(12) United States Patent
O'Keefe et al.

(10) Patent No.: US 11,446,081 B2
(45) Date of Patent: Sep. 20, 2022

(54) MEDICAL INSTRUMENTS FOR PERFORMING MINIMALLY-INVASIVE PROCEDURES

(71) Applicant: Lumendi Ltd., Buckinghamshire (GB)

(72) Inventors: Jonathan O'Keefe, North Attleboro, MA (US); Jeffrey Cerier, Franklin, MA (US); Amos Cruz, Wrentham, MA (US); David Rezac, Westborough, MA (US); Niklas Helmick, Allston, MA (US); Peter Aliski, Melrose, MA (US); Andrew Caunter, Somerville, MA (US)

(73) Assignee: Lumedi Ltd., Maidenhead (GB)

( * ) Notice: Subject to any disclaimer, the term of this patent is extended or adjusted under 35 U.S.C. 154(b) by 187 days.

(21) Appl. No.: 16/780,070

(22) Filed: Feb. 3, 2020

(65) Prior Publication Data
US 2020/0170701 A1  Jun. 4, 2020

Related U.S. Application Data

(63) Continuation-in-part of application No. 15/298,605, filed on Oct. 20, 2016, now Pat. No. 10,617,438.
(Continued)

(51) Int. Cl.
  *A61B 18/14*  (2006.01)
  *A61B 17/00*  (2006.01)
  (Continued)

(52) U.S. Cl.
  CPC .............. *A61B 18/1482* (2013.01); *A61B 2017/00309* (2013.01); *A61B 2017/00323* (2013.01);
  (Continued)

(58) Field of Classification Search
  CPC ............ A61B 17/00234; A61B 17/282; A61B 17/2841; A61B 17/29; A61B 17/2909;
  (Continued)

(56) References Cited

U.S. PATENT DOCUMENTS 4,708,137 A   11/1987  Tsukagoshi
5,273,026 A   12/1993  Wilk
(Continued)

FOREIGN PATENT DOCUMENTS

CN   101849846   6/2013
CN   104586474   5/2015
(Continued)

*Primary Examiner* — George J Ulsh
(74) *Attorney, Agent, or Firm* — Pandiscio & Pandiscio

(57) ABSTRACT

Apparatus for performing a minimally-invasive procedure, the apparatus comprising: a shaft having a distal end and a proximal end; a monopolar knife assembly attached to the distal end of the shaft, the monopolar knife assembly comprising a knife; a handle attached to the proximal end of the shaft; wherein the shaft comprises a flexible portion and an articulating portion, wherein the flexible portion extends distally from the handle and the articulating portion extends distally from the flexible portion; wherein at least one articulation cable extends from the handle to the articulating portion, such that when tension is applied to the at least one articulation cable, the articulating portion deflects; wherein an actuation element extends through the shaft from the handle to the knife, such that when the actuation element is moved, the knife is moved; and wherein the actuation element transmits electrical power from the handle to the knife.

12 Claims, 91 Drawing Sheets

Related U.S. Application Data

(60) Provisional application No. 62/855,308, filed on May 31, 2019, provisional application No. 62/400,759, filed on Sep. 28, 2016, provisional application No. 62/244,026, filed on Oct. 20, 2015.

(51) Int. Cl.
*A61B 18/00* (2006.01)
*A61B 18/12* (2006.01)

(52) U.S. Cl.
CPC .............. *A61B 2018/00601* (2013.01); *A61B 2018/1253* (2013.01); *A61B 2018/1412* (2013.01); *A61B 2218/002* (2013.01)

(58) Field of Classification Search
CPC ........... A61B 2017/00305; A61B 2017/00309; A61B 2017/00323; A61B 2017/00353; A61B 2017/00367; A61B 2017/0046; A61B 2017/00473; A61B 2017/00477; A61B 2017/2905; A61B 2017/2908; A61B 2017/2925; A61B 2017/2932; A61B 90/50

See application file for complete search history.

(56) References Cited

U.S. PATENT DOCUMENTS

| | | |
|---|---|---|
| 5,318,528 A | 6/1994 | Heaven et al. |
| 5,405,344 A | 4/1995 | Williamson et al. |
| 5,419,310 A | 5/1995 | Frassica et al. |
| 5,439,478 A | 8/1995 | Palmer |
| 5,454,827 A | 10/1995 | Aust et al. |
| 5,483,951 A | 1/1996 | Frassica et al. |
| 5,618,294 A | 4/1997 | Aust et al. |
| 5,643,294 A | 7/1997 | Tovey et al. |
| 5,702,408 A | 12/1997 | Wales et al. |
| 5,704,534 A | 1/1998 | Huitema et al. |
| 5,766,196 A | 6/1998 | Griffiths |
| 5,782,834 A | 7/1998 | Lucey et al. |
| 5,797,959 A | 8/1998 | Castro et al. |
| 5,836,960 A | 11/1998 | Kolesa et al. |
| 5,938,678 A | 8/1999 | Zirps et al. |
| 6,210,407 B1 | 4/2001 | Webster |
| 6,350,231 B1 | 2/2002 | Ailinger et al. |
| 6,569,105 B1 | 5/2003 | Kortenbach et al. |
| 6,790,173 B2 | 9/2004 | Saadat et al. |
| 7,090,683 B2 | 8/2006 | Brock et al. |
| 7,125,408 B2 | 10/2006 | Okada |
| 7,147,650 B2 | 12/2006 | Lee |
| 7,169,141 B2 | 1/2007 | Brock et al. |
| 7,214,230 B2 | 5/2007 | Brock et al. |
| 7,338,513 B2 | 3/2008 | Lee et al. |
| 7,364,582 B2 | 4/2008 | Lee |
| 7,371,210 B2 | 5/2008 | Brock et al. |
| D583,051 S | 12/2008 | Lee et al. |
| 7,615,067 B2 | 11/2009 | Lee et al. |
| 7,618,416 B2 | 11/2009 | Ono et al. |
| 7,648,519 B2 | 1/2010 | Lee et al. |
| 7,686,826 B2 | 3/2010 | Lee et al. |
| 7,708,758 B2 | 5/2010 | Lee et al. |
| 7,842,028 B2 | 11/2010 | Lee |
| D631,155 S | 1/2011 | Peine et al. |
| D640,789 S | 6/2011 | Peine et al. |
| 8,016,825 B2 | 9/2011 | Okada |
| 8,029,531 B2 | 10/2011 | Lee et al. |
| 8,048,073 B2 | 11/2011 | Nakamura et al. |
| 8,083,765 B2 | 12/2011 | Lee et al. |
| 8,105,350 B2 | 1/2012 | Lee et al. |
| 8,187,271 B2 | 5/2012 | Yahagi et al. |
| 8,221,450 B2 | 7/2012 | Lee et al. |
| 8,257,386 B2 | 9/2012 | Lee et al. |
| 8,372,071 B2 | 2/2013 | Machiya et al. |
| 8,409,175 B2 | 4/2013 | Lee et al. |
| 8,409,245 B2 | 4/2013 | Lee |
| 8,579,894 B2 | 11/2013 | Falkenstein et al. |
| 8,679,097 B2 | 3/2014 | Jorgensen et al. |
| 8,709,037 B2 | 4/2014 | Lee et al. |
| 8,926,597 B2 | 1/2015 | Lee |
| 9,138,283 B2 | 9/2015 | Wake |
| 9,168,050 B1 | 10/2015 | Peine et al. |
| 9,301,800 B2 | 4/2016 | Suzuki et al. |
| 9,387,034 B2 | 7/2016 | Okada |
| 9,427,256 B2 | 8/2016 | Lee |
| 9,832,980 B2 | 12/2017 | Kovarik et al. |
| 9,901,245 B2 | 2/2018 | Kovarik et al. |
| 9,962,179 B2 | 5/2018 | Castro et al. |
| 10,188,372 B2 | 1/2019 | Lee |
| 10,226,266 B2 | 3/2019 | Kovarik et al. |
| 2003/0135204 A1 | 7/2003 | Lee et al. |
| 2004/0210284 A1 | 10/2004 | Okada |
| 2005/0072280 A1 | 4/2005 | Ono et al. |
| 2005/0113827 A1 | 5/2005 | Dumbauld et al. |
| 2006/0270969 A1 | 11/2006 | Toyonaga et al. |
| 2006/0271079 A1 | 11/2006 | Akiba et al. |
| 2007/0038213 A1 | 2/2007 | Machiya et al. |
| 2008/0027429 A1 | 1/2008 | Oyatsu |
| 2008/0045785 A1 | 2/2008 | Oyatsu |
| 2008/0065116 A1 | 3/2008 | Lee et al. |
| 2008/0188868 A1 | 8/2008 | Weitzner et al. |
| 2008/0300462 A1 | 12/2008 | Intoccia et al. |
| 2010/0168510 A1 | 7/2010 | Rogers et al. |
| 2010/0234831 A1 | 9/2010 | Hinman et al. |
| 2011/0009863 A1 | 1/2011 | Marczyk et al. |
| 2011/0092963 A1 | 4/2011 | Castro |
| 2011/0137123 A1 | 6/2011 | Suzuki et al. |
| 2011/0152609 A1 | 6/2011 | Trusty et al. |
| 2012/0150155 A1 | 6/2012 | Kappel et al. |
| 2013/0012958 A1 | 1/2013 | Marczyk et al. |
| 2013/0267936 A1 | 10/2013 | Stroup et al. |
| 2013/0317375 A1 | 11/2013 | Garcia et al. |
| 2014/0148803 A1 | 5/2014 | Taylor |
| 2014/0188159 A1 | 7/2014 | Steege |
| 2014/0207134 A1 | 7/2014 | Wake |
| 2014/0288554 A1 | 9/2014 | Okada |
| 2015/0025528 A1 | 1/2015 | Arts |
| 2015/0066033 A1 | 3/2015 | Jorgensen |
| 2015/0164524 A1 | 6/2015 | Malkowski et al. |
| 2016/0353979 A1 | 12/2016 | Hashizume et al. |
| 2017/0105746 A1 | 4/2017 | O'Keefe et al. |
| 2017/0231701 A1 | 8/2017 | Cohen et al. |
| 2018/0008805 A1 | 1/2018 | Pleijers |
| 2018/0078249 A1 | 3/2018 | Stoy et al. |
| 2020/0337791 A1 | 10/2020 | Shelton, IV et al. |

FOREIGN PATENT DOCUMENTS

| | | |
|---|---|---|
| CN | 103717147 | 9/2017 |
| JP | 2008-220972 | 9/2008 |
| JP | 2009-112538 | 5/2009 |
| WO | WO2006094242 | 9/2006 |
| WO | WO2017171560 | 10/2017 |

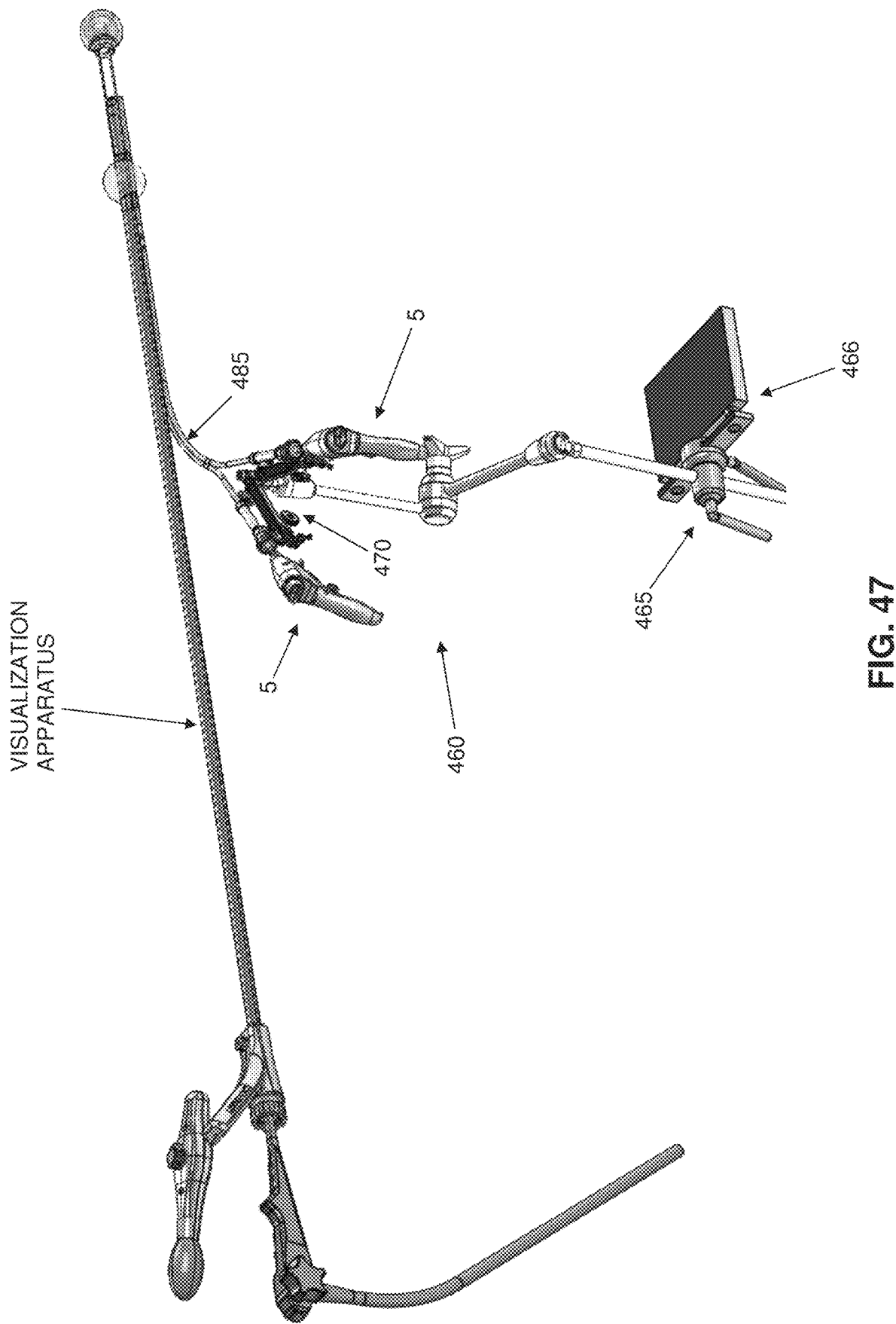

Multi-Pivot

Fixed Wing - 1

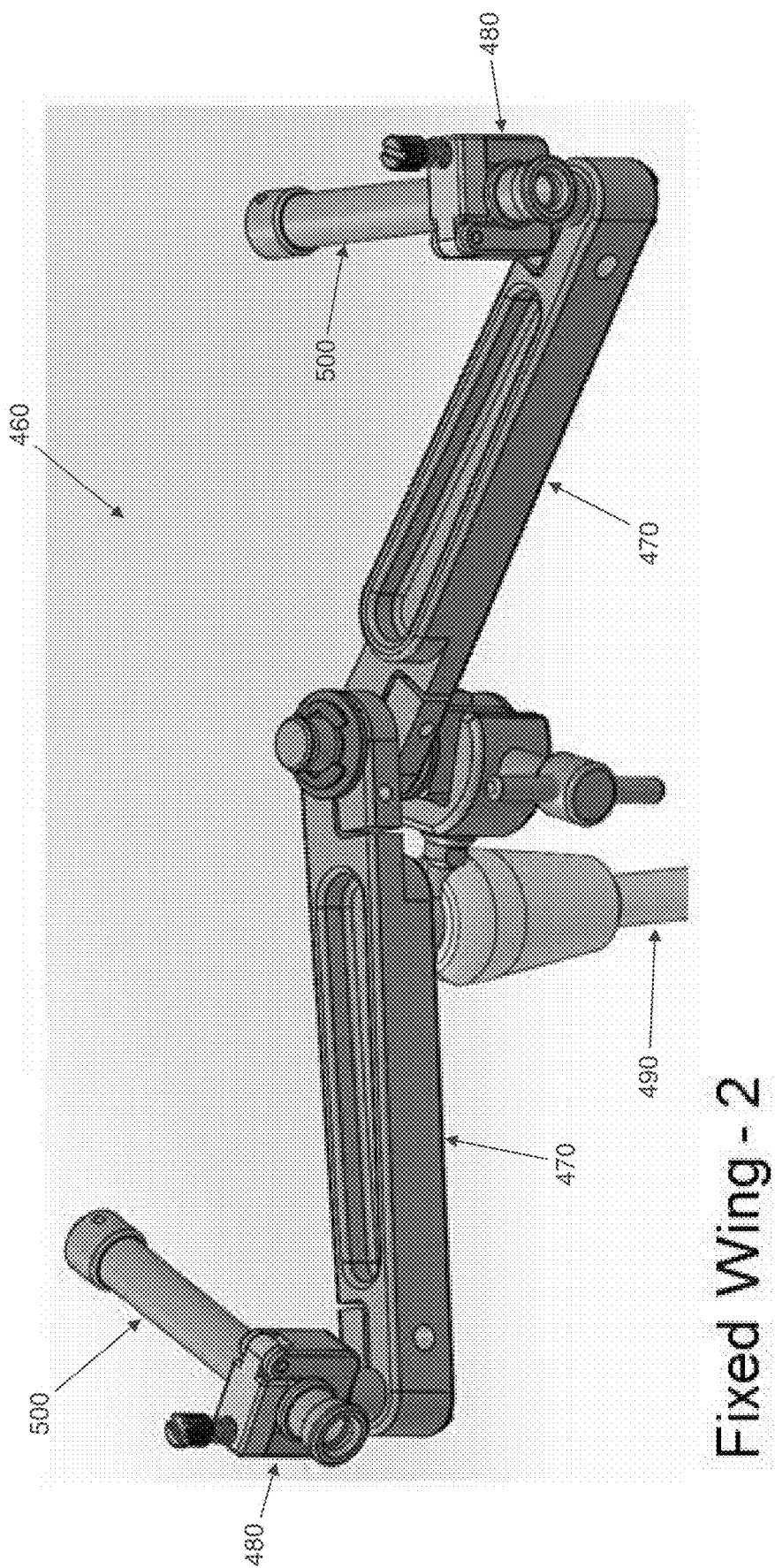
FIG. 55 Fixed Wing - 2

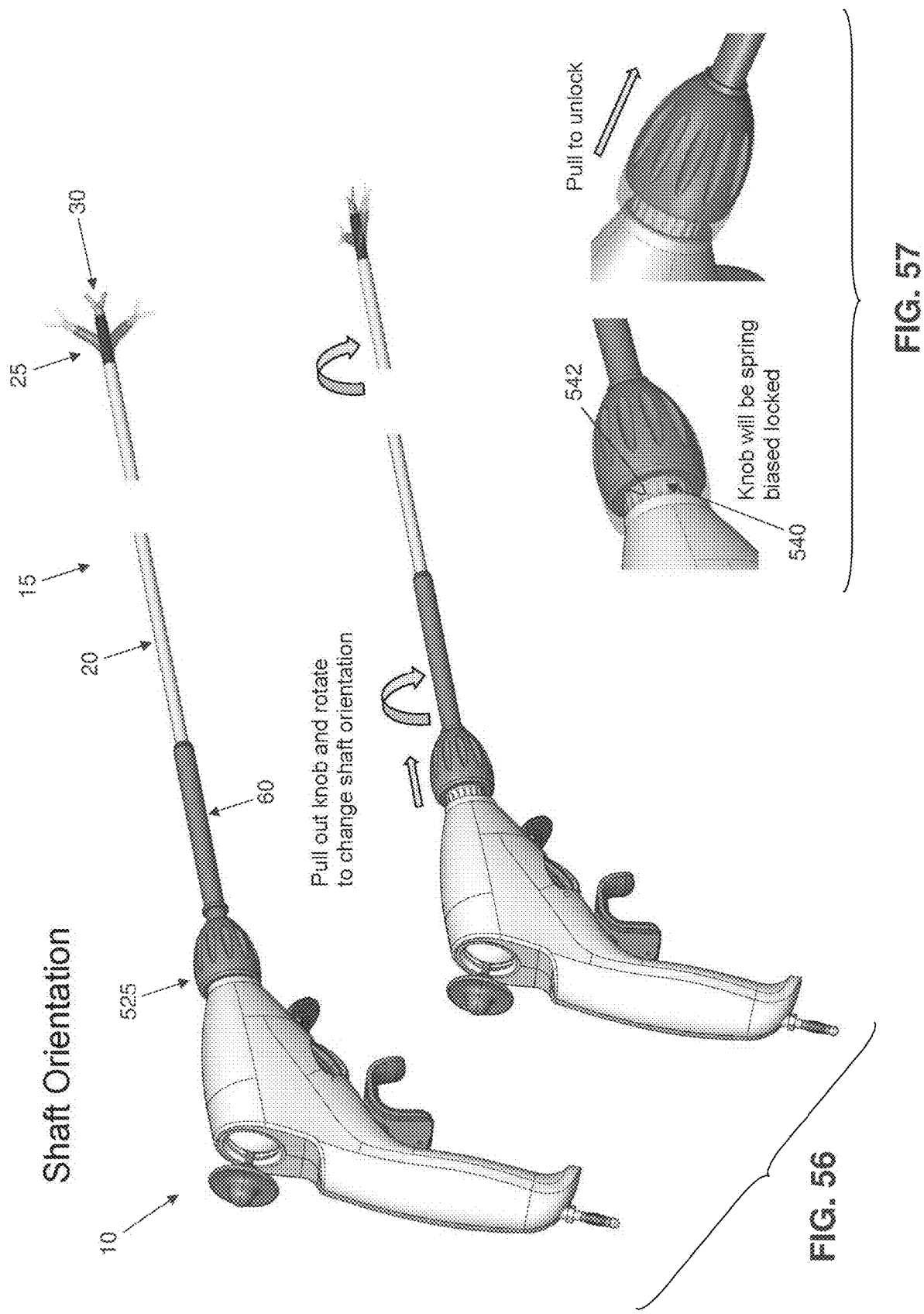

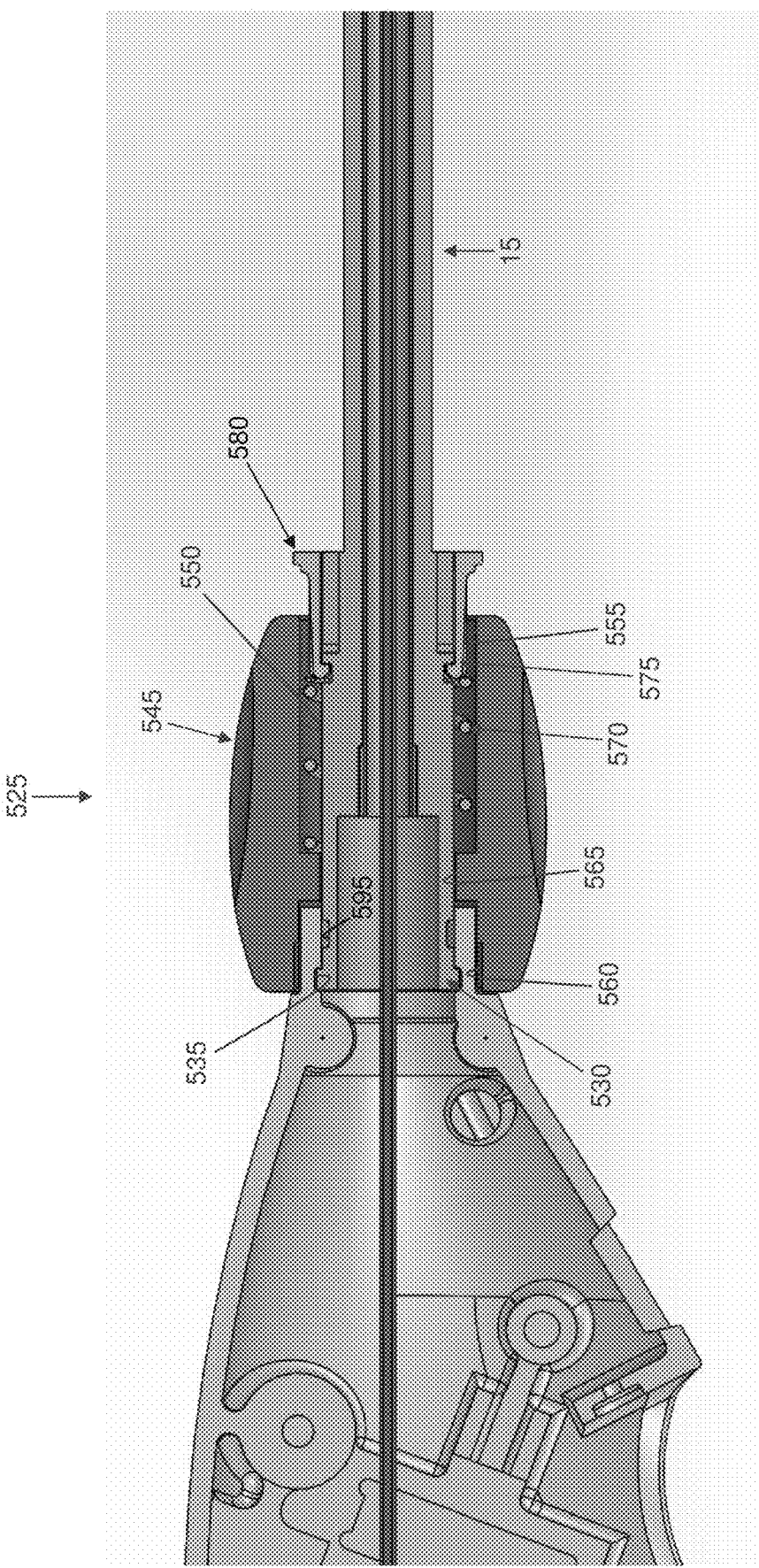

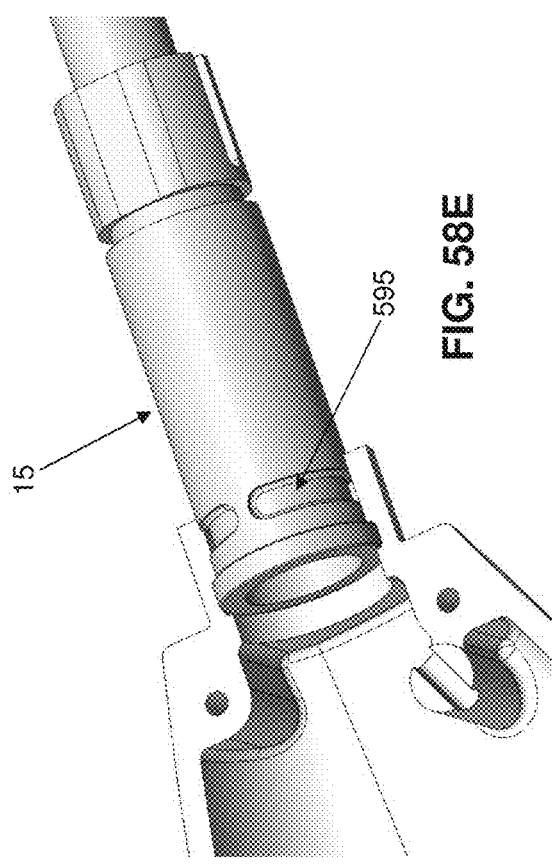
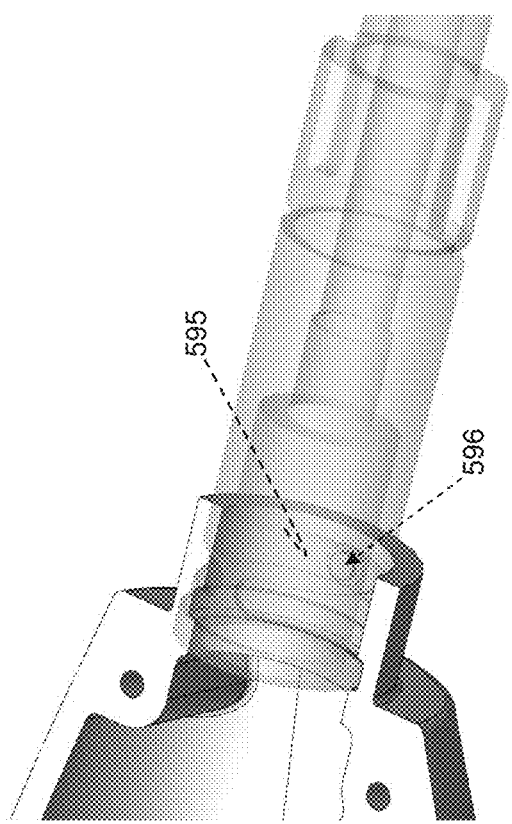

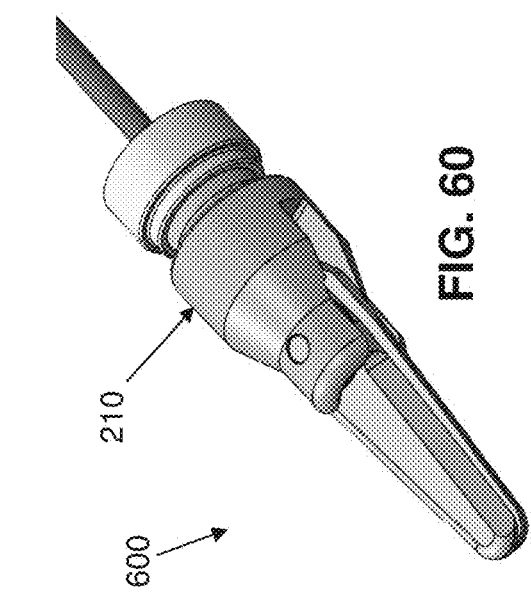
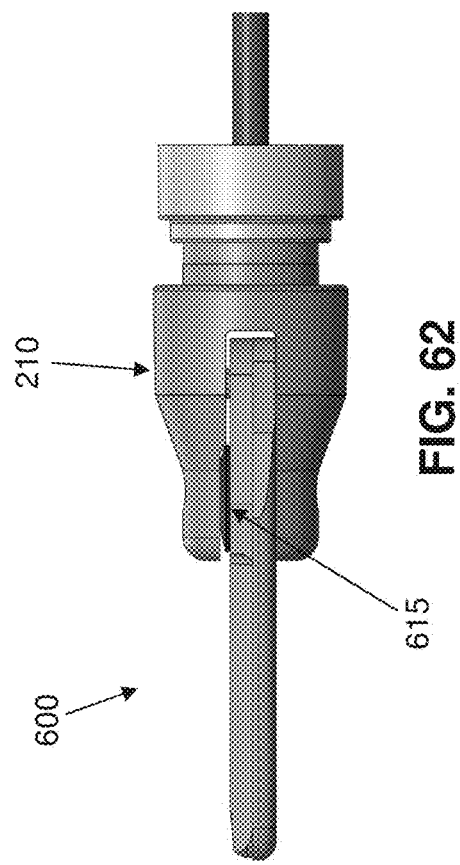
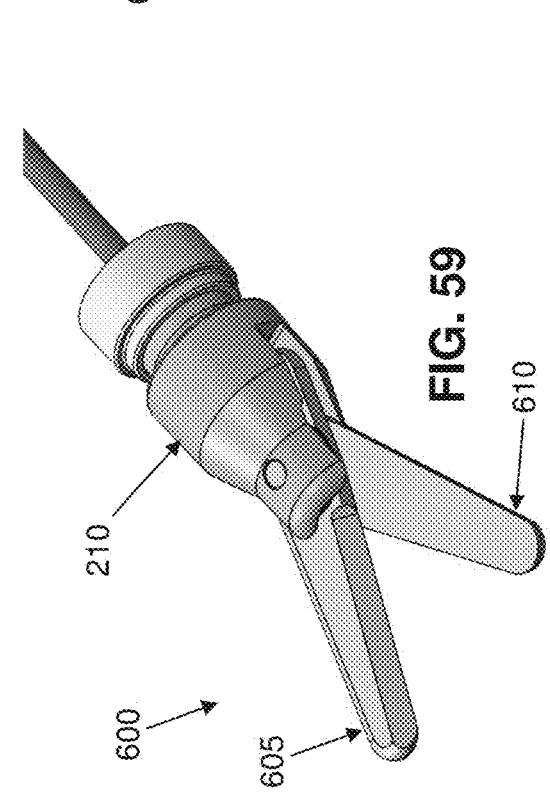
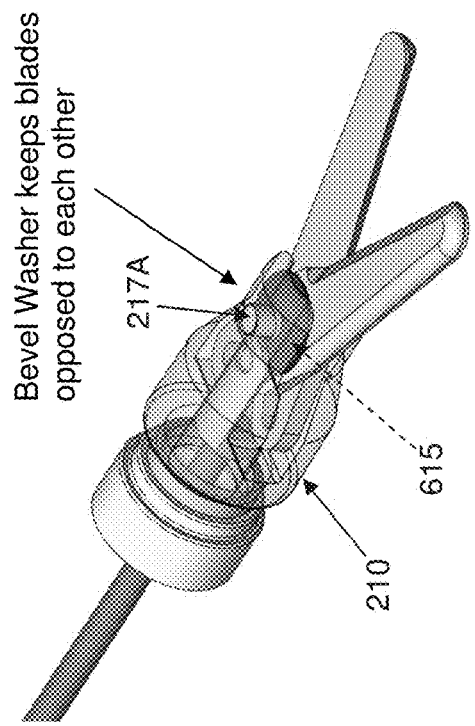

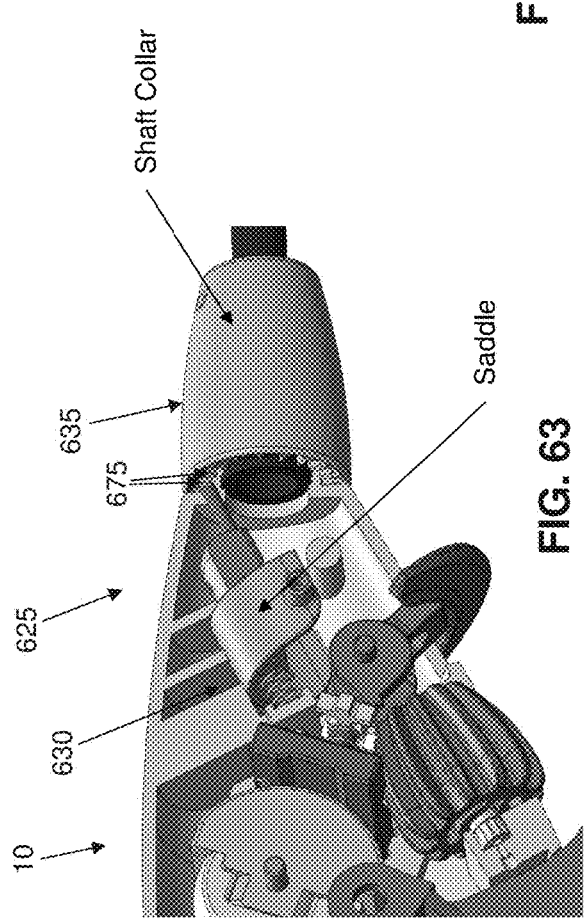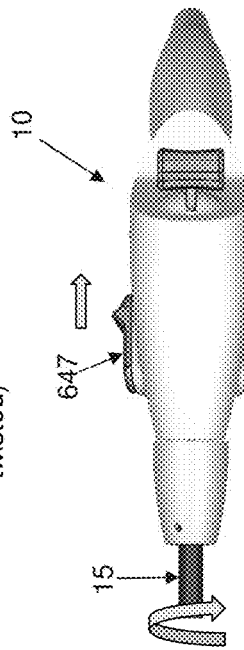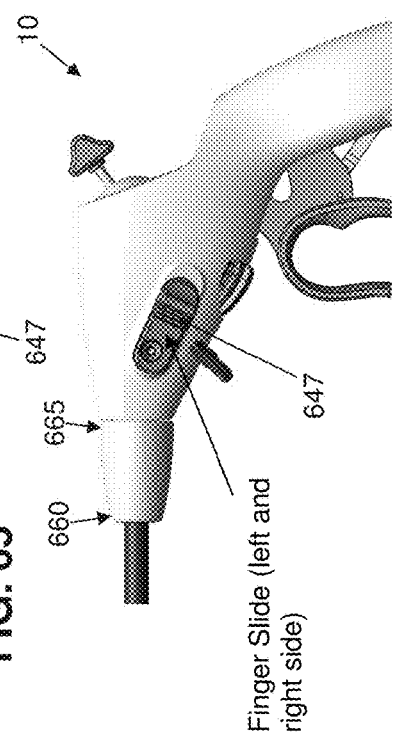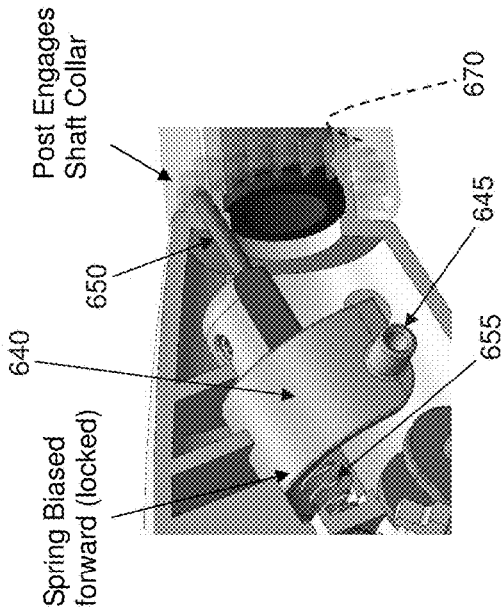
FIG. 63
FIG. 64
FIG. 65
FIG. 66

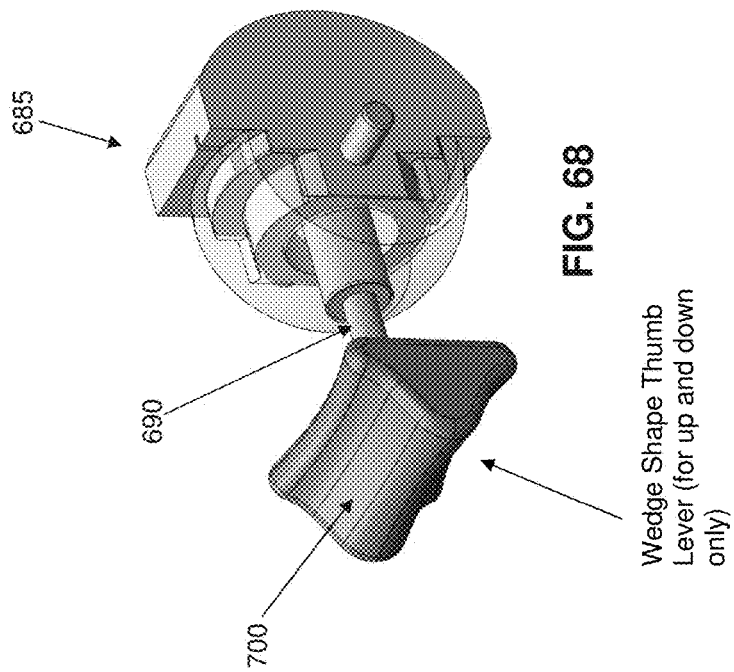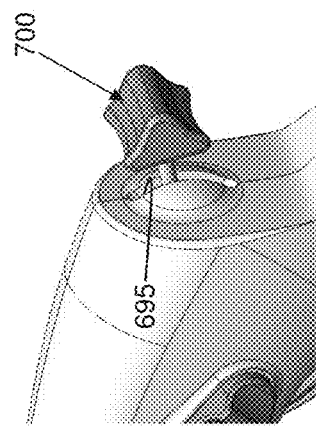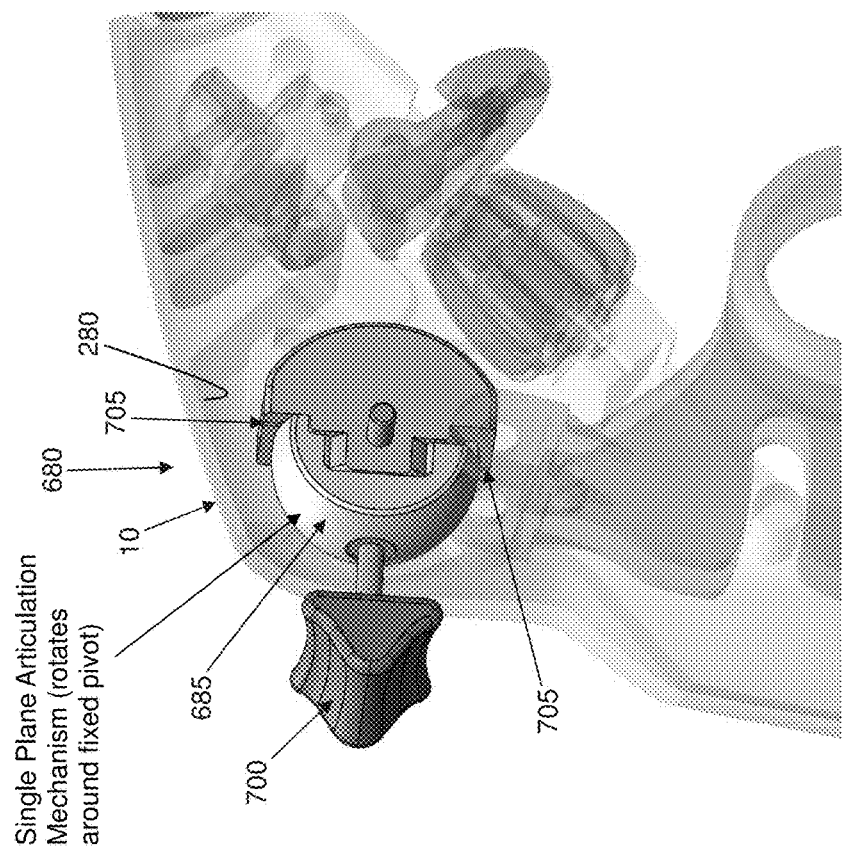
FIG. 68
FIG. 69
FIG. 67

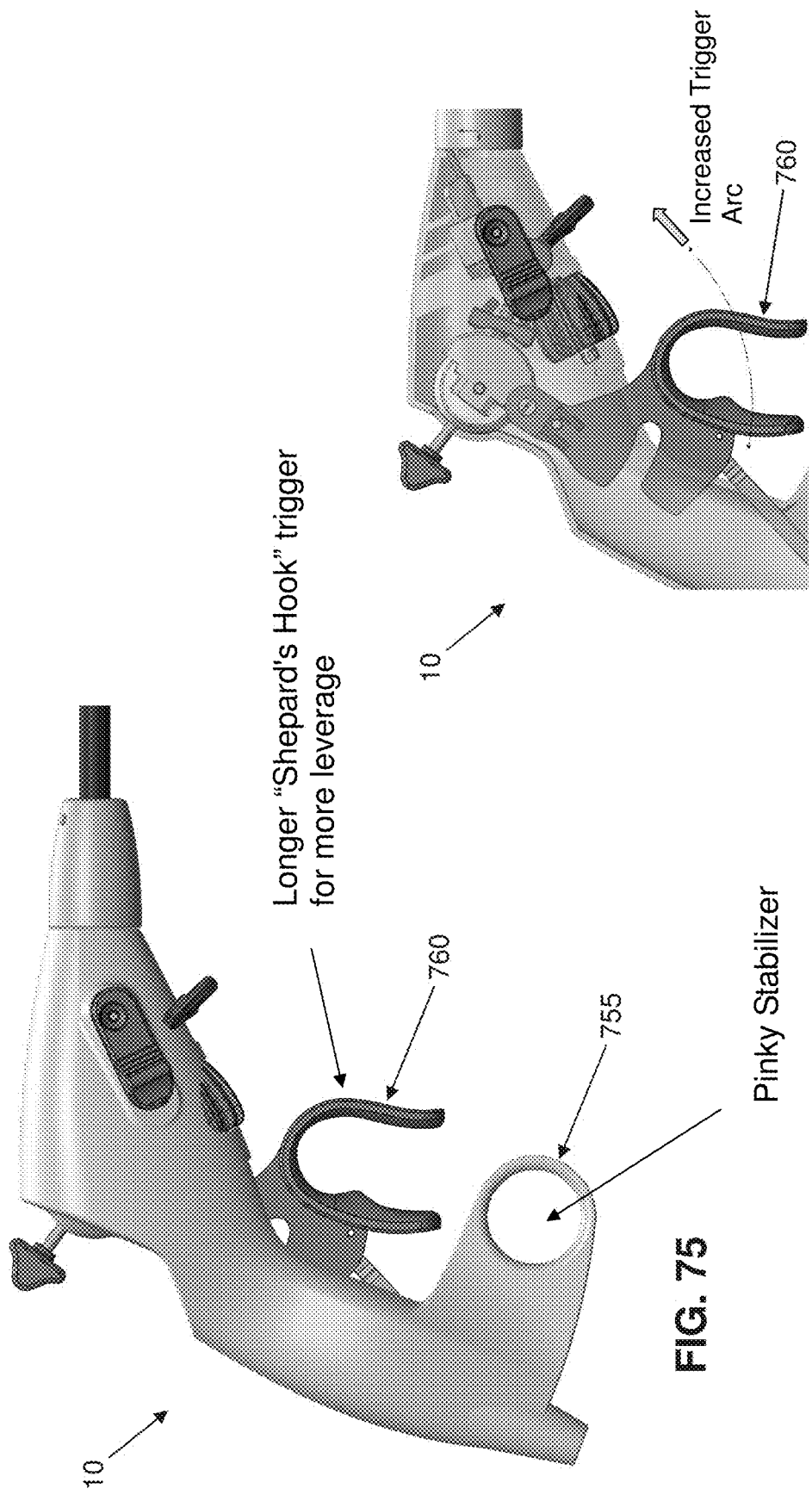

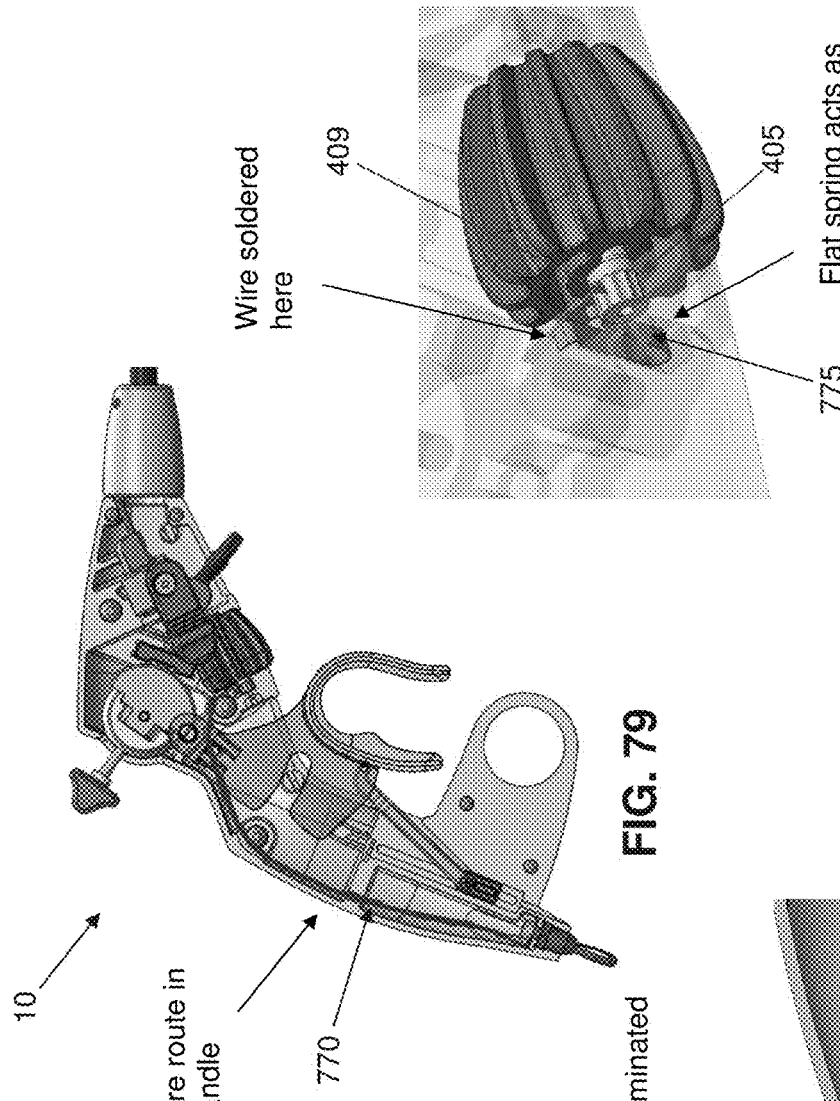
FIG. 80
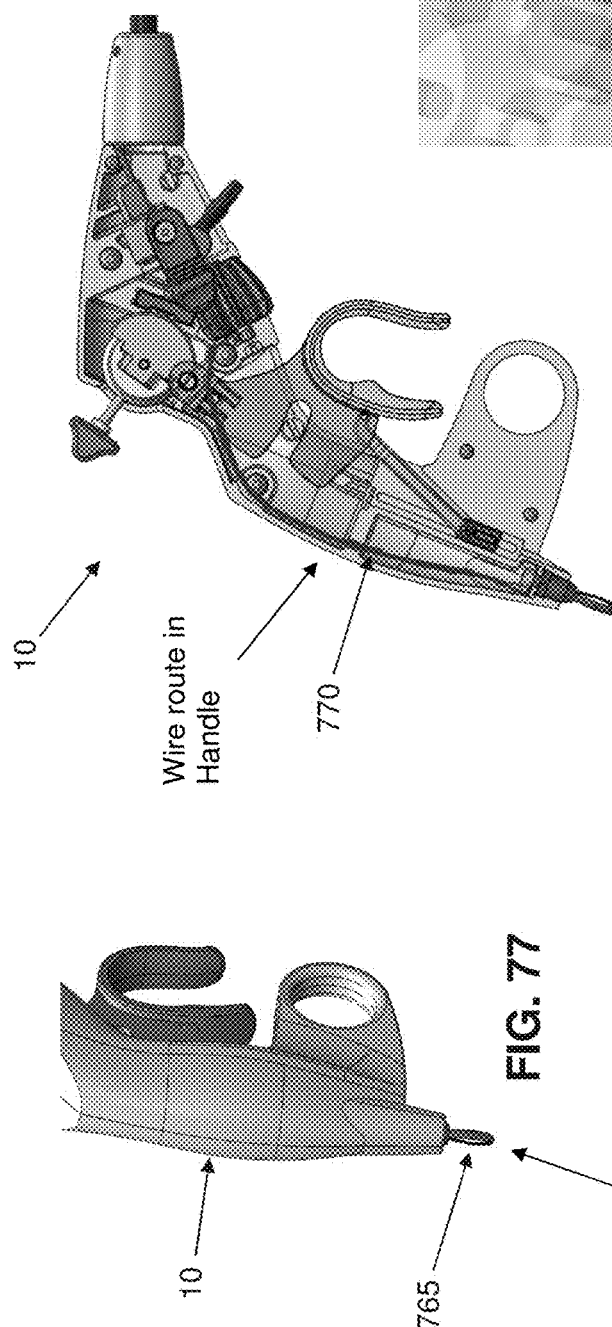
FIG. 79
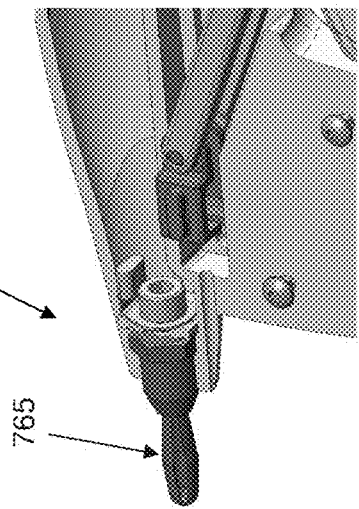
FIG. 78
FIG. 77

PTFE Tubing runs through the center of the shaft

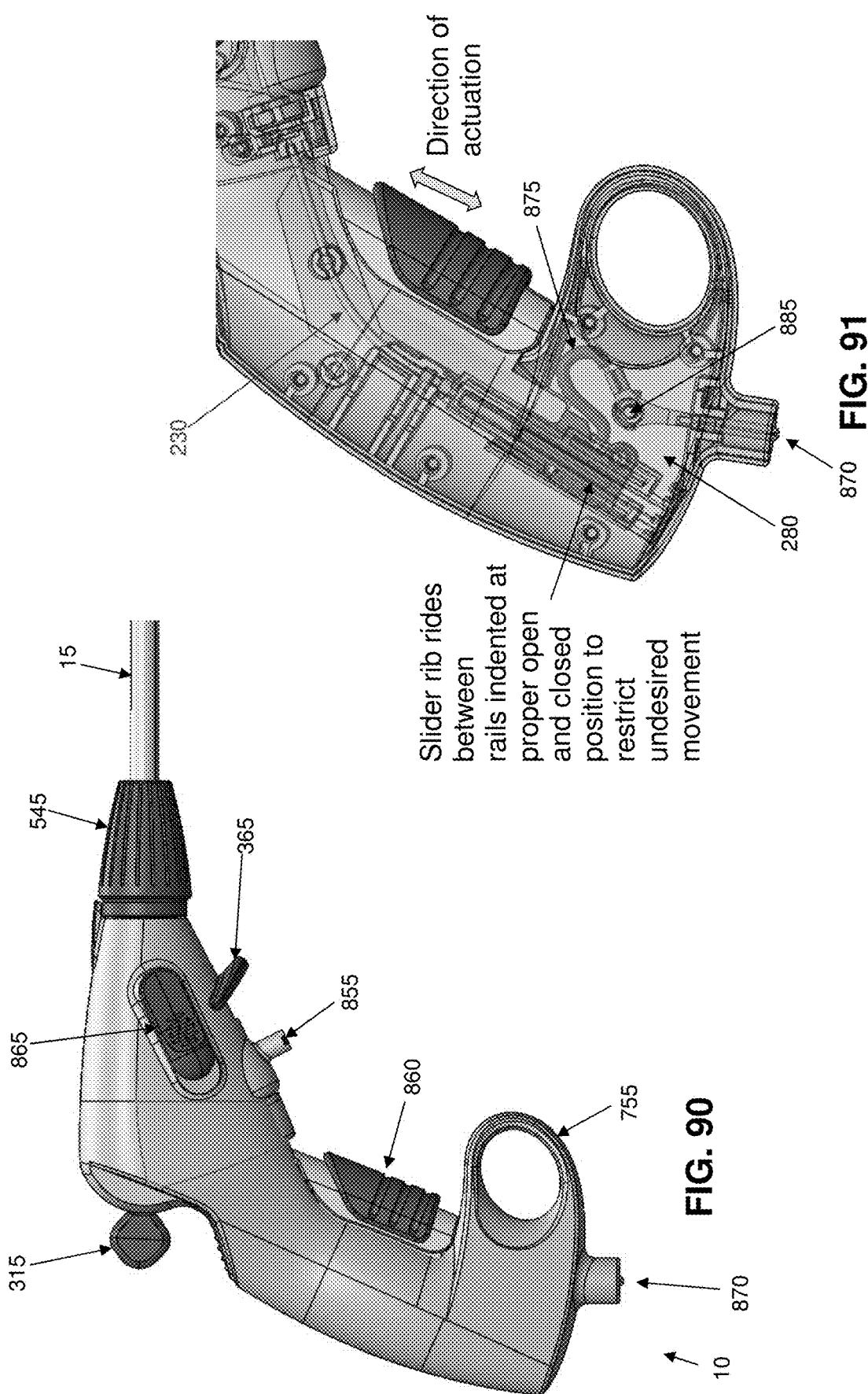

Closeup of wire connection at slider to Pull Cable Power Connector

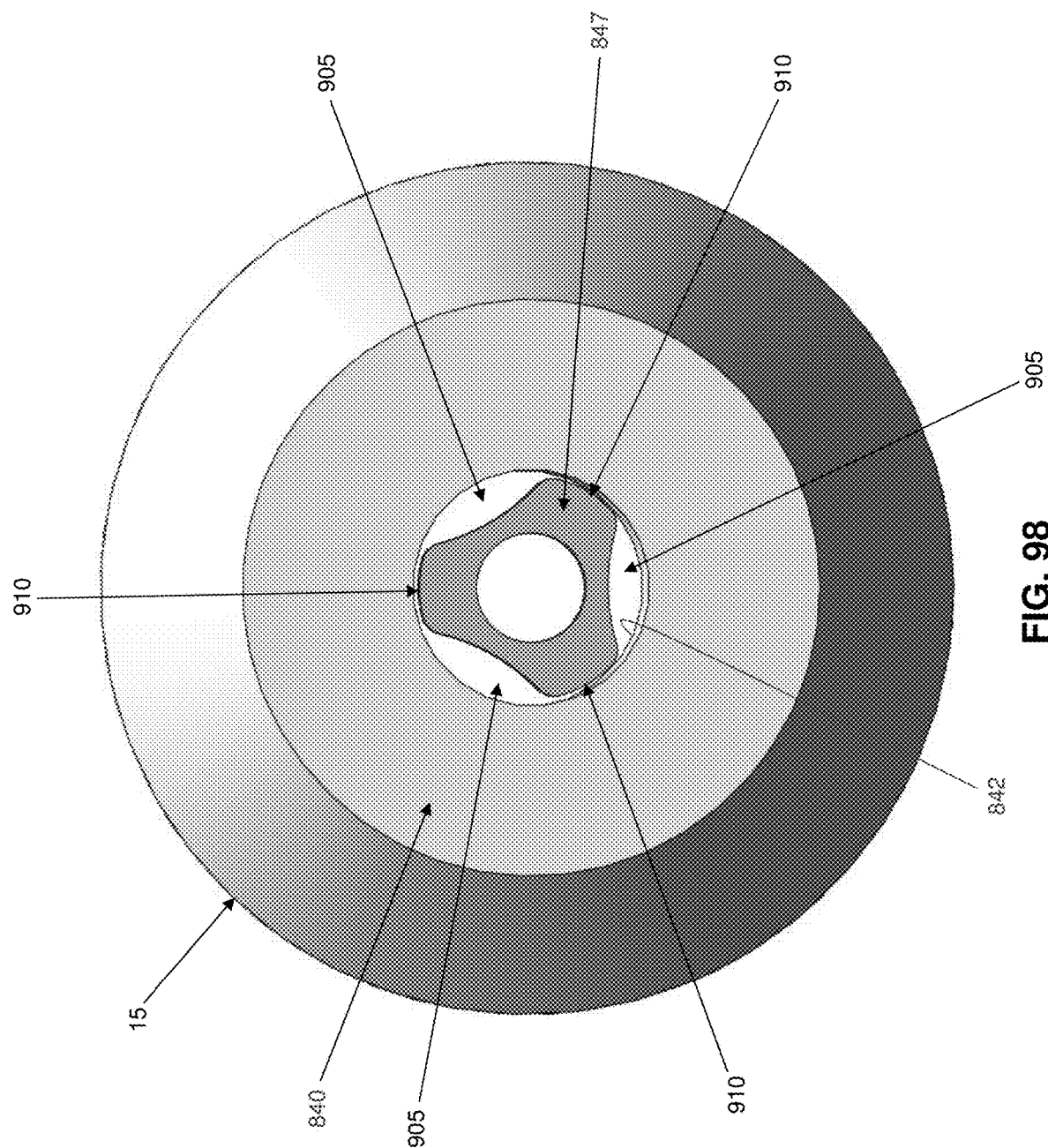

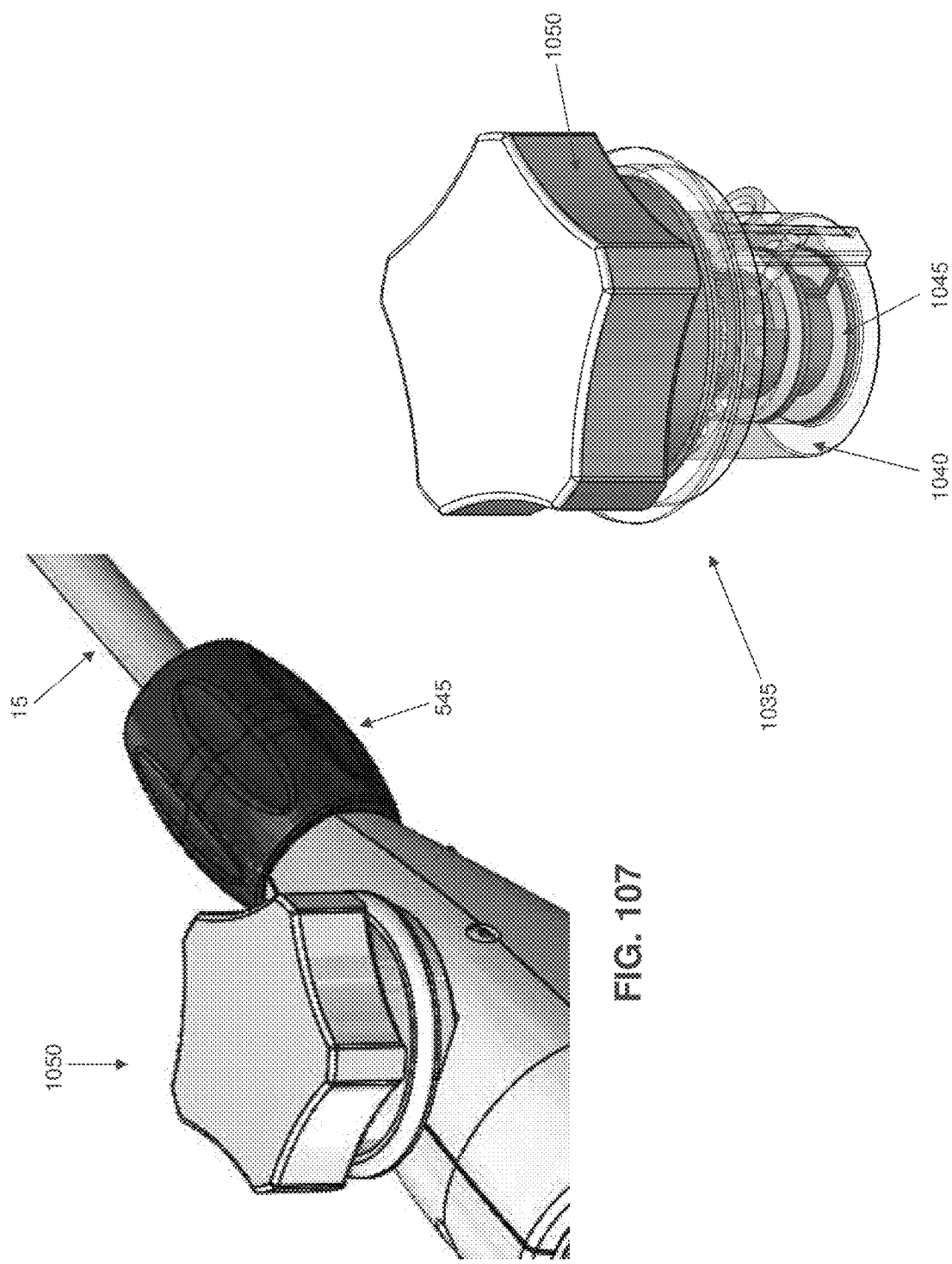

MEDICAL INSTRUMENTS FOR PERFORMING MINIMALLY-INVASIVE PROCEDURES

REFERENCE TO PENDING PRIOR PATENT APPLICATIONS

This patent application:

(1) is a continuation-in-part of pending prior U.S. patent application Ser. No. 15/298,605, filed Oct. 20, 2016 by Lumendi Ltd. and Jonathan O'Keefe et al. for MEDICAL INSTRUMENTS FOR PERFORMING MINIMALLY-INVASIVE PROCEDURES, which patent application claims benefit of (i) prior U.S. Provisional Patent Application Ser. No. 62/244,026, filed Oct. 20, 2015 by Lumendi Ltd. and Jonathan O'Keefe et al. for MEDICAL INSTRUMENTS FOR PERFORMING MINIMALLY-INVASIVE PROCEDURES; and (ii) prior U.S. Provisional Patent Application Ser. No. 62/400,759, filed Sep. 28, 2016 by Lumendi Ltd. and Jonathan O'Keefe et al. for MEDICAL INSTRUMENTS FOR PERFORMING MINIMALLY-INVASIVE PROCEDURES; and (2) claims benefit of prior U.S. Provisional Patent Application Ser. No. 62/855,308, filed May 31, 2019 by Lumendi Ltd. and Jonathan O'Keefe et al. for MEDICAL INSTRUMENTS FOR PERFORMING MINIMALLY-INVASIVE PROCEDURES.

The four (4) above-identified patent applications are hereby incorporated herein by reference.

FIELD OF THE INVENTION

This invention relates to medical instruments in general, and more particularly to medical instruments for performing minimally-invasive procedures.

BACKGROUND OF THE INVENTION

Minimally-invasive medical procedures have become commonplace. In a typical minimally-invasive procedure, access to an internal site is effected through one or more small portals (e.g., a natural body orifice, a small incision in the skin, etc.). A scope (e.g., a colonoscope, an arthroscope, an endoscope, etc.) is inserted through a portal so as to provide visualization of the internal site, and then one or more medical instruments are inserted, either through the same portal (e.g., via an internal channel in the scope) or through another portal, so that the medical instruments can be used to carry out a procedure at the internal site under the visualization provided by the scope.

In many cases the internal site may be difficult to reach due to anatomical constraints, equipment limitations, etc. By way of example but not limitation, in many situations it may be desirable for a medical instrument to be advanced to the internal site through an internal channel of a scope, or for a medical instrument to be advanced to the internal site alongside the scope, and then bent (e.g., along a short radius) so as to enter the visual field of the scope, so that the desired procedure is carried out under the visualization provided by the scope. And in many cases, the path along which the medical instrument needs to be advanced may be tortuous (e.g., endoluminally within the colon). In this situation, it is necessary for the medical instrument to be highly flexible, capable of articulating with a range of different motions, and configured for precise control, while being operated (e.g., along a tortuous path) from only the handle end (i.e., the proximal end) of the medical instrument. In practice, this is extremely difficult to achieve.

The present invention is intended to provide a novel medical instrument capable of such function.

SUMMARY OF THE INVENTION

The present invention comprises a novel medical instrument for performing minimally-invasive procedures. The novel medical instrument is highly flexible, capable of articulating with a range of different motions, and configured for precise control, while being operated (e.g., along a tortuous path) from only the handle end of the medical instrument.

The novel medical instrument generally comprises a handle and a shaft extending distally from the handle. The shaft generally comprises an elongated, flexible proximal portion and a distal articulating portion which is mounted to the distal end of the flexible proximal portion. An end effector is mounted to the distal end of the distal articulating portion. The end effector may take many different forms (e.g., graspers, injection needles, scissors, hot snares, monopolar probes, hemostasis clips, bipolar forceps, suction tubes, single-fire or multi-fire closure devices such as staplers and tackers, dissector forceps, retrieval baskets, monopolar scissors, monopolar knife, monopolar knife with flushing capabilities, etc.). For clarity of illustration, the end effector is shown in the figures as a grasper. The handle may take any one of many different forms (e.g., a pistol grip, a shaft grip, etc.). For clarity of illustration, the handle is shown in the figures as a pistol grip.

In accordance with the present invention, the flexible proximal portion of the shaft is configured to be a highly flexible element capable of extending a significant length (e.g., 95 cm-140 cm) along a tortuous path, the distal articulating portion of the shaft is configured to be capable of universal articulation relative to the distal end of the flexible proximal portion of the shaft, and the end effector is configured to be selectively rotated relative to the distal end of the distal articulating portion and may be selectively actuated, with all functions able to be carried out by a single hand of a user via the handle. In one preferred form of the invention, substantially the entire shaft of the medical instrument is flexible, with the portion of the shaft proximal to a transition point (i.e., the flexible proximal portion) being passively flexible (e.g., able to follow a tortuous path), and the portion of the shaft distal to the transition point (i.e., the distal articulating portion) being actively flexible (e.g., able to be universally articulated to a desired configuration).

As will hereinafter be described in further detail, the novel medical instrument is capable of at least the following motions:

Motion 1—longitudinal movement of the end effector by longitudinal movement of the handle (sometimes hereinafter referred to as a "longitudinal motion function");

Motion 2—rotational movement of the end effector by rotational movement of the handle (sometimes hereinafter referred to as a "torqueing motion function");

Motion 3—articulating movement of the end effector relative to the handle by articulating the distal articulating portion of the shaft relative to the distal end of the flexible proximal portion of the shaft (sometimes hereinafter referred to as a "universal articulation function");

Motion 4—rotational movement of the end effector relative to the distal end of the distal articulating portion of the shaft by rotating the end effector relative to the shaft (sometimes hereinafter referred to as a "roticulation function"); and Motion 5—actuation of the end effector, e.g., selectively moving elements of the end effector relative to one another so as to carry out a medical procedure, e.g., opening and closing the jaws of a grasper-type end effector (sometimes hereinafter referred to as a "jaw open/close function").

In one preferred form of the present invention, there is provided apparatus for performing a minimally-invasive procedure, the apparatus comprising:

a tool comprising:
a shaft having a distal end and a proximal end;
a handle attached to the proximal end of the shaft; and
an end effector attached to the distal end of the shaft;
wherein the shaft comprises a flexible portion extending distally from the proximal end of the shaft, and an articulating portion extending proximally from the distal end of the shaft, and wherein the articulating portion comprises a flexible spine;
wherein a plurality of articulation cables extend through the shaft from the handle to the flexible spine, each of the plurality of articulation cables having an articulation cable housing disposed about the articulation cable such that when tension is applied to at least one of the plurality of articulation cables, the flexible spine bends, with the articulation cable housings providing a counterforce to the flexible spine;
wherein a rotatable element extends through the shaft from the handle to the end effector, such that when the rotatable element is rotated, the end effector rotates; and
wherein an actuation element extends through the shaft from the handle to the end effector, such that when the actuation element is moved, the end effector is actuated.

In another preferred form of the present invention, there is provided a method for performing a minimally-invasive procedure, the method comprising:

obtaining apparatus for performing a minimally-invasive procedure, the apparatus comprising:

a tool comprising:
a shaft having a distal end and a proximal end;
a handle attached to the proximal end of the shaft; and
an end effector attached to the distal end of the shaft;
wherein the shaft comprises a flexible portion extending distally from the proximal end of the shaft, and an articulating portion extending proximally from the distal end of the shaft, and wherein the articulating portion comprises a flexible spine;
wherein a plurality of articulation cables extend through the shaft from the handle to the flexible spine, each of the plurality of articulation cables having an articulation cable housing disposed about the articulation cable such that when tension is applied to at least one of the plurality of articulation cables, the flexible spine bends, with the articulation cable housings providing a counterforce to the flexible spine;
wherein a rotatable element extends through the shaft from the handle to the end effector, such that when the rotatable element is rotated, the end effector rotates; and
wherein an actuation element extends through the shaft from the handle to the end effector, such that when the actuation element is moved, the end effector is actuated; and using the apparatus to perform a minimally-invasive procedure.

In another preferred form of the present invention, there is provided apparatus for performing a minimally-invasive procedure, the apparatus comprising:

a tool comprising:
a shaft having a distal end and a proximal end;
a handle attached to the proximal end of the shaft; and
an end effector attached to the distal end of the shaft;
wherein the shaft comprises a flexible portion extending distally from the proximal end of the shaft, and an articulating portion extending proximally from the distal end of the shaft, and wherein the articulating portion comprises a flexible spine;
wherein a plurality of articulation cables extend through the shaft from the handle to the flexible spine, such that when tension is applied to at least one of the plurality of articulation cables, the flexible spine bends;
wherein a rotatable element extends through the shaft from the handle to the end effector, such that when the rotatable element is rotated, the end effector rotates, wherein the rotatable element comprises a hollow tubular structure extending distally from the handle, the hollow tubular structure being formed out of a plurality of filars which are wound and swaged together, and further wherein the rotatable element further comprises a laser-cut hypotube secured to the hollow tubular structure, such that when the hollow tubular structure is rotated, the laser-cut hypotube is also rotated; and
wherein an actuation element extends through the shaft from the handle to the end effector, such that when the actuation element is moved, the end effector is actuated.

In another preferred form of the present invention, there is provided a method for performing a minimally-invasive procedure, the method comprising:

obtaining apparatus for performing a minimally-invasive procedure, the apparatus comprising:

a tool comprising:
a shaft having a distal end and a proximal end;
a handle attached to the proximal end of the shaft; and
an end effector attached to the distal end of the shaft;
wherein the shaft comprises a flexible portion extending distally from the proximal end of the shaft, and an articulating portion extending proximally from the distal end of the shaft, and wherein the articulating portion comprises a flexible spine;
wherein a plurality of articulation cables extend through the shaft from the handle to the flexible spine, such that when tension is applied to at least one of the plurality of articulation cables, the flexible spine bends;
wherein a rotatable element extends through the shaft from the handle to the end effector, such that when the rotatable element is rotated, the end effector rotates, wherein the rotatable element comprises a hollow tubular structure extending distally from the handle, the hollow tubular structure being formed out of a plurality of filars which are wound and swaged together, and further wherein the rotatable element further comprises a laser-cut hypotube secured to the hollow tubular structure, such that when the hollow tubular structure is rotated, the laser-cut hypotube is also rotated; and wherein an actuation element extends through the shaft from the handle to the end effector, such that when the actuation element is moved, the end effector is actuated; and using the apparatus to perform a minimally-invasive procedure.

In another preferred form of the present invention, there is provided apparatus for performing a minimally-invasive procedure, the apparatus comprising:

a tool comprising:
a shaft having a distal end and a proximal end;
a handle attached to the proximal end of the shaft; and
an end effector attached to the distal end of the shaft;
wherein the shaft comprises a flexible portion extending distally from the proximal end of the shaft, and an articulating portion extending proximally from the distal end of the shaft, and wherein the articulating portion comprises a flexible spine;
wherein a plurality of articulation cables extend through the shaft from the handle to the flexible spine, such that when tension is applied to at least one of the plurality of articulation cables, the flexible spine bends;
wherein a rotatable element extends through the shaft from the handle to the end effector, such that when the rotatable element is rotated, the end effector rotates;
wherein an actuation element extends through the shaft from the handle to the end effector, such that when the actuation element is moved, the end effector is actuated; and
wherein the flexible portion of the shaft comprises an outer coil secured to the flexible spine, a rigid tube configured to rotate relative to the handle, and an outer covering secured to the rigid tube and the flexible spine, such that rotation of the rigid tube causes rotation of the outer covering which causes rotation of the flexible spine.

In another preferred form of the present invention, there is provided a method for performing a minimally-invasive procedure, the method comprising:

obtaining apparatus for performing a minimally-invasive procedure, the apparatus comprising:

a tool comprising:
a shaft having a distal end and a proximal end;
a handle attached to the proximal end of the shaft; and
an end effector attached to the distal end of the shaft;
wherein the shaft comprises a flexible portion extending distally from the proximal end of the shaft, and an articulating portion extending proximally from the distal end of the shaft, and wherein the articulating portion comprises a flexible spine;
wherein a plurality of articulation cables extend through the shaft from the handle to the flexible spine, such that when tension is applied to at least one of the plurality of articulation cables, the flexible spine bends;
wherein a rotatable element extends through the shaft from the handle to the end effector, such that when the rotatable element is rotated, the end effector rotates;
wherein an actuation element extends through the shaft from the handle to the end effector, such that when the actuation element is moved, the end effector is actuated; and
wherein the flexible portion of the shaft comprises an outer coil secured to the flexible spine, a rigid tube configured to rotate relative to the handle, and an outer covering secured to the rigid tube and the flexible spine, such that rotation of the rigid tube causes rotation of the outer covering which causes rotation of the flexible spine; and using the apparatus to perform a minimally-invasive procedure.

In another preferred form of the present invention, there is provided apparatus for performing a minimally-invasive procedure, the apparatus comprising:

a tool comprising:
a shaft having a distal end and a proximal end;
a handle attached to the proximal end of the shaft; and
an end effector attached to the distal end of the shaft;
wherein the shaft comprises a flexible portion extending distally from the proximal end of the shaft, and an articulating portion extending proximally from the distal end of the shaft, and wherein the articulating portion comprises a flexible spine;
wherein a plurality of articulation cables extend through the shaft from the handle to the flexible spine, such that when tension is applied to at least one of the plurality of articulation cables, the flexible spine bends;
wherein a rotatable element extends through the shaft from the handle to the end effector, such that when the rotatable element is rotated, the end effector rotates;
wherein an actuation element extends through the shaft from the handle to the end effector, such that when the actuation element is moved, the end effector is actuated; and
wherein the proximal end of the shaft further comprises a rigid portion, and wherein the apparatus further comprises a tool support mounted to a patient support, the tool support comprising an opening for receiving the rigid portion.

In another preferred form of the present invention, there is provided a method for performing a minimally-invasive procedure, the method comprising:

obtaining apparatus for performing a minimally-invasive procedure, the apparatus comprising:

a tool comprising:
a shaft having a distal end and a proximal end;
a handle attached to the proximal end of the shaft; and
an end effector attached to the distal end of the shaft;
wherein the shaft comprises a flexible portion extending distally from the proximal end of the shaft, and an articulating portion extending proximally from the distal end of the shaft, and wherein the articulating portion comprises a flexible spine;
wherein a plurality of articulation cables extend through the shaft from the handle to the flexible spine, such that when tension is applied to at least one of the plurality of articulation cables, the flexible spine bends;
wherein a rotatable element extends through the shaft from the handle to the end effector, such that when the rotatable element is rotated, the end effector rotates;
wherein an actuation element extends through the shaft from the handle to the end effector, such that when the actuation element is moved, the end effector is actuated; and
wherein the proximal end of the shaft further comprises a rigid portion, and wherein the apparatus further comprises a tool support mounted to a patient support, the tool support comprising an opening for receiving the rigid portion; and using the apparatus to perform a minimally-invasive procedure.

In another preferred form of the present invention, there is provided apparatus for performing a minimally-invasive procedure, the apparatus comprising:
a tool comprising:
a shaft having a distal end and a proximal end;
a handle attached to the proximal end of the shaft; and
an end effector attached to the distal end of the shaft;
wherein the shaft comprises a flexible portion extending distally from the proximal end of the shaft, and an articulating portion extending proximally from the distal end of the shaft, and wherein the articulating portion comprises a flexible spine;
wherein a plurality of articulation cables extend through the shaft from the handle to the flexible spine, such that when tension is applied to at least one of the plurality of articulation cables, the flexible spine bends;
wherein a rotatable element extends through the shaft from the handle to the end effector, such that when the rotatable element is rotated, the end effector rotates; and
wherein an actuation element extends through the shaft from the handle to the end effector, such that when the actuation element is moved, the end effector is actuated;
the shaft being configured such that when the articulating portion has been articulated, rotation of the rotatable element occurs without the build-up of spring energy within the shaft.

In another preferred form of the present invention, there is provided a method for performing a minimally-invasive procedure, the method comprising:
obtaining apparatus for performing a minimally-invasive procedure, the apparatus comprising:
a tool comprising:
a shaft having a distal end and a proximal end;
a handle attached to the proximal end of the shaft; and
an end effector attached to the distal end of the shaft;
wherein the shaft comprises a flexible portion extending distally from the proximal end of the shaft, and an articulating portion extending proximally from the distal end of the shaft, and wherein the articulating portion comprises a flexible spine;
wherein a plurality of articulation cables extend through the shaft from the handle to the flexible spine, such that when tension is applied to at least one of the plurality of articulation cables, the flexible spine bends;
wherein a rotatable element extends through the shaft from the handle to the end effector, such that when the rotatable element is rotated, the end effector rotates; and
wherein an actuation element extends through the shaft from the handle to the end effector, such that when the actuation element is moved, the end effector is actuated;
the shaft being configured such that when the articulating portion has been articulated, rotation of the rotatable element occurs without the build-up of spring energy within the shaft; and
using the apparatus to perform a minimally-invasive procedure.

In another preferred form of the present invention, there is provided apparatus for performing a minimally-invasive procedure, the apparatus comprising:
a tool comprising:
a shaft having a distal end and a proximal end;
a handle attached to the proximal end of the shaft; and
an end effector attached to the distal end of the shaft;
wherein the shaft comprises a flexible portion extending distally from the proximal end of the shaft, and an articulating portion extending proximally from the distal end of the shaft, and wherein the articulating portion comprises a flexible spine;
wherein a plurality of articulation cables extend through the shaft from the handle to the flexible spine, such that when tension is applied to at least one of the plurality of articulation cables, the flexible spine bends;
wherein a rotatable element extends through the shaft from the handle to the end effector, such that when the rotatable element is rotated, the end effector rotates; and
wherein an actuation element extends through the shaft from the handle to the end effector, such that when the actuation element is moved, the end effector is actuated.

In another preferred form of the present invention, there is provided a method for performing a minimally-invasive procedure, the method comprising:
obtaining apparatus for performing a minimally-invasive procedure, the apparatus comprising:
a tool comprising:
a shaft having a distal end and a proximal end;
a handle attached to the proximal end of the shaft; and
an end effector attached to the distal end of the shaft;
wherein the shaft comprises a flexible portion extending distally from the proximal end of the shaft, and an articulating portion extending proximally from the distal end of the shaft, and wherein the articulating portion comprises a flexible spine;
wherein a plurality of articulation cables extend through the shaft from the handle to the flexible spine, such that when tension is applied to at least one of the plurality of articulation cables, the flexible spine bends;
wherein a rotatable element extends through the shaft from the handle to the end effector, such that when the rotatable element is rotated, the end effector rotates; and
wherein an actuation element extends through the shaft from the handle to the end effector, such that when the actuation element is moved, the end effector is actuated; and
using the apparatus to perform a minimally-invasive procedure.

In another form of the invention, there is provided a novel monopolar knife.

And in another form of the invention, there is provided a novel method for cutting tissue using a monopolar knife.

In still another form of the invention, there is provided a novel monopolar knife with flushing capabilities.

And in another form of the invention, there is provided a novel method for cutting tissue using a monopolar knife with flushing capabilities.

In one preferred form of the present invention, there is provided apparatus for performing a minimally-invasive procedure, the apparatus comprising:
a shaft having a distal end and a proximal end;
a monopolar knife assembly attached to the distal end of the shaft, the monopolar knife assembly comprising a knife;
a handle attached to the proximal end of the shaft;
wherein the shaft comprises a flexible portion and an articulating portion, wherein the flexible portion extends distally from the handle and the articulating portion extends distally from the flexible portion;

wherein at least one articulation cable extends from the handle to the articulating portion, such that when tension is applied to the at least one articulation cable, the articulating portion deflects;

wherein an actuation element extends through the shaft from the handle to the knife, such that when the actuation element is moved, the knife is moved; and wherein the actuation element transmits electrical power from the handle to the knife.

In another preferred form of the present invention, there is provided a method for creating a bleb in tissue, the method comprising:

providing apparatus comprising:
a shaft having a distal end and a proximal end;
a monopolar knife assembly attached to the distal end of the shaft, the monopolar knife assembly comprising a knife;
a handle attached to the proximal end of the shaft;
wherein the shaft and the handle are configured to so that fluid can be passed from the handle to the distal end of the shaft and into tissue;
wherein an actuation element extends through the shaft from the handle to the knife, such that when the actuation element is moved, the knife is moved; and
wherein the actuation element transmits electrical power from the handle to the knife;
inserting the knife through tissue to be excised; and injecting fluid into the tissue to lift the tissue to be excised away from underlying tissue.

In another preferred form of the present invention, there is provided a method for performing a minimally-invasive procedure, the method comprising:

providing apparatus for performing a minimally-invasive procedure, the apparatus comprising:
a shaft having a distal end and a proximal end;
a monopolar knife assembly attached to the distal end of the shaft, the monopolar knife assembly comprising a knife;
a handle attached to the proximal end of the shaft;
wherein the shaft comprises a flexible portion and an articulating portion, wherein the flexible portion extends distally from the handle and the articulating portion extends distally from the flexible portion;
wherein at least one articulation cable extends from the handle to the articulating portion, such that when tension is applied to the at least one articulation cable, the articulating portion deflects;
wherein an actuation element extends through the shaft from the handle to the knife, such that when the actuation element is moved, the knife is moved; and
wherein the actuation element transmits electrical power from the handle to the knife; and
using the apparatus to perform a minimally-invasive procedure.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein:

FIGS. 47-55 are schematic views showing a novel tool support which may be used in conjunction with the novel medical instrument shown in FIG. 1;

FIGS. 56-58F are schematic views showing another novel medical instrument formed in accordance with the present invention;

FIGS. 59-62 are schematic views showing another form of end effector for the novel medical instrument of the present invention;

FIGS. 63-66 are schematic views showing another novel medical instrument formed in accordance with the present invention;

FIGS. 67-72 are schematic views showing another novel medical instrument formed in accordance with the present invention;

FIGS. 75 and 76 are schematic views showing another novel medical instrument formed in accordance with the present invention;

FIGS. 77-80 are schematic views showing another novel medical instrument formed in accordance with the present invention;

FIGS. 81-98 are schematic views showing another novel medical instrument formed in accordance with the present invention;

FIGS. 100-108 are schematic views showing another novel medical instrument formed in accordance with the present invention.

Figure 1:
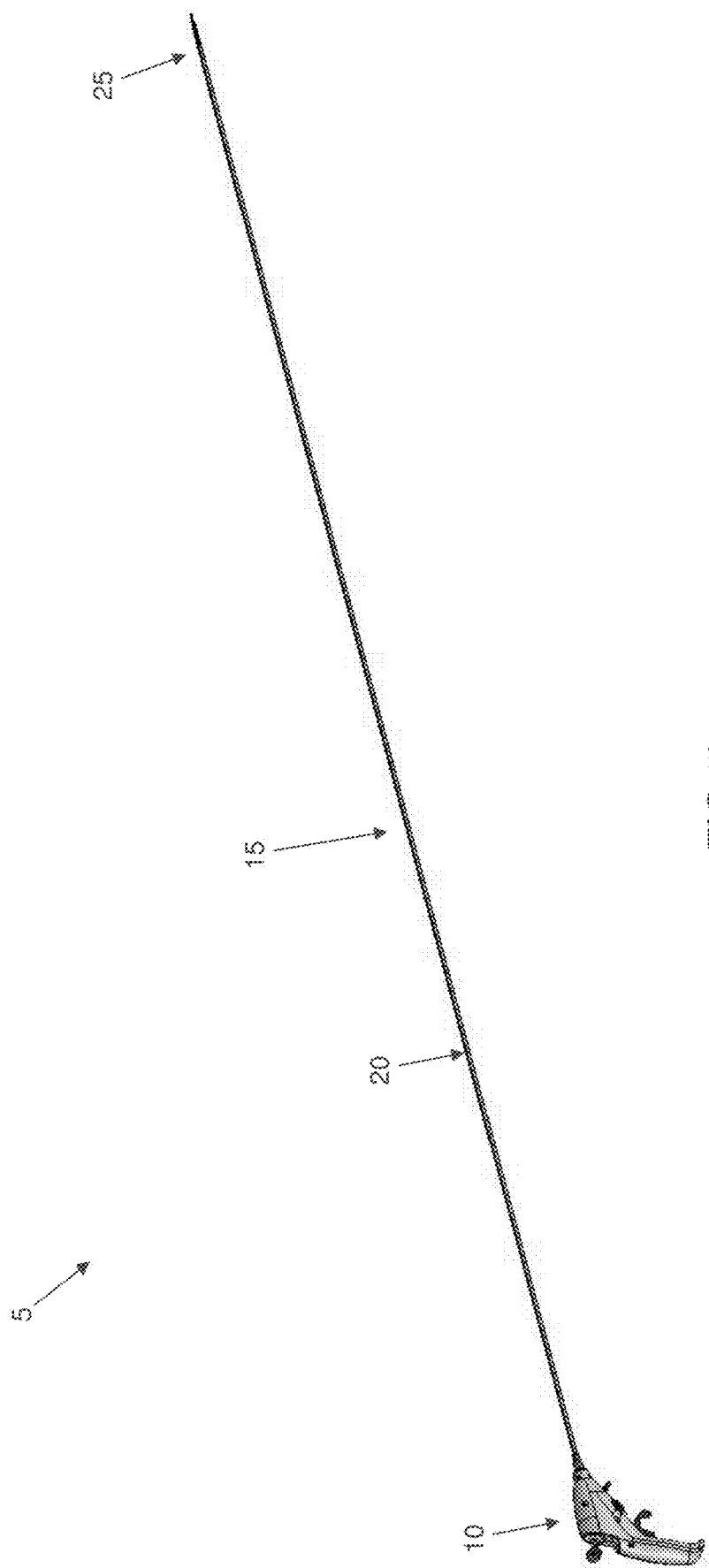
FIG. 1 is a schematic view showing a novel medical instrument formed in accordance with the present invention.
Figure 1A:
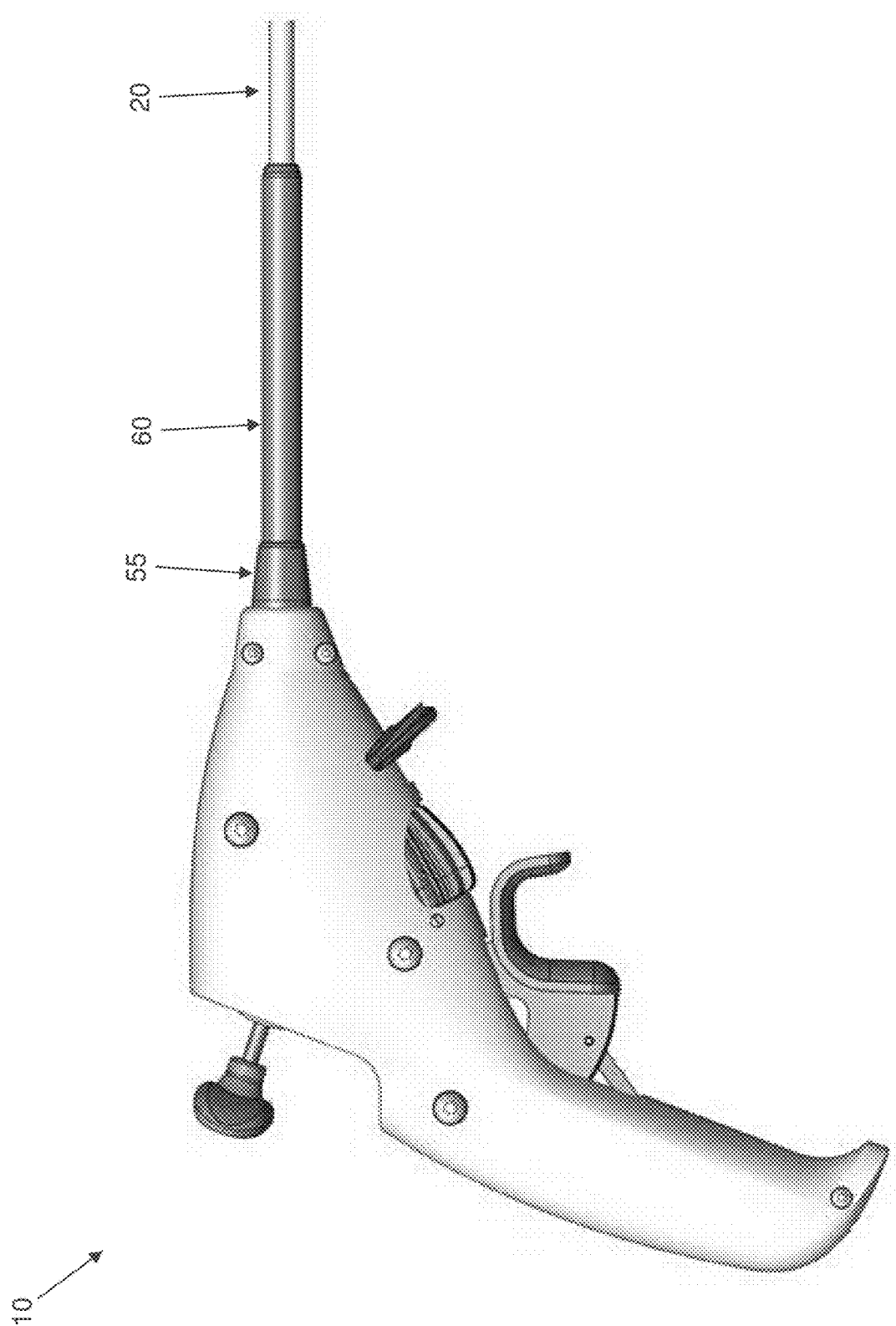
FIG. 1A is a schematic view showing the handle and proximal end of the shaft of the novel medical instrument shown in FIG. 1.
Figure 1B:
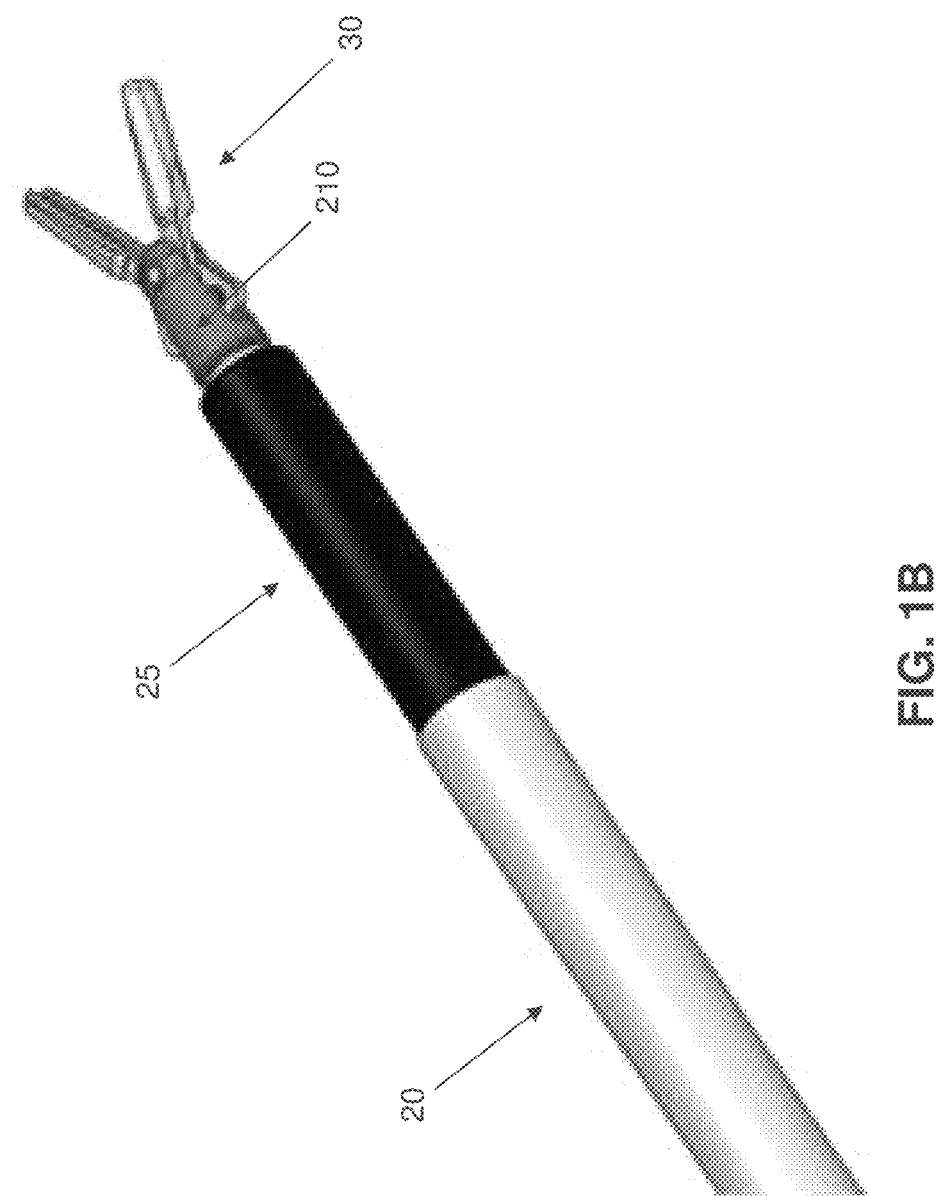
FIG. 1B is a schematic view showing the distal end of the shaft and the end effector of the novel medical instrument shown in FIG. 1.

DETAILED DESCRIPTION OF THE PREFERRED EMBODIMENTS 1 the Novel Medical Instrument in General The present invention comprises a novel medical instrument for performing minimally-invasive procedures. The novel medical instrument is highly flexible, capable of articulating with a range of different motions, and configured for precise control, while being operated (e.g., along a tortuous path) from only the handle end of the medical instrument.

Looking first at FIGS. 1, 1A, 1B and 2, there is shown a novel medical instrument 5 formed in accordance with the present invention. Novel medical instrument 5 generally comprises a handle 10 and a shaft 15 extending distally from handle 10. Shaft 15 generally comprises an elongated, flexible proximal portion 20 and a distal articulating portion 25 which is mounted to the distal end of flexible proximal portion 20. An end effector 30 is mounted to the distal end of distal articulating portion 25. End effector 30 may take many different forms (e.g., graspers, injection needles, scissors, hot snares, monopolar probes, hemostasis clips, bipolar forceps, suction tubes, single-fire or multi-fire closure devices such as staplers and tackers, dissector forceps, retrieval baskets, monopolar scissors, monopolar knife, monopolar knife with flushing capabilities, etc.). For clarity of illustration, end effector 30 is shown in the figures as a grasper. Handle 10 may take any one of many different forms (e.g., a pistol grip, a shaft grip, etc.). For clarity of illustration, handle 10 is shown in the figures as a pistol grip.

In accordance with the present invention, flexible proximal portion 20 of shaft 15 is configured to be a highly flexible element capable of extending a significant length (e.g., 95 cm-140 cm) along a tortuous path, distal articulating portion 25 of shaft 15 is configured to be capable of universal articulation relative to the distal end of flexible proximal portion 20 of shaft 15, and end effector 30 is configured to be selectively rotated relative to the distal end of distal articulating portion 25 and may be selectively actuated, with all functions able to be carried out by a single hand of a user via handle 10. In one preferred form of the invention, substantially the entire shaft 15 of medical instrument 5 is flexible, with the portion of shaft 15 proximal to a transition point 32 (i.e., flexible proximal portion 20) being passively flexible (e.g., able to follow a tortuous path), and the portion of shaft 15 distal to transition point 32 (i.e., distal articulating portion 25) being actively flexible (e.g., able to be universally articulated to a desired configuration).

As will hereinafter be described in further detail, novel medical instrument 5 is capable of at least the following motions:

Motion 1—longitudinal movement of end effector 30 by longitudinal movement of handle 10 (sometimes referred to herein as a "longitudinal motion function");

Motion 2—rotational movement of end effector 30 by rotational movement of handle 10 (sometimes referred to herein as a "torqueing motion function");

Motion 3—articulating movement of end effector 30 relative to handle 10 by articulating distal articulating portion 25 of shaft 15 relative to the distal end of flexible proximal portion 20 of shaft 15 (sometimes referred to herein as a "universal articulation function");

Motion 4—rotational movement of end effector 30 relative to the distal end of distal articulating portion 25 of shaft 15 by rotating end effector 30 relative to shaft 15 (sometimes referred to herein as a "roticulation function"); and Motion 5—actuation of end effector 30, e.g., selectively moving elements of end effector 30 relative to one another so as to carry out a medical procedure, e.g., opening and closing the jaws of a grasper-type end effector (sometimes referred to herein as a "jaw open/close function").

2 Construction of Shaft 15

2.1 Flexible Proximal Portion 20

Looking now at FIGS. 1, 1A, 1B and 2-4, flexible proximal portion 20 of shaft 15 generally comprises an elongated flexible outer coil 35 (FIGS. 2 and 3) having a distal end 40, a proximal end 45 and a lumen 50 extending therebetween. Distal articulating portion 25 of shaft 15 is mounted to distal end 40 of outer coil 35 via intervening elements (see below). Proximal end 45 of outer coil 35 is secured to a shaft adapter 55 which is, in turn, secured to handle 10 (see below).

Means for selectively articulating distal articulating portion 25 relative to the distal end of flexible proximal portion 20 (i.e., relative to distal end 40 of outer coil 35), means for selectively rotating end effector 30 relative to distal articulating portion 25, and means for selectively actuating end effector 30 extend through lumen 50 of outer coil 35, as will hereinafter be discussed in further detail.

In one preferred form of the invention, a rigid tube 60 (FIGS. 1A and 4) is provided at the proximal end of flexible proximal portion 20 (i.e., disposed about the proximal end 45 of outer coil 35 and secured to shaft adapter 55), whereby to provide a region of increased rigidity for mounting novel medical instrument 5 to a tool support (e.g., a table-mounted tool support) as will hereinafter be discussed in further detail. If desired, rigid tube 60 may comprise a fillet 65 (FIG. 4) at the distal end of rigid tube 60 which provides a smooth transition between the outer surface of rigid tube 60 and the outer surface of the portion of flexible proximal portion 20 located distal to rigid tube 60.

2.2 Distal Articulating Portion 25 in General

As discussed above, distal articulating portion 25 is configured to selectively articulate relative to the distal end of flexible proximal portion 20. To this end, and looking now at FIGS. 2 and 5, distal articulating portion 25 generally comprises a distal articulation link assembly 70, a proximal articulation link assembly 75 and a flex spine 80 extending between distal articulation link assembly 70 and proximal articulation link assembly 75. Proximal articulation link assembly 75 is configured to be mounted to the distal end of flexible proximal portion 20 of shaft 15 and to provide a counterforce surface to enable selective articulation of distal articulation link assembly 70 and flex spine 80, as will hereinafter be discussed in further detail.

2.2.1 Proximal Articulation Link Assembly 75

Figure 2:
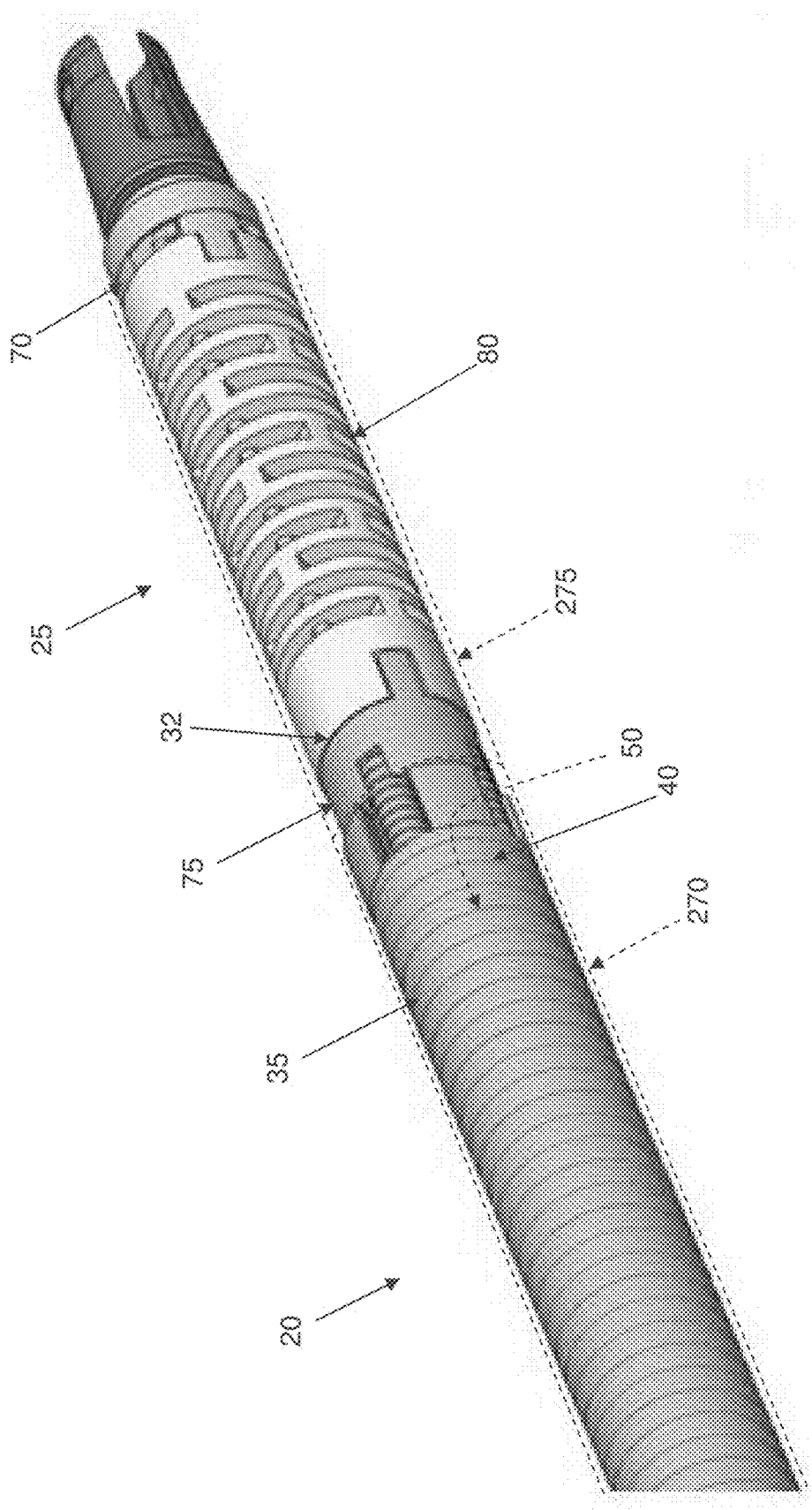
FIGS. 2-23 are schematic views showing further details of the shaft and the end effector of the novel medical instrument shown in FIG. 1.
Figure 3:
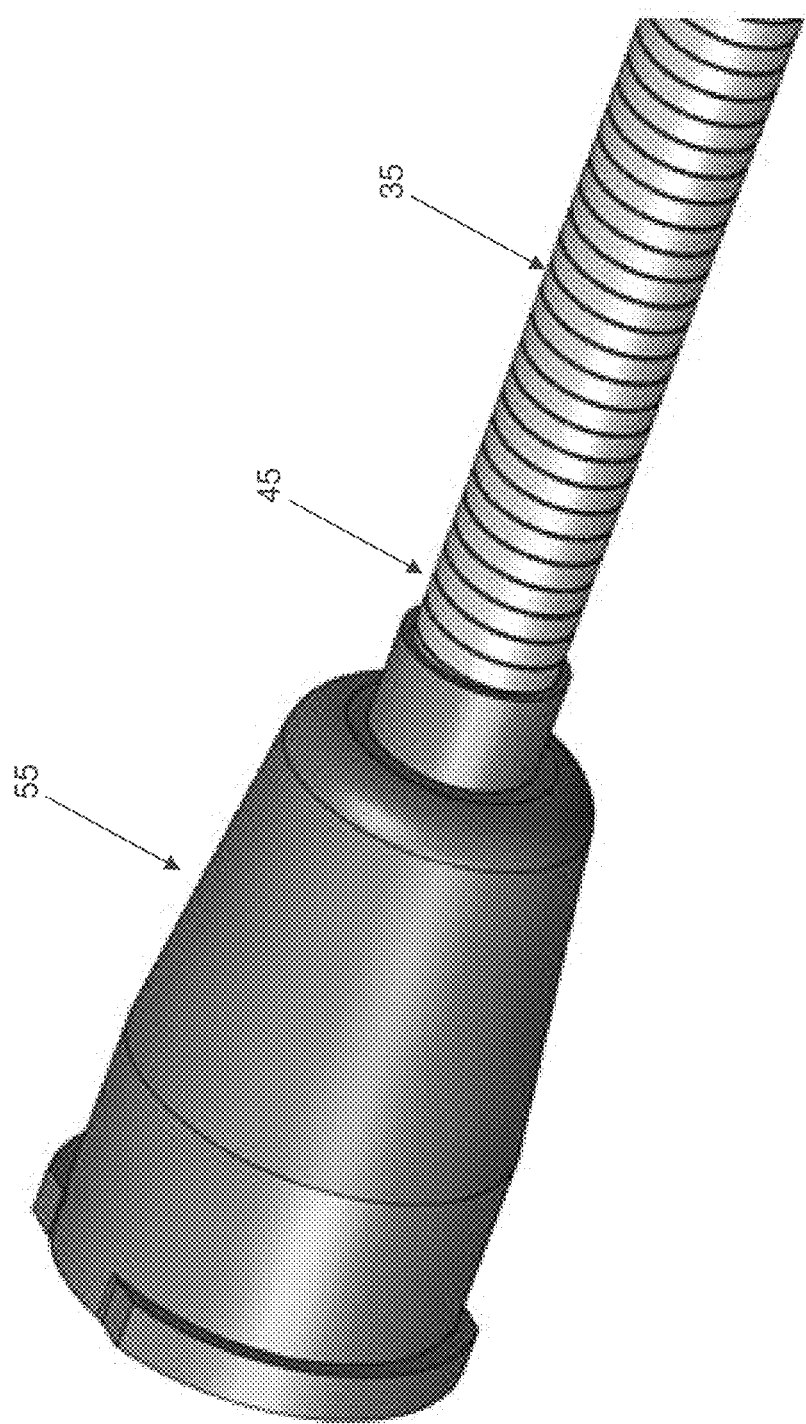
Figure 4:
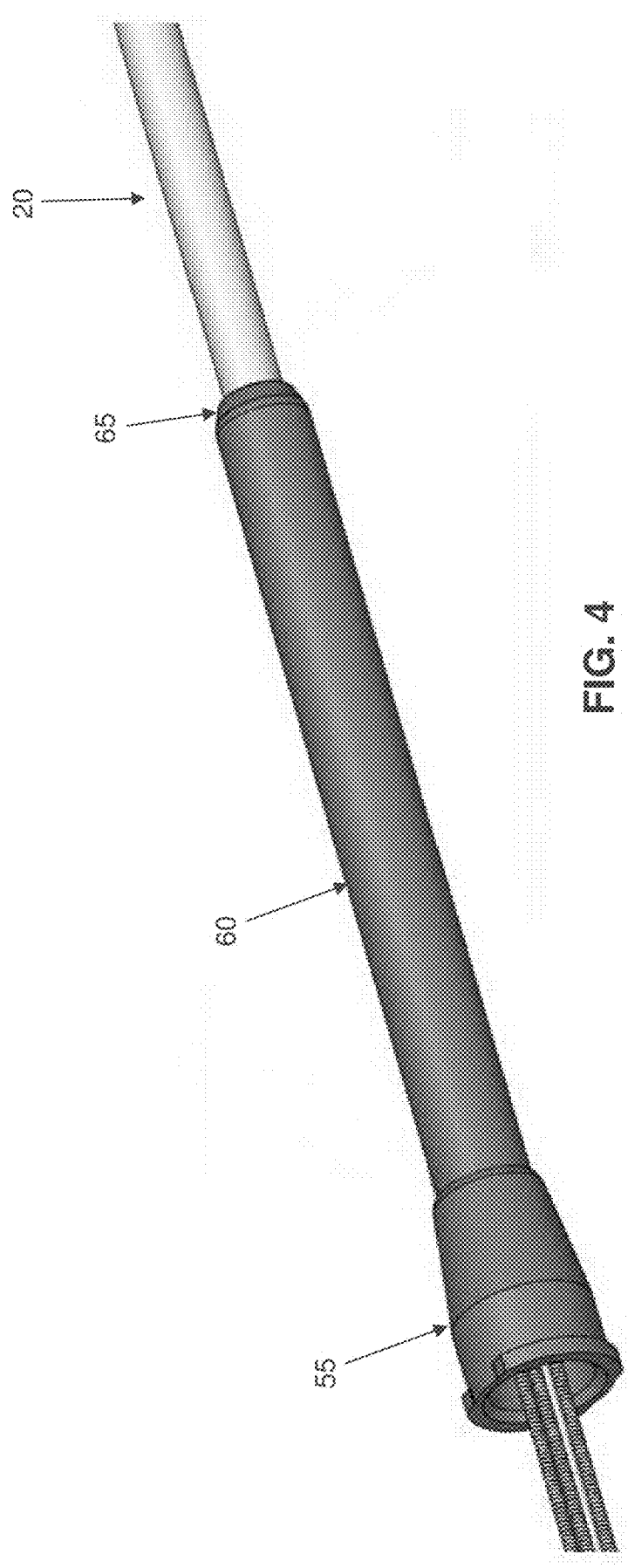
Figure 6:
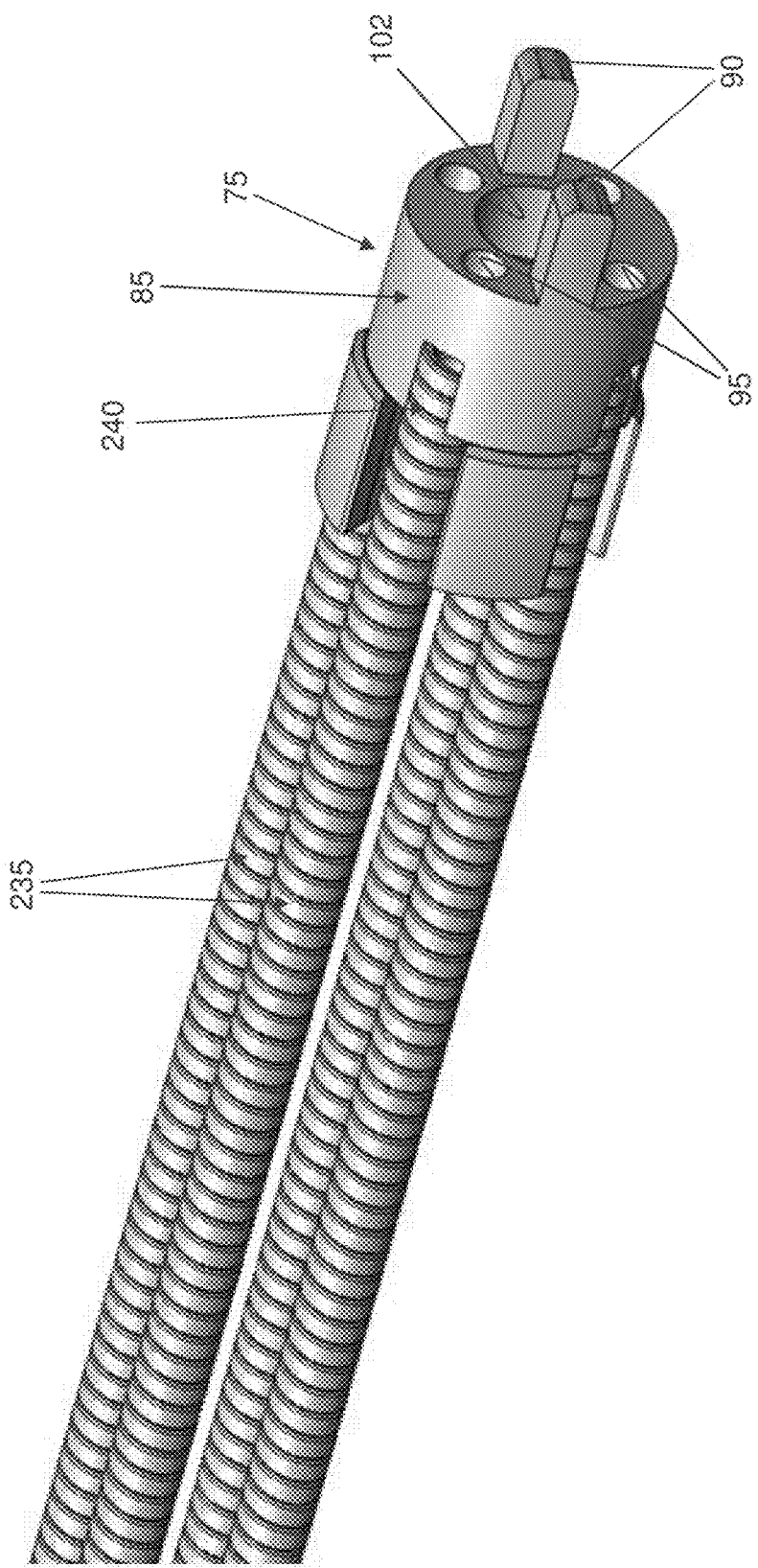

Looking now at FIGS. 2 and 6, proximal articulation link assembly 75 is disposed at the distal end 40 of outer coil 35 of flexible proximal portion 20. The distal end of proximal articulation link assembly 75 provides a counterforce surface to enable selective flexing of distal articulation link assembly 70 and flex spine 80 relative to the distal end of flexible proximal portion 20 of shaft 15 (i.e., in order to effect universal articulation of distal articulating portion 25).

Figure 18:
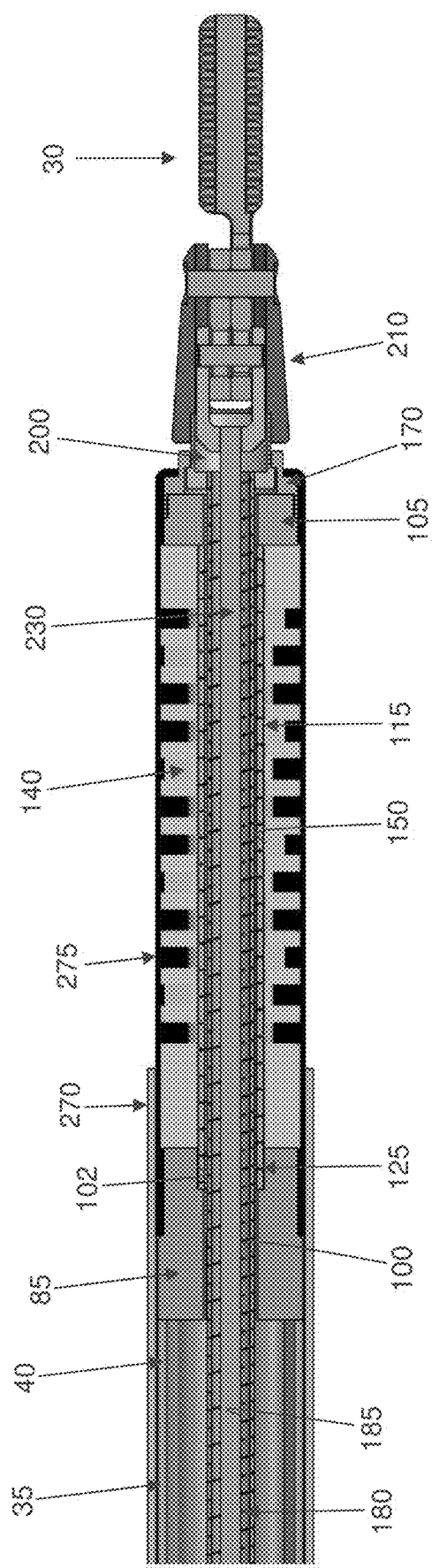
Figure 19:
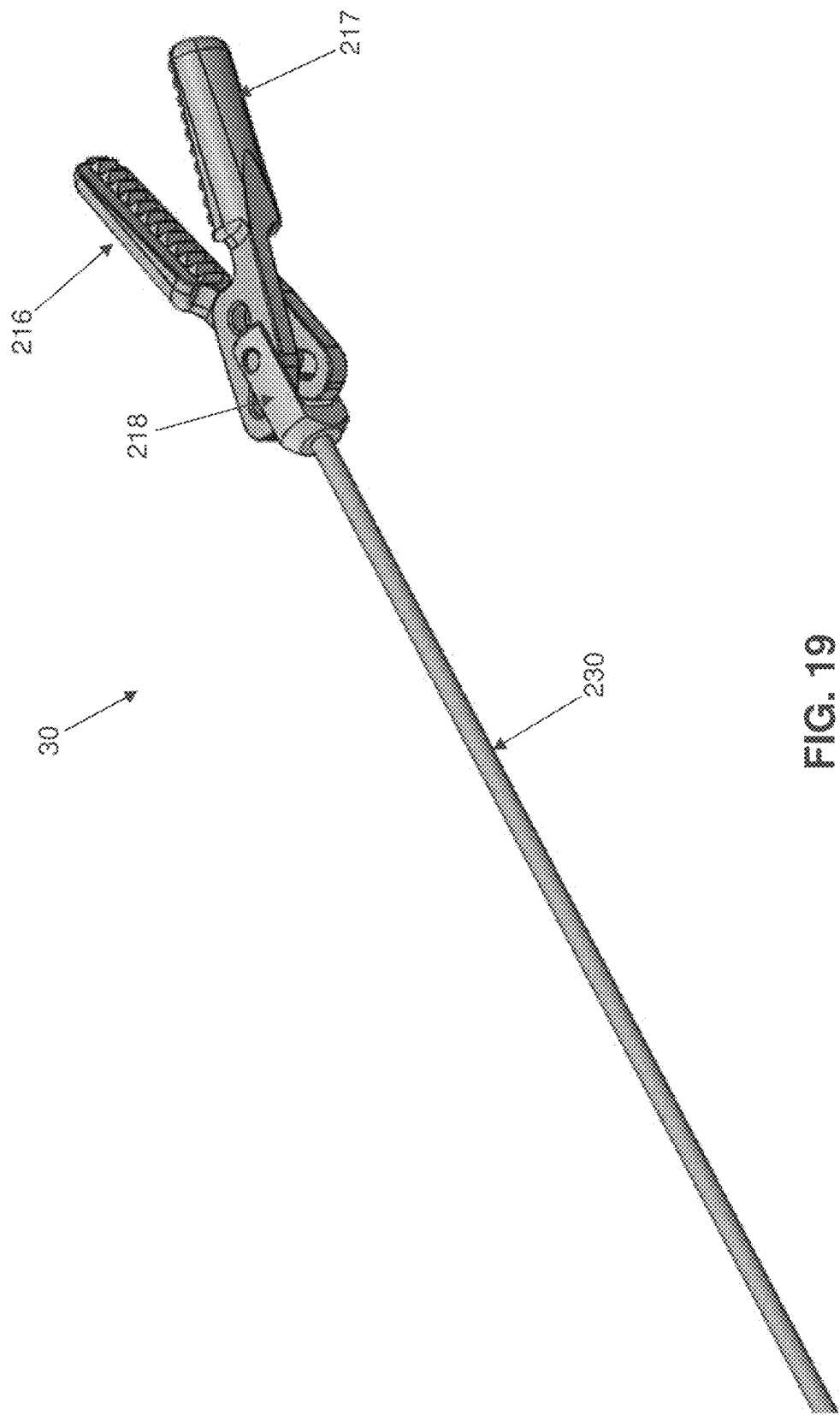
Figure 20:
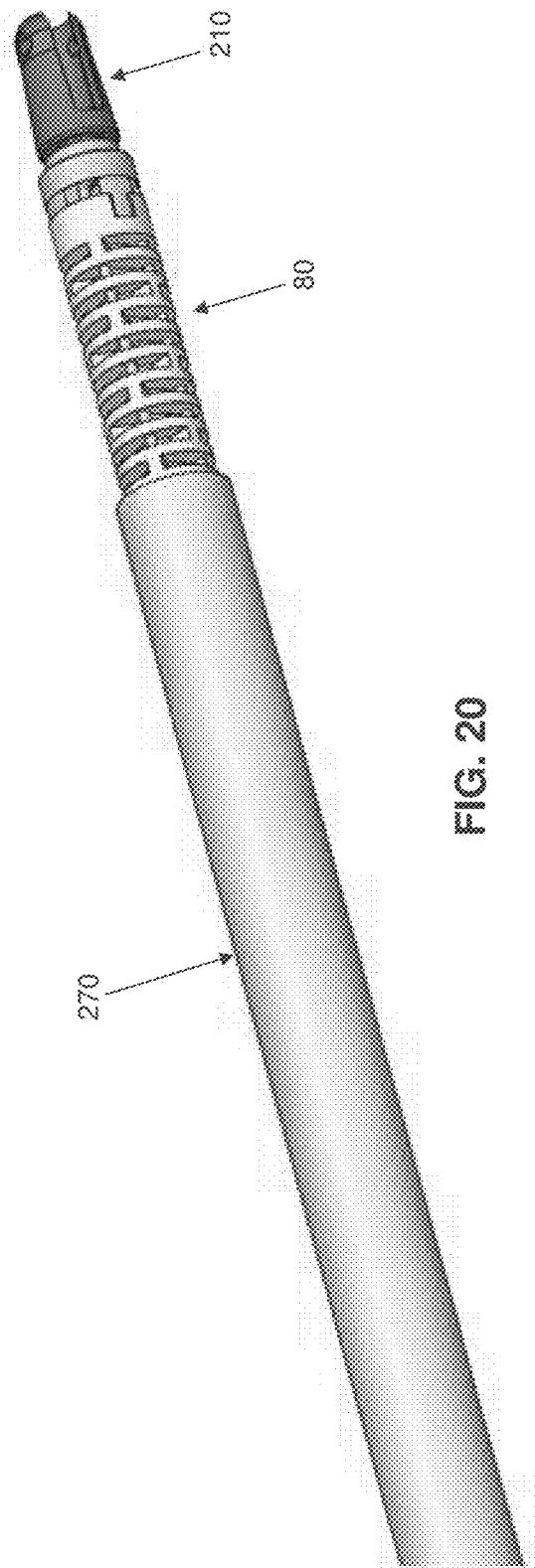
Figure 21:
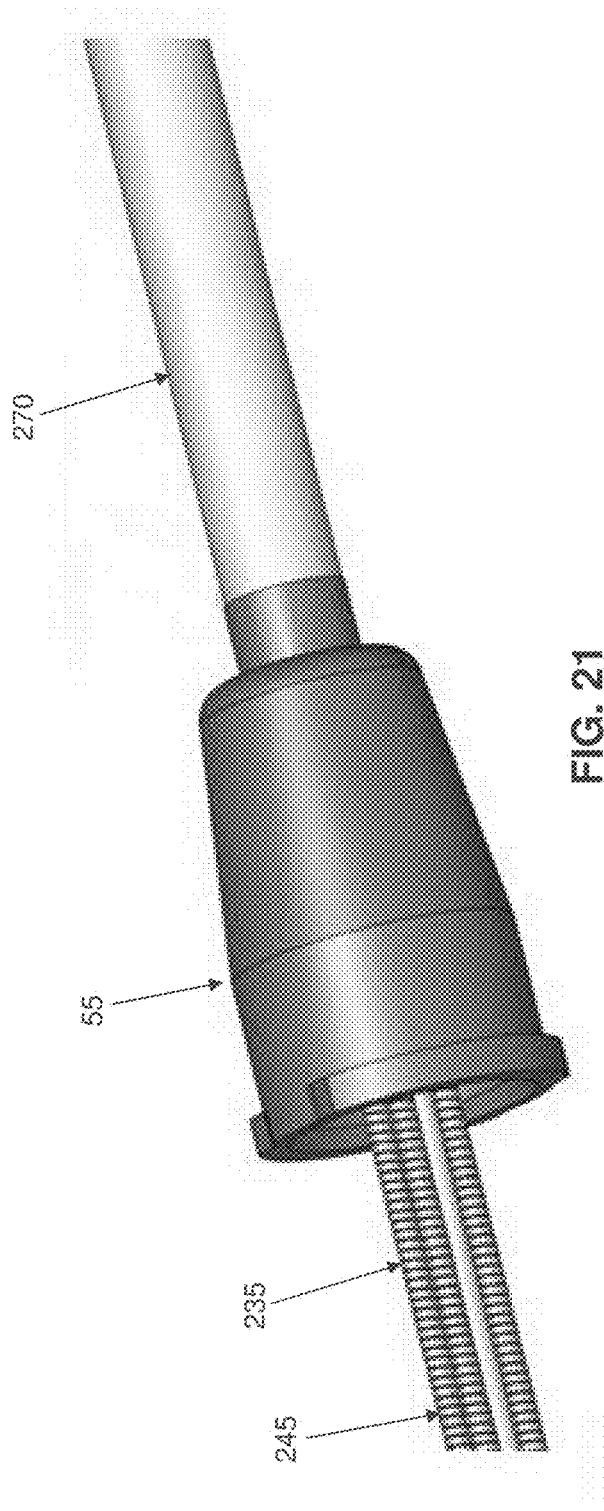
Figure 22:
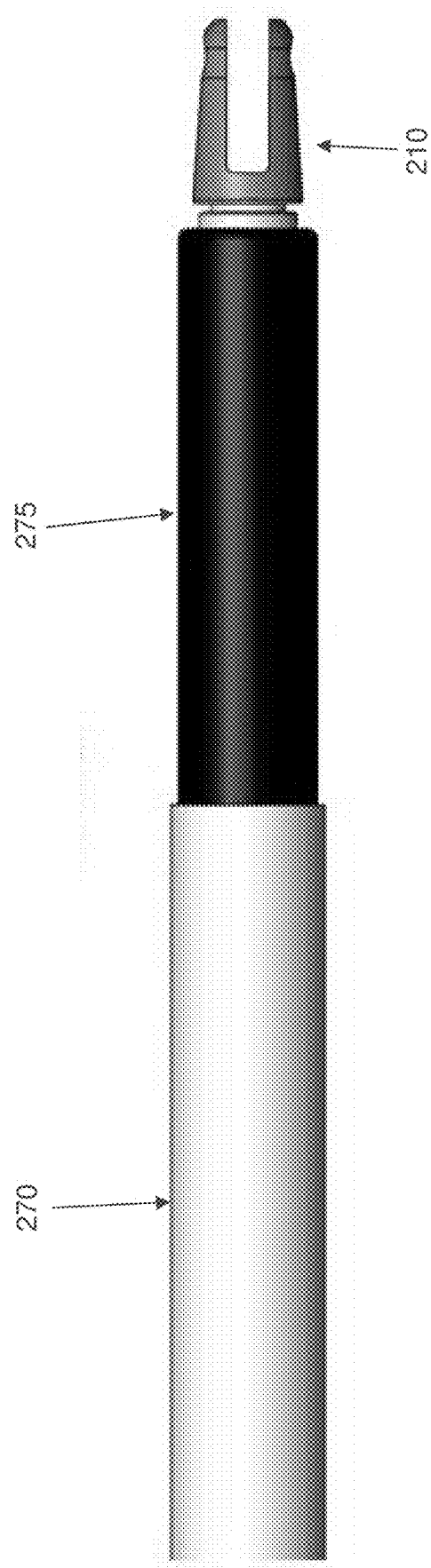
Figure 23:
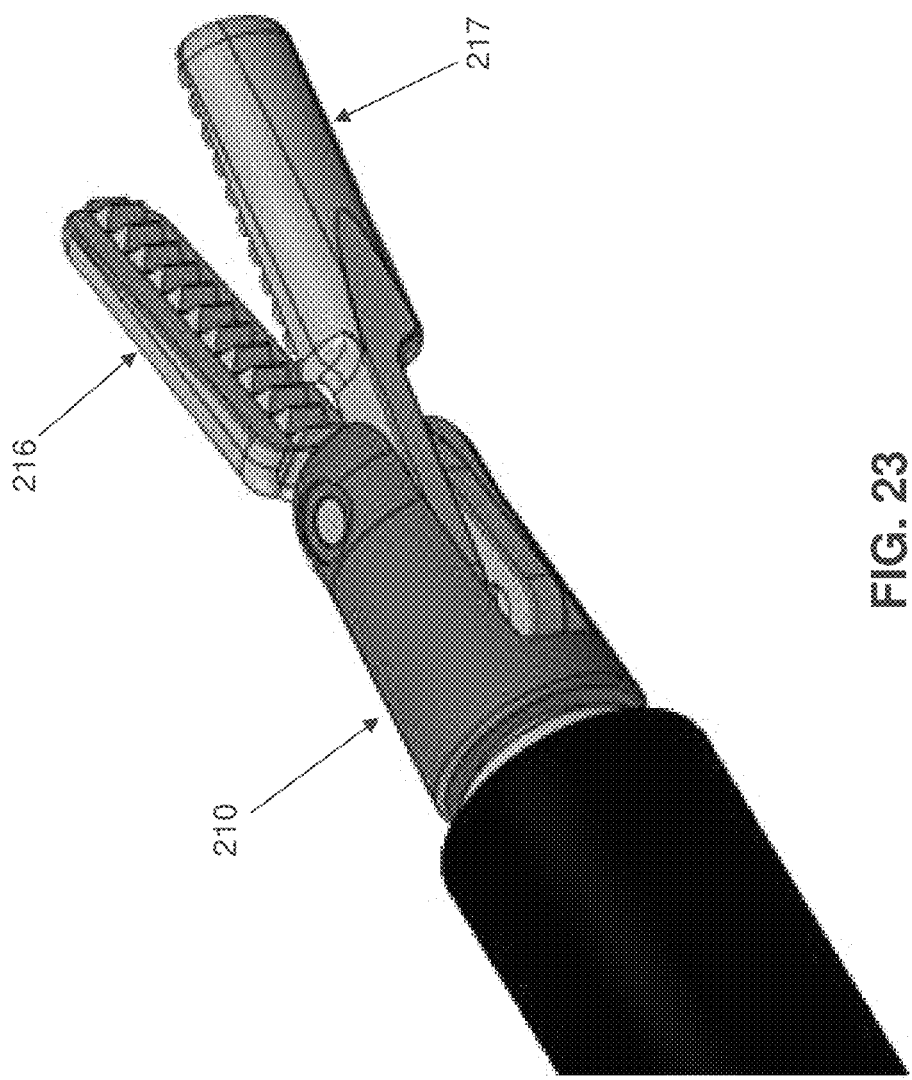

More particularly, proximal articulation link assembly 75 (FIG. 6) comprises a body 85 having a pair of distally-extending fingers 90 which are configured to engage flex spine 80 (FIG. 5) as will hereinafter be discussed in further detail. A plurality of bores 95 (FIG. 6), disposed about a central bore 100 (FIG. 18), are formed in body 85 and sized to receive a plurality of articulation cables (see below). If desired, bores 95 may comprise counterbores (not shown) disposed at their proximal ends for receiving articulation cable housings as will hereinafter be discussed. Central bore 100 (FIG. 18) may comprise a counterbore 102 (FIGS. 6 and 18) disposed at its distal end for facilitating mounting of distal articulating link assembly 70 to body 85, as will hereinafter be discussed.

Body 85 of proximal articulation link assembly 75 bears against a plurality of articulation cable housings 235 (see below) which, in turn, bear against handle 10 in order for proximal articulation link assembly 75 to provide a counterforce surface for selective flexing of distal articulating portion 25 of shaft 15, as will hereinafter be discussed. Note that outer coil 35 is secured to body 85 of proximal articulation link assembly 75, but provides substantially no counterforce to body 85—the counterforce to body 85 is provided by the articulation cable housings.

2.2.2 Distal Articulation Link Assembly 70

Figure 5:
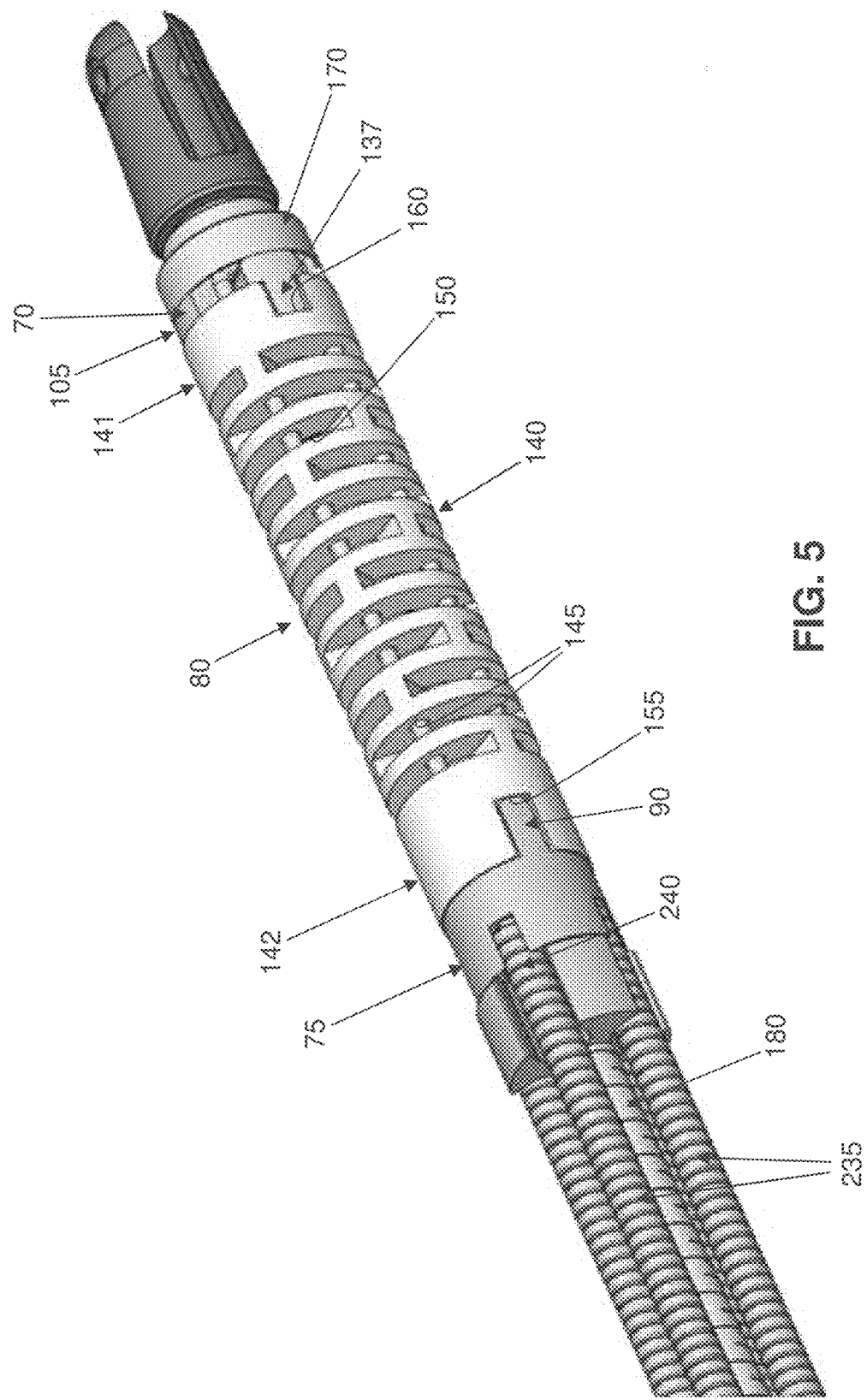
Figure 7:
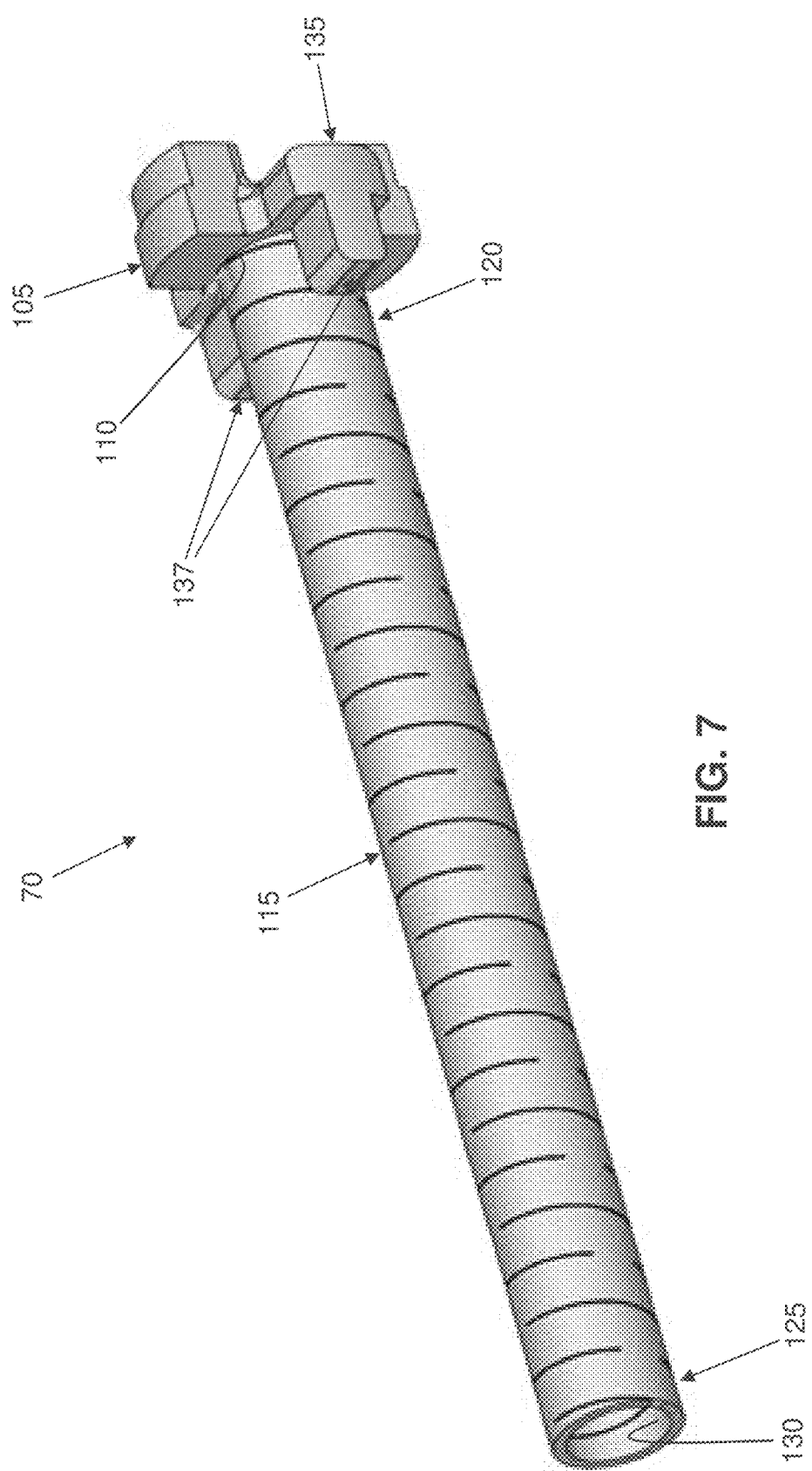

Looking now at FIGS. 2, 5 and 7, distal articulation link assembly 70 generally comprises a body 105 (FIG. 7) having a central opening 110 passing therethrough, and a short laser-cut hypotube 115 extending proximally therefrom. Short laser-cut hypotube 115 comprises a distal end 120, a proximal end 125 and a lumen 130 extending therebetween. Short laser-cut hypotube 115 is configured to be highly flexible, but with sufficient column strength, so as to permit selective articulation of body 105 relative to proximal articulation link assembly 75 when proximal end 125 of short laser-cut hypotube 115 bears against body 85 (FIG. 6) of proximal articulation link assembly 75 and an off-center proximal force is applied to body 105, as will hereinafter be discussed. Proximal end 125 of short laser-cut hypotube 115 is mounted to body 85 of proximal articulation link assembly 75 (e.g., via welding). Distal end 120 of short laser-cut hypotube 115 is mounted to body 105 (e.g., via welding), with lumen 130 of short laser-cut hypotube 115 being aligned with central opening 110 of body 105 when distal articulation link assembly 70 is in its relaxed (i.e., unbiased) condition. As a result of this construction, rotation of body 85 of proximal articulation link assembly 75 causes rotation of laser-cut hypotube 115, whereby to cause rotation of body 105 of distal articulation link assembly 70. Body 105 also comprises a pair of distal seats 135 (only one of which is shown in FIG. 7) for mounting one or more articulation cables to body 105, as will hereinafter be discussed in further detail. Body 105 also comprises two proximally-extending fingers 137 for mating with flex spine 80 (FIG. 5), as will hereinafter be discussed in further detail.

2.2.3 Flex Spine 80

Looking now at FIG. 5, flex spine 80 generally comprises a flexible body 140 having a distal end 141 and a proximal end 142. A plurality of axially-aligned openings 145, and a central bore 150, extend between distal end 141 and proximal end 142. Openings 145 are sized to each receive an articulation cable therein as will hereinafter be discussed. Central bore 150 is sized to receive short laser-cut hypotube 115 (FIG. 7) of distal articulation link assembly 70. Proximal end 142 of flex spine 80 comprises proximal seats 155 for seating the aforementioned distally-extending fingers 90 (FIG. 6) of proximal articulation link assembly 75, and distal end 141 of flex spine 80 comprises distal seats 160 for receiving the aforementioned proximally-extending fingers 137 (FIG. 7) of distal articulation link assembly 70. It will be appreciated that when flex spine 80 is mounted in this fashion, flex spine 80 is fixed against rotation relative to either distal articulation link assembly 70 or proximal articulation link assembly 75.

2.2.4 Rotatable Housing Assembly 165

Looking next at FIGS. 5 and 8-12, the distal end of distal articulating portion 25 comprises a rotatable housing assembly 165 (FIG. 9) for rotatably mounting end effector 30 to distal articulation link assembly 70, as will hereinafter be discussed.

More particularly, rotatable housing assembly 165 generally comprises a collar 170, a long laser-cut hypotube 180 having a distal end 185, a proximal end 190 and a lumen 195 extending therebetween. Rotatable housing assembly 165 also comprises a rotation connector 200 (FIGS. 9 and 10) having an opening 205 formed therein which is fixedly mounted to distal end 185 of long laser-cut hypotube 180 such that lumen 195 of long laser-cut hypotube 180 is aligned with opening 205 of rotation connector 200 when rotatable housing assembly 165 is in its relaxed (i.e., unbiased) condition, and such that long laser-cut hypotube 180 and rotation connector 200 can rotate as a unit. An end effector mount 210 (FIGS. 8, 9, 11 and 12), is mounted to rotation connector 200 such that end effector mount 210 rotates when rotation connector 200 rotates (i.e., when long laser-cut hypotube 180 rotates). End effector 30 is mounted to end effector mount 210 (see below). Rotation connector 200 and end effector mount 210 are rotatably mounted to body 105 of distal articulation link assembly 70 (FIGS. 5 and 7) via collar 170 (FIG. 5). More particularly, rotation connector 200 (FIG. 9) is rotatably mounted to collar 170 and is able to rotate relative to collar 170. End effector mount 210 is mounted to rotation connector 200 and engages a distal shoulder 215 (FIG. 10) of rotation connector 200. Collar 170 is fixedly mounted to body 105 of distal articulation link assembly 70 (FIG. 7). Thus, end effector mount 210 (FIG. 9) is fixedly mounted to rotation connector 200 which is in turn fixedly connected to long laser-cut hypotube 180, and the foregoing subassembly (end effector mount 170, rotation connector 200 and long laser-cut hypotube 180) is rotatably mounted to collar 170, with collar 170 being fixedly mounted to distal articulation link assembly 70 (FIG. 5), and with long laser-cut hypotube 180 extending through central bore 150 of flex spine 80 and through bore 100 (FIG. 18) of body 85 of proximal articulating link assembly 75.

2.3 End Effector 30

End effector 30 may take many different forms (e.g., graspers, injection needles, scissors, hot snares, monopolar probes, hemostasis clips, bipolar forceps, suction tubes, single-fire or multi-fire closure devices such as staplers and tackers, dissector forceps, retrieval baskets, monopolar scissors, monopolar knife, monopolar knife with flushing capabilities, etc.). For clarity of illustration, end effector 30 is shown in the figures as a grasper.

Figure 8:
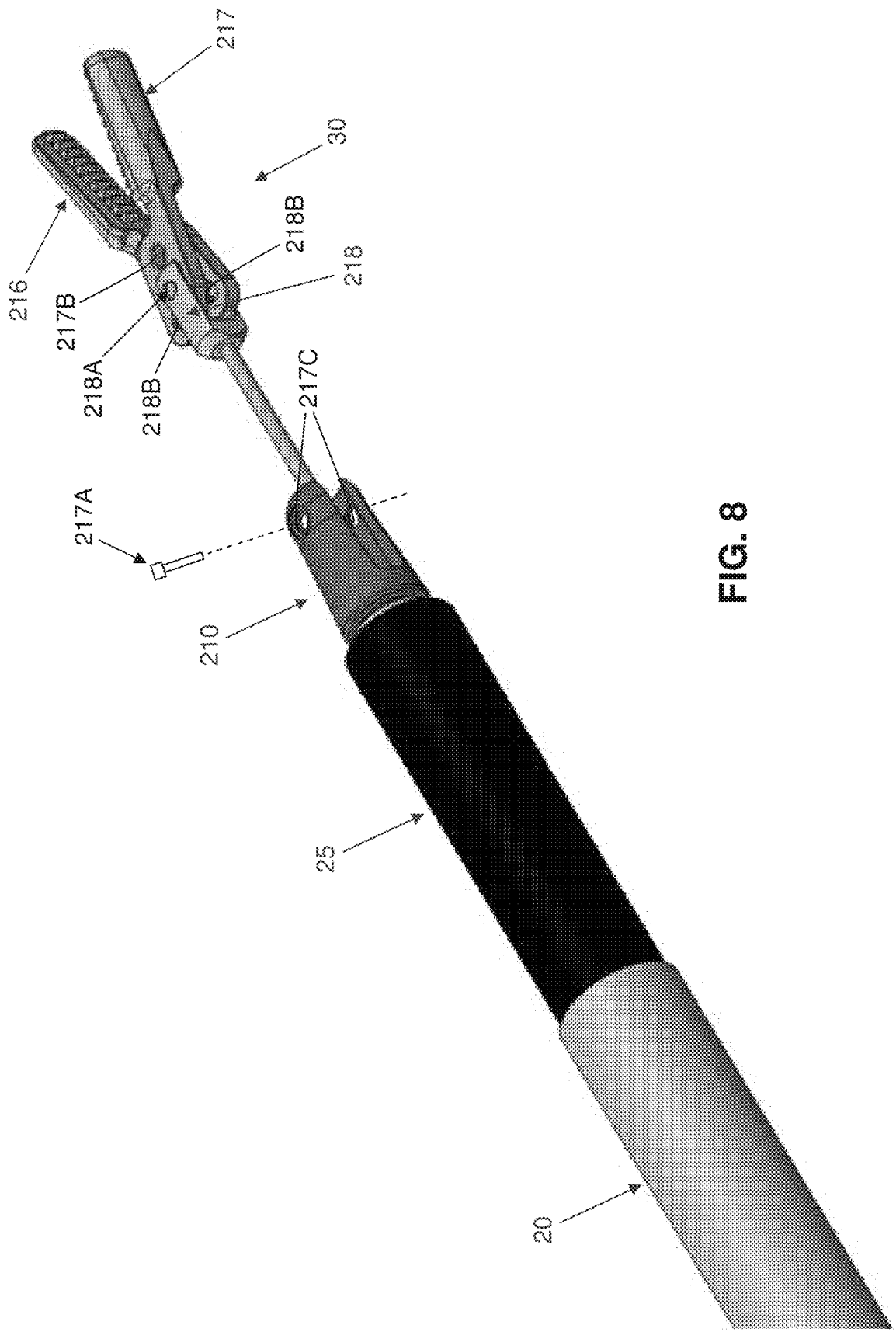
Figure 9:
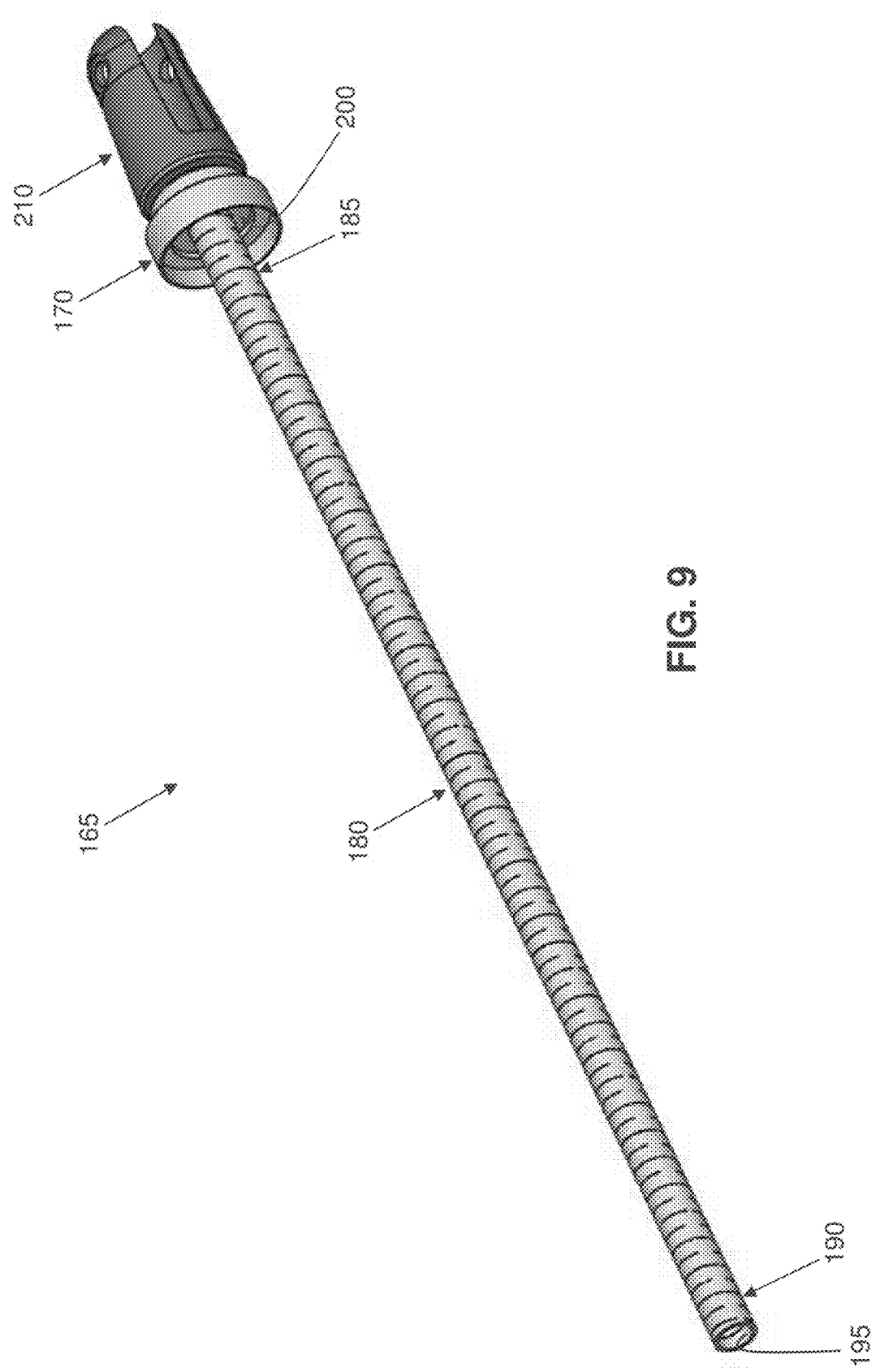
Figure 10:
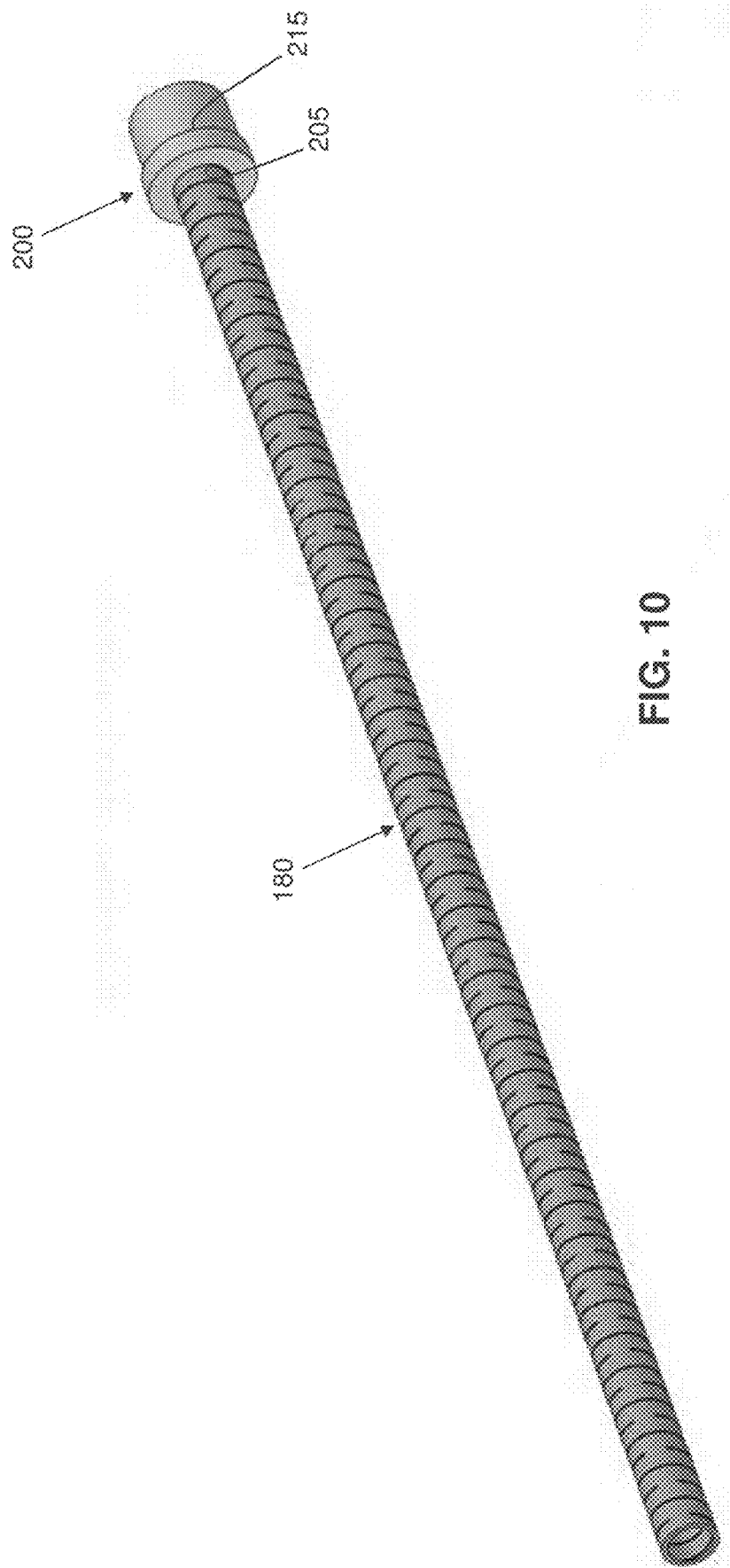
Figure 11:
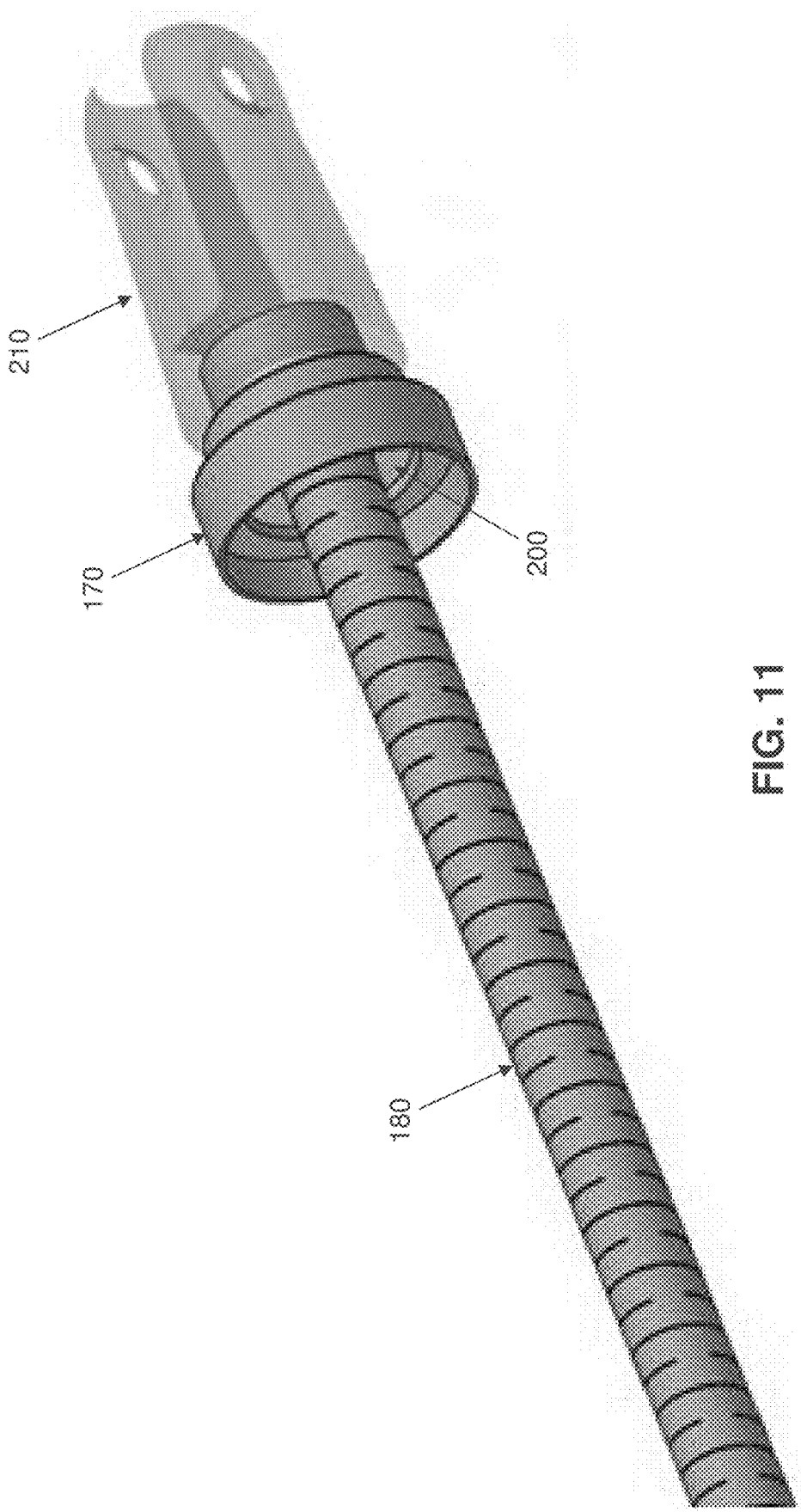
Figure 12:
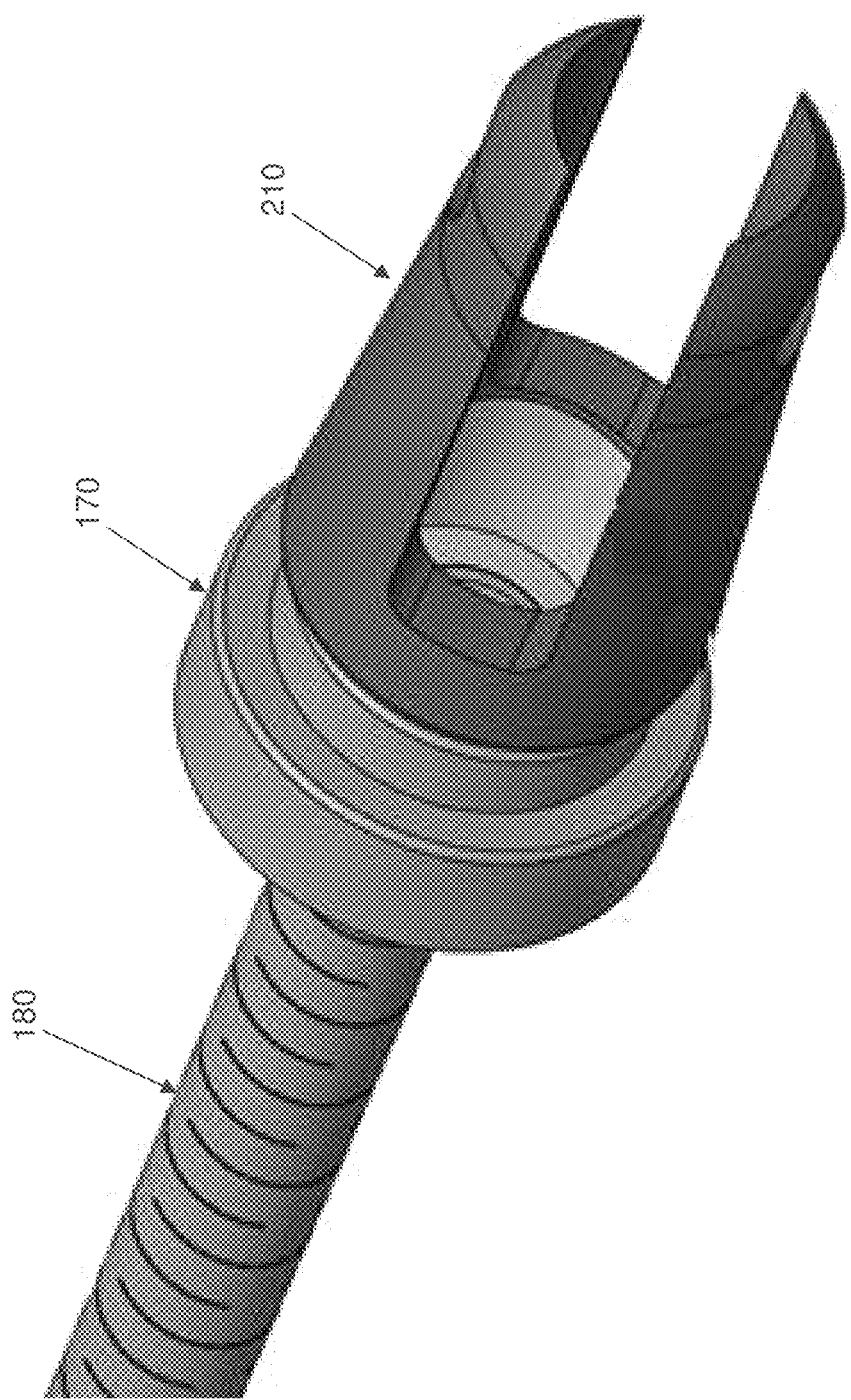

In one preferred form of the invention, and looking now at FIG. 8, end effector 30 is mounted to end effector mount 210. More particularly, in one preferred form of the invention, end effector 30 comprises a grasper having two opposed jaws 216, 217 which are pivotally mounted to end effector mount 210 via a pin 217A which passes through holes 217B in jaws 216, 217 and through holes 217C in end effector mount 210. A clevis 218 is mounted to jaws 216, 217 via a pin 218A disposed in slots 218B formed in the proximal portions of jaws 216, 217 such that reciprocal movement of a pull wire mounted to clevis 218 (see below) causes the opposing jaws 216, 217 of the grasper to open and close relative to one another, as will hereinafter be discussed.

2.4 Articulation Means in General

As discussed above, shaft 15 also comprises (i) means for selectively articulating distal articulating portion 25 (FIG. 2) relative to flexible proximal portion 20, (ii) means for selectively rotating rotatable housing assembly 165 (FIG. 9) relative to shaft 15, and hence for selectively rotating end effector 30 relative to shaft 15, and (iii) means for selectively actuating end effector 30 (FIG. 8). All of the foregoing means are actuated via handle 10, as will hereinafter be discussed.

Figure 13:
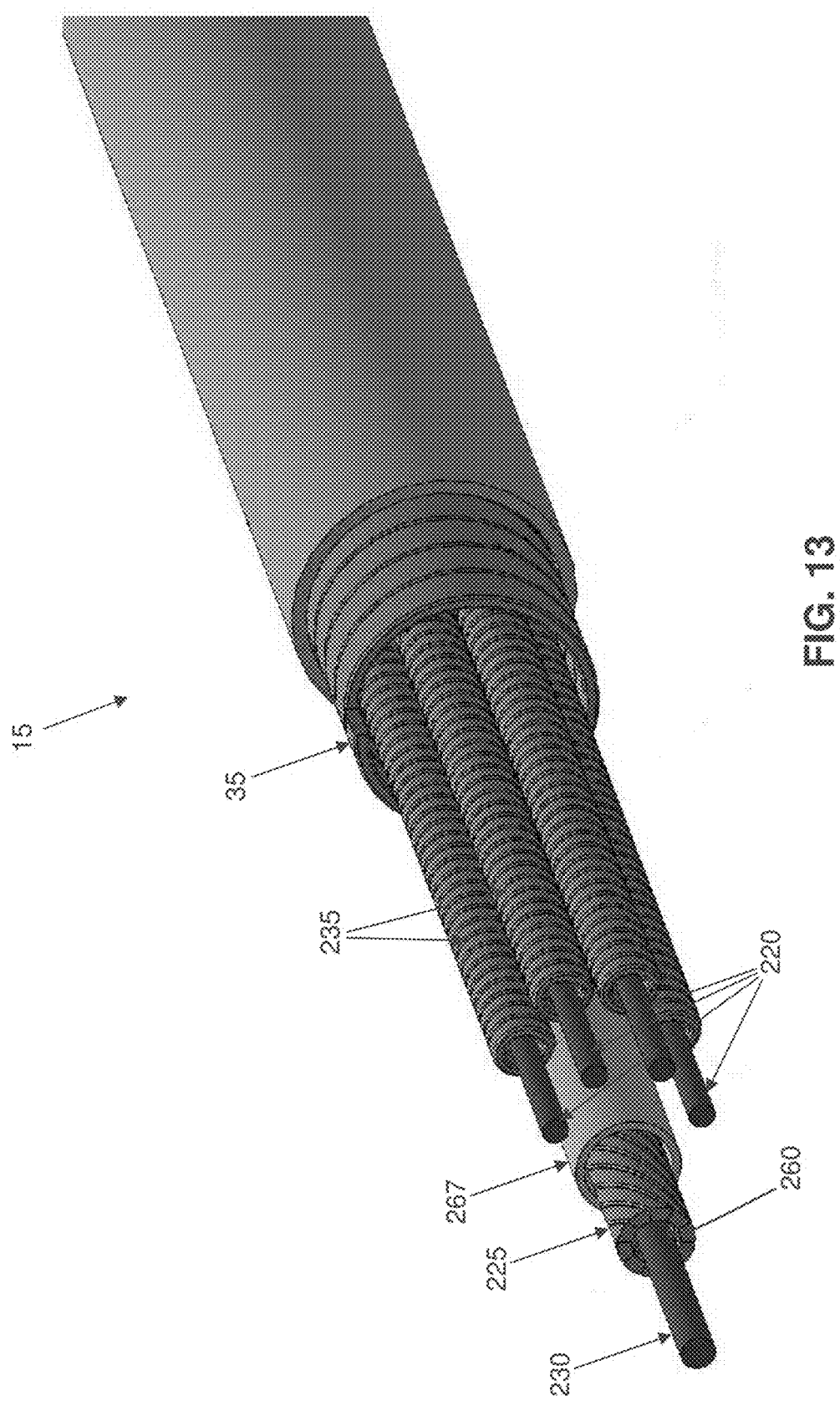
Figure 14:
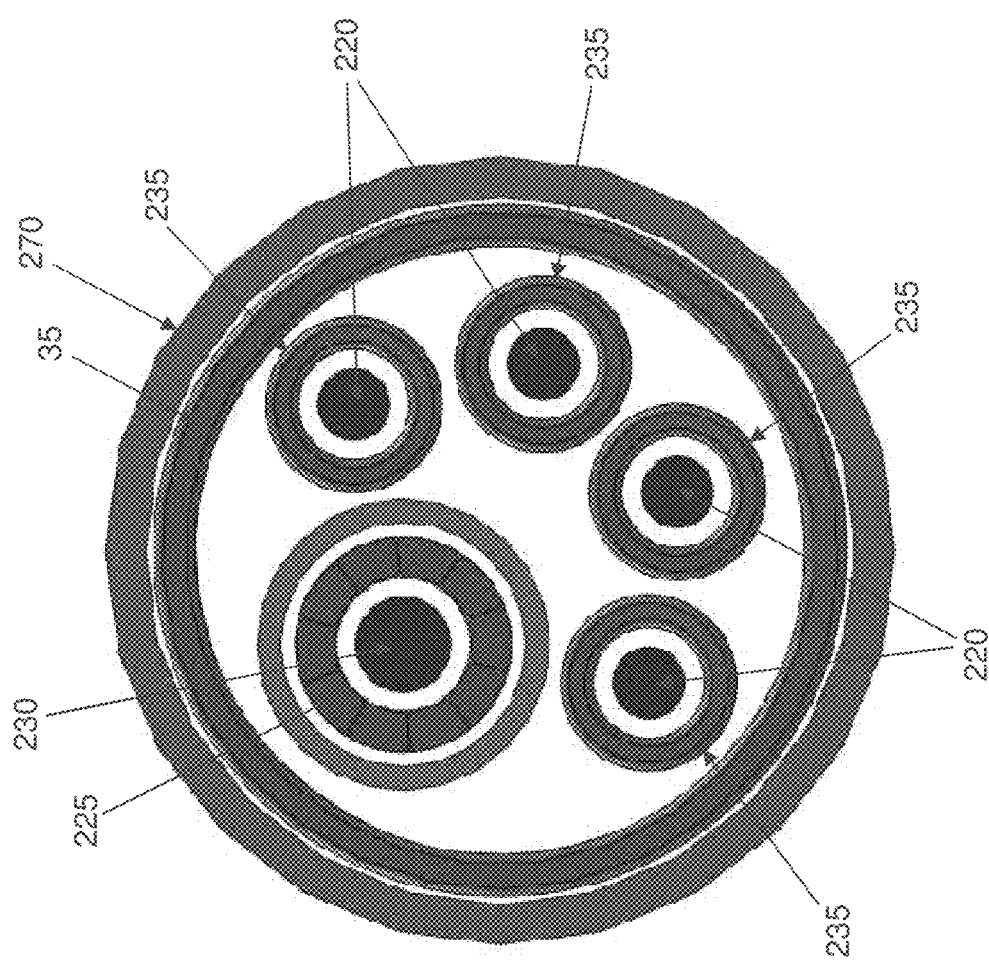

More particularly, and looking now at FIGS. 13 and 14, shaft 15 generally comprises (i) four articulation cables 220 for selectively articulating distal articulating portion 25 relative to the distal end of flexible proximal portion 20, (ii) an HHS coil 225 (e.g., a hollow helical strand of the sort sold by Fort Wayne Metals of Fort Wayne, Ind.) for selectively rotating rotatable housing assembly 165 (FIG. 9) relative to shaft 15, and hence for selectively rotating end effector 30 relative to shaft 15, and (iii) a pull wire 230 for selectively actuating end effector 30.

2.4.1 Articulation Cables 220

Figure 15:
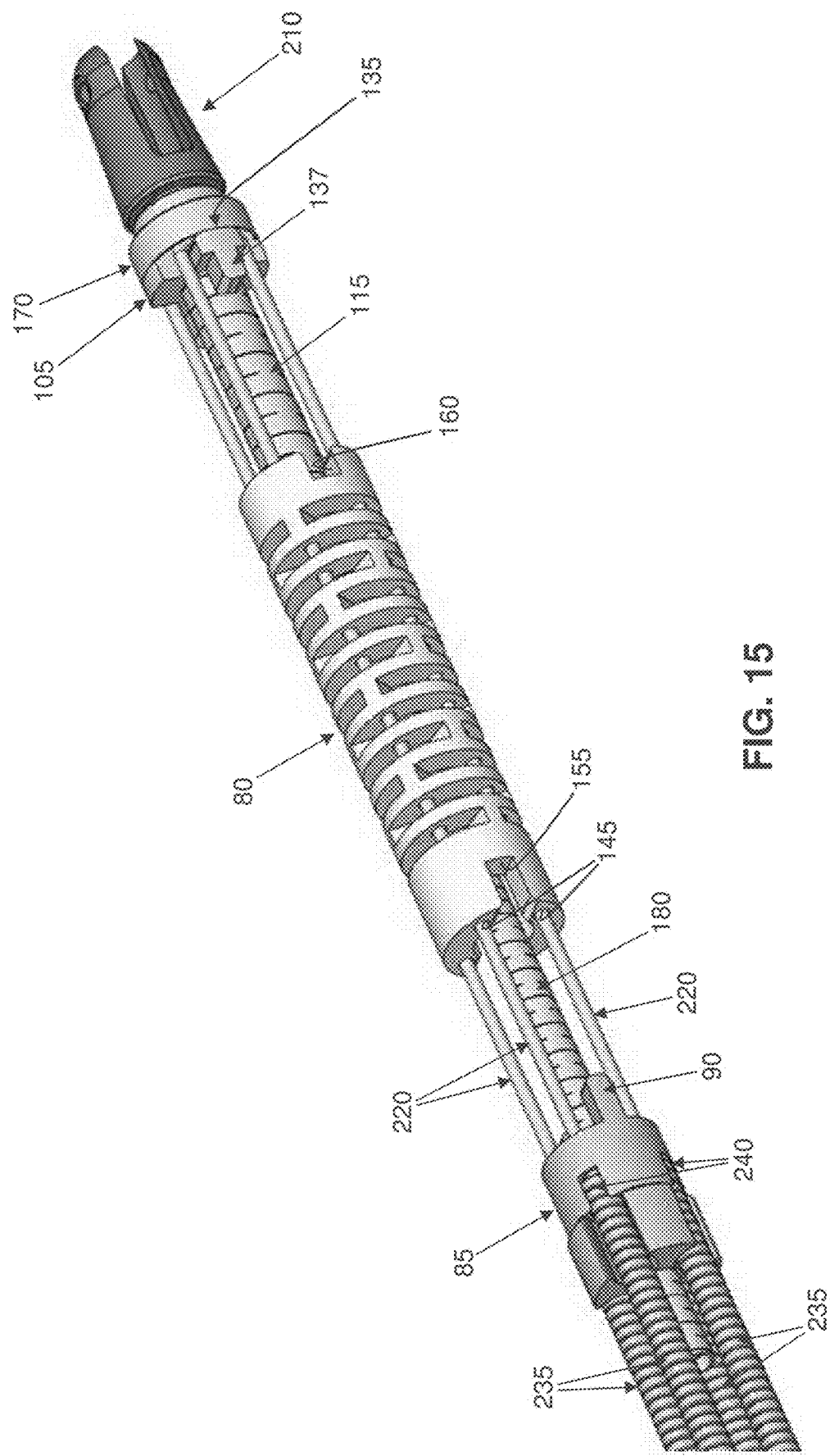
Figure 16:
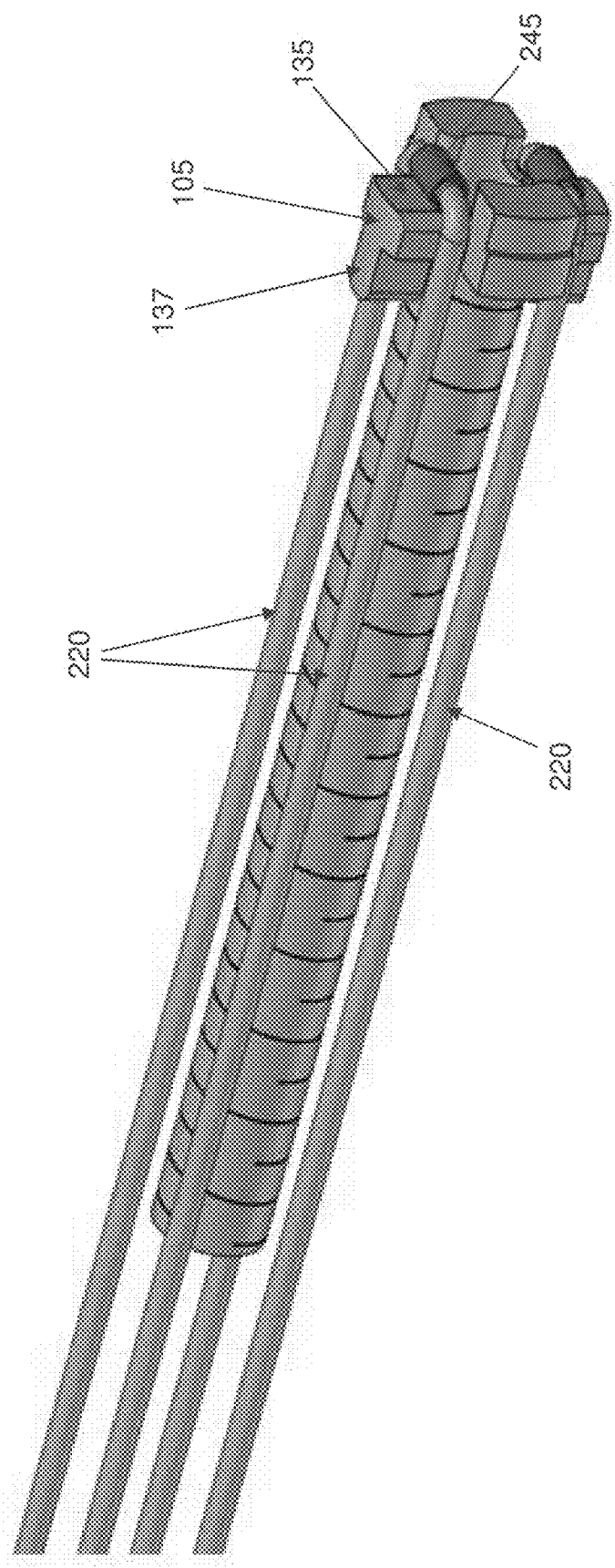

Looking next at FIGS. 13-16, in a preferred form of the invention, four articulation cables 220 run from handle 10 to distal seats 135 (FIGS. 15 and 16) of distal articulation link assembly 70, with articulation cables 220 extending through bores 95 of body 85 (FIG. 6), through openings 145 of flex spine 80 (FIG. 5) to distal seats 135 of body 105 (FIG. 16). Articulation cables 220 are preferably each slidably disposed within an articulation cable housing 235 (FIG. 13). The distal ends 240 of articulation cable housings 235 are mounted to body 85 (FIG. 15) of proximal articulation link assembly 75 (i.e., via thread adjusters 330, as will hereinafter be discussed). Articulation cable housings 235 bear against body 85 of proximal articulation link assembly 75 and provide a counterforce to body 85 for articulation of distal articulating portion 25 of shaft 15 relative to flexible proximal portion 20 of shaft 15. Articulation cable housings 235 also separate articulation cables 220 from one another and from HHS coil 225, and help ensure smooth sliding movement of articulation cables 220 within flexible proximal portion 20 of shaft 15 (i.e., over the distance between handle 10 and proximal articulation link assembly 75, which may be substantial in length (e.g., 95 cm-140 cm) and follow a tortuous path when medical instrument 5 is disposed in a patient). If desired, in order to facilitate mounting the distal ends of articulation cable housings 235 to the body 85 (FIG. 15), the proximal end of each bore 95 may comprise a counterbore (not shown) sized to receive the distal end 240 of a given articulation cable housing 235.

Looking now at FIGS. 15 and 16, after articulation cables 220 pass distally through openings 145 (FIG. 5) in flex spine 80, articulation cables 220 are attached (e.g., via welding, crimping, etc.) to distal seats 135 of body 105 of distal articulation link assembly 70. By way of example but not limitation, two of the articulation cables 220 may be provided by a single length of cable, with that single length of cable having a tube 245 (FIG. 16) crimped thereto and with tube 245 being welded (or otherwise affixed) to a distal seat 135.

As a result of this construction, by selectively pulling proximally on a proximal end of an articulation cable 220, body 105 (FIG. 7) of distal articulation link assembly 70 can be articulated laterally, whereby to articulate distal articulating portion 25 of shaft 15. Furthermore, by providing at least three articulation cables 220, with the three or more articulation cables being positioned about the perimeter of body 105, substantially universal articulation of distal articulation link assembly 70 can be achieved, whereby to provide substantially universal articulation for distal articulating portion 25 of shaft 15.

2.4.2 HHS Coil 225

Figure 17:
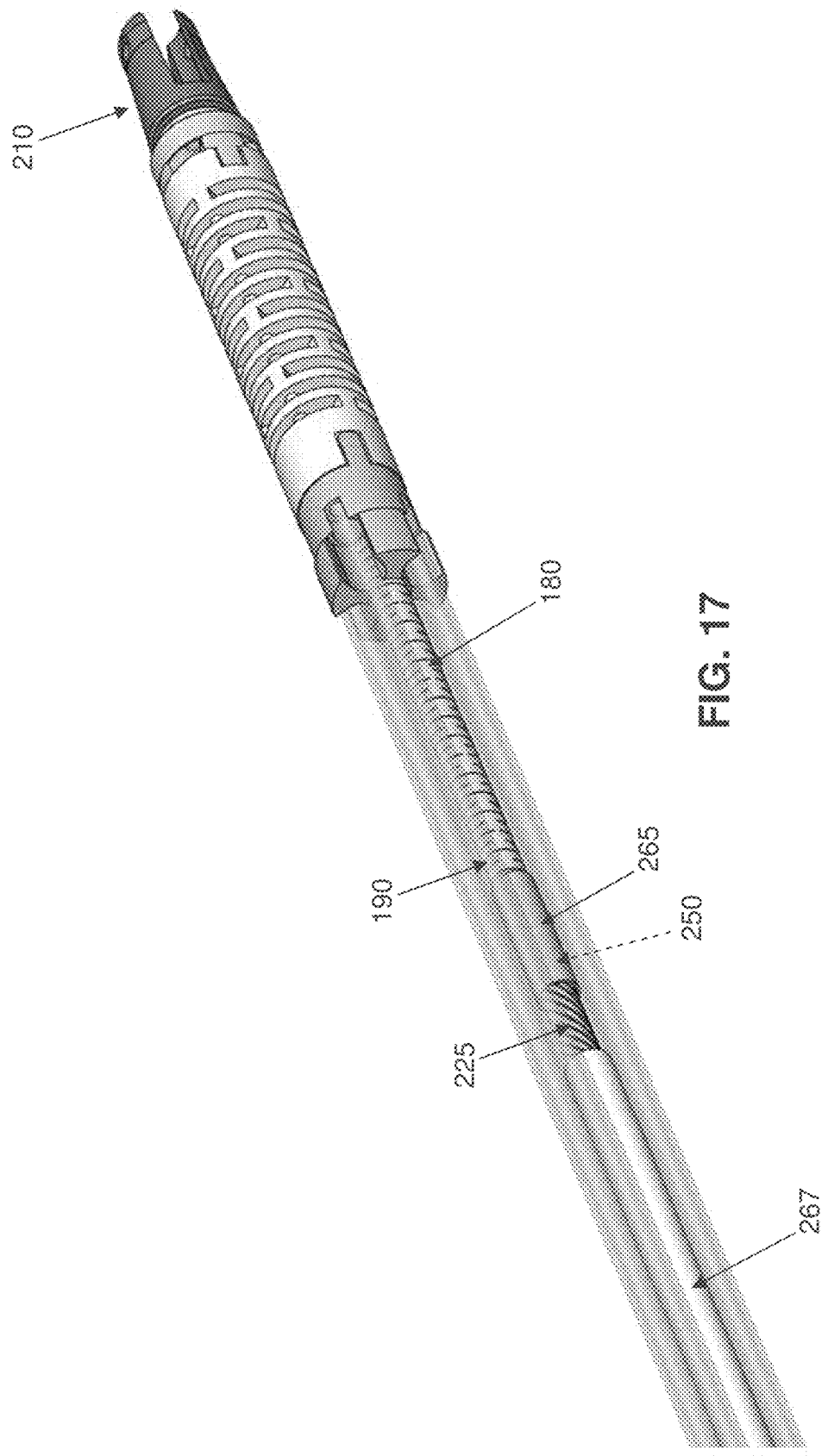

Looking next at FIGS. 13, 14 and 17, HHS coil 225 comprises a distal end 250 (FIG. 17), a proximal end 255 (FIG. 26) and a lumen 260 (FIG. 13) extending therebetween. In order to facilitate rotation of HHS coil 225 within shaft 15, HHS coil 225 is preferably disposed within a flexible, friction-reducing sleeve 267 (FIG. 13). More particularly, HHS coil 225 preferably comprises a plurality of filars which are wound and swaged together so as to together form a hollow tubular structure. By way of example but not limitation, HHS coil 225 may comprise a hollow helical strand of the sort sold by Fort Wayne Metals of Fort Wayne, Ind. In one preferred form of the present invention, HHS coil 225 comprises 10 filars which are wound and swaged together into a singular flexible structure. Distal end 250 (FIG. 17) of HHS coil 225 is mounted to long laser-cut hypotube 180 (FIG. 17) of rotatable housing assembly 165 (FIG. 9) via a sleeve (or crimp) 265 (FIG. 17), such that long laser-cut hypotube 180 (and hence end effector mount 210 carrying end effector 30) rotate when HHS coil 225 rotates.

It will be appreciated that, as a result of this construction, the rotational disposition of end effector 30 can be adjusted by selectively rotating HHS coil 225, whereby to rotate long laser-cut hypotube 180 and hence end effector mount 210, to which end effector 30 is secured. Significantly, by using HHS coil 225 and long laser-cut hypotube 180 to transmit torque down shaft 15, any build-up of torqueing spring energy within the shaft is minimized, even when shaft 15 follows a tortuous path and distal articulating portion 25 has been articulated relative to the longitudinal axis of shaft 15.

2.4.3 Pull Wire 230

Looking next at FIGS. 13, 14, 18 and 19, pull wire 230 is provided for selectively actuating end effector 30. The distal end of pull wire 230 (FIG. 19) is secured to clevis 218 of end effector 30, with clevis 218 being slidably mounted to jaws 216, 217 of end effector 30, and with jaws 216, 217 being pinned to end effector mount 210, such that reciprocal movement of pull wire 230 causes the opposing jaws 216, 217 of end effector 30 to open and close relative to one another.

2.5 Further Details on the Construction of Shaft 15

When shaft 15 is fully assembled, and looking now at FIGS. 18-23, body 85 (FIG. 18) of proximal articulation link assembly 75 (FIG. 6) is mounted to distal end 40 (FIG. 2) of flexible outer coil 35, with distal ends 240 (FIG. 15) of articulation cable housings 235 being mounted to body 85 of proximal articulation link assembly 75, and with articulation cables 220 passing through bores 95 (FIG. 6) formed in body 85. Distal articulation link assembly 70 (FIG. 7) is mounted to proximal articulation link assembly 75 by mounting proximal end 125 of short laser-cut hypotube 115 in counterbore 102 (FIG. 6) of body 85. Flexible body 140 (FIG. 5) of flex spine 80 is "sandwiched" between body 105 (FIG. 7) of distal articulation link assembly 70 and body 85 (FIG. 6) of proximal link assembly 75, with distally-extending fingers 90 of body 85 being disposed in proximal seats 155 (FIG. 5) of flex spine 80 and with proximally-extending fingers 137 of body 105 being disposed in distal seats 160 of flex spine 80. Short laser-cut hypotube 115 (FIG. 7) of distal articulation link assembly 70 passes through central bore 150 (FIG. 5) of flexible body 140 of flex spine 80. When articulation cables 220 are pulled proximally, the distal end of short laser-cut hypotube 115 bears against body 85 of proximal articulation link assembly 75 (which, in turn, bears against articulation cable housings 235), whereby to selectively articulate distal articulating portion 25 of shaft 15.

Long laser-cut hypotube 180 (FIGS. 9, 10 and 17) of rotatable housing assembly 165 extends proximally through short laser-cut hypotube 115 (FIG. 18) such that the proximal end 190 (FIG. 17) of long laser-cut hypotube 180 passes through body 85 of proximal articulation link assembly 75 (i.e., by passing through counterbore 102 and central bore 100 of body 85) and is secured to HHS coil 225 (FIG. 17), e.g., via sleeve 265. Collar 170 (FIG. 18) of rotatable housing assembly 165 (FIG. 9) is mounted to body 105 of distal articulation link assembly 70 and covers distal seats 135 (and the portions of articulation cables 220 mounted thereto). Rotation connector 200 (FIGS. 9 and 10) is mounted to the distal end of long laser-cut hypotube 180. Rotation connector 200 is also mounted to end effector mount 210. End effector 30 is mounted to end effector mount 210. As a result of this construction, when HHS coil 225 is rotated, long laser-cut hypotube 180 is rotated and rotation connector 200 is rotated and end effector mount 210 is rotated, whereby to cause rotation of end effector 30.

Pull wire 230 (FIG. 18) extends distally through lumen 260 of HHS coil 225 (FIGS. 13 and 14) and distally through lumen 195 (FIG. 9) of long laser-cut hypotube 180, exiting rotation connector 200. The distal end of pull wire 230 is connected to end effector 30. As a result of this construction, reciprocal movement of a pull wire 230 causes the opposing jaws 216, 217 (FIG. 8) of the grasper to open and close relative to one another.

Flexible proximal portion 20 of shaft 15 is preferably covered with a protective sleeve or outer covering (e.g., Pebax®) 270 (FIGS. 18, 20 and 21), with the proximal end of protective sleeve or outer covering 270 being secured (e.g., bonded) to rigid tube 60 and with the distal end of protective sleeve or outer covering 270 being secured (e.g., bonded) to body 85 of proximal articulation link assembly 75, and distal articulating portion 25 of shaft 15 is preferably covered with a protective sleeve or outer covering 275 (FIGS. 18 and 22), with the proximal end of protective sleeve or outer covering 275 being secured to body 85 of proximal articulation link assembly 75 and with the distal end of protective sleeve or outer covering 275 extending up to and over the proximal portion of end effector 30, whereby to protect shaft 15 and permit easy insertion of shaft 15 into the body of a patient via a natural body orifice, a cannula, the lumen of another surgical instrument, etc.

The proximal end of shaft 15 is mounted to handle 10 (FIG. 1) such that articulation cables 220, HHS coil 225 and pull wire 230 may be selectively actuated using handle 10, as will hereinafter be discussed in further detail.

3 Handle 10 in General

Figure 24:
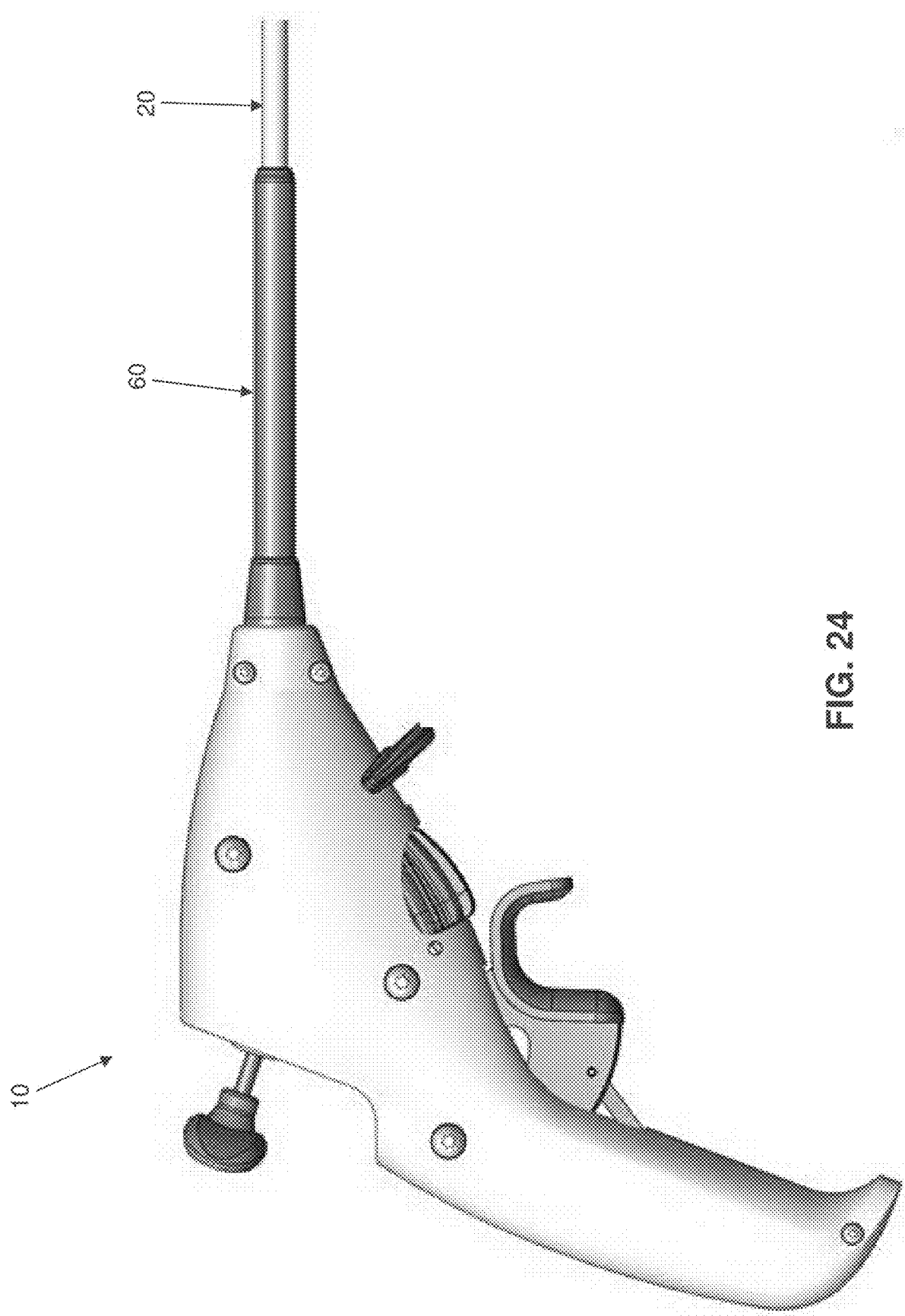
FIGS. 24-46B are schematic views showing further details of the handle and the proximal end of the shaft of the novel medical instrument shown in FIG. 1.
Figure 25:
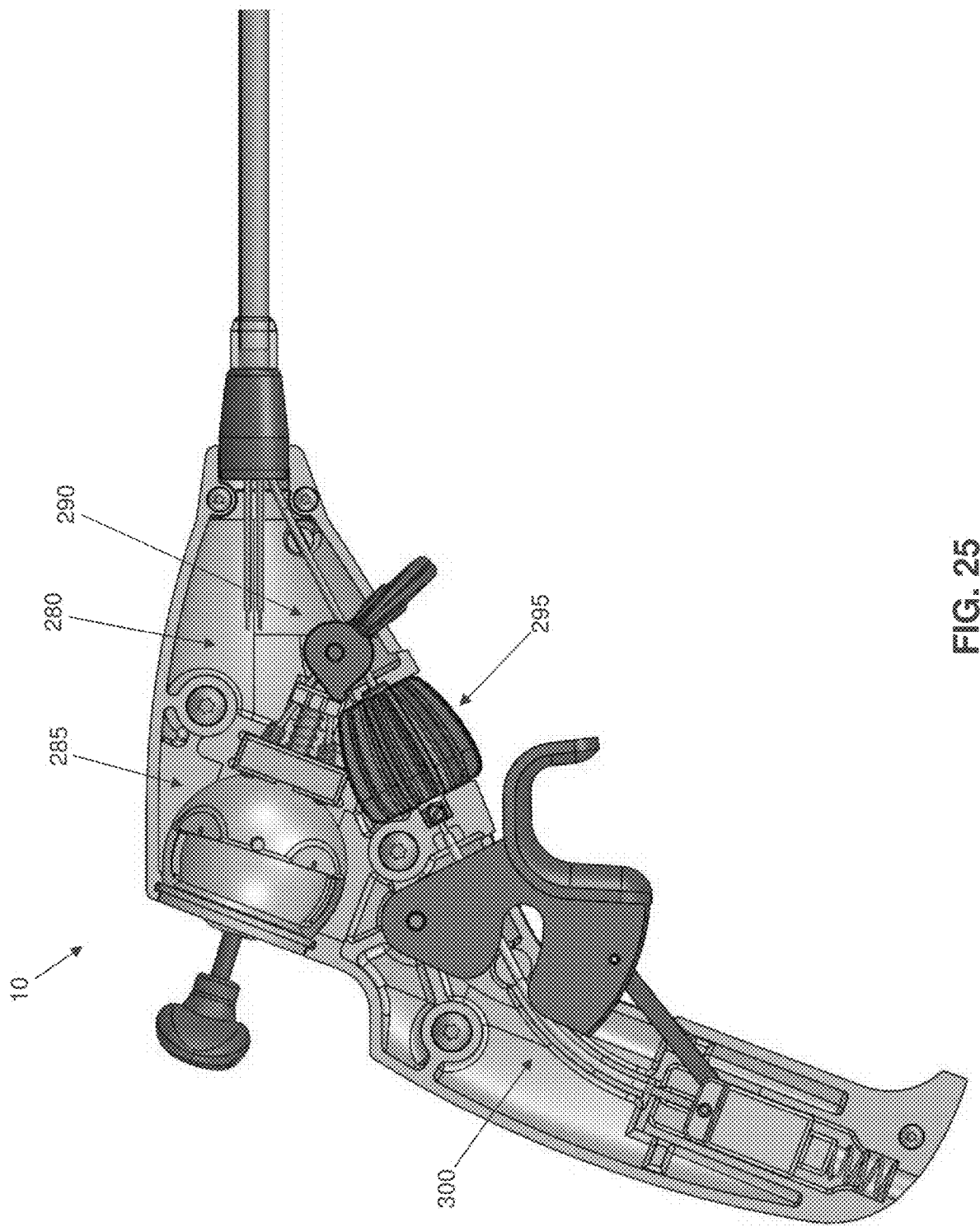
Figure 26:
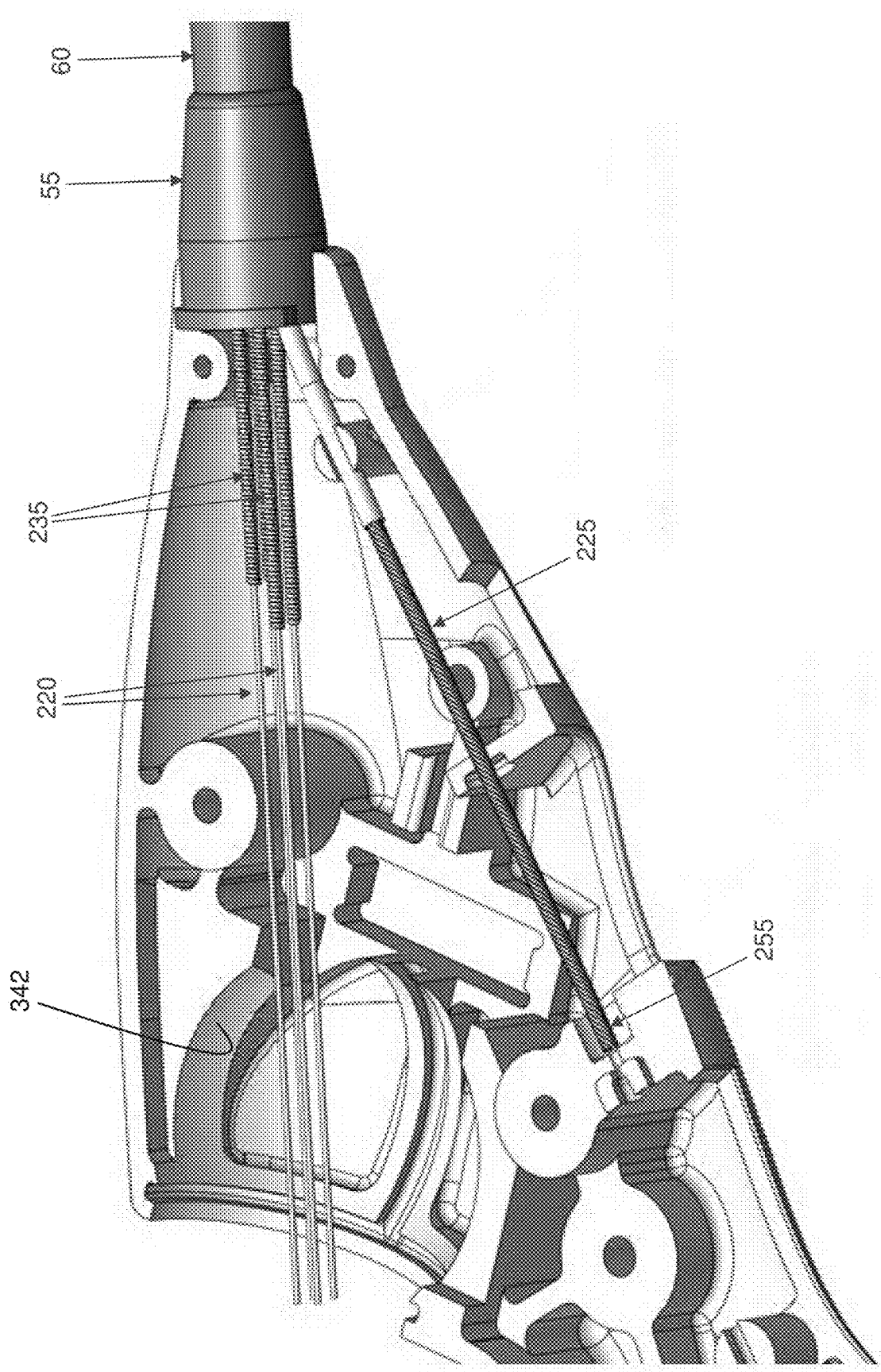
Figure 27:
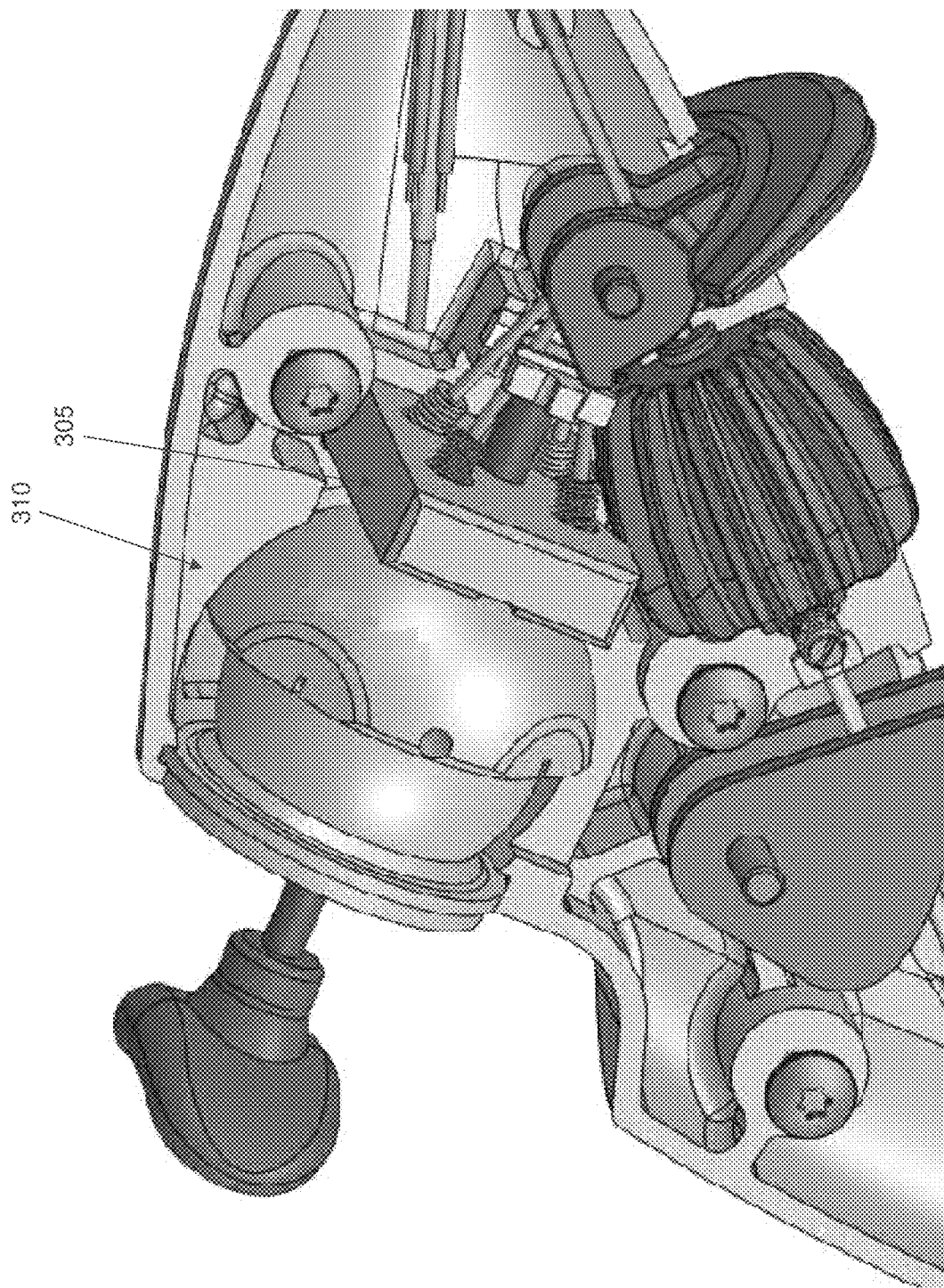
Figure 28:
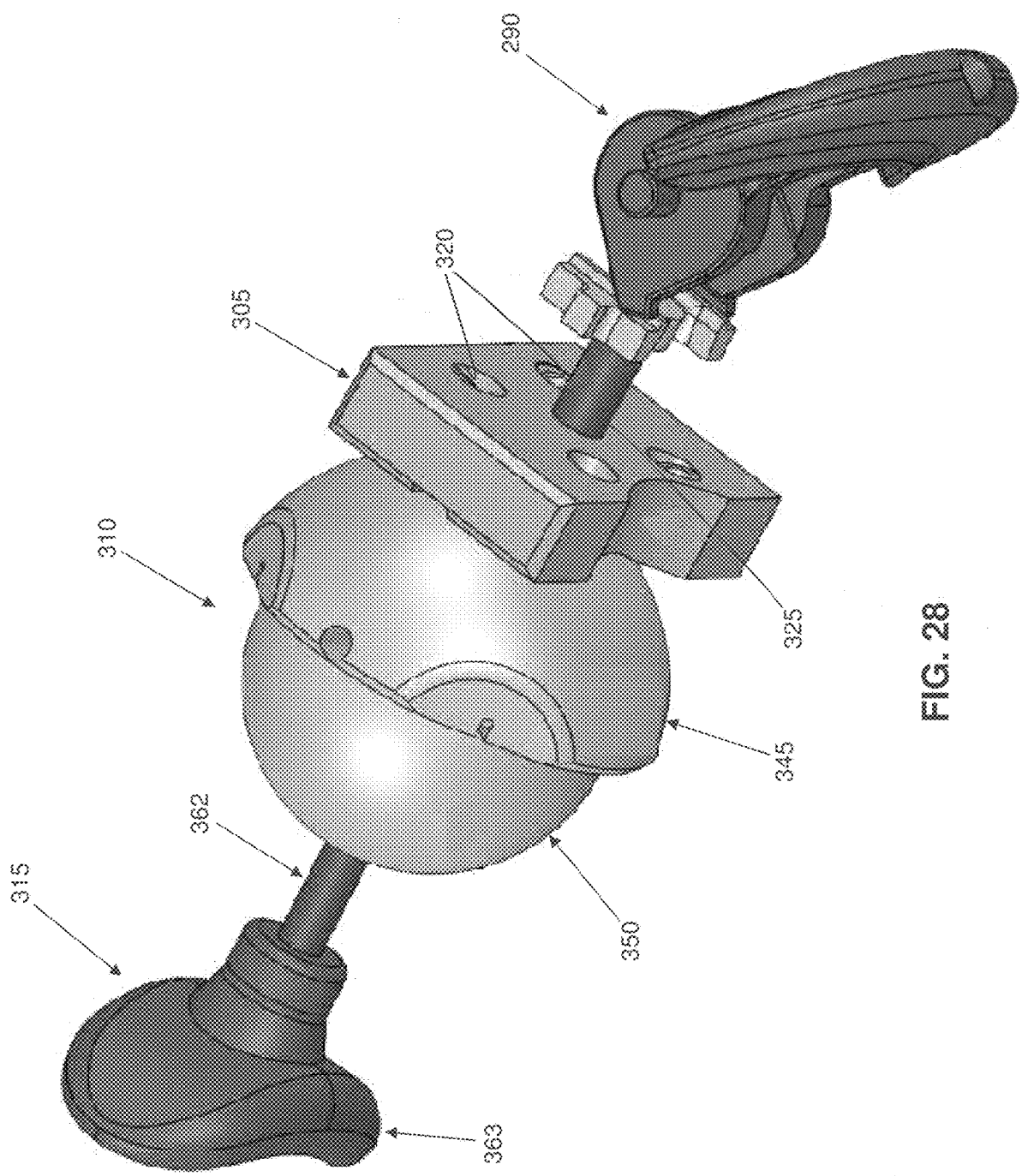
Figure 29:
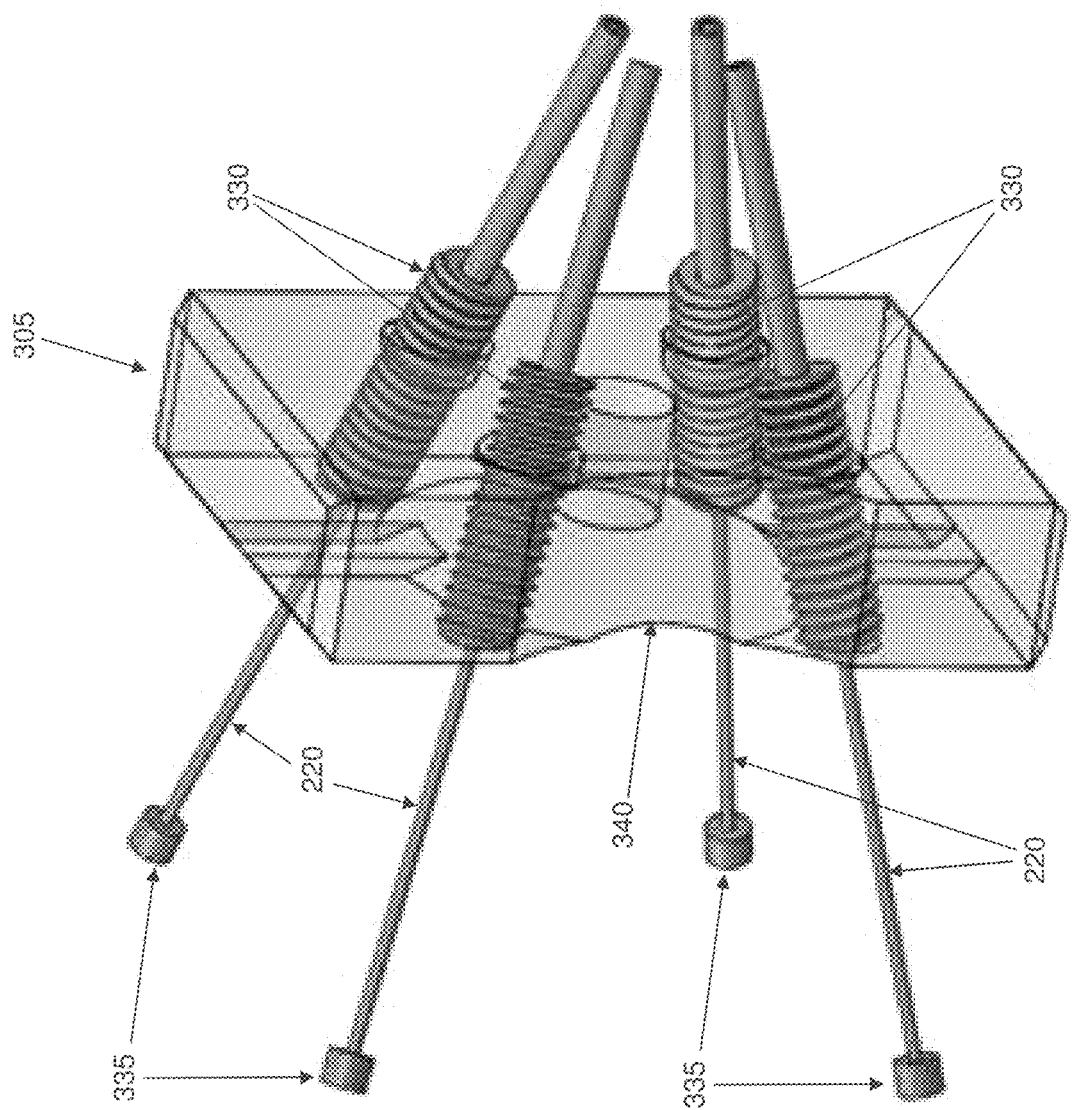
Figure 30:
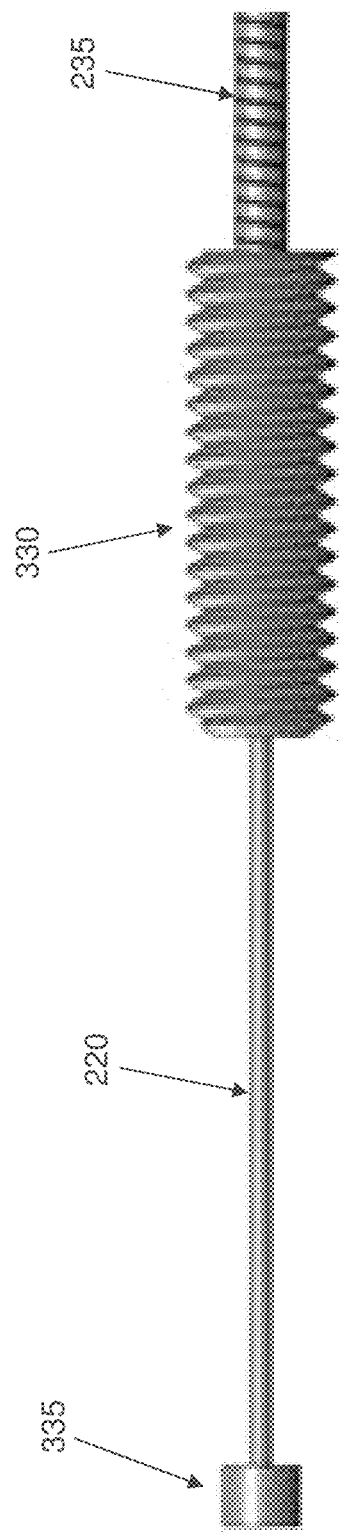
Figure 31:
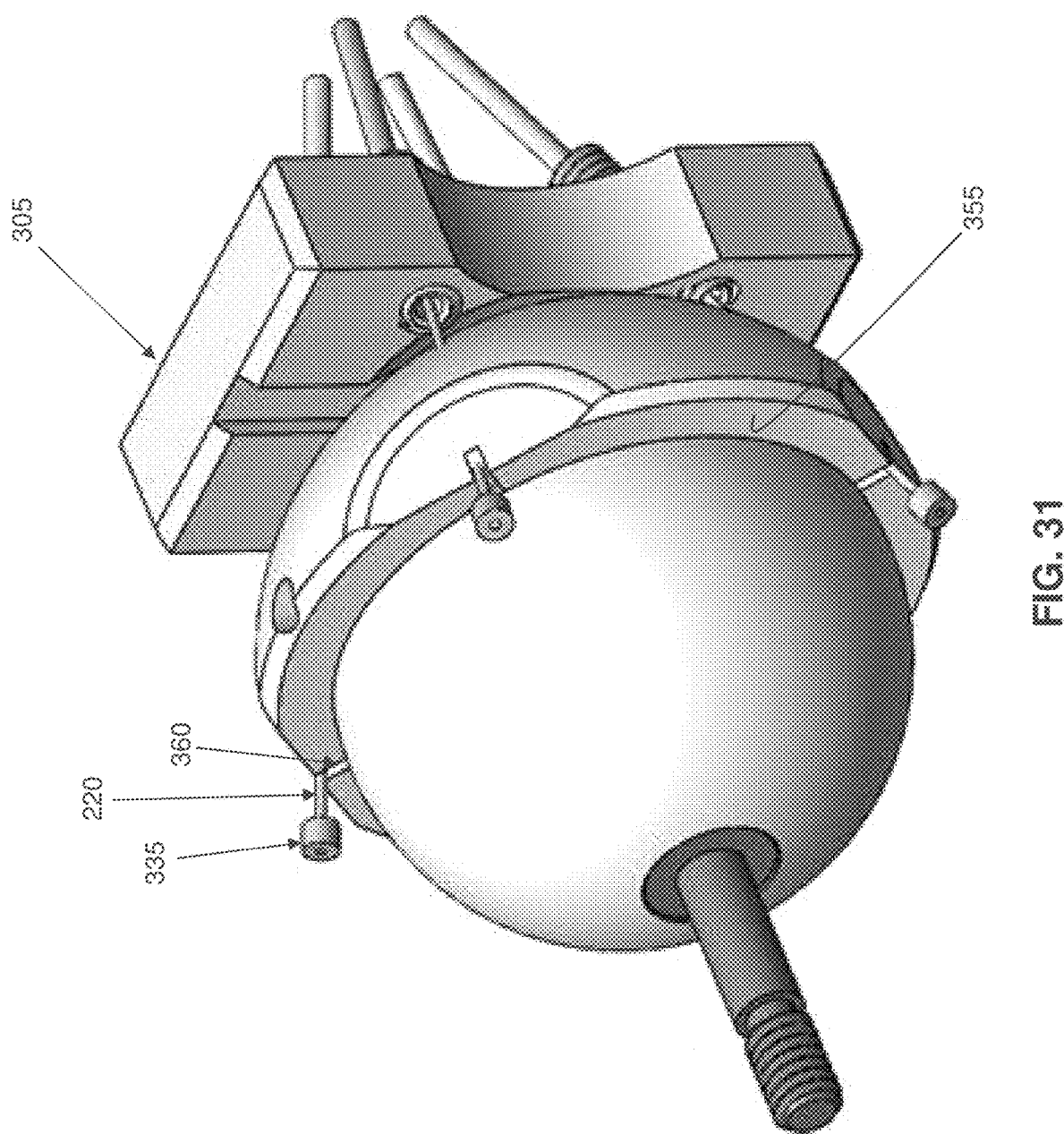
Figure 32:
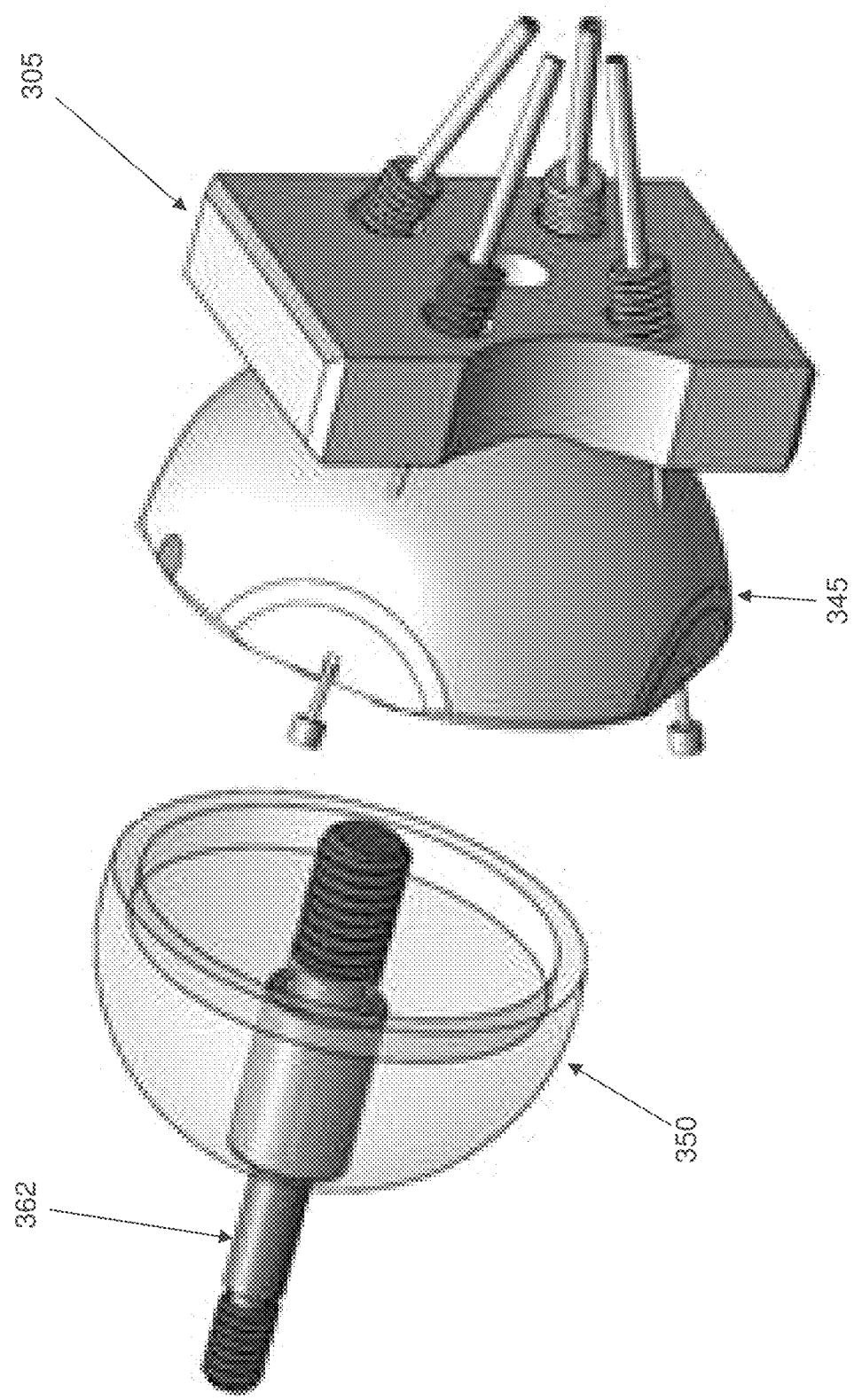

Looking now at FIGS. 24-26, handle 10 generally comprises an internal cavity 280, an articulation control assembly 285 for selectively moving articulation cables 220 (and hence selectively articulating distal articulating portion 25 of shaft 15), a push rod lock assembly 290 for selectively locking articulation control assembly 285 in a desired position (and hence locking distal articulating portion 25 of shaft 15 in a selected position), a roticulation control assembly 295 for selectively rotating HHS coil 225 (and hence selectively rotating end effector 30), and a trigger assembly 300 for selectively actuating pull wire 230 (and hence selectively actuating end effector 30).

3.1 Articulation Control Assembly 285

Looking now at FIGS. 27-36, articulation control assembly 285 generally comprises a ball plate 305 (FIG. 28) fixedly mounted within internal cavity 280 of handle 10, a thumbstick ball assembly 310 configured to be selectively pivoted relative to ball plate 305, and a thumbstick 315 configured to be engaged by the thumb of a user.

Ball plate 305 comprises a plurality of threaded openings 320 (FIG. 28) and a center opening 325 for receiving pushrod lock assembly 290, as will hereinafter be discussed in further detail. Threaded openings 320 are configured to receive a plurality of threaded adjusters 330 (FIGS. 29 and 30) which are, in turn, mounted to the proximal ends (FIGS. 21 and 30) of each articulation cable housing 235. It will be appreciated that, as a result of this construction, the proximal ends of articulation cable housings 235 bear against ball plate 305 (which is, in turn, fixedly mounted to handle 10), such that articulation cable housings 235 can provide a counterforce to body 85 of proximal articulation link assembly 75 when articulation cables 220 are pulled proximally. Each threaded adjuster 330 comprises a central lumen passing therethrough, such that an articulation cable 220 (FIG. 30) may pass through the threaded adjuster (and hence, through threaded openings 320 of ball plate 305) to be mounted to thumbstick ball assembly 310, as will hereinafter be discussed. An enlargement 335 (FIG. 30) is formed on (or attached to) the proximal end of each articulation cable 220, whereby to facilitate mounting articulation cables 220 to thumbstick ball assembly 310. Ball plate 305 also comprises a proximally-facing concave recess 340 (FIG. 29) for providing clearance to thumbstick ball assembly 310 which is pivotally seated within a seat 342 disposed within internal cavity 280 of handle 10, as will hereinafter be discussed in further detail.

Thumbstick ball assembly 310 comprises a hemispherical distal ball 345 (FIG. 32) and a hemispherical proximal ball 350. Hemispherical distal ball 345 preferably has a maximum diameter (i.e., the diameter at its proximal end) which is greater than the maximum diameter of hemispherical distal ball 345 (i.e., the diameter at its distal end), whereby to provide a proximal circumferential seat 355 (FIG. 31) about the proximal end of hemispherical distal ball 345. A plurality of openings (or grooves) 360 (FIG. 31) are formed in the proximal circumferential seat 355 for receiving articulation cables 220 when enlargements 335 are seated on proximal circumferential seat 355, as will hereinafter be discussed. As a result of this construction, when the rounded distal end of hemispherical distal ball 345 is pivotally disposed within seat 342 in internal cavity 280 of handle 10 (FIG. 27) and spaced from ball plate 305 (FIG. 33), articulation cables 220 may be passed through openings (or grooves) 360 in proximal circumferential seat 355 as enlargements 335 seat on proximal circumferential seat 355. Hence, articulation cables 220 may be selectively moved by selectively pivoting hemispherical distal ball 345 within its seat 342 inside internal cavity 280 of handle 10 (i.e., by selectively pivoting thumbstick 315, as will hereinafter be discussed in further detail).

Thumbstick 315 comprises a threaded stem 362 (FIG. 33) and a thumb seat 363. The distal end of threaded stem 362 secures hemispherical proximal ball 350 to hemispherical distal ball 345. Thumb seat 363 is secured to the proximal end of threaded stem 362. As a result of this construction, thumbstick 315 can be used to selectively move hemispherical distal ball 345, whereby to selectively move articulation cables 220, whereby to selectively articulate distal articulating portion 25 of shaft 15 relative to flexible proximal portion 20 of shaft 15.

3.1.1 Push Rod Lock Assembly 290

Figure 33:
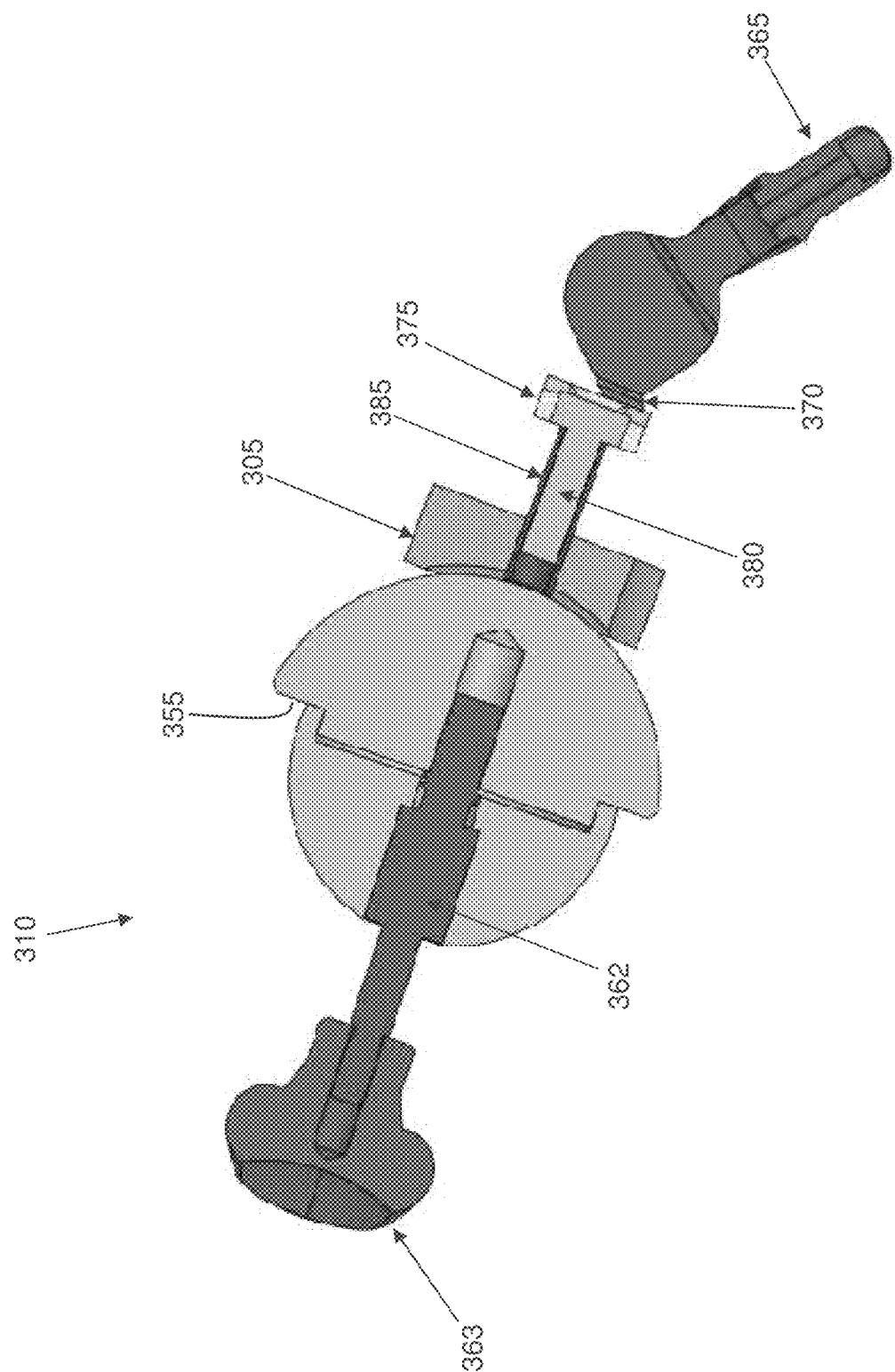
Figure 34:
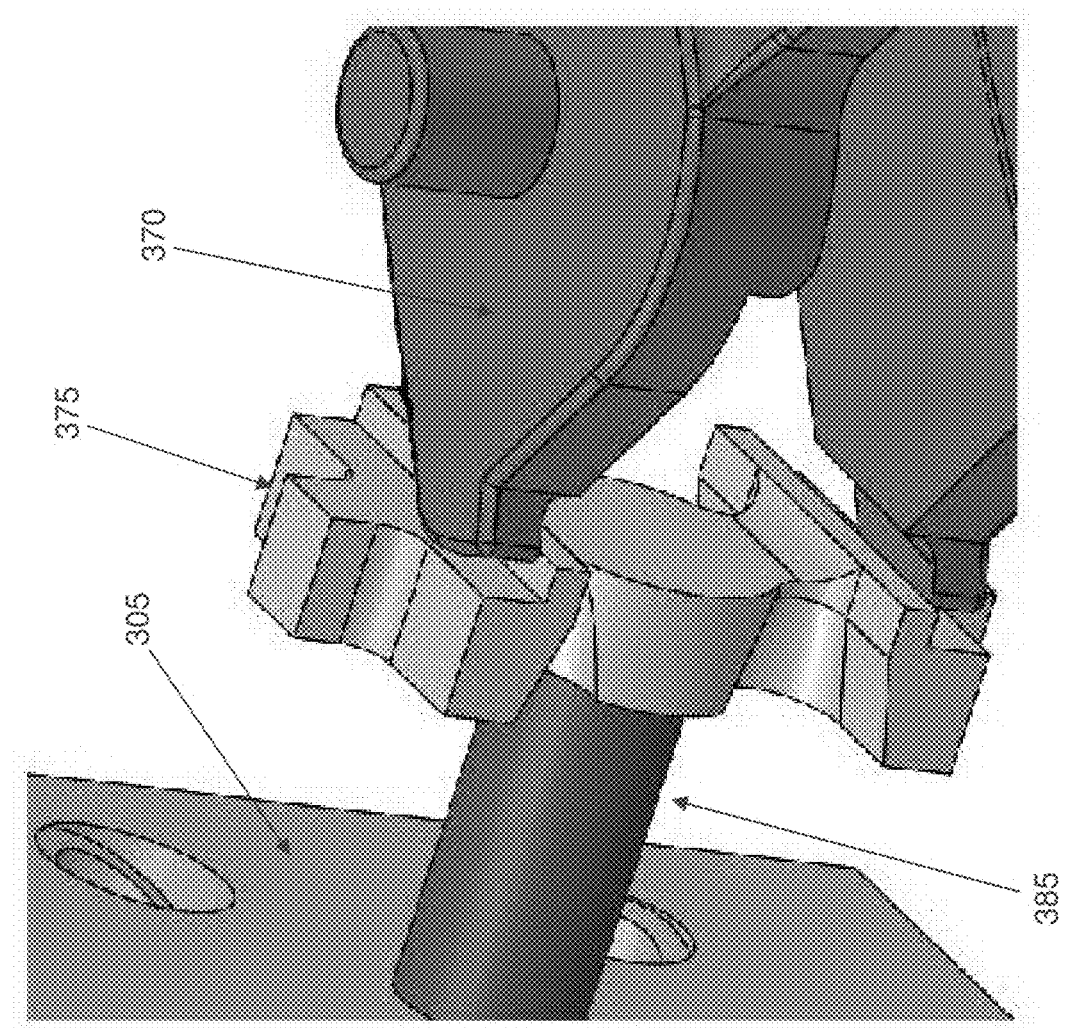
Figure 35:
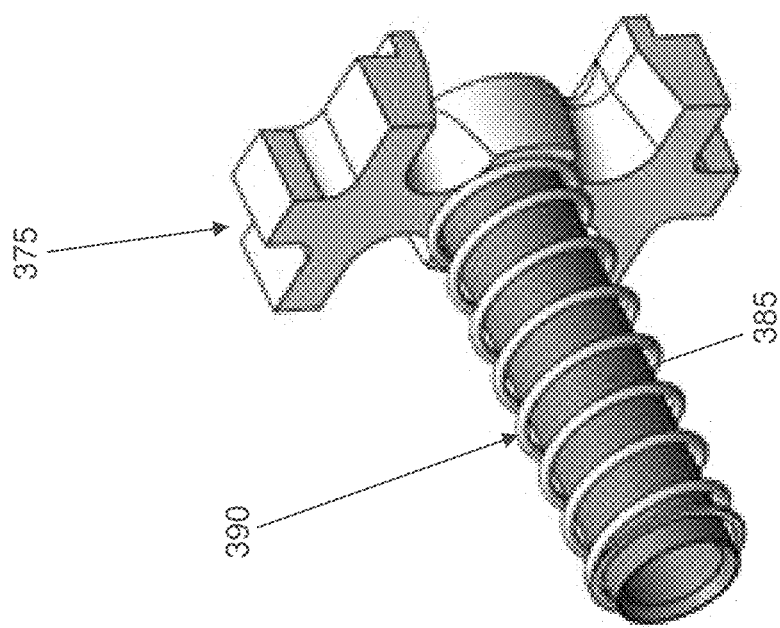
Figure 36:
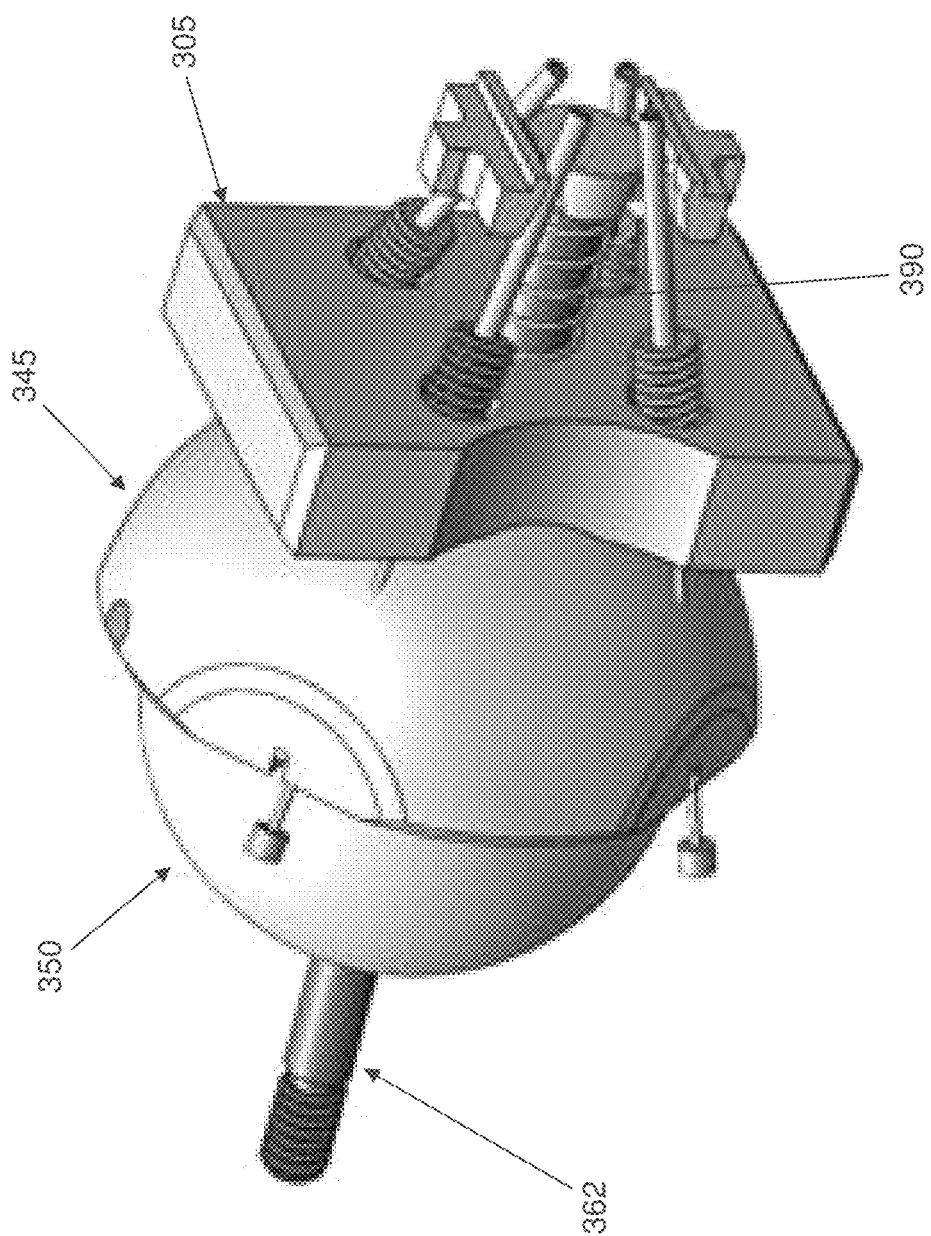
Figure 37:
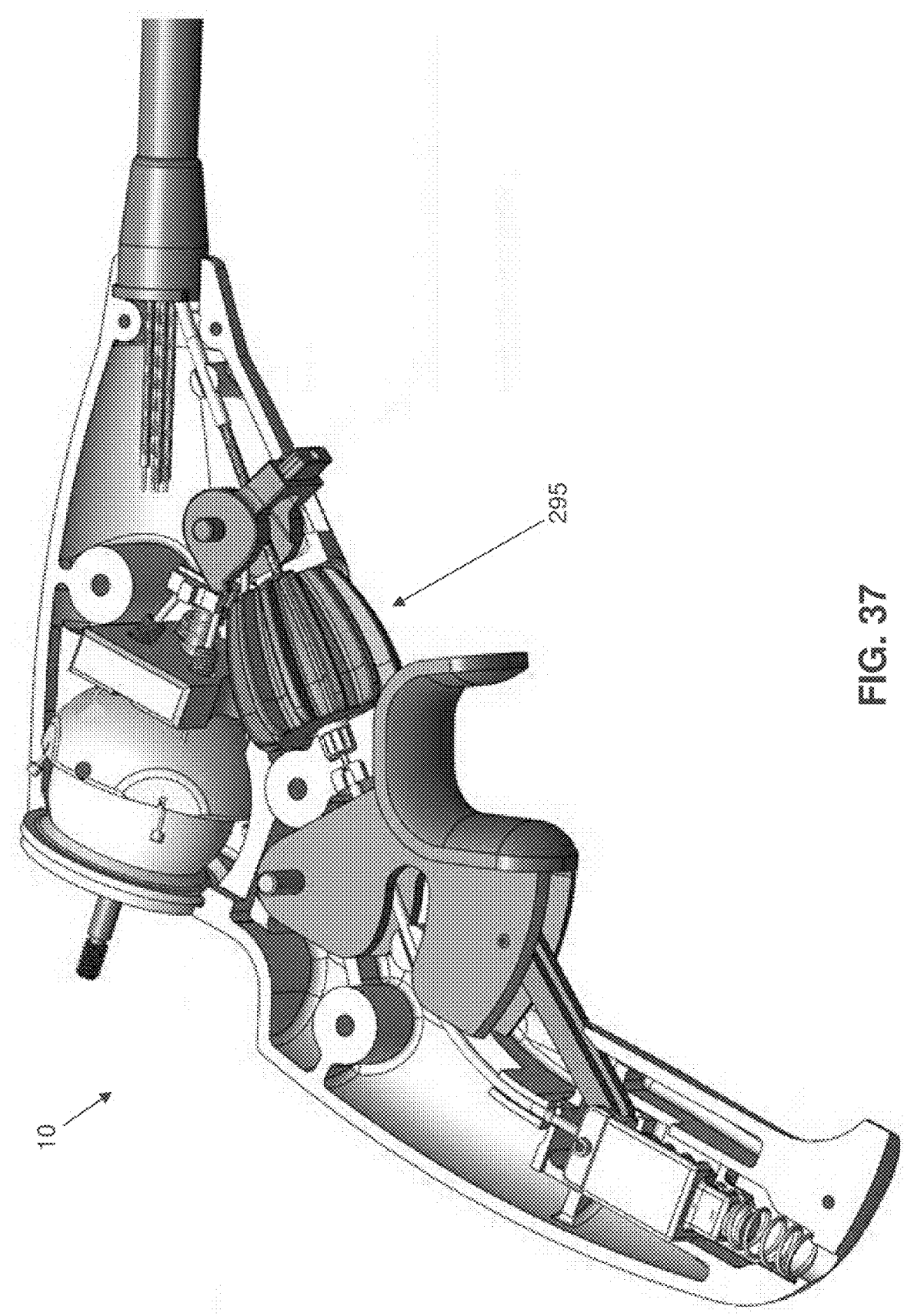
Figure 38:
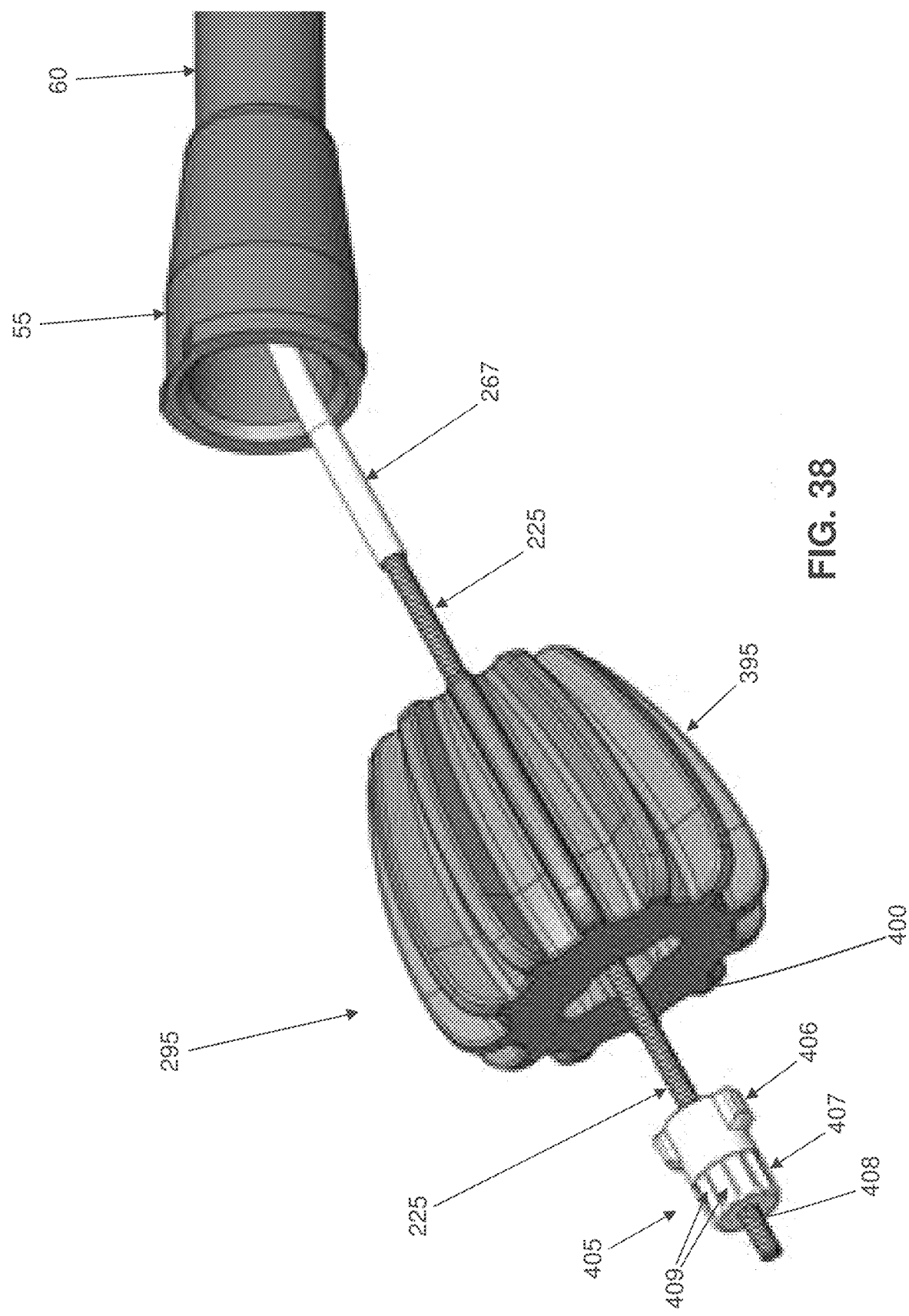

Looking next at FIGS. 27, 28 and 33-36, pushrod lock assembly 290 generally comprises an actuation lever 365 (FIG. 33), a cam 370 mounted to actuation lever 365, and a pushrod lock assembly plate 375 having a pushrod 380 mounted thereto and extending proximally therefrom. Pushrod 380 is preferably disposed within a sleeve 385. In one preferred form of the invention, a spring 390 (FIG. 35) is disposed over sleeve 385 so as to bias pushrod lock assembly plate 375 distally away from ball plate 305 (FIG. 36). Pushrod 380 is slidably disposed in center opening 325 (FIG. 28) of ball plate 305 and extends proximally therefrom toward thumbstick ball assembly 310 (FIG. 33). Actuation lever 365 and cam 370 are rotatably mounted within cavity 280 of handle 10, with cam 370 contacting pushrod lock assembly plate 375 such that movement of actuation lever 365 cams pushrod lock assembly plate 375 (and hence pushrod 380) proximally against the power of spring 390, whereby to cause the free end of pushrod 380 to engage hemispherical distal ball 345, thereby locking thumbstick ball assembly 310 against movement. When actuation lever 365 is moved in a second, opposite direction, cam 370 is moved so as to allow pushrod lock assembly plate 375 (and hence pushrod 380) to move distally under the power of spring 390, away from hemispherical distal ball 345, whereby to allow free movement of thumbstick ball assembly 310. As a result, it will be appreciated that pushrod lock assembly 290 can be used to selectively lock thumbstick ball assembly 310 in a desired position, whereby to selectively lock distal articulating portion 25 of shaft 15 in a desired (e.g., articulated) configuration.

3.2 Roticulation Control Assembly 295

Looking next at FIGS. 37-41, roticulation control assembly 295 generally comprises a roticulation knob 395 (FIGS. 37 and 38) having a keyway 400 (FIG. 38) passing therethrough, and a roticulation key 405. Roticulation key 405 comprises a distal end 406, a proximal end 407 and a lumen 408 extending therebetween. HHS coil 225 is received within lumen 408 of roticulation key 405 and is secured to roticulation key 405 such that rotation of roticulation key 405 effects rotation of HHS coil 225. As noted above, HHS coil 225 is secured to long laser-cut hypotube 180, and long laser-cut hypotube 180 is secured to end effector mount 210, such that rotation of HHS coil 225 causes rotation of long laser-cut hypotube 180 which causes rotation of end effector mount 210 (and hence rotation of end effector 30). Distal end 406 of rotaticulation key 405 is received in keyway 400 of roticulation knob 395 such that roticulation key 405 is engaged by roticulation knob 395 and rotates when roticulation knob 395 rotates. As a result of this construction, rotation of roticulation knob 395 causes rotation of roticulation key 405 which causes rotation of HHS coil 225 and hence rotation of end effector 30. In a preferred form of the invention, keyway 400 of roticulation knob 395 comprises a non-circular cross-sectional profile which matches the non-circular cross-sectional profile of distal end 406 of roticulation key 405.

Roticulation knob 395 is rotatably mounted within cavity 280 of handle 10 such that a portion of roticulation knob 395 protrudes out of handle 10 (FIG. 37), whereby to permit roticulation knob 395 to be selectively rotated by a user. Pull wire 230 (FIG. 40), which is disposed within HHS coil 225, extends through roticulation key 405 and is selectively actuated using trigger assembly 300 (FIG. 25), as will hereinafter be discussed.

Figure 39:
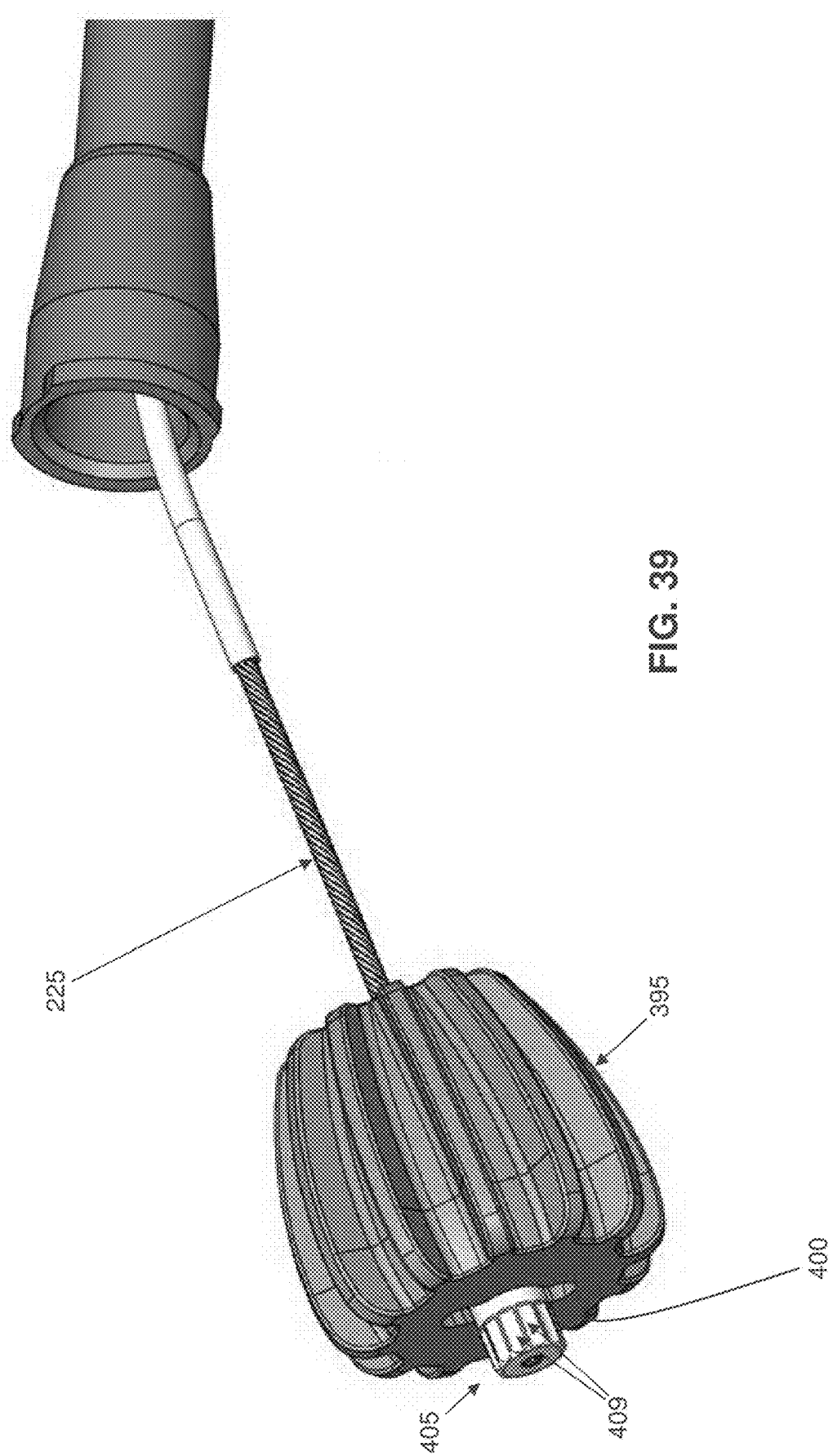
Figure 40:
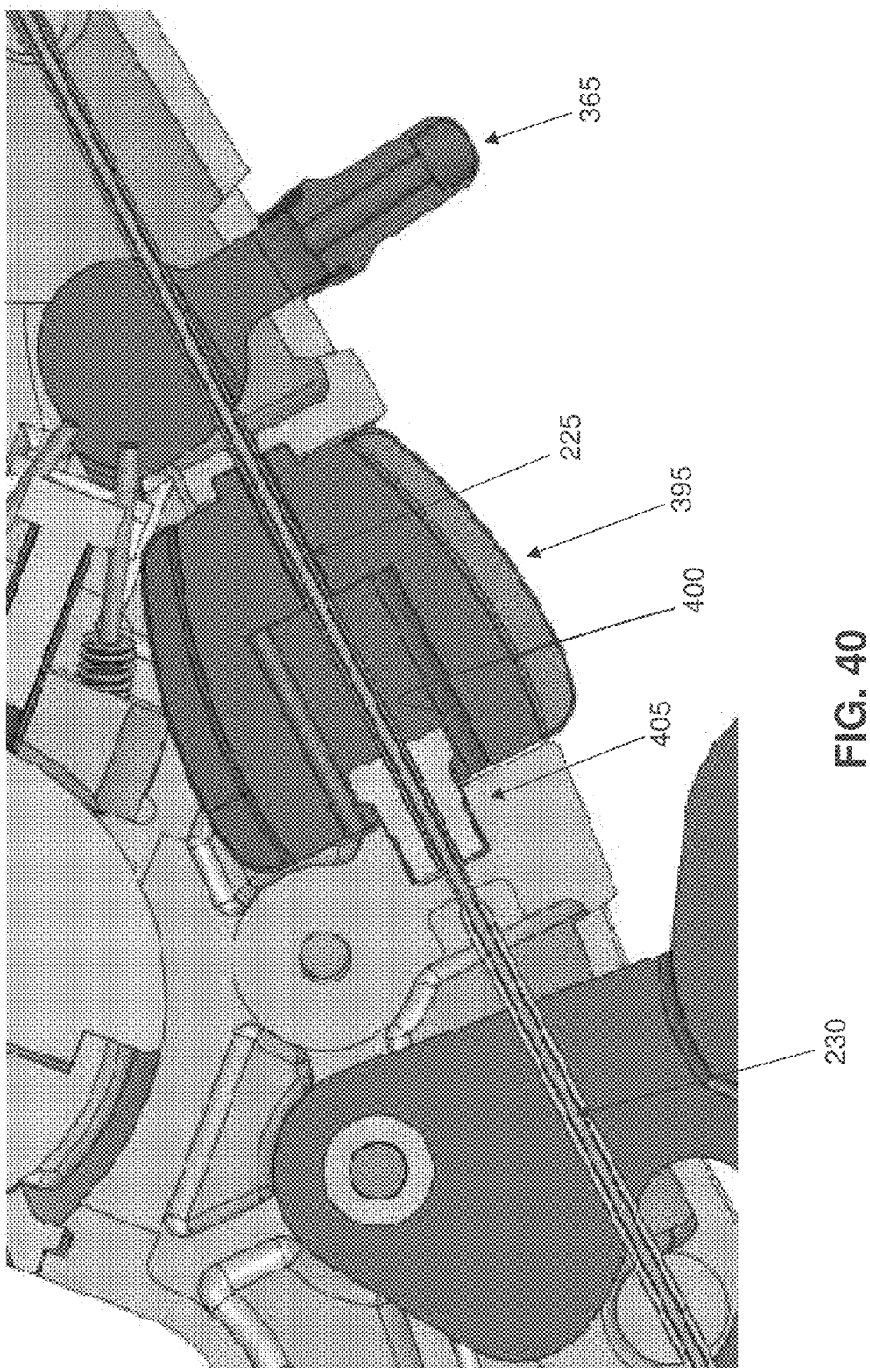
Figure 41:
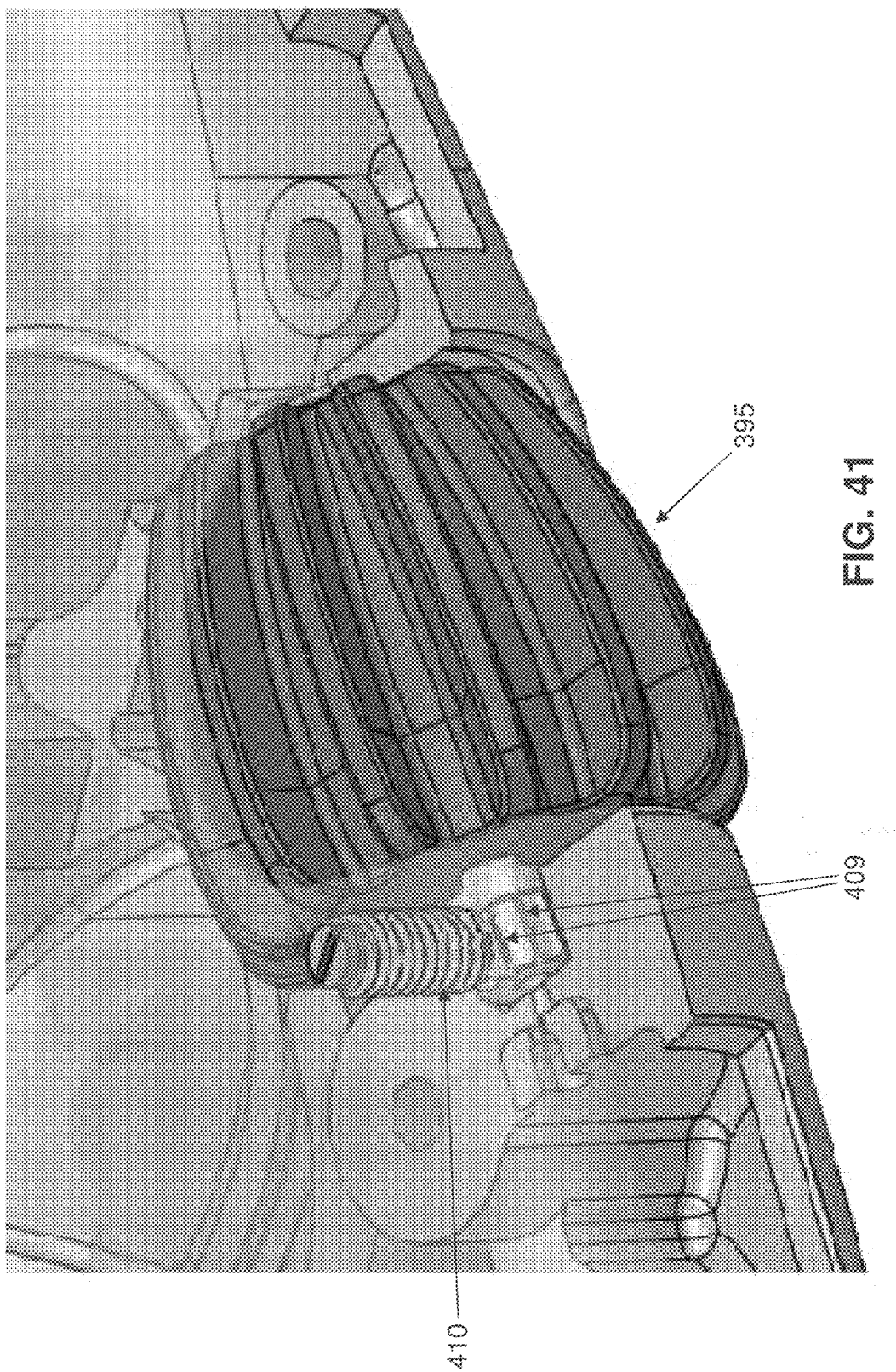
Figure 42:
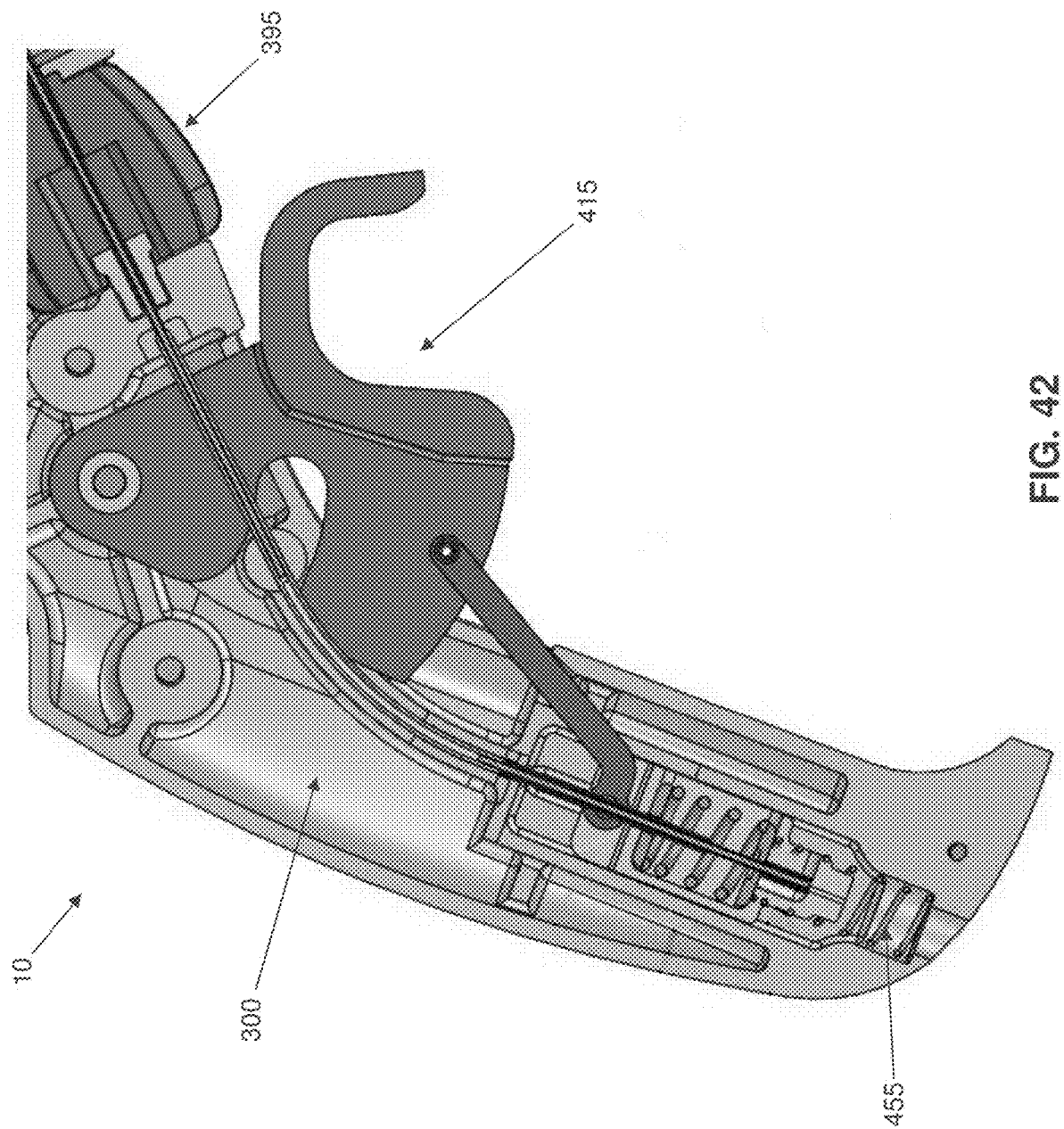
Figure 43:
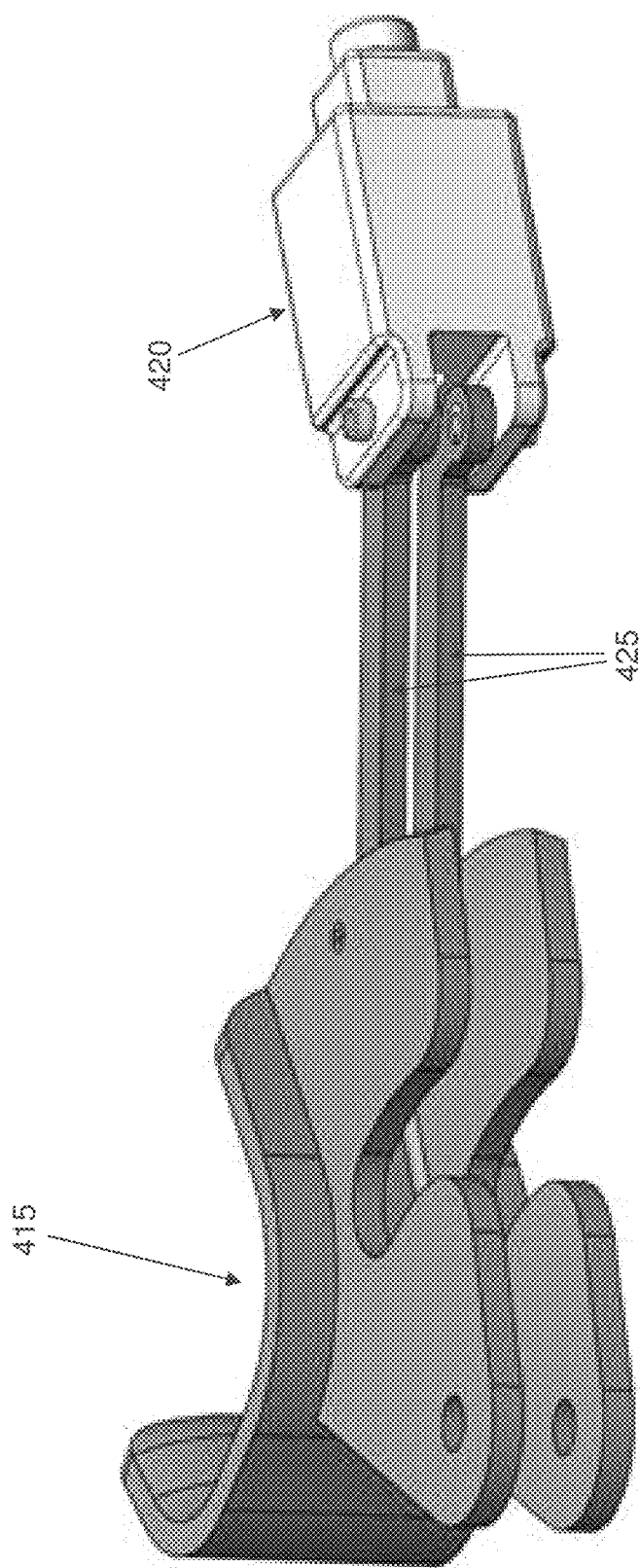
Figure 44:
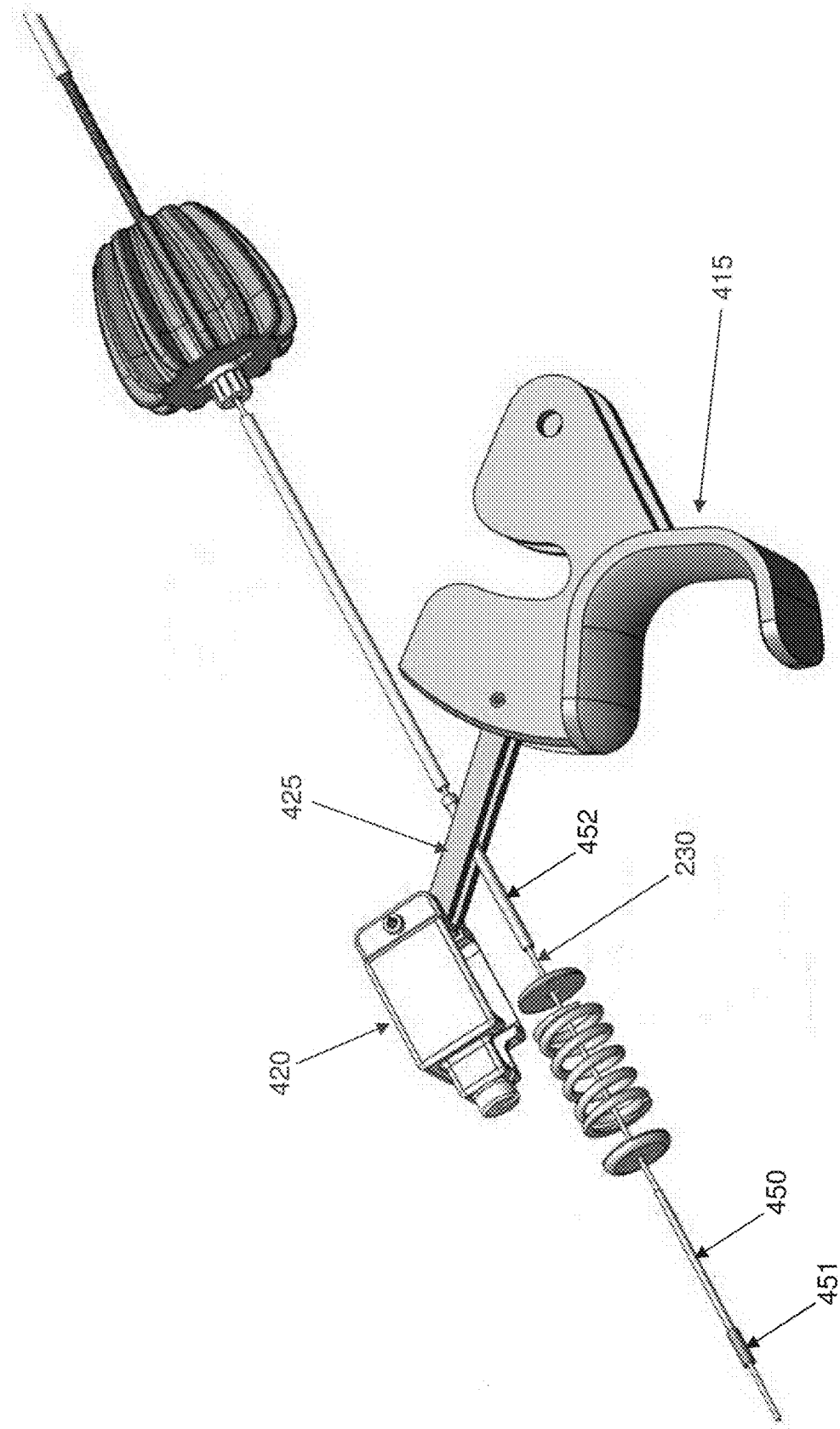
Figure 45:
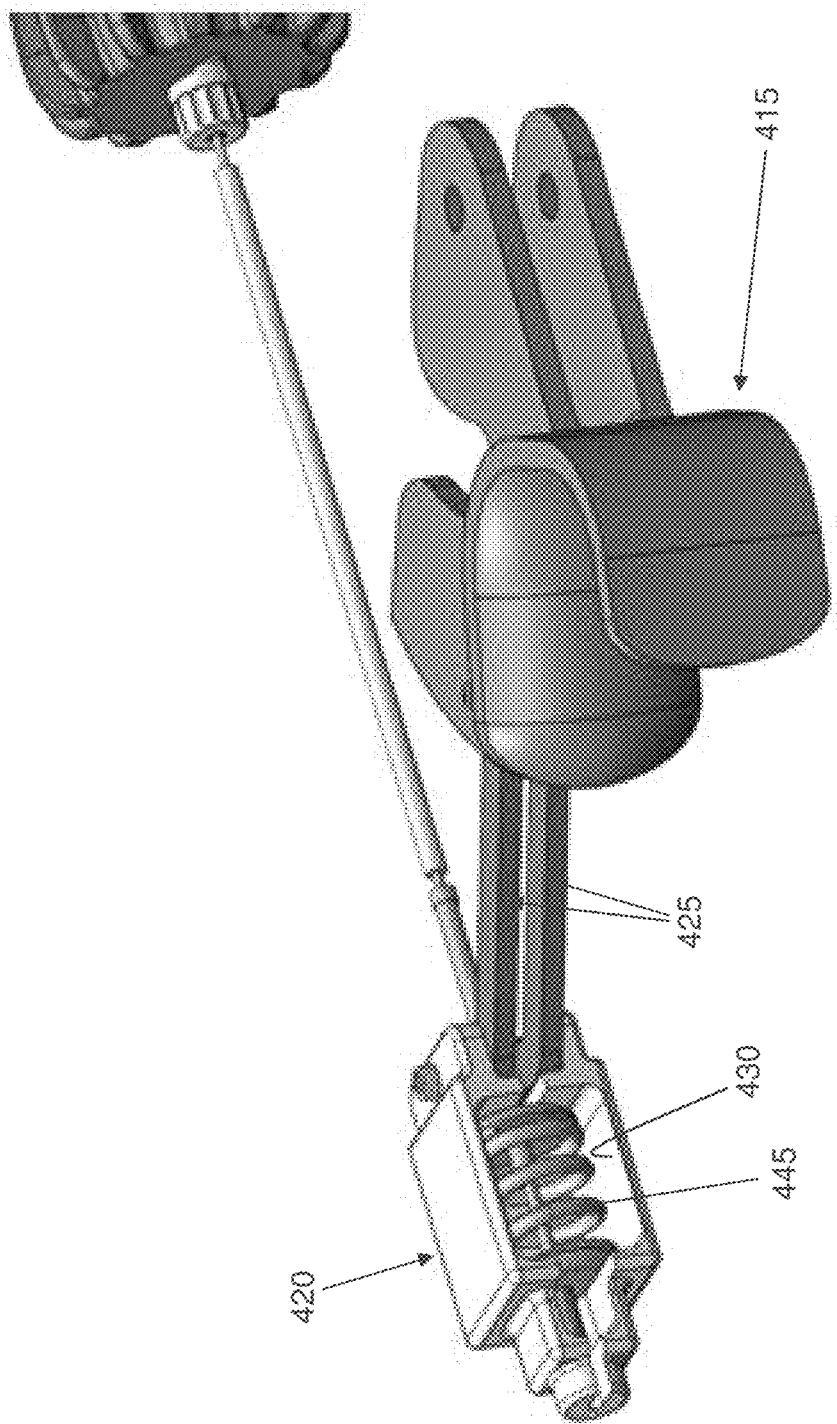
Figure 46:
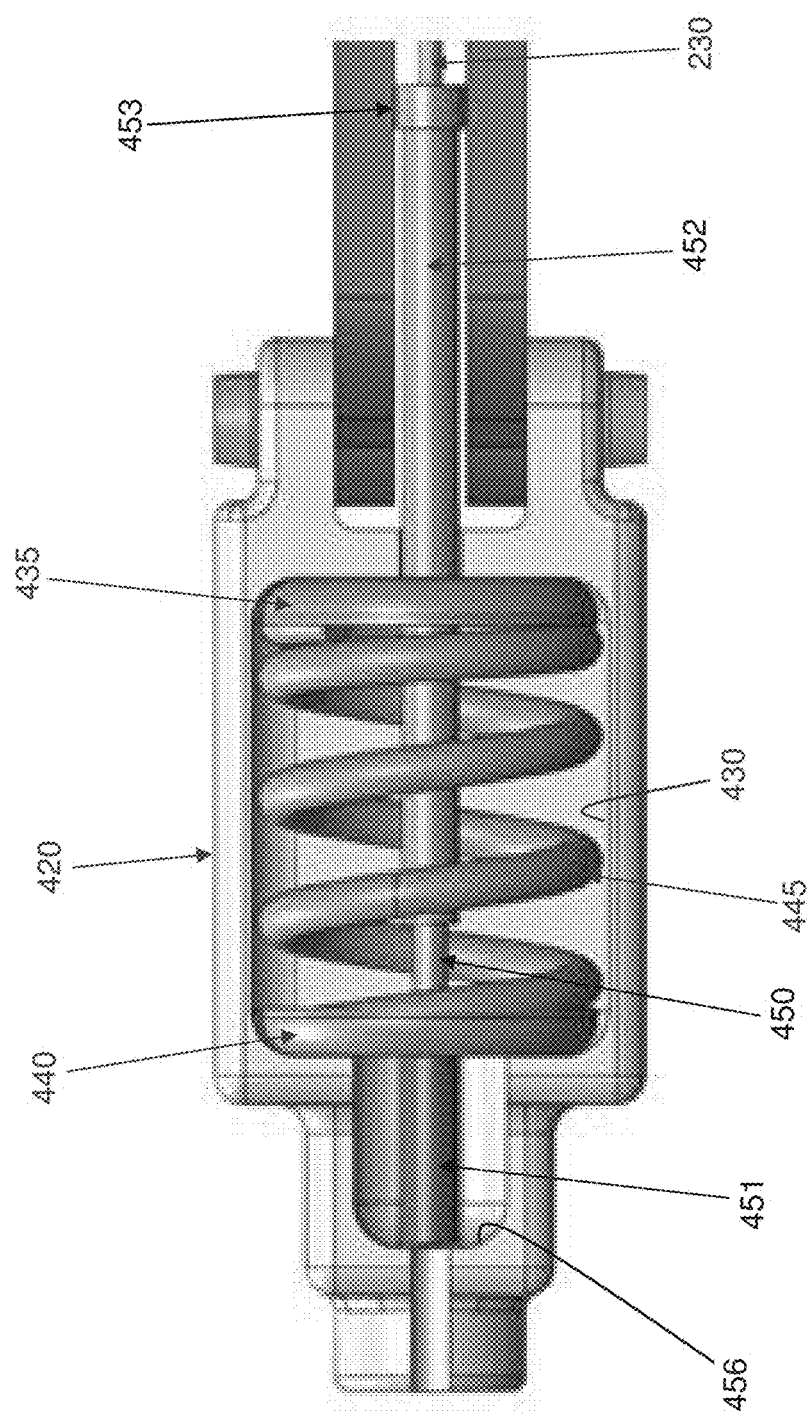
Figure 46A:
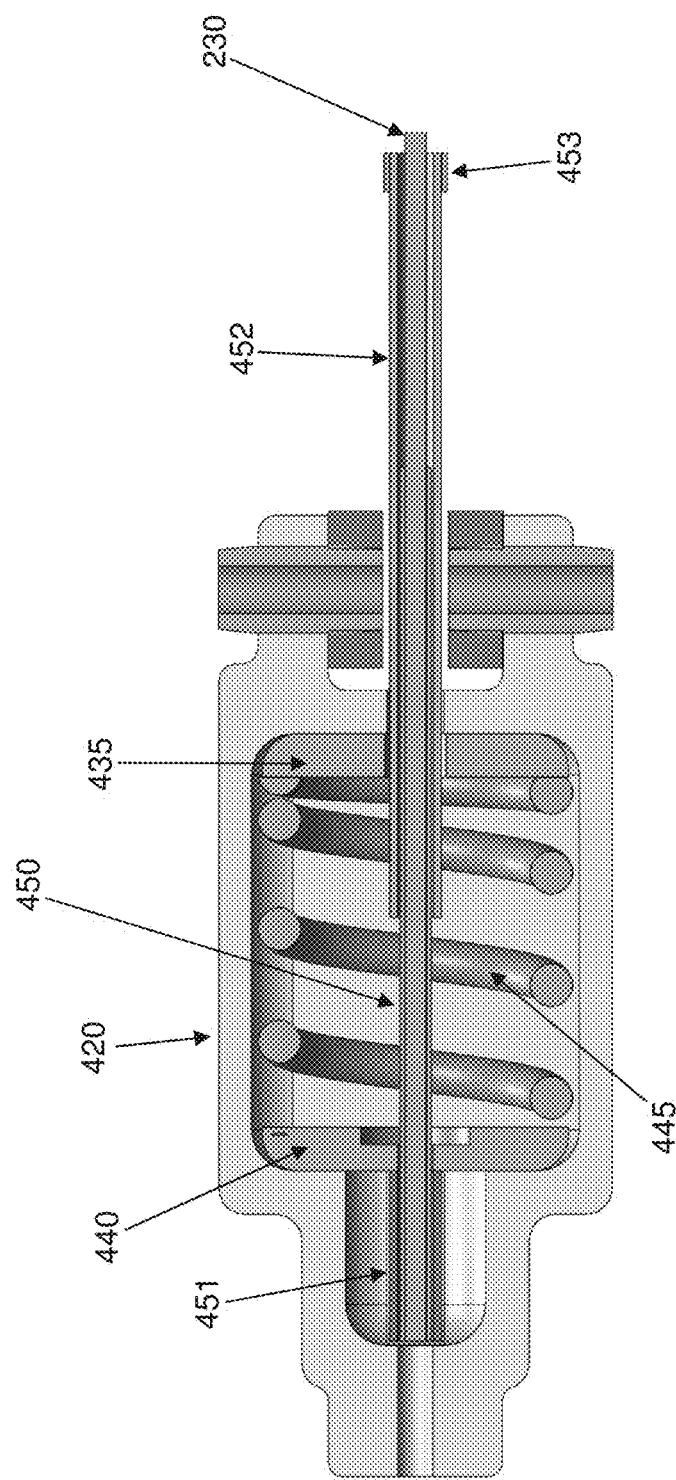
Figure 46B:
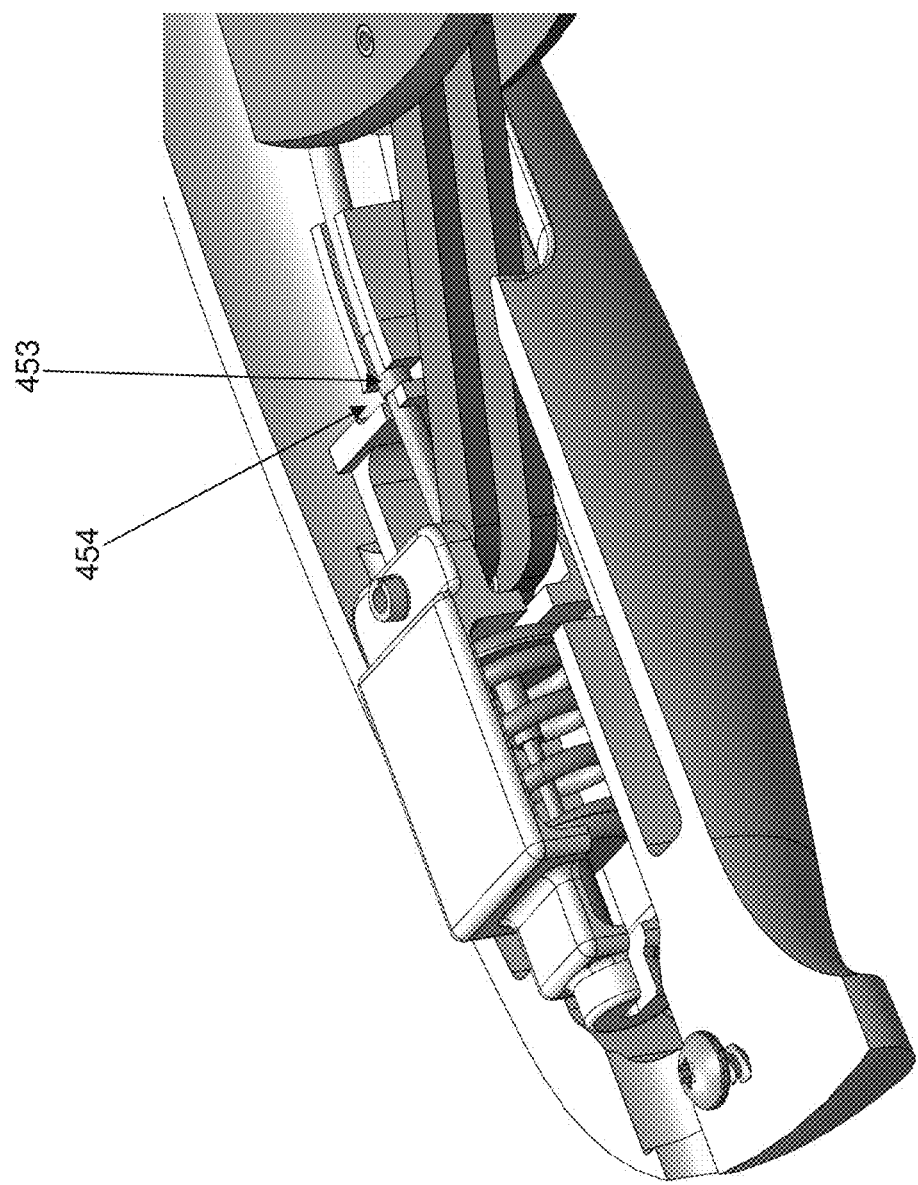

Proximal end 407 of roticulation key 405 extends out of roticulation knob 395 (FIG. 39). In one preferred form of the present invention, proximal end 407 (FIG. 38) of roticulation key 405 comprises a plurality of teeth 409 for releasably engaging a ball nose spring plunger 410 (FIG. 41). Ball nose spring plunger 410 is mounted within cavity 280 of handle 10 such that ball nose spring plunger 410 releasably engages teeth 409 disposed on proximal end 407 of roticulation key 405. By virtue of the engagement between ball nose spring plunger 410 and roticulation key 405, roticulation key 405 (and hence HHS coil 225 which is mounted to roticulation key 405) are prevented from "spontaneously" rotating absent deliberate rotation of roticulation knob 395. Thus, ball nose spring plunger 410 prevents accumulated spring tension (e.g., spring tension which can build up when rotating HHS coil 225 using roticulation knob 395) from "unraveling" HHS coil 225 and thereby causing unintentional rotation of HHS coil 225 (and hence unintentional rotation of end effector 30).

3.3 Trigger Assembly 300

Looking next at FIGS. 42-46, 46A, 46B and 47, trigger assembly 300 generally comprises a trigger 415 pivotally mounted to handle 10, a sled 420 (FIG. 43) movably disposed within cavity 280 of handle 10, and one or more lever arms 425 which connect trigger 415 to sled 420 such that when trigger 415 is actuated (i.e., pulled), sled 420 moves proximally within cavity 280 of handle 10, whereby to move pull wire 230 proximally, whereby to actuate end effector 30, as will hereinafter be discussed in further detail.

More particularly, sled 420 comprises a cavity 430 (FIG. 45), a distal bushing 435 (FIG. 46) disposed within cavity 430, a proximal bushing 440 disposed within cavity 430, and a spring 445 disposed between distal bushing 435 and proximal bushing 440. An inner support tube 450 is secured to pull wire 230 (e.g., by a crimp sleeve 451 disposed at the proximal end of inner support tube 450). An outer support tube 452 is disposed over the distal portion of inner support tube 450, with inner support tube 450 able to slide freely within outer support tube 452. Outer support tube 452 also comprises an outer support tube collar 453 which is sized to be mounted within a seat 454 (FIG. 46B) formed in internal cavity 280 of handle 10. A spring 455 (FIG. 42) is disposed in the proximal end of handle 10 so as to bias sled 420 distally.

As a result of this construction, when sled 420 is moved proximally (i.e., by pulling trigger 415) against the power of spring 455 (FIG. 42), distal bushing 435 (FIG. 46) moves proximally, bearing against spring 445 which, in turn, bears against proximal bushing 440, which bears against crimp sleeve 451 and pulls pull wire 230 proximally. Thus, as sled 420 moves proximally, proximal bushing 440 and crimp sleeve 451 also move proximally, whereby to move pull wire 230 proximally and thereby actuate end effector 30. It should be appreciated, however, that inasmuch as sled 420 is not mounted directly to pull wire 230, proximal bushing 440 and spring 445 act as a force limiter, with spring 445 yielding when the force on pull wire 230 exceeds a given level, whereby to cease applying a proximal force to pull wire 230. Put another way, if the force applied to move sled 420 proximally exceeds the force biasing proximal bushing 440 away from distal bushing 435 (i.e., the biasing force provided by spring 445), spring 445 will compress, thereby allowing proximal bushing 440 and crimp sleeve 451 (and hence inner support tube 450 and pull wire 230) to remain stationary as sled 420 moves proximally. In this way trigger 415 can be pulled through a "full stroke" without the danger of breaking pull wire 230.

It should also be appreciated that since spring 455 biases sled 420 distally, and since crimp sleeve 451 is engaged by a shoulder 456 when sled 420 moves proximally, sled 420 will return to its distal position within handle 10 and pull wire 230 will be moved distally.

4 Exemplary Method of Use

In an exemplary use of novel medical instrument 5 in a minimally-invasive procedure, the profile of end effector 30 is reduced (e.g., where end effector 30 comprises a grasper, the jaws of the grasper are closed); shaft 15 is straightened; handle 10 is longitudinally advanced so as to longitudinally advance the distal end of medical instrument 5 through a portal and into the body (e.g., along a tortuous path); handle 10 is longitudinally advanced and/or rotated, and/or distal articulating portion 25 of shaft 15 is bent and/or end effector 30 is roticulated, so that end effector 30 appropriately addresses the target tissue at the internal site; end effector 30 is used to perform the desired procedure (e.g., where end effector 30 comprises a surgical grasper the jaws of the grasper are opened and closed to grasp tissue) at the internal site; and the distal end of medical instrument 5 is withdrawn from the body, e.g., handle 10 is longitudinally withdrawn through the portal (during which the handle may also be rotated, and/or distal articulating portion 25 of shaft 15 is unbent and/or the end effector roticulated as necessary), so that the end effector is withdrawn from the body.

It will be appreciated that novel medical instrument 5 is capable of at least the following motions:

Motion 1—longitudinal movement of end effector 30 by longitudinal movement of handle 10 (sometimes referred to herein as a "longitudinal motion function");

Motion 2—rotational movement of end effector 30 by rotational movement of handle 10 (sometimes referred to herein as a "torqueing motion function");

Motion 3—articulating movement of end effector 30 relative to handle 10 by articulating distal articulating portion 25 of shaft 15 relative to the distal end of flexible proximal portion 20 of shaft 15 (sometimes referred to herein as a "universal articulation function");

Motion 4—rotational movement of end effector 30 relative to the distal end of distal articulating portion 25 of shaft 15 by rotating end effector 30 relative to shaft 15 (sometimes referred to herein as a "roticulation function"); and Motion 5—actuation of end effector 30, e.g., selectively moving elements of end effector 30 relative to one another so as to carry out a medical procedure, e.g., opening and closing the jaws of a grasper-type end effector (sometimes referred to herein as a "jaw open/close function").

It will be appreciated by those skilled in the art that, if desired, the medical instrument may be modified so as to provide less (or more) than the five aforementioned motions, e.g., the roticulation function may be eliminated, an additional rotational function such as selective rotation of shaft 15 may be added, etc.

5 Novel Tool Support

Figure 48:
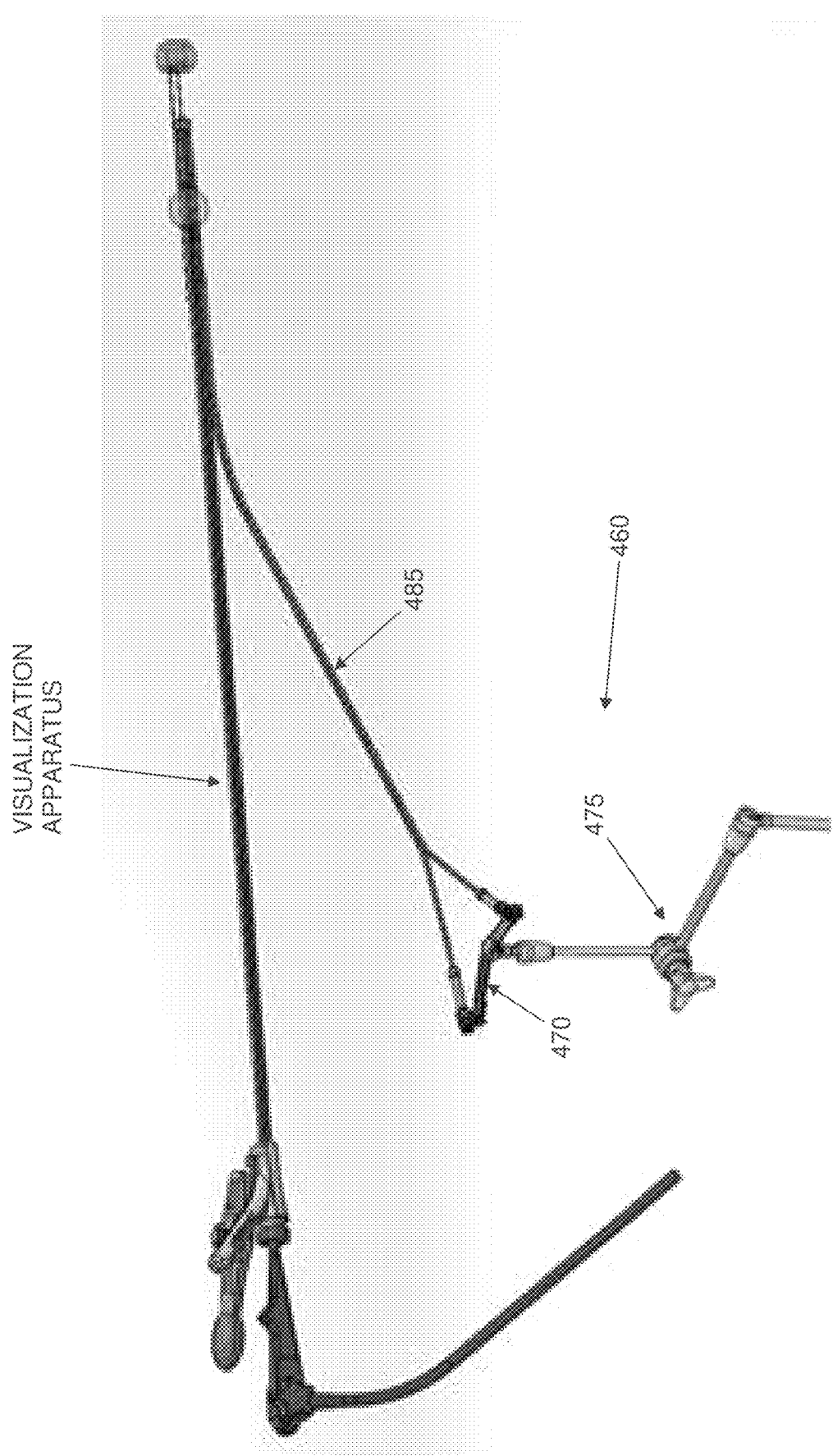
Figure 49:
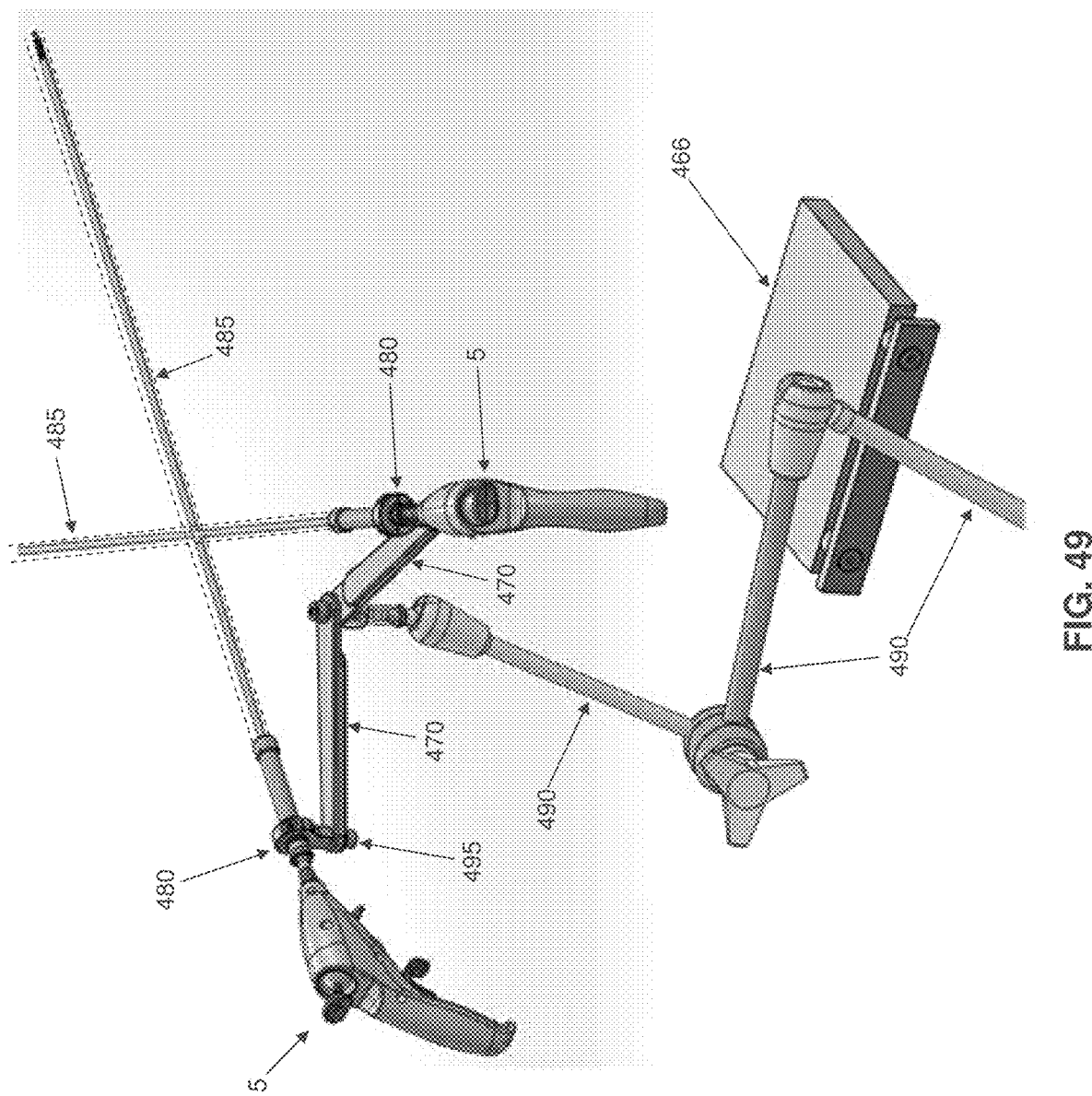

Looking next at FIGS. 47-49, there is shown a novel tool support 460 which may be used to support medical instrument 5. Tool support 460 generally comprises a clamp 465 for mounting tool support 460 to a surgical table 466, an adjustable base 470 for mounting one or more medical instrument(s) 5 to tool support 460, and an adjustable arm 475 (FIG. 48) for adjustably mounting base 470 to clamp 465. One or more instrument adapters 480 (FIG. 49) are mounted to base 470, whereby to permit mounting of one or more medical instrument(s) 5 to tool support 460 (i.e., by providing a support for handle 10 and/or rigid tube 60 at the proximal end of shaft 15), as will hereinafter be discussed in further detail.

One or more tool channels 485, configured for passing shaft 15 into a patient (or into the working lumen of another medical instrument), are mounted to the one or more instrument adapters 480, as will hereinafter be discussed in further detail.

More particularly, and still looking at FIGS. 47-50, clamp 465 is configured to be mounted to a stable object (e.g., to surgical table 466) in order to permit a surgeon to manipulate tool support 460 (and hence the one or more medical instruments 5 mounted thereto) relative to the patient and/or relative to other surgical instruments, as will hereinafter be discussed.

Adjustable arm 475 preferably comprises one or more segments 490 (FIG. 49) which are adjustably mounted to one another, and to clamp 465 and to base 470, whereby to permit the surgeon to precisely adjust the disposition of base 470 relative to the patient (and/or relative to another surgical instrument).

Figure 50:
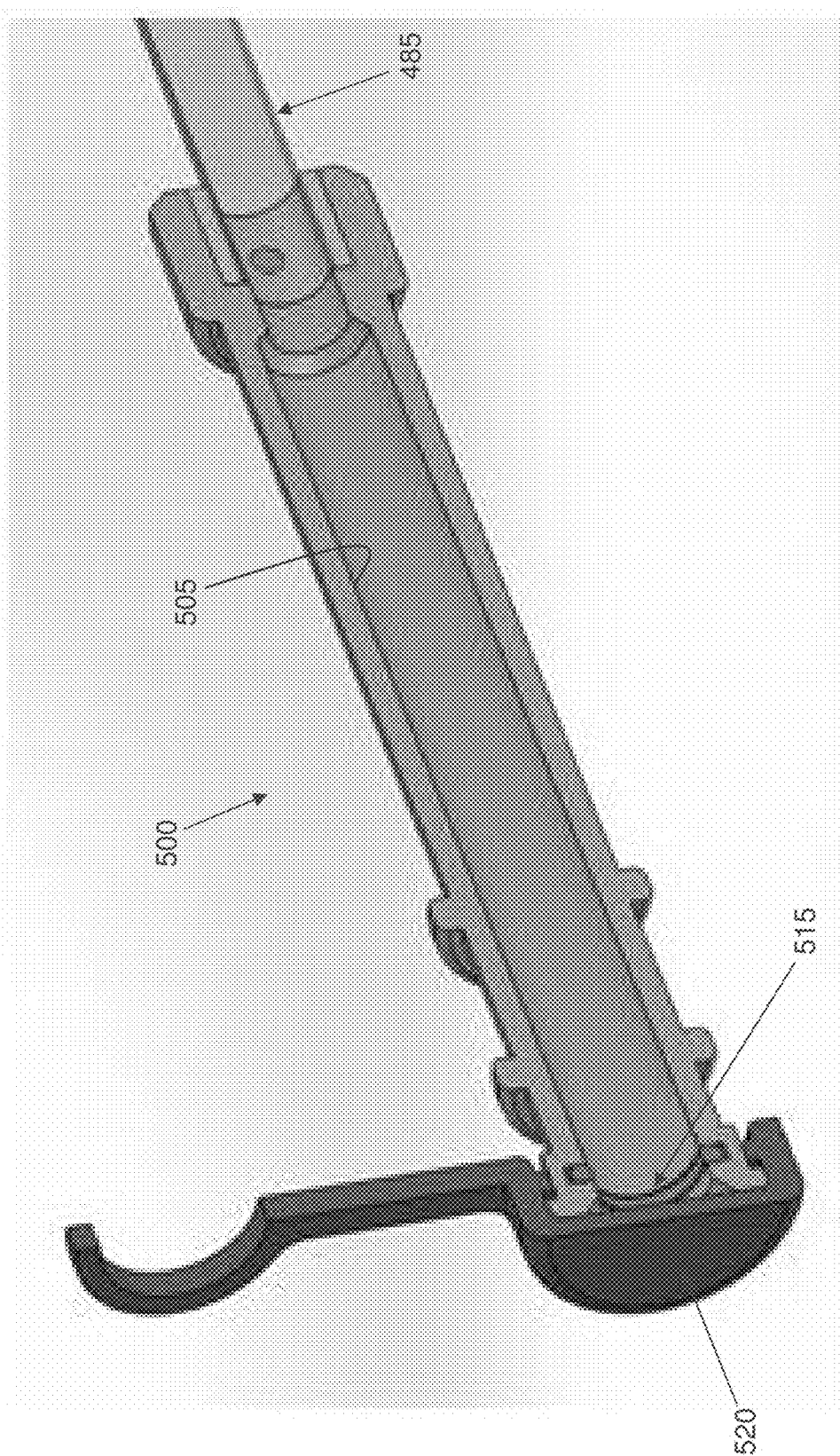
Figure 51:
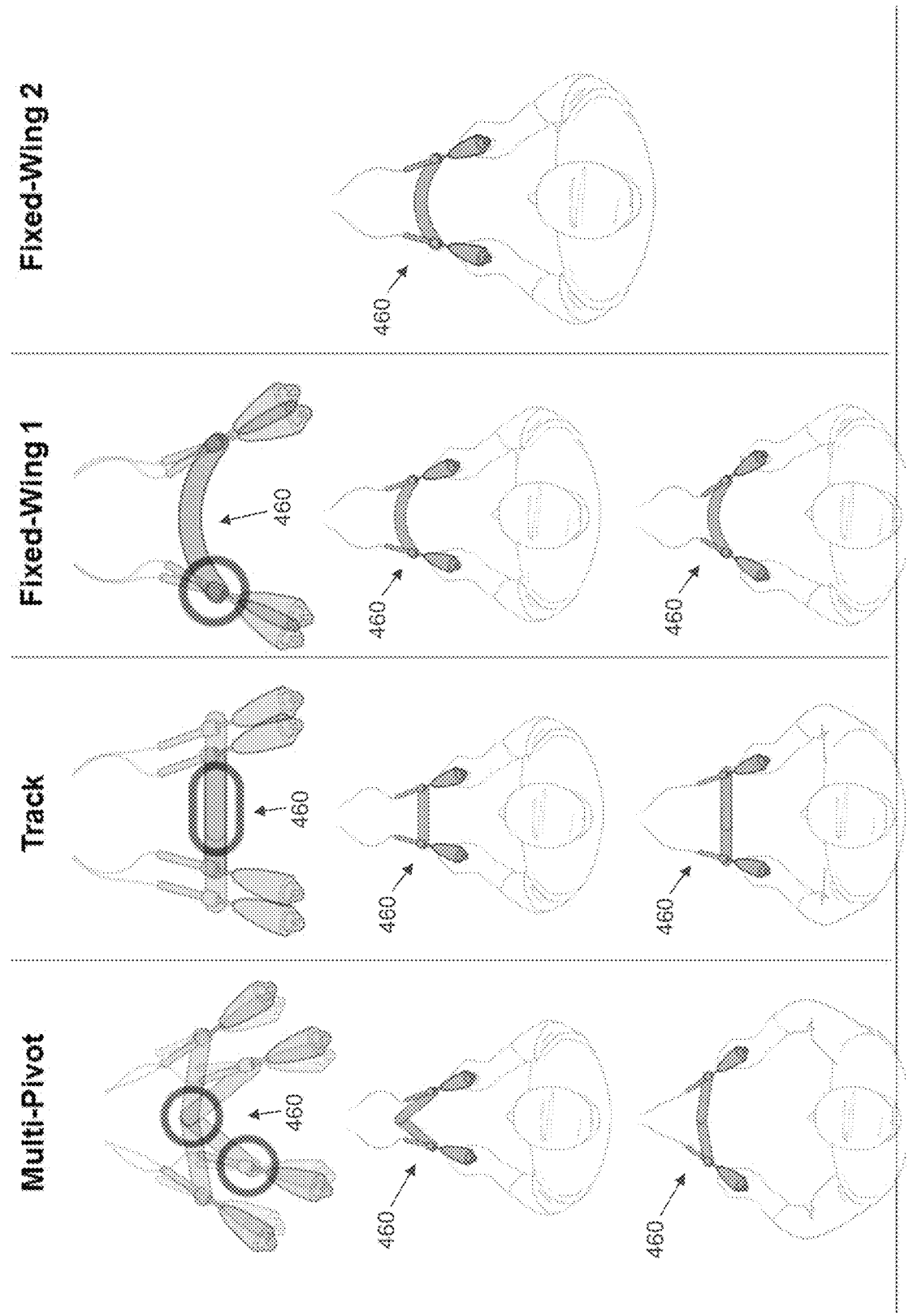
Figure 52:
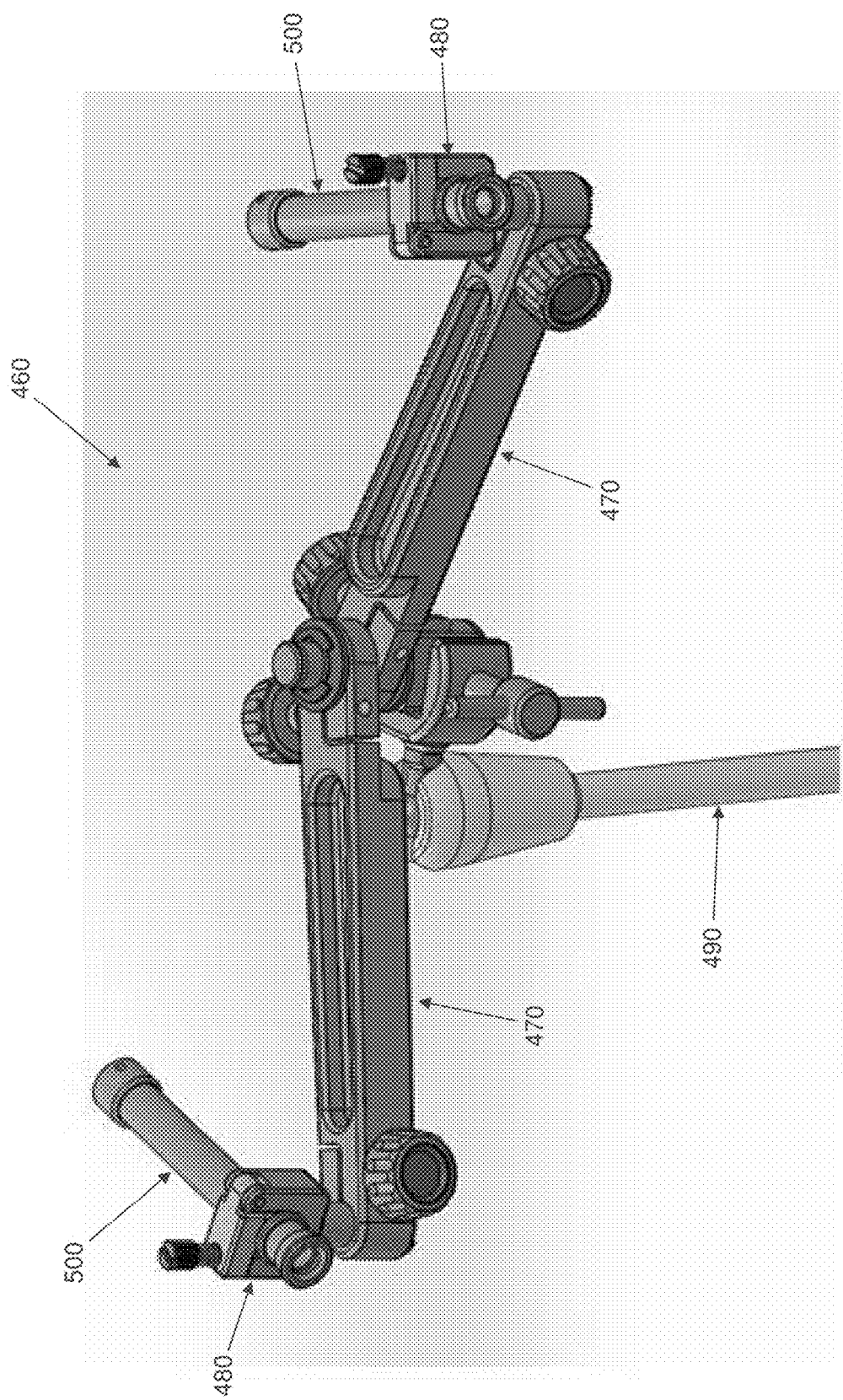
Figure 53:
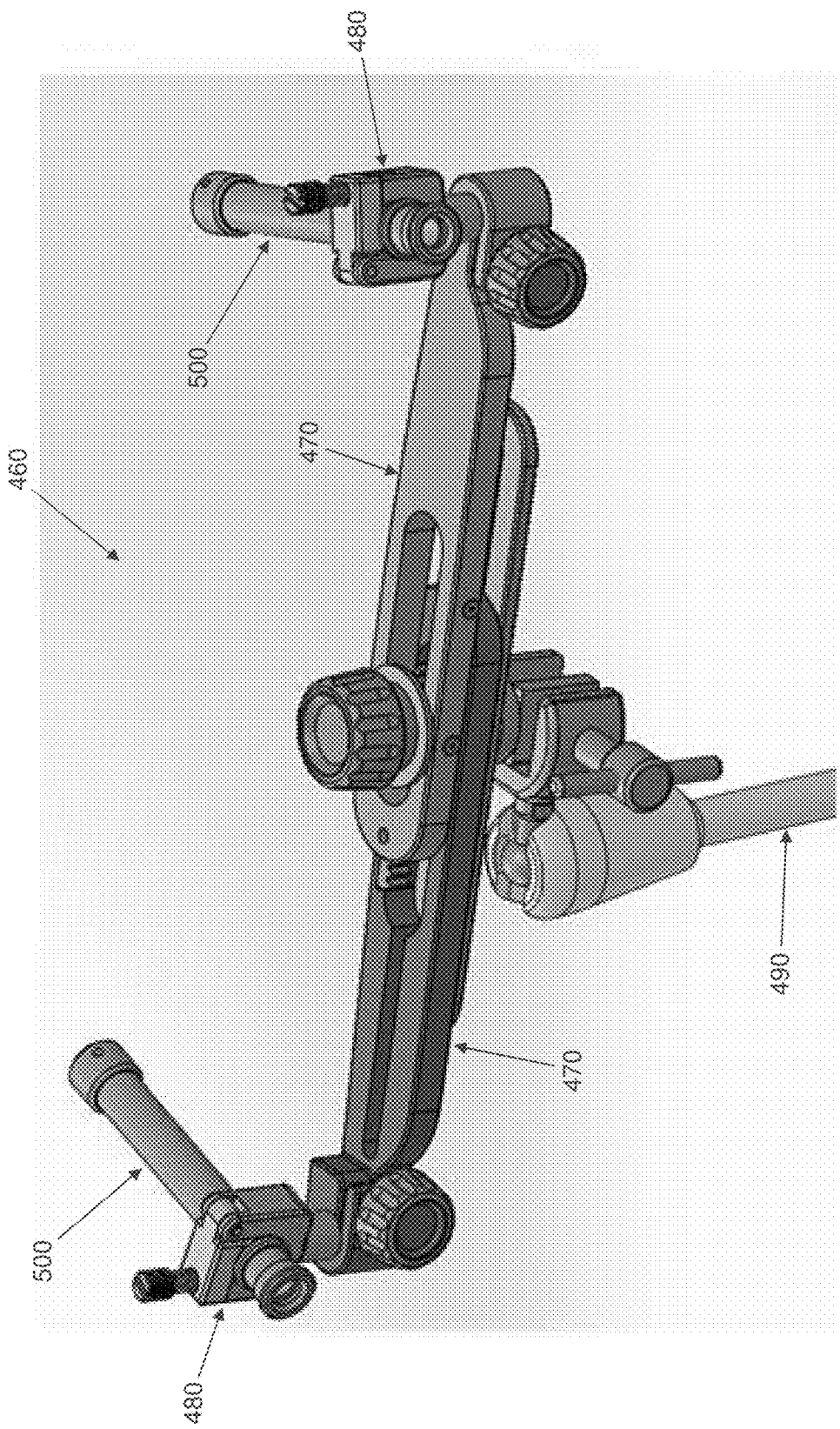
Figure 54:
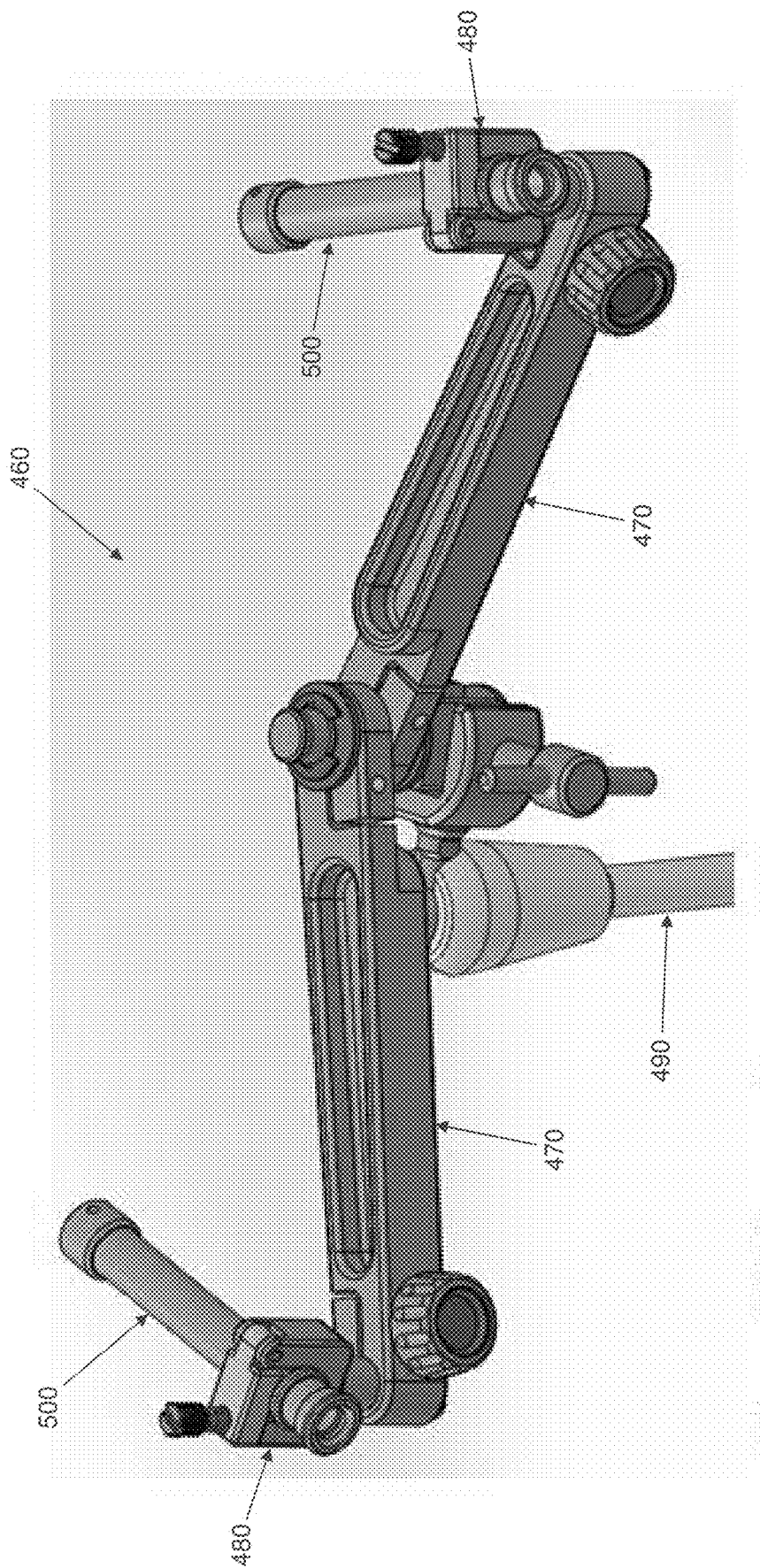
Figure 58A:
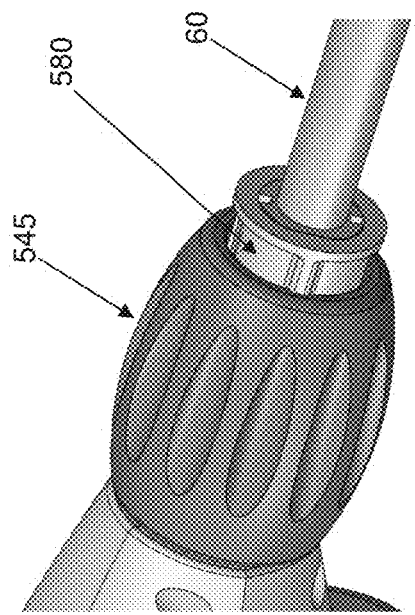
Figure 58B:
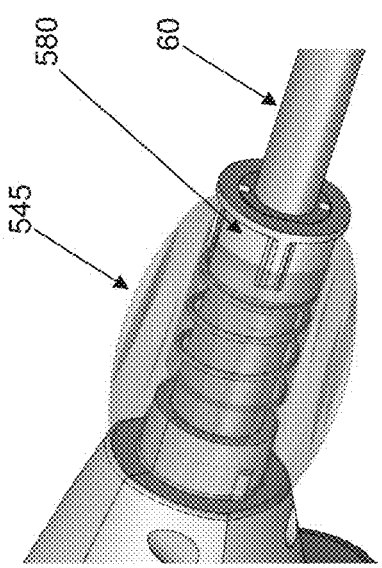
Figure 58C:
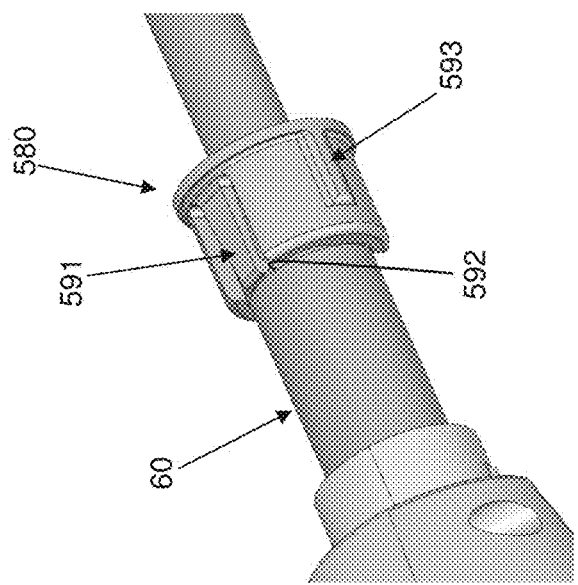
Figure 58D:
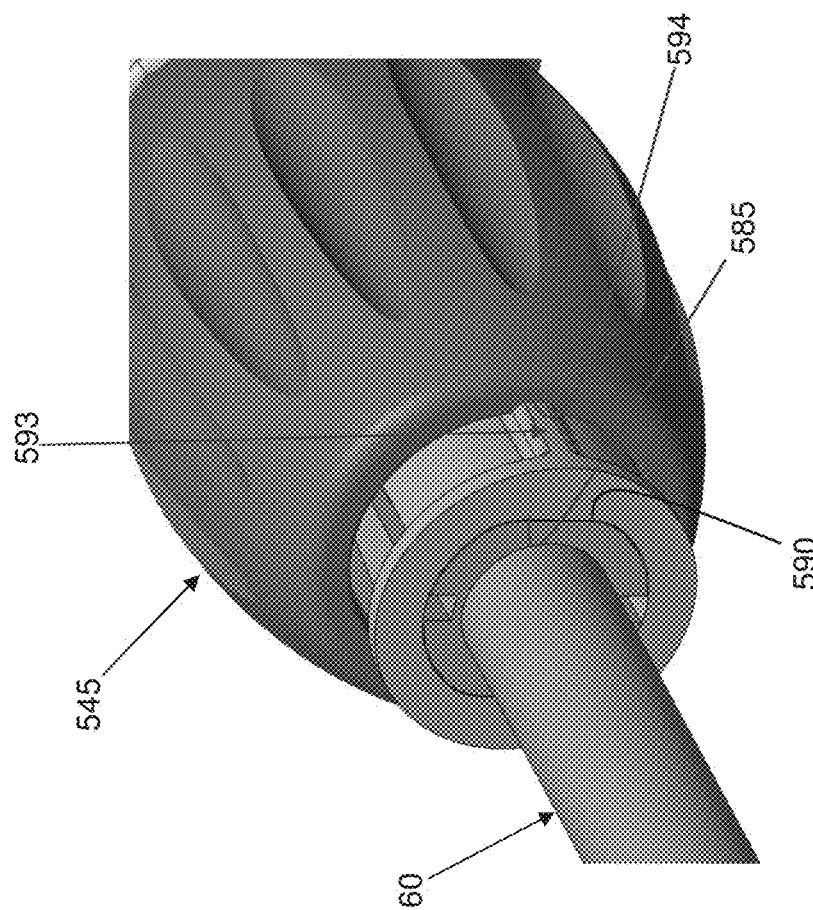

Looking now at FIGS. 49 and 50, instrument adapters 480 each comprise a mount 495 and a tube 500. Mount 495 is pivotally mounted to base 470 (FIG. 49). Tube 500 has a lumen 505 sized to receive the proximal end of shaft 15 of medical instrument 5 (i.e., rigid tube 60 located at the proximal end of shaft 15). If desired, lumen 505 may comprise a septum 515 for fluidically sealing tube 500 (and hence fluidically sealing tool chamber 485), and/or tube 500 may comprise an end cap 520 for fluidically sealing tube 500 (and hence, for fluidically sealing tool chamber 485).

Looking now at FIGS. 51-55, there are shown some exemplary configurations for tool support 460. It should be appreciated that base 470 of tool support 460 may comprise a plurality of pivots and/or arms, may be shaped in the form of an arc, and/or may comprise other geometries, etc., in order to accommodate the needs and/or preferences of the surgeon.

6 Medical Instrument 5 with Rotatable Shaft 15

As discussed above, novel medical instrument 5 comprises a shaft 15 having a flexible proximal portion 20, a distal articulating portion 25 which can be selectively articulated relative to the distal end of flexible proximal portion 20, and an end effector 30 which can be selectively rotated relative to the distal end of distal articulating portion 25. With this construction, longitudinal movement of handle 10 can be used to move shaft 15 distally and proximally, whereby to move end effector 30 distally and proximally; rotational movement of handle 10 can be used to rotate shaft 15, whereby to rotate end effector 30; articulation control assembly 285 (FIG. 25) can be used to articulate distal articulating portion 25 of shaft 15, whereby to redirect end effector 30; roticulation control assembly 295 (FIG. 25) can be used to rotate end effector 30; and trigger assembly 300 (FIG. 25) can be used to actuate end effector 30. With the foregoing construction, flexible proximal portion 20 rotates as a unit with handle 10.

However, it has been recognized that it may be desirable to be able to rotate flexible proximal portion 20 of shaft 15 independently of handle 10. To this end, and looking now at FIGS. 56-58, a novel rotatable shaft adapter mechanism 525 may be provided between shaft 15 and handle 10, whereby to allow shaft 15 (i.e., both flexible proximal portion 20 and distal articulating portion 25) to be selectively rotated relative to handle 10.

More particularly, rotatable shaft adapter mechanism 525 is mounted to the proximal end of shaft 15 (i.e., mounted to the proximal end of flexible proximal portion 20) and connects shaft 15 to handle 10. It should be appreciated that, in this form of the invention, rotatable shaft adapter mechanism 525 replaces the aforementioned shaft adapter 55 (where the aforementioned shaft adapter 55 was fixedly secured to handle 10 and fixedly secured to the proximal end of outer coil 35, and where rigid tube 60 was fixedly secured to shaft adapter 55). More particularly, in this form of the invention, shaft 15 is rotatably mounted to the distal end of handle 10 and selectively locked/unlocked from rotation via rotatable shaft adapter mechanism 525, as will hereinafter be discussed in further detail.

Still looking now at FIGS. 56-58, in this form of the invention, rigid tube 60 of shaft 15 comprises a flange 530 disposed around the proximalmost end of rigid tube 60. Flange 530 is received within a corresponding groove 535 formed in the distal end of handle 10 (i.e., formed within cavity 280 of handle 10 near the distalmost end of handle 10), whereby to rotatably mount rigid tube 60 of shaft 15 to handle 10. In this form of the invention, the proximal end of outer coil 35 is fixedly secured to rigid tube 60 (and the distal end of outer coil 35 is secured to body 85 of proximal articulation link assembly 75). The outer circumference of the distalmost end of handle 10 comprises a plurality of keyways 540 (FIG. 57) which are sized to receive a plurality of projections 542 formed on rotatable shaft adapter mechanism 525, as will hereinafter be discussed in further detail. Note that, if desired, the locations of keyways 540 and projections 542 may be reversed from the foregoing, i.e., keyways 540 may be formed on rotatable shaft adapter mechanism 525 and projections 542 may be formed on the distalmost end of handle 10.

Rotatable shaft adapter mechanism 525 generally comprises a shaft rotation knob 545 having a lumen 550 extending therethrough. Lumen 550 comprises a distal end 555, a proximal end 560 and an annular shoulder 565 disposed therebetween. A spring 570 is disposed within distal end 555 of lumen 550, extending between annular shoulder 565 and the proximal end 575 of a retaining cap 580 (FIGS. 58, 58A, 58B, 58C and 58D) which is mounted circumferentially about the outer perimeter of shaft 15, whereby to bias shaft rotation knob 545 proximally, so that projections 542 of shaft adapter mechanism 525 are received within keyways 540 of handle 10, whereby to lock shaft rotation knob 545 against rotation. More particularly, retaining cap 580 comprises a pair of flats 585 which key to corresponding flats 590 formed on the outer surface of rigid tube 60 of shaft 15. One or more spring fingers 591 engage a groove 592 on the outer surface of rigid tube 60, whereby to lock retaining cap 580 to rigid tube 60. Retaining cap 580 also comprises a plurality of key features 593 sized to be received in corresponding keyways 594 of shaft rotation knob 545. As a result of this construction, rotation knob 545 is able to slide longitudinally (distally or proximally) relative to rigid tube 60 of shaft 15, however, rotation knob 545 is locked against rotation relative to rigid tube 60 (and hence, relative to shaft 15). Therefore, rotation knob 545 can be moved longitudinally without causing longitudinal motion of rigid tube 60 and shaft 15, but rotation of rotation knob 545 will be transferred to rigid tube 60 (and to shaft 15 as will hereinafter be discussed).

Shaft rotation knob 545 is connected to rigid tube 60 of shaft 15 (e.g., via projections, a friction fit, etc.) so that shaft rotation knob 545 is longitudinally movable relative to rigid tube 60 but rotationally fixed to rigid tube 60.

In this form of the invention, the proximal end of protective sleeve or outer covering (e.g., Pebax®) 270 is secured (e.g., bonded) to rigid tube 60 and the distal end of protective sleeve or outer covering 270 is secured (e.g., bonded) to body 85 of proximal articulation link assembly 75. Significantly, protective sleeve or outer covering 270 is capable of transmitting torque between rigid tube 60 and body 85 of proximal articulation link assembly 75.

As a result of this construction, spring 570 normally biases shaft rotation knob 545 proximally, whereby to cause projections 542 to engage keyways 540 and lock shaft 15 against rotation relative to handle 10. However, when shaft rotation knob 545 is moved distally, against the power of spring 570, projections 542 disengage from keyways 540, thereby allowing shaft rotation knob 545 to be selectively rotated relative to handle 10, whereby to selectively rotate rigid tube 60 relative to handle 10, whereby to selectively rotate protective sleeve or outer covering 270 relative to handle 10, whereby to selectively rotate body 85 of proximal articulation link assembly 75, whereby to selectively rotate distal articulating portion 25 of shaft 15 relative to handle 10. When shaft 15 has been rotated to the desired position relative to handle 10, shaft rotation knob 545 is released and shaft rotation knob 545 moves proximally under the power of spring 570 such that projections 542 re-engage keyways 540, thereby locking shaft 15 against further rotation relative to handle 10.

Thus it will be seen that in this form of the invention, rigid tube 60 is rotatable relative to handle 10 but longitudinally fixed relative to handle 10; shaft rotation knob 545 is connected to rigid tube 60 such that shaft rotation knob 545 can be moved longitudinally relative to rigid tube 60 but not rotationally relative to rigid tube 60, such that shaft rotation knob 545 can be selectively locked to, or unlocked from, handle 10 so as to permit shaft rotation knob 545 to selectively rotate rigid tube 60; and protective sleeve or outer covering 270 transmits torque between rigid tube 60 and body 85 of proximal articulation link assembly 75, such that rotation of rigid tube 60 causes rotation of body 85 of proximal articulation link assembly 75, whereby to rotate distal articulating portion 25 of shaft 15 relative to handle 10.

It will be appreciated that unlimited rotation of rigid tube 60 and shaft 15 will cause articulation cables 220 and articulation cable housings 235 to wind on themselves; therefore, in one preferred form of the present invention, means are provided for limiting rotation of rigid tube 60 and shaft 15. More particularly, in one preferred form of the invention, and looking now at FIGS. 58E and 58F, rigid tube 60 of shaft 15 preferably comprises a groove 595 extending partially circumferentially about the outer surface of shaft 15. Groove 595 is disposed just distal to the proximal end of shaft 15 and extends partially, but not entirely, around the circumference of shaft 15. A corresponding boss 596 is formed on the distal end of handle 10 and received within groove 595. As a result of this construction, shaft 15 can be rotated only until boss 596 reaches one end of groove 595. In a preferred form of the present invention, groove 580 is sized so that shaft 15 can be rotated up to 350 degrees.

7 Additional Constructions

In the foregoing disclosure, there is described a novel medical instrument 5 comprising a handle, an elongated flexible shaft and an end effector disposed at the distal end of the shaft configured for performing a medical procedure. It should be appreciated that medical instrument 5 may be modified in a variety of ways in order to support different types of end effectors, to facilitate single-handed use of medical instrument 5, to enhance the functionality of medical instrument 5, etc.

7.1 Alternative End Effector

As discussed above, in a preferred form of the present invention, end effector 30 comprises a surgical grasper having two opposed jaws 216, 217 (FIG. 8).

In another preferred form of the present invention, and looking now at FIGS. 59-62, end effector 30 comprises scissors 600 having opposing blades 605, 610. Blades 605, 610 comprise sharp edges that contact one another in order to facilitate cutting (e.g., of tissue, suture, etc.) when blades 605, 610 are brought together (i.e., closed). In order to ensure clean cutting by blades 605, 610, it is desirable to maintain blades 605, 610 in tight contact with one another as blades 605, 610 are brought together (i.e., closed). To this end, a beveled washer 615 (FIGS. 61 and 62) is disposed between one of the blades 605, 610 and the inner wall of end effector mount 210. Beveled washer 615 is preferably disposed over the pin 217A which pivotally mounts blades 605, 610 to end effector mount 210. By mounting beveled washer 615 in this manner, blades 605, 610 are kept in tight engagement as they are brought together (i.e., closed), whereby to facilitate clean cutting (e.g., of tissue, of suture, etc.).

7.2 Finger Slide for Single-Handed Shaft Rotation

As discussed above, in one form of the present invention, shaft 15 is rotatably mounted to the distal end of handle 10 and can be selectively rotated using rotatable shaft adapter mechanism 525 (FIGS. 56-58 and 58A-58F). With this form of the invention, the proximal end of shaft 15 is rotationally mounted to the distal end of handle 10 (e.g., by means of the aforementioned flange 530 (FIG. 58) on rigid tube 60 being rotationally received within the aforementioned corresponding groove 535 formed in the distal end of handle 10), and rotatable shaft adapter mechanism 525 is moved distally (i.e., pushed distally by the user against the power of spring 570) in order to "unlock" shaft 15 (i.e., to allow shaft rotation knob 545, and hence shaft 15, to rotate). A user can then rotate shaft 15 as desired (i.e., by rotating rotatable shaft adapter mechanism 525, and hence rotating shaft 15). After the user has rotated shaft 15 as desired, shaft adapter mechanism 525 is released and automatically moves proximally (i.e., under the power of spring 570) so as to "lock" shaft 15 against further rotation. This action typically requires that the user use one hand to push rotatable shaft adapter mechanism 525 distally (and thereafter rotate shaft 15) while the user uses their other hand to keep handle 10 stationary.

However, it should be appreciated that it may also be desirable for a user to rotate shaft 15 using a single hand. To this end, in another form of the present invention, shaft 15 is kept stationary (e.g., via friction between the outer surface of shaft 15 and the interior of a tool channel (e.g., tool channel 485 (FIG. 48), the lumen of a tool channel provided in another medical instrument such as an endoscope, etc.), handle 10 is selectively rotationally de-coupled from shaft 15, and handle 10 is selectively rotated by a user to a desired rotational position using a single hand. Handle 10 is then rotationally re-coupled to shaft 15 and then rotated by the user (whereby to also rotate shaft 15).

More particularly, with this form of the invention, and looking now at FIGS. 63-66, a shaft rotation finger slide assembly 625 is provided in order to enable single-handed rotation of shaft 15, as will hereinafter be discussed in further detail. Shaft rotation finger slide assembly 625 generally comprises a finger slide mechanism 630 which is slidably disposed within handle 10, and a shaft collar 635 which is fixedly mounted to the proximal end of shaft 15 (e.g., fixedly mounted to rigid tube 60).

Finger slide mechanism 630 comprises a saddle 640 having a pair of projections 645 extending through corresponding slots (not shown) formed in the side wall of handle 10. A pair of finger slides 647 are secured to projections 645. A post 650 extends distally from saddle 640 and is configured to selectively lock shaft collar 635 against rotation, as will hereinafter be discussed in further detail. A spring 655 biases saddle 640 (and hence post 650) distally, such that post 650 engages shaft collar 635 when finger slide mechanism 630 is in its resting state, as will hereinafter be discussed in further detail.

Shaft collar 635 is fixedly mounted to the proximal end of shaft 15 (e.g., to rigid tube 60). Shaft collar 635 comprises a distal end 660, a proximal end 665 and a lumen 670 extending therebetween. A plurality of teeth 675 are disposed about the inside perimeter of lumen 670 at proximal end 665 of shaft collar 635, with teeth 675 being spaced such that post 650 of finger slide mechanism 630 can be received within the gap between a pair of adjacent teeth 675, whereby to lock shaft collar 635 (and hence shaft 15) against rotation, as will hereinafter be discussed in further detail.

When a user desires to rotate shaft 15, the user moves finger slides 647 proximally, whereby to move projections 645 proximally, whereby to move saddle 640 proximally against the power of spring 655. As this occurs, post 650 is also moved proximally, whereby to disengage post 650 from teeth 675 of shaft collar 635 (and thereby rotationally de-couple handle 10 from shaft 15). While holding projections 645 proximally, the user can then rotate handle 10 as desired relative to shaft 15. Shaft 15 does not rotate as handle 10 is rotated (i.e., shaft 15 is maintained stationary by virtue of friction between the outer surface of shaft 15 and the interior of the lumen that shaft 15 is disposed in, e.g., tool channel 485). After the user has rotated handle 10 to the desired degree, the user releases finger slides 647, which allows projections 645 and saddle 640 (and hence post 650) to move distally under the power of spring 655, with post 650 moving distally into a space between a pair of teeth 675 of shaft collar 635, whereby to rotationally re-couple handle 10 to shaft collar 635 (and hence shaft 15). At this point, the user can rotate handle 10 as desired in order to rotate shaft 15. By way of example but not limitation, if a user desires to rotate shaft 15 clockwise 90 degrees, the user can rotationally de-couple shaft 15 from handle 10 in the manner discussed above, rotate handle 10 counterclockwise 90 degrees (e.g., rotate the grip of handle 10 from the "6 o'clock" position to the "3 o'clock" position), re-couple shaft 15 to handle 10 in the manner discussed above, and then rotate handle 10 (and hence shaft 15) clockwise 90 degrees (e.g., rotate the grip of handle 10 from the "3 o'clock" position to the "6 o'clock" position).

7.3 Single-Plane Articulation Mechanism

As discussed above, in one preferred form of the present invention, articulation control assembly 285 comprises thumbstick ball assembly 310, which is configured to selectively pull one or more of four articulation cables 220 proximally, whereby to allow selective universal articulation of distal articulating portion 25 of shaft 15 relative to flexible proximal portion 20 of shaft 15 via movement of thumbstick ball assembly 310.

However, it has been recognized that it is also sometimes desirable to provide a simplified articulation control assembly which may be used with only two articulation cables, e.g., to provide single-plane articulation of distal articulating portion 25 of shaft 15 relative to flexible proximal portion 20 of shaft 15. To that end, in one form of the present invention, and looking now at FIGS. 67-69, there is shown an articulation control assembly 680 which is similar to the articulation control assembly 285 discussed above, but which is configured to provide single-plane articulation, as will hereinafter be discussed in further detail.

More particularly, articulation control assembly 680 comprises a rocker 685 pivotally mounted within internal cavity 280 of handle 10. Rocker 685 may be pivotally mounted within internal cavity 280 via an appropriately-formed seat disposed within internal cavity 280 of handle 10 or by other means (e.g., a pivot pin). A thumb lever 690 is mounted to rocker 685 and extends proximally through a slot 695 formed in the housing of handle 10 (FIG. 69). A wedge-shaped thumb rest 700 is preferably mounted to the free end of thumb lever 690. two articulation cables 220 (not shown) are mounted to rocker 685 (e.g., by mounting the proximal ends of articulation cables 220 within diametrically-opposed slots 705 formed on rocker 685).

As a result of this construction, a user can selectively articulate, in a single plane, distal articulating portion 25 of shaft 15 by selectively moving thumb lever 690, whereby to selectively pivot rocker 685 in a single plane, and thereby selectively pull one of the two articulation cables 220 which are mounted to rocker 685 proximally.

7.4 HHS Coil Comprising Compressive Outer Wrap

As discussed above, pull wire 230 is disposed within lumen 260 of HHS coil 225 and is able to slide freely relative to HHS coil 225 in order to selectively actuate end effector 30 (i.e., when a user pulls trigger 415 of handle 10, whereby to move pull wire 230 proximally).

It has been found that inasmuch as shaft 15 (and hence, HHS coil 225) can extend a substantial distance along a tortuous path (e.g., though the colon of a patient), HHS coil 225 can sometimes longitudinally compress (i.e., longitudinally shorten) while pull wire 230 does not longitudinally compress (i.e., longitudinally shorten). When this occurs, since HHS coil 225 provides the counterforce for pull wire 230, pull wire 230 needs to be moved a further distance proximally in order to actuate end effector 30. However, further proximal movement of pull wire 230 may not be possible if trigger 415 has reached the end of its "throw" (i.e., if trigger 415 cannot be pulled further).

Figure 72:
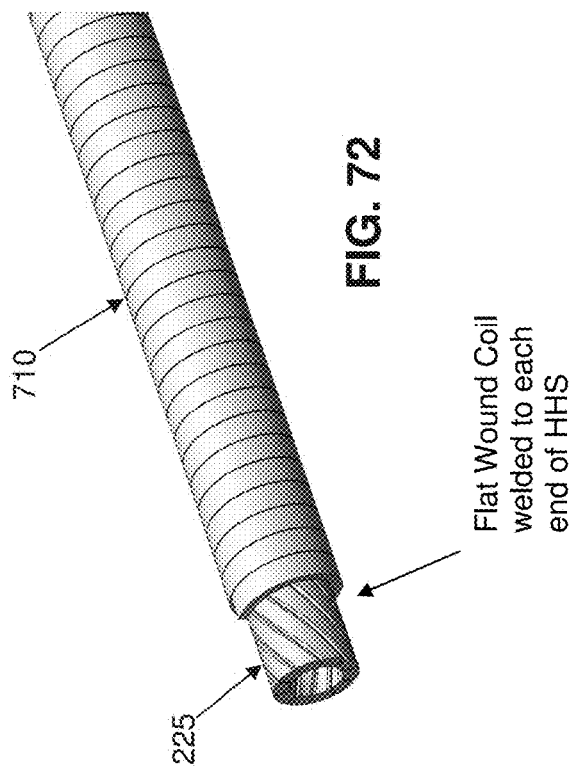
Figure 70:
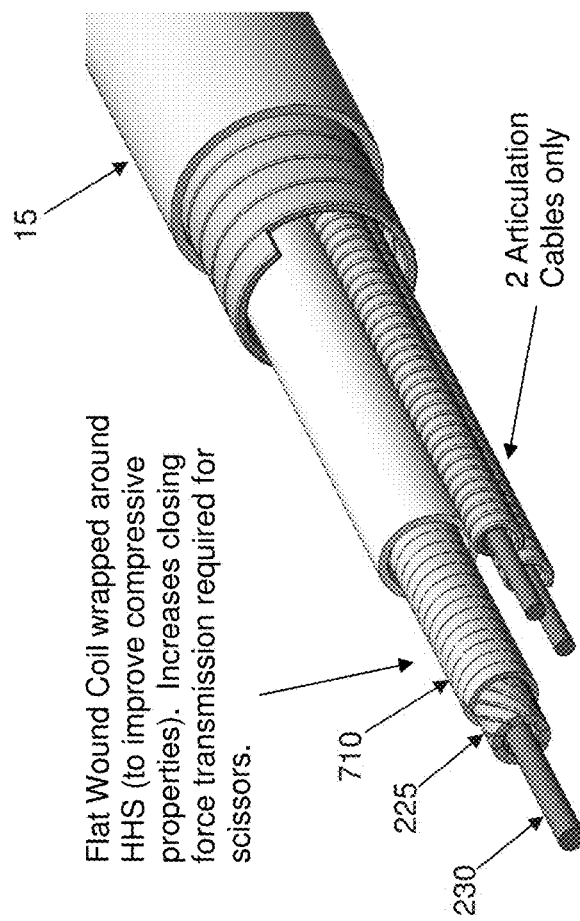
Figure 71:
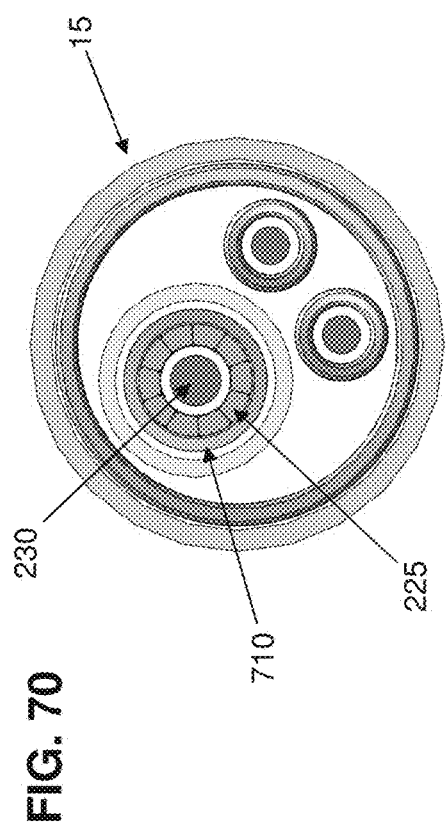

In order to minimize longitudinal compression of HHS coil 225, and looking now at FIGS. 70-72, in one form of the present invention there is provided a flat wound coil 710 which is wound around HHS coil 225. Flat wound coil 710 is welded to distal end 250 of HHS coil 225 and is welded to proximal end 255 of HHS coil 225. Coil 710 rotates with HHS coil 225 and provides support to HHS coil 225, whereby to minimize longitudinal compression of HHS coil 225. As a result of this construction, HHS coil 225 does not compress longitudinally (i.e., HHS coil 225 does not shorten) when shaft 15 is disposed along a tortuous path.

7.5 Cover for End Effector Mount 210

As discussed above, end effector 30 may be pivotally mounted within end effector mount 210 via a pin 217A passing through the end effector and jaws 216, 217 of the grasper.

Figure 73:
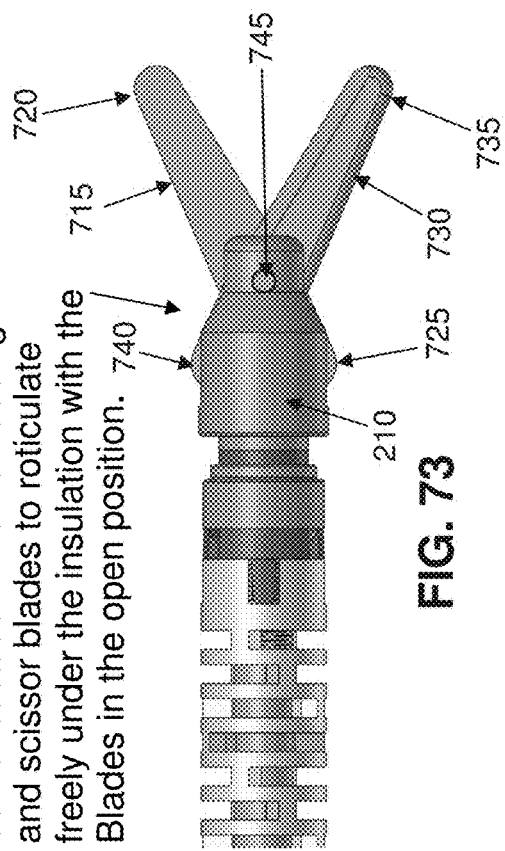
FIGS. 73 and 74 are schematic views showing another novel medical instrument formed in accordance with the present invention.
Figure 74:
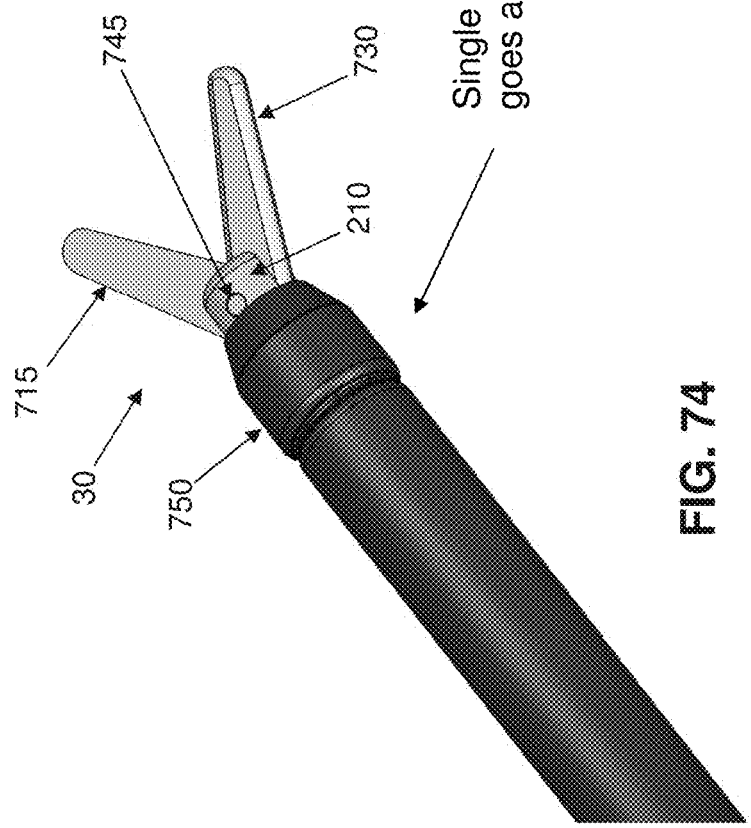

However, with certain end effectors, it is necessary to provide openings in the sides of end effector mount 210 so that the proximal ends of the elements of the end effector have room to move when the end effector is in certain configurations. By way of example but not limitation, and looking now at FIGS. 73 and 74, in one form of the present invention, end effector 30 comprises scissors. More particularly, in this form of the invention, end effector 30 comprises a first blade 715 having a distal end 720 and a proximal end 725, and a second blade 730 having a distal end 735 and a proximal end 740. First blade 715 and second blade 730 are pivotally mounted to one another and to end effector mount 210 via a pin 745. When first blade 715 and second blade 730 are opened (i.e., to receive tissue, suture, etc. that is to be cut), proximal end 725 of first blade 715, and proximal end 740 of second blade 730, project laterally out of end effector mount 210 (FIG. 73). It has been found that proximal ends 725, 740 can present a sharp surface which can damage surrounding equipment and/or the anatomy when end effector 30 is used in a surgical procedure, particularly when end effector 30 is rotated at a surgical site while blades 715, 730 are in their opened position. To eliminate this issue, a cover 750 may be provided which covers the proximal portion of end effector mount 210. As a result, the proximal ends 725, 740 of blades 715, 730 remain covered even when blades 715, 730 are in their open position, whereby to prevent damage to the anatomy or other surgical equipment. In one preferred form of the invention, cover 750 is formed out of an electrically-insulating material so that cover 750 also provides electrical insulation. This can be advantageous where end effector 30 comprises monopolar scissors, etc.

7.6 Enhanced Handle and Trigger Ergonomics

As discussed above, in one preferred form of the present invention, trigger 415 (FIG. 25) is pivotally mounted to handle 10 and may be selectively pulled by a user in order to selectively actuate end effector 30. For the purposes of illustration, trigger 415 is shown in FIG. 25 as a traditional "pistol type" trigger, and handle 10 is shown as comprising a traditional "pistol type" grip.

However, it has been found that it is sometimes desirable to provide additional stabilization elements on handle 10 (e.g., to facilitate single-handed use of medical instrument 5) and/or to provide a trigger having a longer throw (i.e., an increased arc of movement) for providing better leverage.

To these ends, and looking now at FIGS. 75 and 76, in one form of the invention, a handle 10 comprises a "pinky" stabilizer ring 755 for receiving the "pinky" finger of a user and a "shepard's hook"-type trigger 760 for providing greater leverage and superior ergonomics to a user. This construction facilitates a better single-handed grip of handle 10 by a user and also allows a user to easily move trigger 415 proximally or distally (e.g., to pull or push pull wire 230 in order to selectively close/open the jaws of a grasper, etc.)

7.7 Monopolar Electrical Current Delivery

In some circumstances it is desirable to be able to deliver monopolar electrical power to end effector 30. By way of example but not limitation, where end effector 30 comprises monopolar ("hot") scissors, it is necessary to transmit electrical power from handle 10, along (or through) shaft 15, to end effector 30.

To that end, and looking now at FIGS. 77-80, in one preferred form of the present invention, there is provided an electrical connection port (e.g., a "banana jack") 765 disposed on the proximal end of the grip of handle 10 for connection to an external power supply (not shown), and a wire 770 (FIG. 79) disposed within internal cavity 280 of handle 10 for routing electrical power from electrical connection port 765 to a flat conductive spring 775 disposed within handle 10 (FIG. 80). Flat conductive spring 775 contacts the plurality of teeth 409 disposed on roticulation key 405, whereby to make electrical contact with roticulation key 405 and hence HHS coil 225 and/or pull wire 230 via roticulation key 405. It should be appreciated that, with this form of the invention, ball nose spring plunger 410 is preferably omitted (i.e., it is replaced by flat conductive spring 775). In addition, with this form of the invention, roticulation key 405 (and teeth 409 of roticulation key 405) are formed out of an electrically-conductive material (e.g., metal), as is long laser-cut hypotube 180, rotation connector 200 and end effector mount 210. As a result, electrical power can pass from an external power supply (not shown) to electrical connection port 765, along wire 770 to flat conductive spring 775, from conductive spring 775 to roticulation key 405, and then to HHS coil 225 (and also to pull wire 230), along HHS coil 225 (and pull wire 230) through flexible proximal portion 20 of shaft 15, through sleeve (or crimp) 265 to long laser-cut hypotube 180, along long laser-cut hypotube 180 (and pull wire 230) through distal articulating portion 25 of shaft 15, to rotation connector 200 and end effector mount 210, and from end effector mount 210 to end effector 30. In this way, monopolar power can be supplied to end effector 30.

7.8 Alternative End Effector

As discussed above, in a preferred form of the present invention, end effector 30 comprises a surgical grasper having two opposed jaws 216, 217 (FIG. 8), in another preferred form of the present invention, end effector 30 comprises scissors 600 having opposing blades 605, 610 (FIGS. 59-62), and in another preferred form of the present invention, end effector 30 comprises monopolar ("hot") scissors and handle 10 is modified to transmit electrical power from handle 10, along (or through) shaft 15, to end effector 30 (FIGS. 77-80).

In yet another preferred form of the present invention, and looking now at FIGS. 81-98, end effector 30 comprises a monopolar knife assembly 800 which comprises a knife tip that can be electrified for use in marking tissue, cutting tissue and/or cauterizing tissue. More particularly, knife assembly 800 comprises a knife 805, a knife housing 820 and a pull wire 230 for (i) delivering monopolar electrical power to knife 805 so as to electrify knife 805, and (ii) moving knife 805 distally and proximally, whereby to extend and retract knife 805 relative to knife housing 820.

Furthermore, in this embodiment, handle 10 of knife assembly 800 is configured to (i) transmit monopolar electrical power along pull wire 230 to knife 805, and (ii) introduce fluid so that the fluid can be passed through shaft 15 and into the tissue for cleaning the knife (or area surrounding the knife) during use, and/or for creating a bleb (i.e., a blister) in the tissue, as will be discussed in further detail below.

Figure 81:
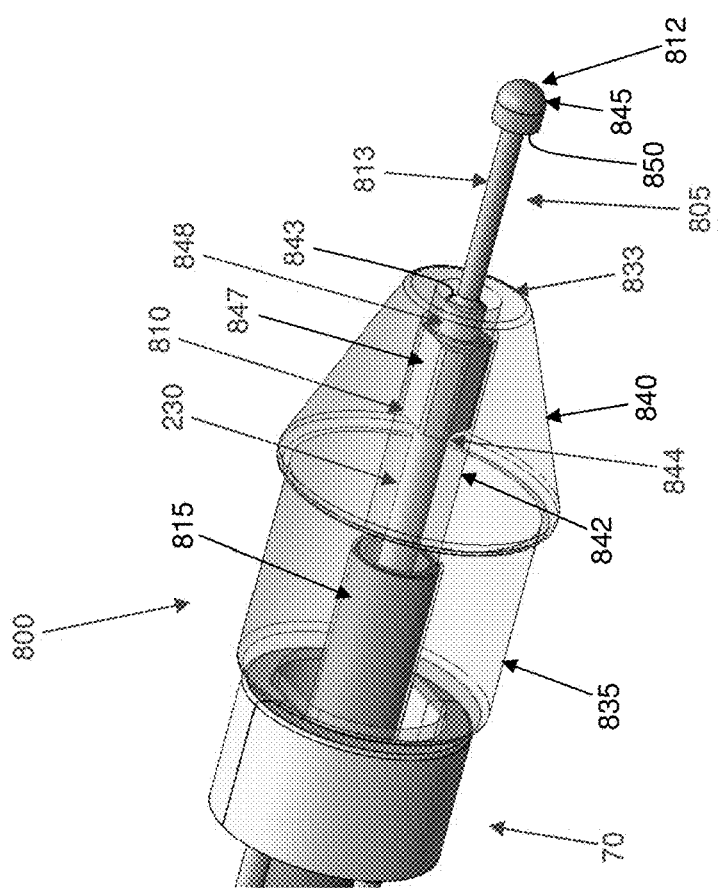
Figure 85:
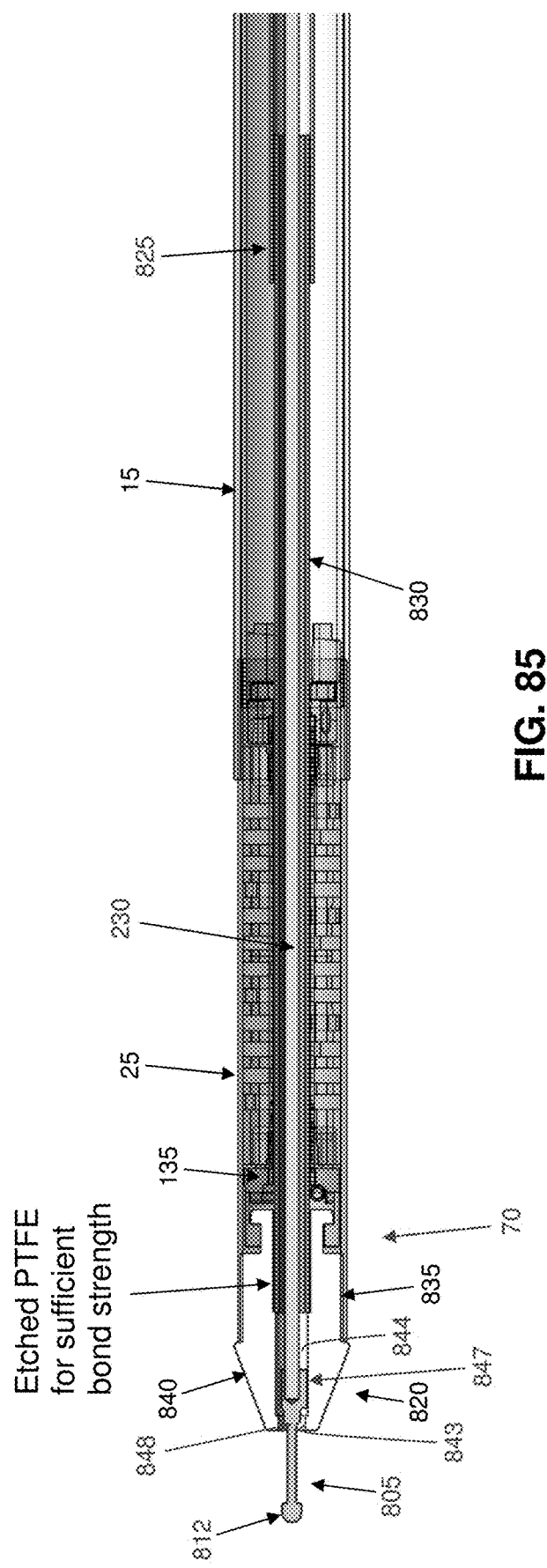
Figure 87:
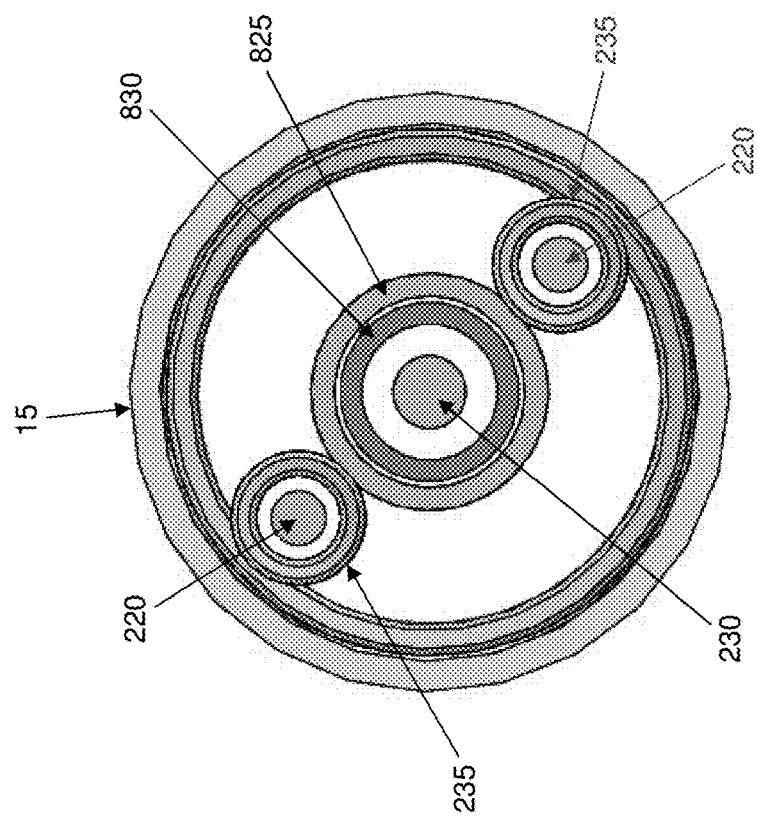
Figure 86:
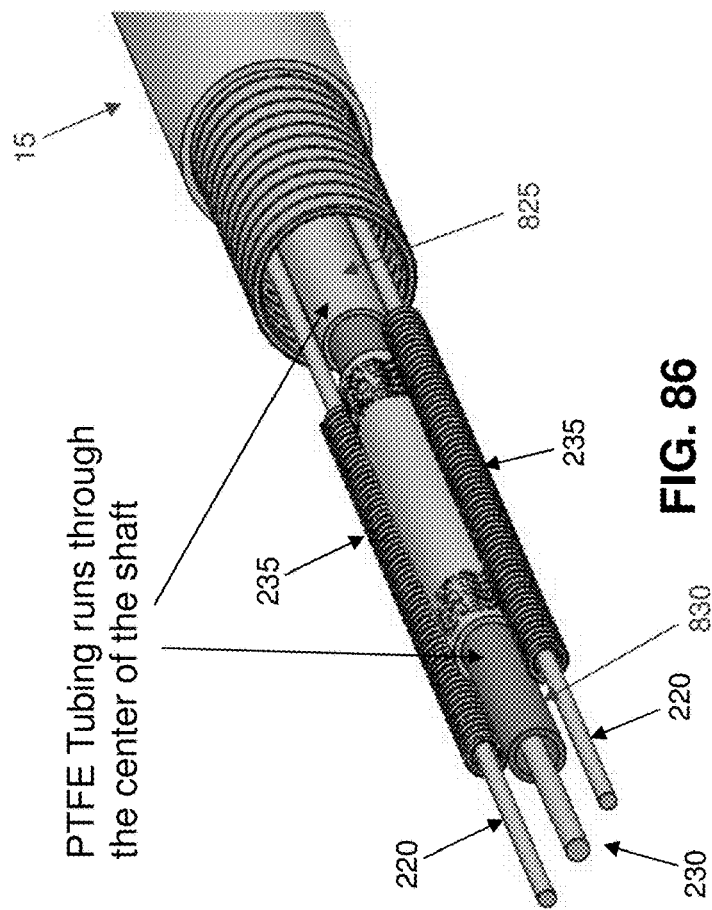
Figure 89:
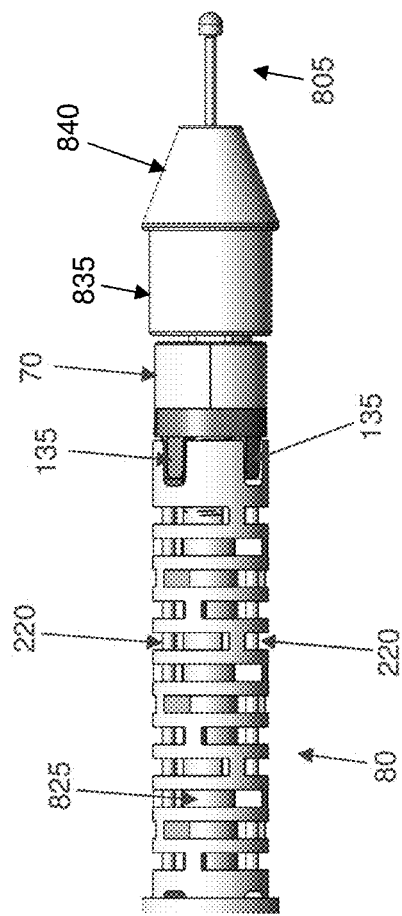
Figure 88:
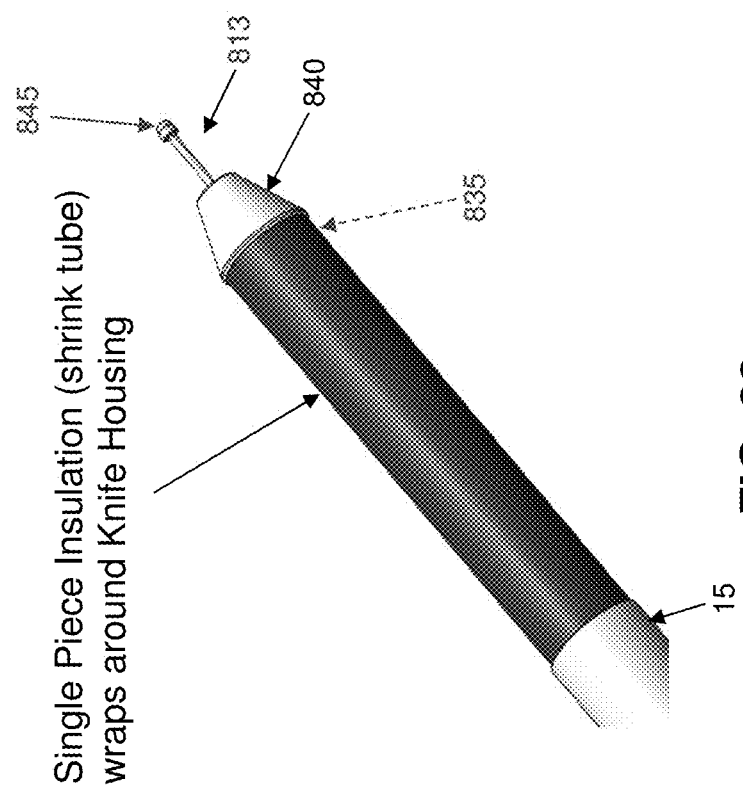
Figure 94:
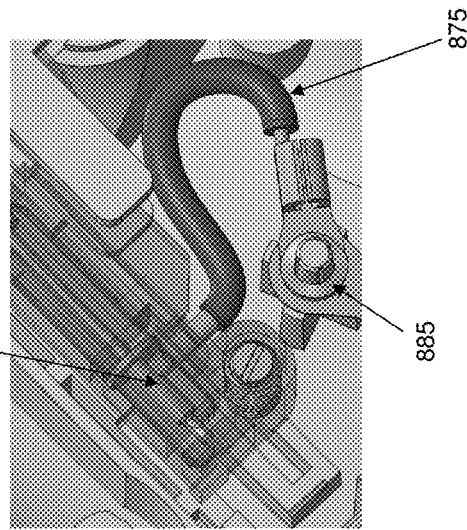
Figure 92:
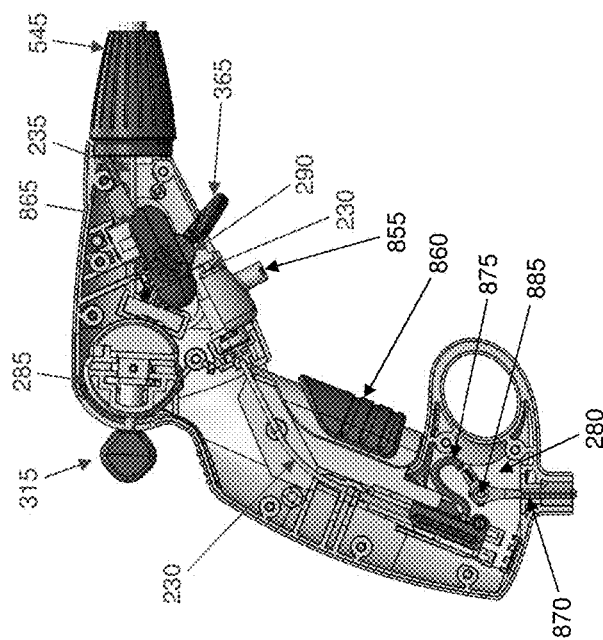
Figure 93:
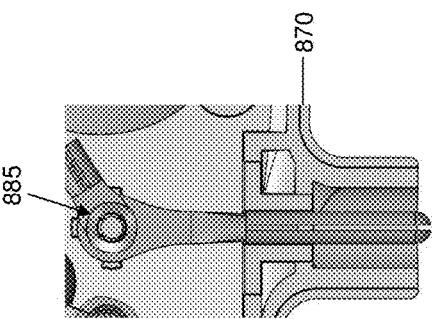
Figure 95:
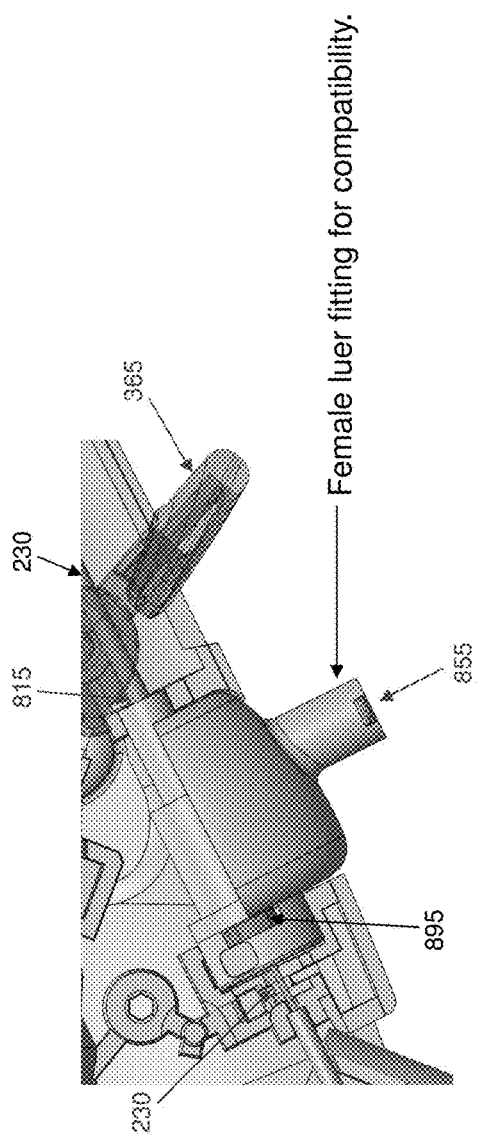
Figure 97:
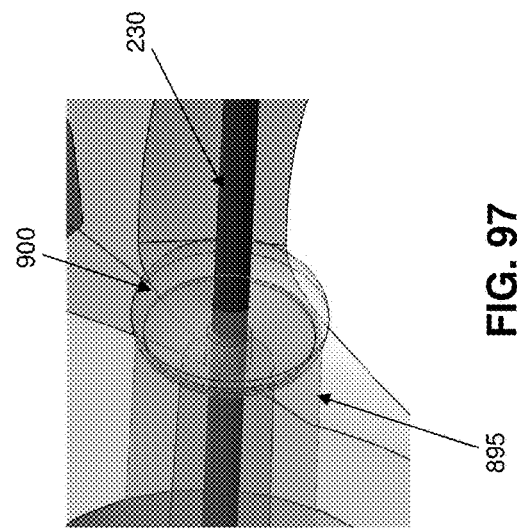
Figure 96:
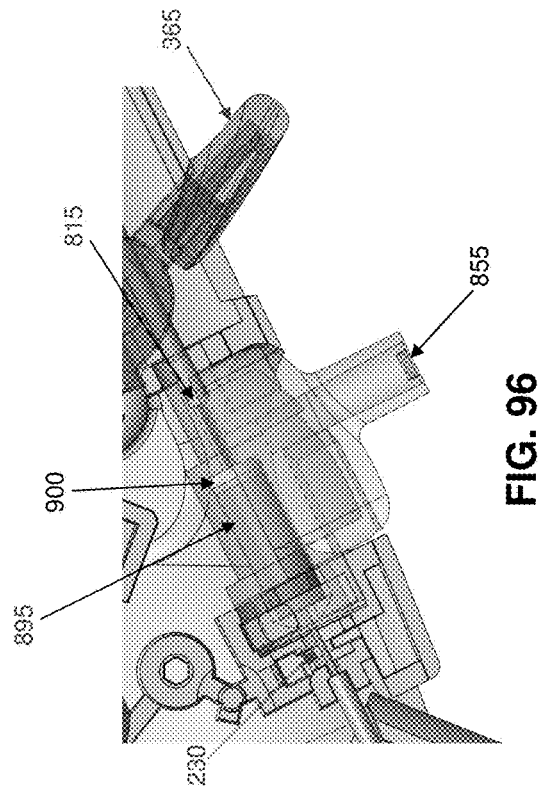

As can be seen in FIGS. 81 and 85, knife 805 comprises a proximal end 810, a distal end 812 and a knife blade 813 extending between proximal end 810 and distal end 812. Preferably, distal end 812 of knife 805 comprises a knife tip with a rounded front portion 845 and a flattened back portion 850. Proximal end 810 of knife 805 comprises a mount 847 having a tapered distal portion 848. Preferably, proximal end 810 of knife 805 is welded to the distal end of pull wire 230 at mount 847 so that when pull wire 230 is moved distally, knife 805 moves distally, and when pull wire 230 is moved proximally, knife 805 moves proximally, whereby to extend and retract knife 805 relative to knife housing 820. In a preferred form of the present invention, pull wire 230 comprises a braided cable.

Figure 82:
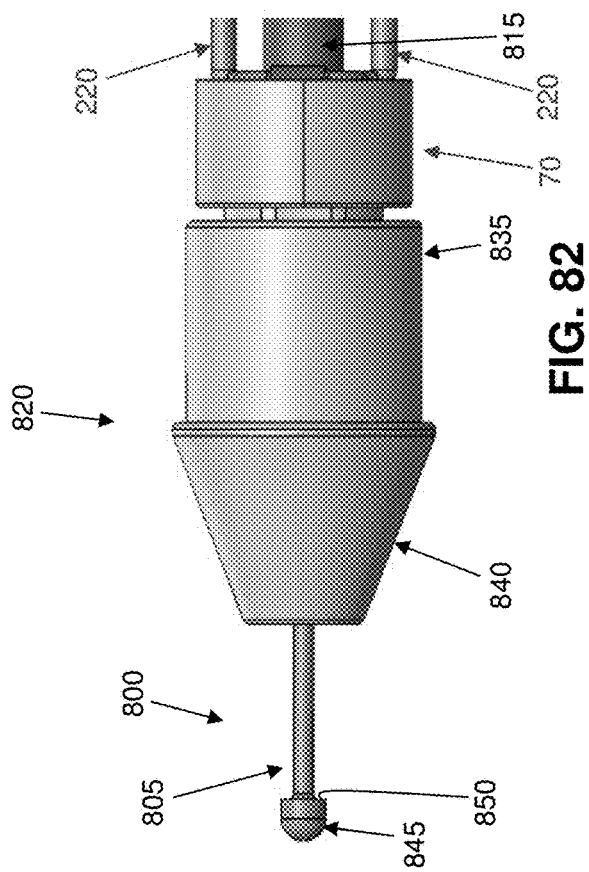

Looking now at FIGS. 81, 82 and 85, knife housing 820 comprises a cylindrical proximal portion 835 and a conical distal portion 840. Cylindrical proximal portion 835 is configured to be received within the distal end of shaft 15 and connected to distal articulation link assembly 70 of distal articulating portion 25. Conical distal portion 840 extends distally from the distal end of shaft 15. A bore 842 extends through cylindrical proximal portion 835 and conical distal portion 840 and opens on the distal end 833 of conical distal portion 840. Preferably, knife housing 820 is formed out of a non-conductive material, e.g., ceramic, which insulates electricity and isolates the electrical current being delivered from handle 10 to knife 805.

As pull wire 230 passes from proximal end 810 of knife 805 to handle 10, pull wire 230 extends through a tube 815. Tube 815 extends from handle 10 through shaft 15 and the distal end of tube 815 terminates within bore 842 of knife housing 820, with the opening at the distal end of tube 815 aligned with bore 842 of knife housing 820. Tube 815 acts as electrical insulation for the electrical power traveling through pull wire 230 from the handle to knife 805, as will also be discussed in further detail below. Tube 815 and bore 842 also serve as a fluid pathway for fluid passing from a fluid inlet port in handle 10, through tube 815, through bore 842 and out distal end 833 of knife housing 820, as will also be discussed in further detail below.

In FIGS. 81-87, tube 815 is shown as two separate tubes (i.e., proximal tube 825 and distal tube 830), with proximal tube 825 having a larger diameter lumen than the diameter of the lumen of distal tube 830. However, tube 815 can also be formed as a single tube which tapers from the proximal end to the distal end (not shown). It should be appreciated that forming tube 815 with a small diameter along the entire length of the lumen may create too much friction between pull wire 230 and the wall(s) defining tube 815, or cause fluid passing from the fluid inlet port to the distal end of knife housing 820 to build up within lumen 815. Therefore, whether tube 815 is formed by two separate tubes or a single tapered tube, it is preferable that the lumen be sized to have a large diameter along a significant portion of the lumen in order to reduce friction between pull wire 230 and the wall(s) defining tube 815 and/or to enable fluid to easily flow through tube 815 as the fluid travels from the fluid inlet port in handle 10 and out distal end 833 of knife housing 820. Preferably, tube 815 is formed out of polytetrafluoroethylene (PTFE).

As stated above, pull wire 230 can be pushed distally, and pulled proximally, through tube 815 to extend and retract knife 805 relative to knife housing 820. Significantly, proximal end 810 of knife 805 and knife housing 820 are sized and shaped to (i) prevent retraction of knife 805 into tube 815, and (ii) limit the distance knife 805 can be projected beyond distal end 833 of knife housing 820.

Figure 84:
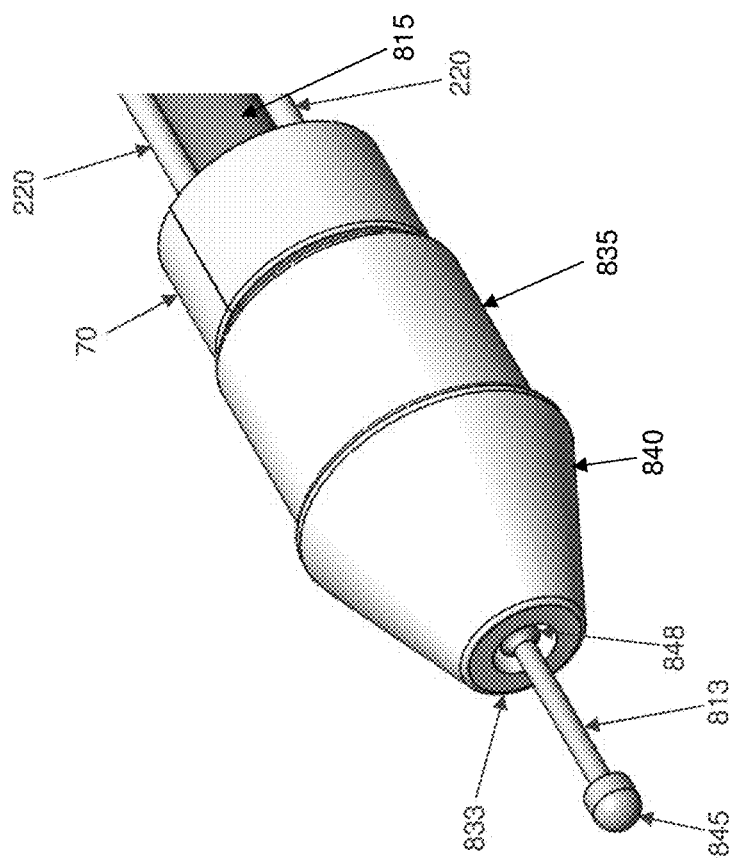
Figure 83:
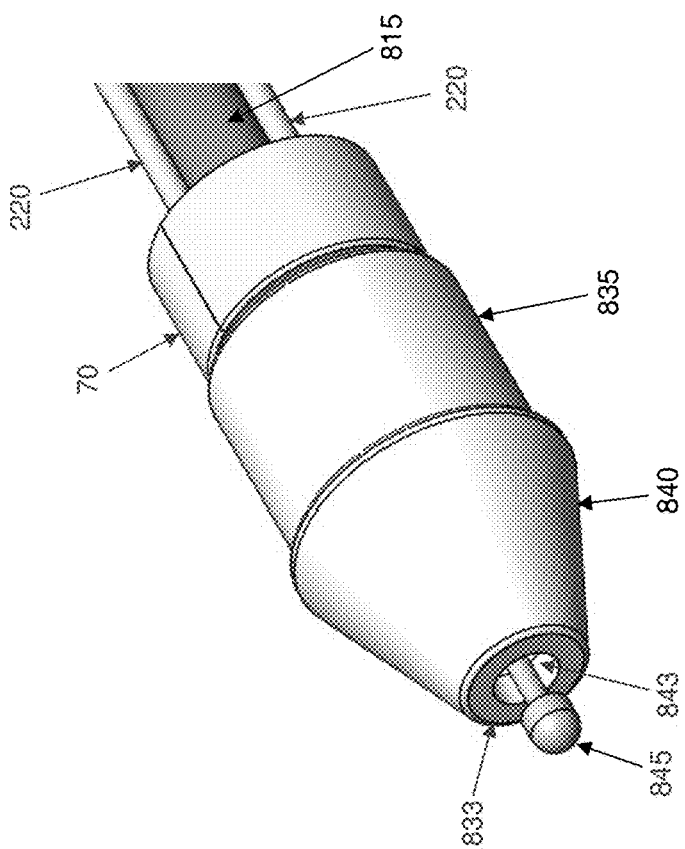

More particularly, as shown in FIG. 81, bore 842 of knife housing 820 preferably comprises a stepped bore, with the distal end 843 of stepped bore 842 having a smaller diameter than the proximal end 844 of stepped bore 842. Knife 805 moves within stepped bore 842 so as to move knife 805 between its fully retracted position (FIG. 83) and its fully extended position (FIG. 84). Mount 847 at proximal end 810 of knife 805 has a diameter which is greater than the diameter of tube 815, whereby to prevent retraction of knife 805 into tube 815. Furthermore, mount 847 also has a diameter which is greater than the diameter of distal end 843 of stepped bore 842, whereby to prevent extension of mount 847 of knife 805 beyond distal end 843 of stepped bore 842. As can be seen in FIG. 85, tapered distal portion 848 of mount 847 has a diameter that is smaller than the diameter of distal end 843 of stepped bore 842 so that when knife 805 is moved distally within bore 842, tapered distal portion 848 moves distally within distal end 843 of stepped bore 842 until further distal movement is prevented by mount 847 contacting the shoulder separating distal end 843 of stepped bore 842 from proximal end 844 of stepped bore 842.

Significantly, when knife 805 is in its fully retracted position (FIG. 83), a portion of knife 805 still extends beyond distal end 833 of knife housing 820. The distance that the portion of knife 805 projects out of knife housing 820 when knife 805 is in its fully retracted position is designed to be less than the distance between the innermost layer of the intestinal wall (i.e., the mucosa layer) and the outermost layer of the intestinal wall (i.e., the serosa layer) in order to minimize the possibility that the knife will perforate the intestinal wall when the knife passes through the mucosa layer, as will be discussed in further detail below and as shown in FIGS. 98A-98F.

In addition to moving knife 805 distally and proximally within tube 815 so as to extend and retract knife 805 relative to knife housing 820, knife 805 may also be articulated relative to handle 10. Looking now at FIGS. 85-87, two articulation cables 220 run through articulation cable housings 235 from handle 10 to distal seats 135 of distal articulation link assembly 70 (FIG. 89) so that articulation cables 220 can be pulled proximally to articulate distal articulating portion 25 of shaft 15 (and thereby, knife housing 820 and knife 805), in the same manner discussed above. However, since there are only two articulation cables (and not the four articulation cables shown in FIGS. 15 and 16), knife housing 820 (and thus, knife 805) can only be articulated in a single plane instead of the universal articulation provided by the three or more articulation cables discussed above.

If desired, the plane of articulation can be modified by rotating shaft 15 from handle 10, which in turn rotates (i) flexible proximal portion 20, (ii) distal articulating portion 25, and (iii) knife housing 820, as will be discussed in further detail below. Because of the manner that knife housing 820 is connected to shaft 15 (i.e., with a clam shell connector), pull wire 230 and knife 805 do not rotate when shaft 15 and knife housing 820 rotate.

Since knife 805 is substantially uniform (i.e., symmetrical), there is no need to provide independent rotational movement of knife 805 and/or knife housing 820 relative to the distal end of distal articulating portion 25 of shaft 15 (i.e., the roticulation function referred to above). Therefore, roticulation mechanism 295 (including HHS coil 225 and roticulation knob 395) may be removed from this version of the instrument. In place of roticulation knob 395, fluid inlet port 855 is provided for receiving fluid for flushing, as will be discussed in further detail below.

Looking now at FIGS. 90-97, a further embodiment of handle 10 is shown. Handle 10 has been specifically designed to provide the motion necessary for actuating knife 805. More particularly, in this form of the invention, handle 10 comprises:

(i) a slider 860 for selectively actuating pull wire 230 (and hence selectively moving pull wire 230 proximally and distally so as to retract and extend, respectively, knife 805 relative to knife housing 820);

(ii) a thumb stick 315 of articulation control assembly 285 for selectively moving articulation cables 220 (and hence selectively articulating distal articulating portion 25 of shaft 15 and knife 805 away from the shaft axis, within a single plane);

(iii) actuation lever 365 of push rod lock assembly 290 for selectively locking articulation control assembly 285 in a desired position (and hence locking thumb stick 315 and distal articulating portion 25 of shaft 15 in a selected position); and (iv) rotation knob 545 of rotatable shaft adapter mechanism 525 for allowing shaft 15 (i.e., both flexible proximal portion 20 and distal articulating portion 25) and knife housing 820 to be selectively rotated relative to handle 10 in order to modify the plane of articulation. In this embodiment, rotation knob 545 is selectively locked to handle 10 by a finger latch 865.

As stated above, handle 10 is configured to transmit monopolar electrical power along pull wire 230 to knife 805. To that end, and looking at FIGS. 90-94, in one preferred form of the present invention, there is provided an electrical connection port (e.g., a "banana jack") 870 disposed on the proximal end of the grip of handle 10 for connection to an external power supply (not shown), and a wire 875 (FIGS. 91, 92 and 94) disposed within internal cavity 280 of handle 10 for routing electrical power from electrical connection port 870 to pull wire 230. Wire 875 is connected to pull wire 230 with at least one crimp. Flat conductive spring 885 acts as a detent feature and also acts as a conductor to apply voltage through pull wire 230 to knife 805, whereby to make electrical contact from electrical connection port 870 to knife 805 via pull wire 230. As a result, electrical power can pass from an external power supply (not shown) to electrical connection port 870, along wire 875 to pull wire 230, and along pull wire 230 to knife 805. In this way, monopolar power can be supplied to knife 805.

As also stated above, handle 10 is provided with a fluid inlet port 855 so that fluid may be introduced into handle 10, passed through tube 815, out of distal end 833 of knife housing 820 and into the tissue surrounding knife 805. More particularly, and looking now at FIGS. 95-97, the proximal end of tube 815 is bonded to fluid inlet port 855 in handle 10, whereby fluid may be introduced into fluid inlet port 855 and flow distally through tube 815 and out of distal end 833 of knife housing 820. Preferably, an insert 895 is provided to prevent fluid from flowing proximally within handle 10 along the path of pull wire 230 (which extends through the handle to provide the electrical path from the handle to the knife). Pull wire 230 extends through insert 895 and insert 895 is sealed with an O-ring 900. The seal around pull wire 230 is created when insert 895 applies pressure to (i.e., deforms) O-ring 900 around pull wire 230.

At the distal end of the instrument, and as shown in further detail in FIG. 98, mount 847 of knife 805 is formed with concave portions 905 in between convex portions 910 in order to permit fluid to flow through tube 815 through bore 842, and out distal end 833 of knife housing 820. More particularly, concave portions permit fluid to be passed out of the distal end of knife housing 820 even when knife 805 is in its fully extended position (FIGS. 81 and 84) (i.e., when mount 847 of knife 805 is in contact with the shoulder separating proximal end 844 of stepped bore 842 from distal end 843 of stepped bore 842). Therefore, fluid can be passed out of the distal end of knife housing 820 regardless of whether knife 805 is extended or retracted from knife housing 820.

Fluid is passed out of the distal end of knife housing 820 in order to flush away debris that builds up on knife 805 or in the surrounding tissue during tissue cutting or cauterization.

Figure 98B:
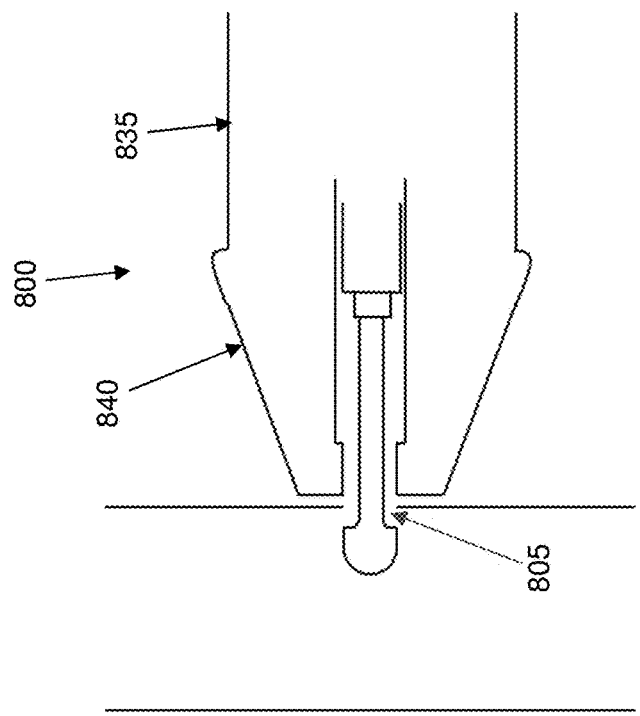
FIGS. 98A-98F are schematic views of the novel medical instrument of FIGS. 81-98 being used to create a bleb and cut tissue.
Figure 98A:
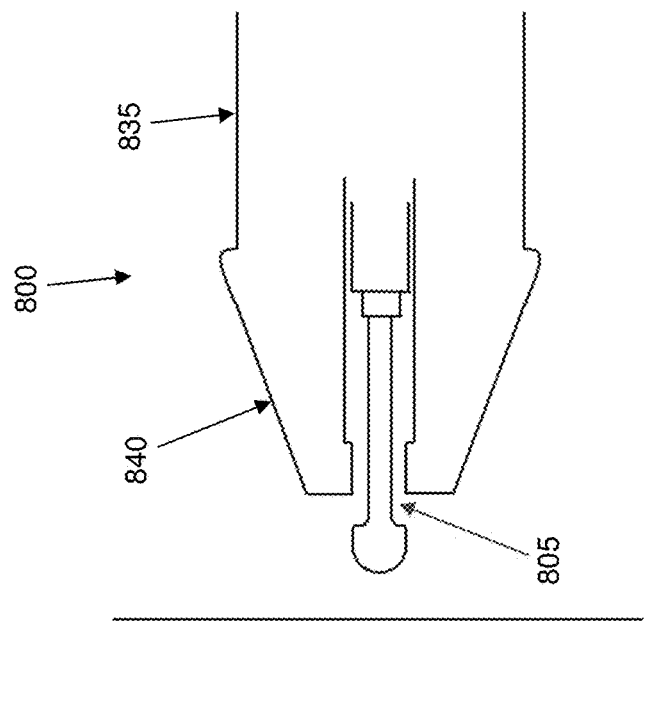
Figure 98D:
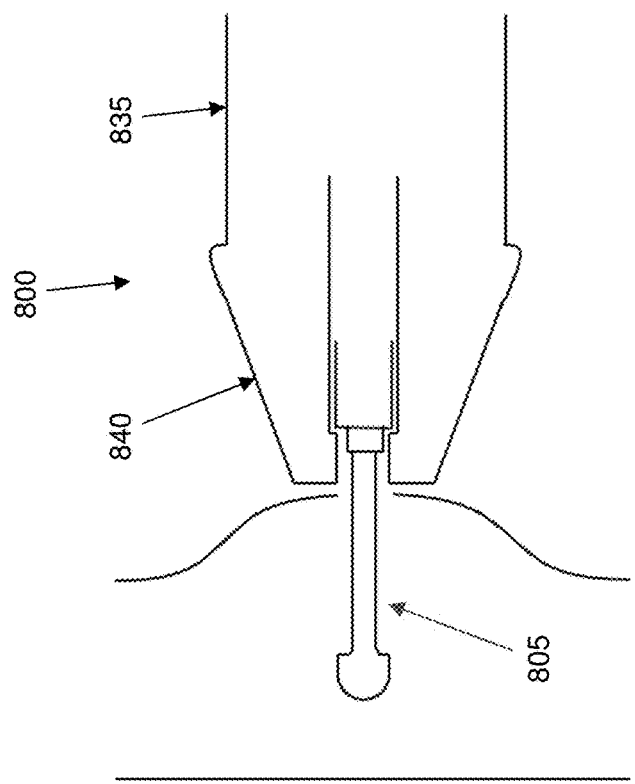
Figure 98C:
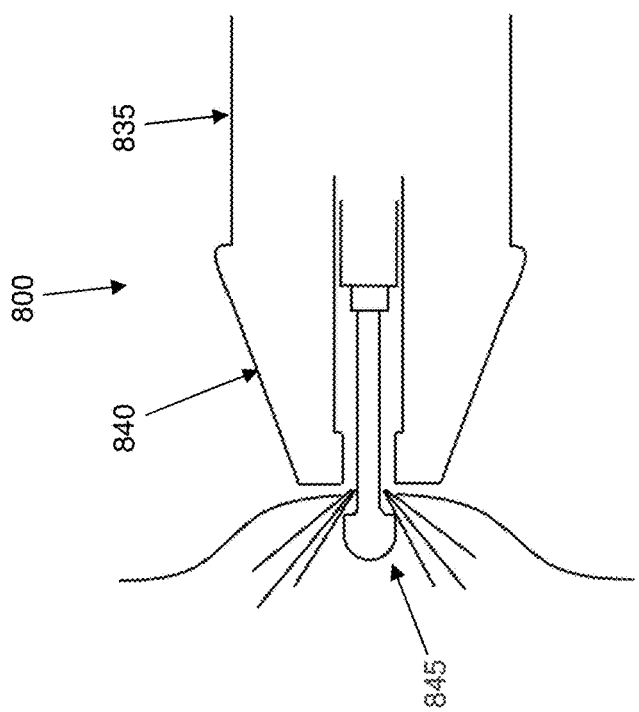
Figure 98F:
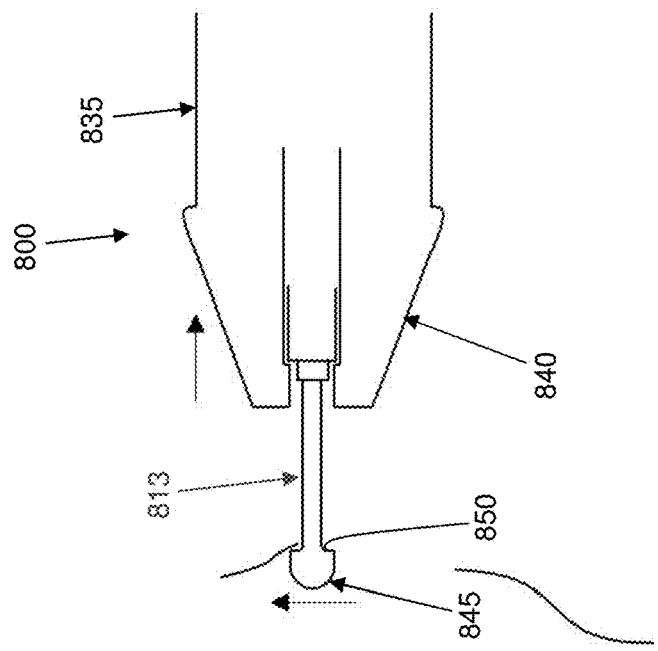
Figure 98E:
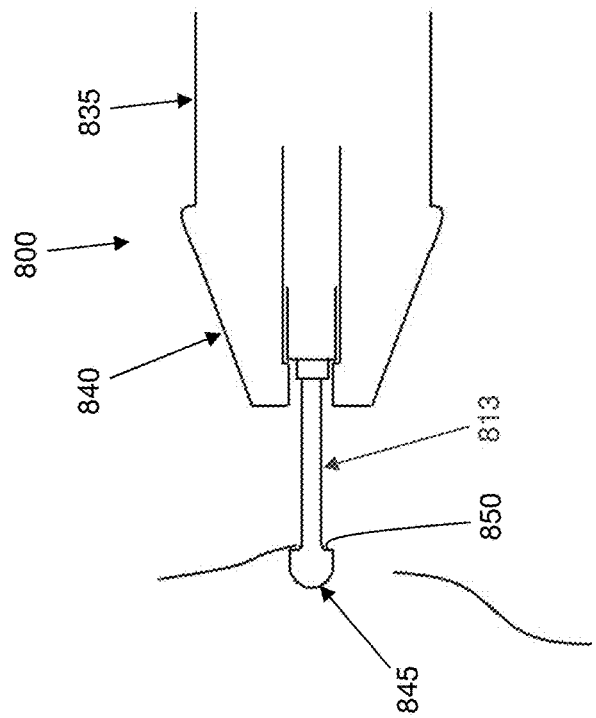

Fluid can also be passed out of the distal end of knife housing 820 to create a bleb (i.e., a blister) in the tissue to separate the sub-mucosal layer from the muscularis mucosal layer so that the mucosal and sub-mucosal layers can be excised. More particularly, and looking now at FIGS. 98A-98F, to create a bleb, knife 805 is electrified and inserted through the mucosa layer while knife 805 is in its retracted position (FIG. 98A). It is preferable to inject knife 805 through the mucosa layer while the knife is in its retracted position (FIG. 83) so that the knife does not penetrate too far into the intestinal wall and unintentionally perforate the intestinal wall. After knife 805 has been inserted through the mucosa layer (FIG. 98B), fluid is injected under the mucosa layer in order to lift the sub-mucosal layer away from the underlying tissue (i.e., muscularis mucosae) (FIG. 98C). Knife 805 is now extended (FIG. 98D) and power is delivered to knife 805 to cut tissue. Significantly, knife 805 can be moved laterally and pulled proximally against the wall of the mucosa so that flattened back portion 850 retracts the mucosa (i.e., tensions the mucosa) while knife blade 813 cuts the mucosa (FIGS. 98E and 98F). If desired, prior to creating the bleb, power can be delivered to knife 805 to mark a border around the tissue that is to be excised.

The fluid injected through knife housing 820 is typically saline. However, if desired, methylene blue dye can be added to the saline to assist the user in viewing where the user is cutting. Furthermore, other fluids could be injected with (or instead of) saline (e.g., gel-like fluids to increase duration of bleb formation, temperature sensitive fluids, etc.).

In an exemplary use of knife assembly 800 in a minimally-invasive procedure, knife 805 is retracted; shaft 15 is straightened; handle 10 is longitudinally advanced so as to longitudinally advance knife 805 through a portal (e.g., through a tool channel of an endoscope) and into the body (e.g., along a tortuous path); handle 10 is longitudinally advanced and/or rotated, and/or distal articulating portion 25 of shaft 15 is bent, so that knife 805 is adjacent to the target tissue at the internal site; knife 805 is extended; monoelectric power is delivered to knife 805; knife 805 is used to perform the desired procedure (e.g., mark tissue, cut tissue, etc.) at the internal site; knife 805 is retracted; and the knife 805 is withdrawn from the internal site, e.g., handle 10 is longitudinally withdrawn through the portal (during which the handle may also be rotated, and/or distal articulating portion 25 of shaft 15 is unbent as necessary), so that knife assembly 800 is withdrawn from the body.

If desired, a syringe (or another suitable pressurized liquid source) filled with sterile water (or another fluid) may be used to inject fluid into fluid inlet port 855 to flush water out of the distal end of knife housing 820 to clean knife 805 (or the target area) while knife 805 is being used to perform the desired procedure. Additionally, if desired, fluid may be injected into the fluid inlet port 855 to flush fluid out of the distal end of knife housing 820 in order to create a bleb (in the manner discussed above).

It will be appreciated that medical instrument 5 with knife assembly 800 is capable of at least the following motions:

Motion 1—longitudinal movement of knife 805 by sliding slider 860 of handle 10 (sometimes referred to herein as a "longitudinal motion function");

Motion 2—articulating movement of shaft 15 and knife 805 relative to handle 10 by articulating thumb stick 315 of handle 10 to articulate distal articulating portion 25 of shaft 15 relative to the distal end of flexible proximal portion 20 of shaft 15 (sometimes referred to herein as a "universal articulation function"); and Motion 3—rotational movement of shaft 15 (and hence knife housing 820) by rotational movement of rotational knob 545 of handle 10 (sometimes referred to herein as a "torqueing motion function").

It will also be appreciated that, if desired, the medical instrument may be modified so as to provide less (or more) than the three aforementioned motions, e.g., the roticulation function may be added, an additional rotational function such as selective rotation of shaft 15 may be added, additional articulation cables may be added, etc.

It will be further appreciated that medical instrument 5 with knife assembly 800 of FIGS. 81-98 is capable of (i) transmitting monopolar electrical power from handle 10 to knife 805; and (ii) passing fluid from handle 10 out of the distal end of knife housing 820.

8. Additional Constructions

In the foregoing disclosure, there is described a novel medical instrument comprising a handle, an elongated flexible shaft and various end effectors disposed at the distal end of the shaft configured for performing a medical procedure. It should be appreciated that medical instrument 5 may be modified in a variety of ways in order to support different types of end effectors, to facilitate single-handed use of medical instrument 5, to enhance the functionality of medical instrument 5, etc.

Figure 99:
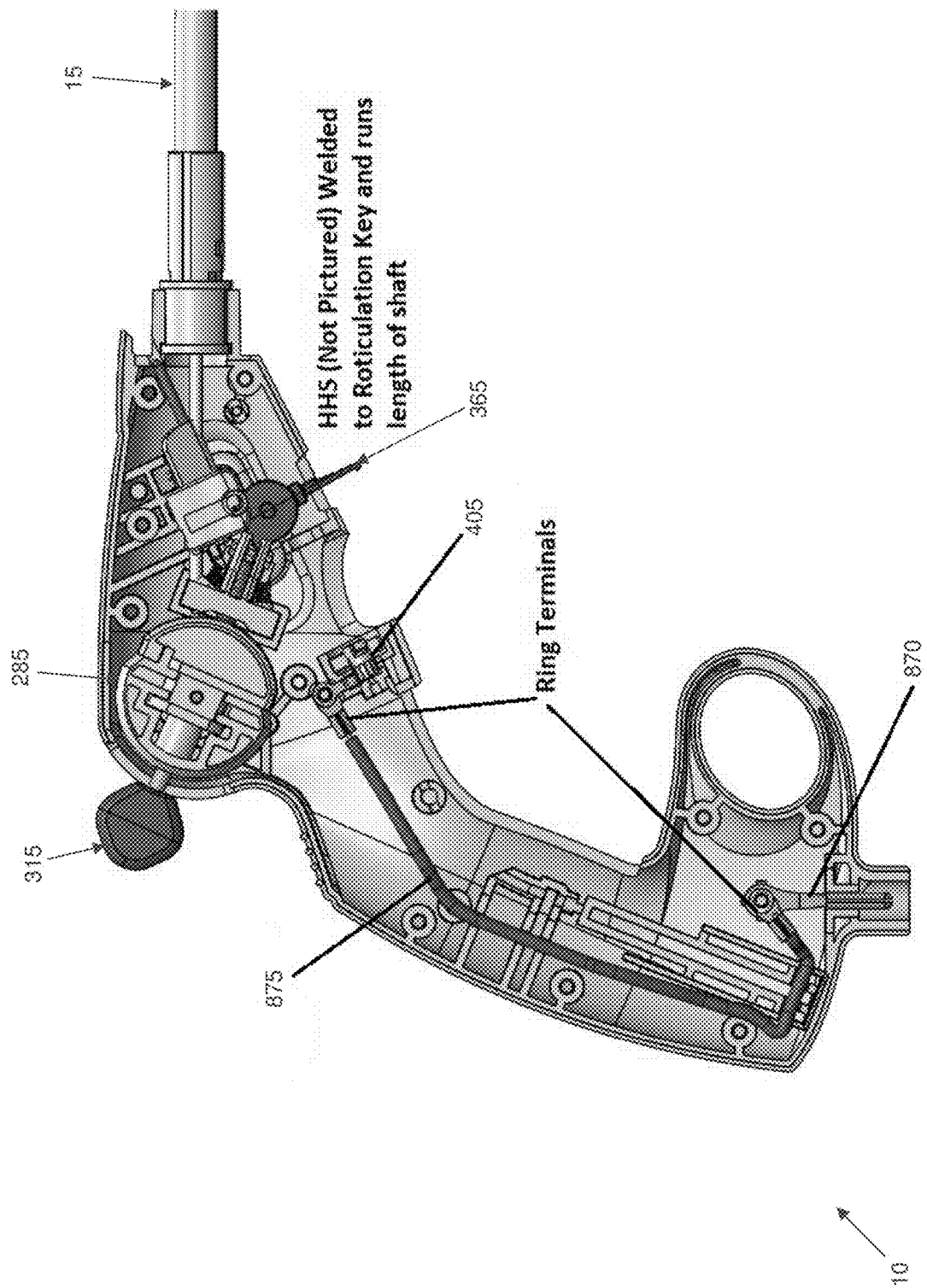
FIG. 99 is a schematic view showing another handle construction that can be used to deliver monopolar electrical power to an end effector.

Specifically, handle 10 can be modified in a variety of ways in order support different types of end effectors, to facilitate single-handed use of medical instrument 5, to enhance the functionality of medical instrument 5, etc. By way of example but not limitation, the distal tip of knife 805 could be formed with a spade configuration or another configuration (instead of the rounded front/flattened back configuration shown in FIGS. 81-85, 88 and 89). Furthermore, slider 860 of FIGS. 90 and 91 can be replaced with a trigger (e.g., trigger 415 of FIGS. 75 and 76). Additionally, the electrical connection for delivering monopolar electrical energy to "hot" scissors can follow the path shown in FIG. 99 instead of the path shown in FIG. 79.

9. Medical Instrument 5 with an Additional Degree of Articulation

As discussed above, in one form of the invention, novel medical instrument 5 generally comprises a shaft 15 having a flexible proximal portion 20, a distal articulating portion 25 configured to be selectively articulated relative to the distal end of flexible proximal portion 20, and an end effector 30 configured to be selectively rotated relative to the distal end of distal articulating portion 25. With this form of the invention, longitudinal movement of handle 10 can be used to selectively move shaft 15 distally or proximally, whereby to move end effector 30 distally or proximally; rotational movement of handle 10 can be used to rotate shaft 15 (and hence, to also rotate end effector 30); articulation control assembly 285 (FIG. 25) can be used to selectively articulate distal articulating portion 25 of shaft 15 relative to flexible proximal portion 20 of shaft 15, whereby to permit control over the positioning of end effector 30; roticulation control assembly 295 (FIG. 25) can be used to selectively rotate end effector 30 relative to distal articulating portion 25 of shaft 15; and trigger assembly 300 (FIG. 25) can be used to selectively actuate end effector 30. It should be appreciated that, in this form of the invention, flexible proximal portion 20 of shaft 15 rotates as a unit together with handle 10.

As also discussed above, in another form of the present invention, novel medical instrument 5 may further comprise a rotatable shaft adapter mechanism 525 actuated with a rotation knob 545 (FIGS. 56-58) which can be selectively rotated so as to allow shaft 15 (i.e., both flexible proximal portion 20 and distal articulating portion 25) to be selectively rotated relative to handle 10.

Furthermore, as also discussed above, end effector 30 may comprise a monopolar knife assembly 800, wherein knife 805 can be extended and retracted relative to knife housing 820 by sliding slider 860 on handle 10, wherein shaft 15 and knife 805 can be articulated relative to handle 10 by articulating thumb stick 315 of handle 10 to articulate distal articulating portion 25 of shaft 15 relative to the distal end of flexible proximal portion 20 of shaft, and wherein shaft 15 (and hence knife housing 820) can be rotated relative to handle 10 by rotating rotational knob 545 of handle 10.

However, it should also be appreciated that, in some circumstances, it may be desirable to add an additional degree of articulation to shaft 15 of novel medical instrument 5. By way of example but not limitation, when medical instrument 5 is passed along a sharp bend in the colon (or other anatomical structure), shaft 15 of medical instrument 5 is constrained by the anatomy and is forced to deflect along the outer curve of the bend in the colon (or other anatomical structure), thereby making it difficult for knife 805 to cut tissue disposed along the corresponding inner curve of the bend in the colon (or other anatomical structure). Thus there is a need for a medical instrument that permits a greater degree of articulation, and hence greater options for addressing the anatomy with knife 805.

Figure 100:
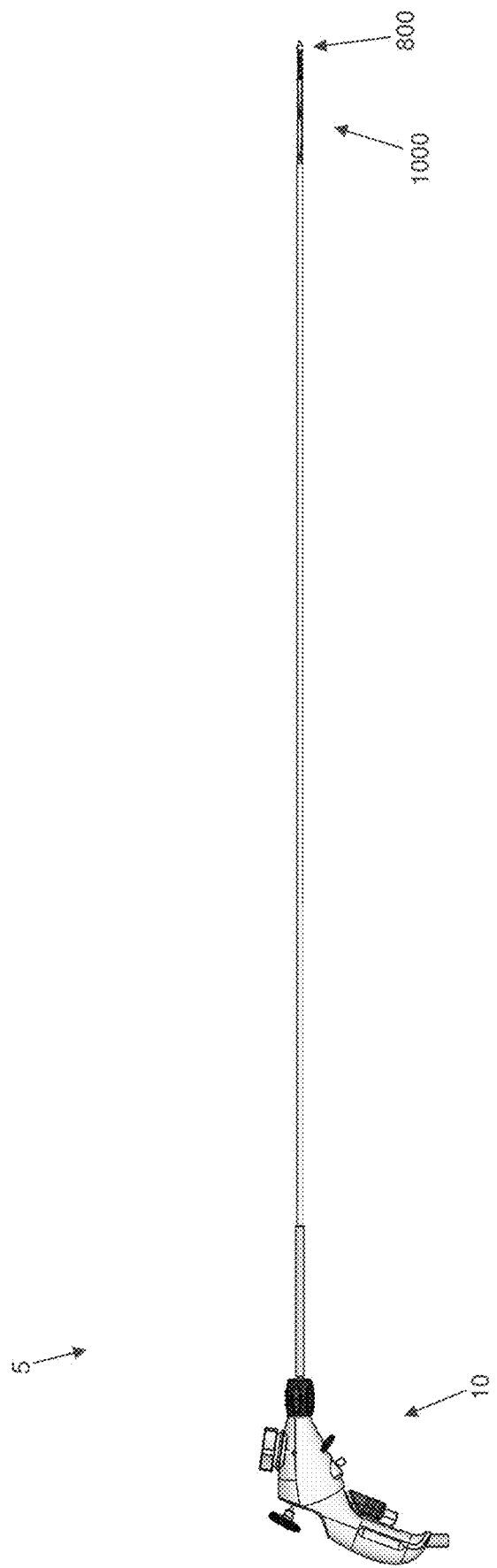
Figure 101:
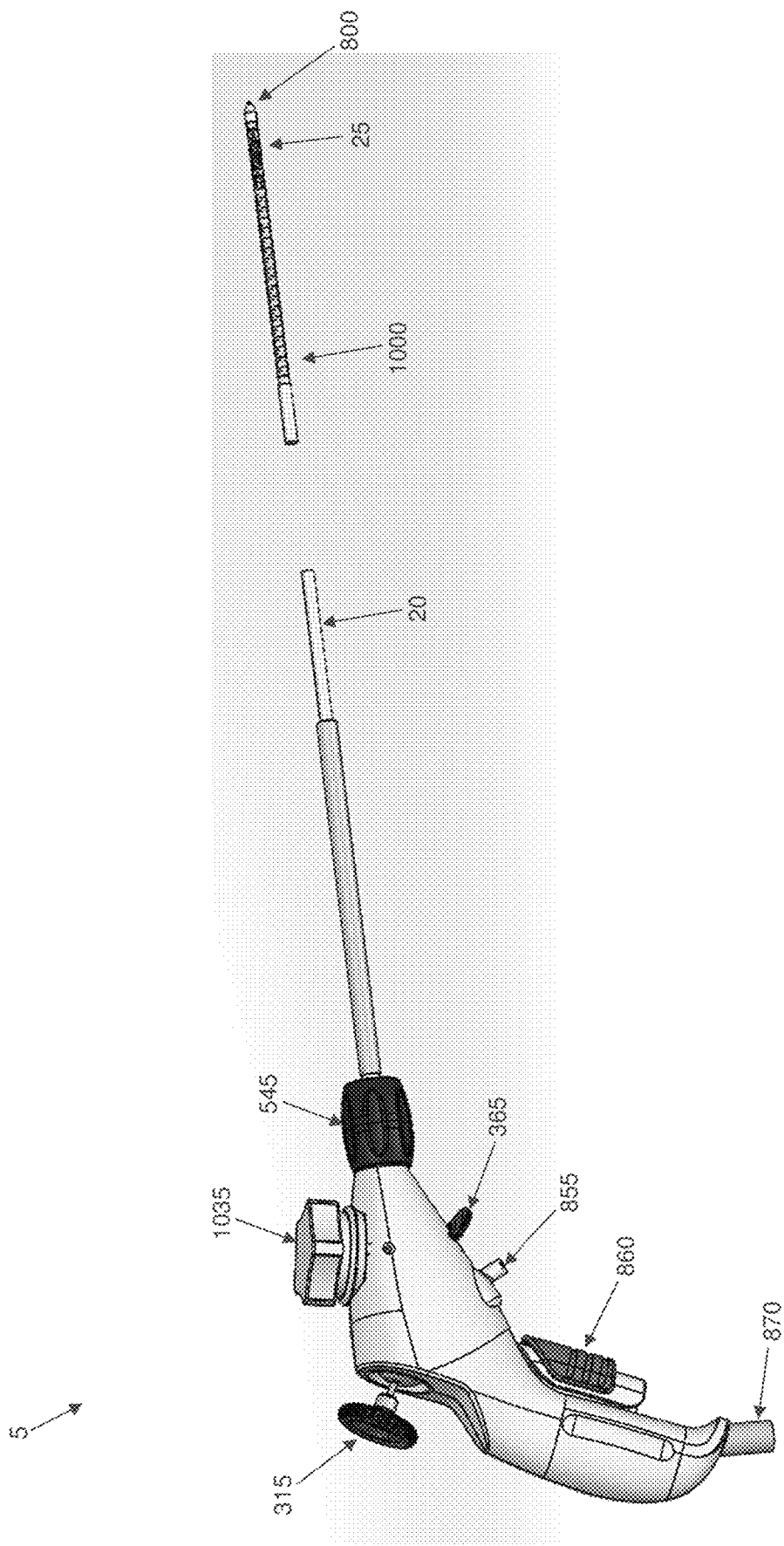

To this end, and looking now at FIGS. 100 and 101, in another preferred form of the present invention, novel medical instrument 5 further comprises an intermediate articulating portion 1000 disposed between the distal end of flexible proximal portion 20 and the proximal end of distal articulating portion 25. Intermediate articulating portion 1000 can be articulated in a single plane (e.g., in a manner analogous to the human "elbow" joint) in order to provide another degree of articulation to distal articulating portion 25 of medical instrument 5, as will hereinafter be discussed in further detail. This additional degree of articulation is sometimes hereinafter referred to as a "gross articulation function". With the additional degree of articulation provided by the gross articulation function provided by intermediate articulating portion 1000, novel medical instrument 5 is capable of at least the following motions:

Motion 1—longitudinal movement of knife 805 by longitudinal movement of handle 10 (sometimes referred to herein as a "longitudinal motion function"); Motion 2—rotational movement of knife 805 by rotational movement of handle 10 (sometimes referred to herein as a "torquing motion function");

Motion 3—articulating movement of knife 805 relative to handle 10 by articulating distal articulating portion 25 of shaft 15 relative to the distal end of intermediate articulating portion 1000 of shaft 15 (sometimes referred to herein as a "universal articulation function");

Motion 4—rotation of shaft 15 independently of handle 10, e.g., selectively rotating rotation knob 545 of rotatable shaft adapter mechanism 525 to allow shaft 15 (and hence flexible proximal portion 20, intermediate articulating portion 1000 and distal articulating portion 25) to be selectively rotated relative to handle 10;

Motion 5—extension and retraction of knife 805 relative to knife housing 820, e.g., selectively moving slider 860 so as to move pull wire 230 distally and proximally, whereby to extend and retract knife 805 relative to knife housing 820; and Motion 6—articulating movement of distal articulating portion 25 and knife 805 relative to flexible proximal portion 20 of shaft 15 by articulating intermediate articulating portion 1000 of shaft 15 relative to the distal end of flexible proximal portion 20 of shaft 15 (sometimes referred to herein as a "gross articulation function").

Figure 102:
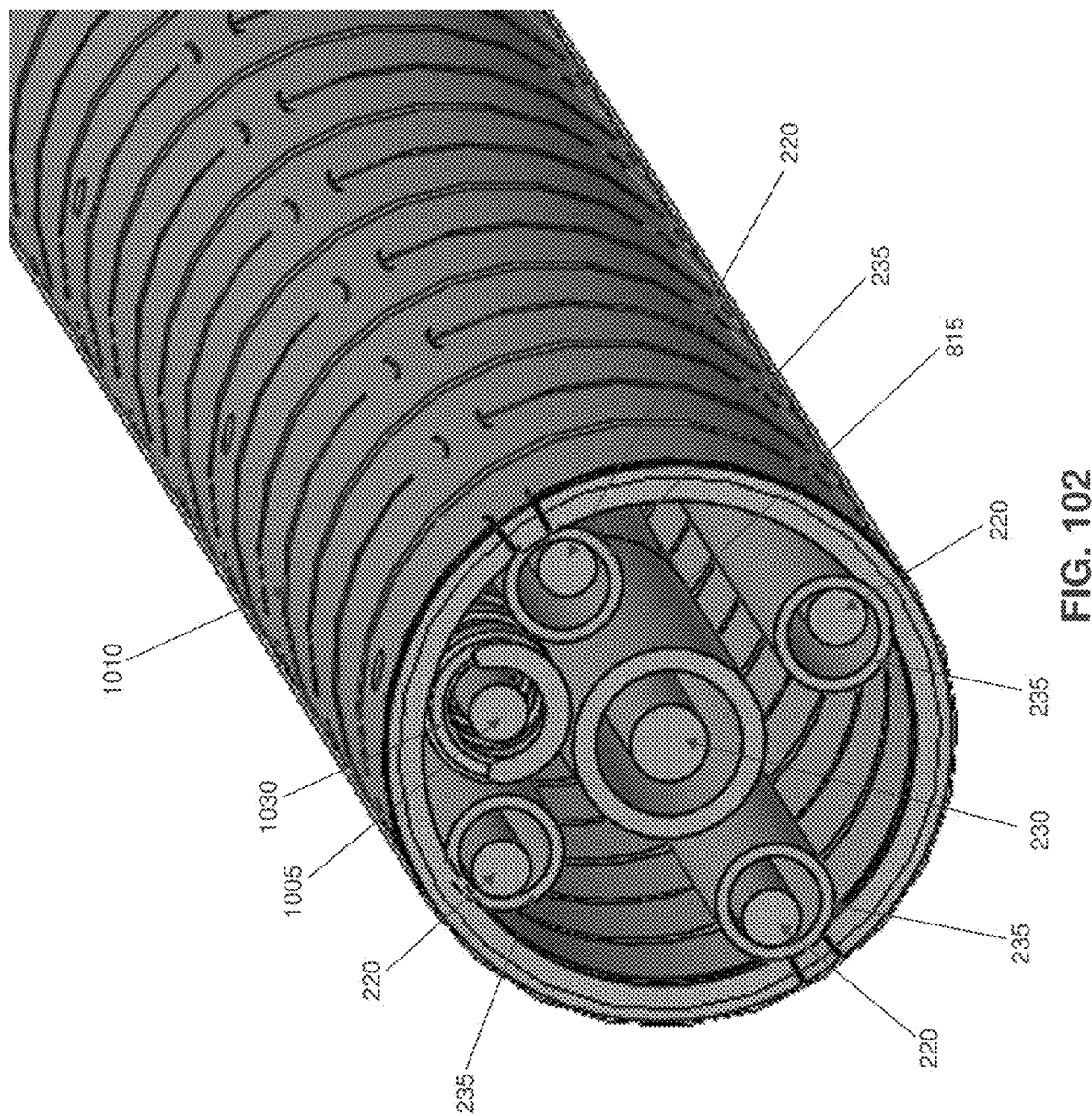
Figure 103:
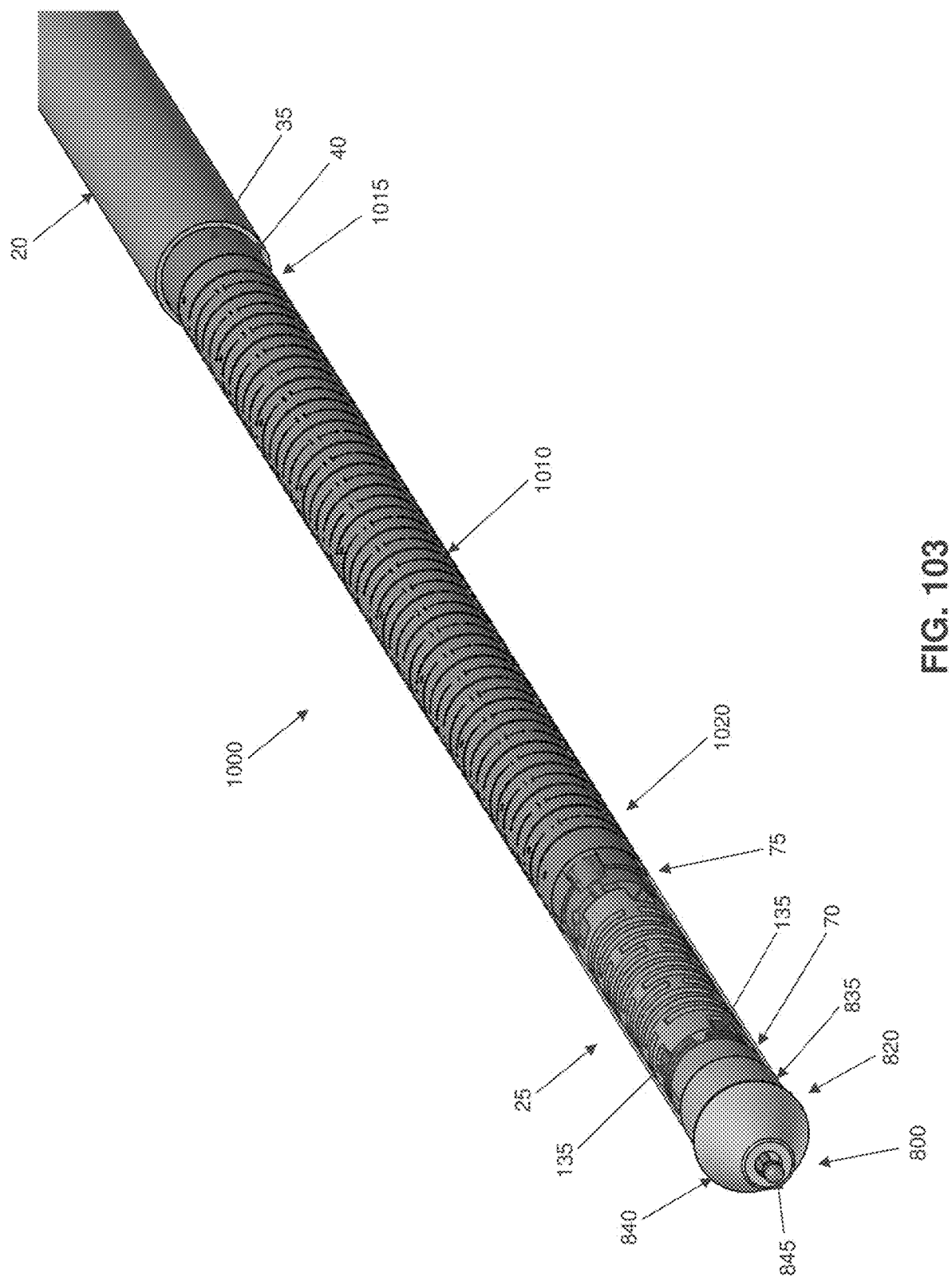
Figure 104:
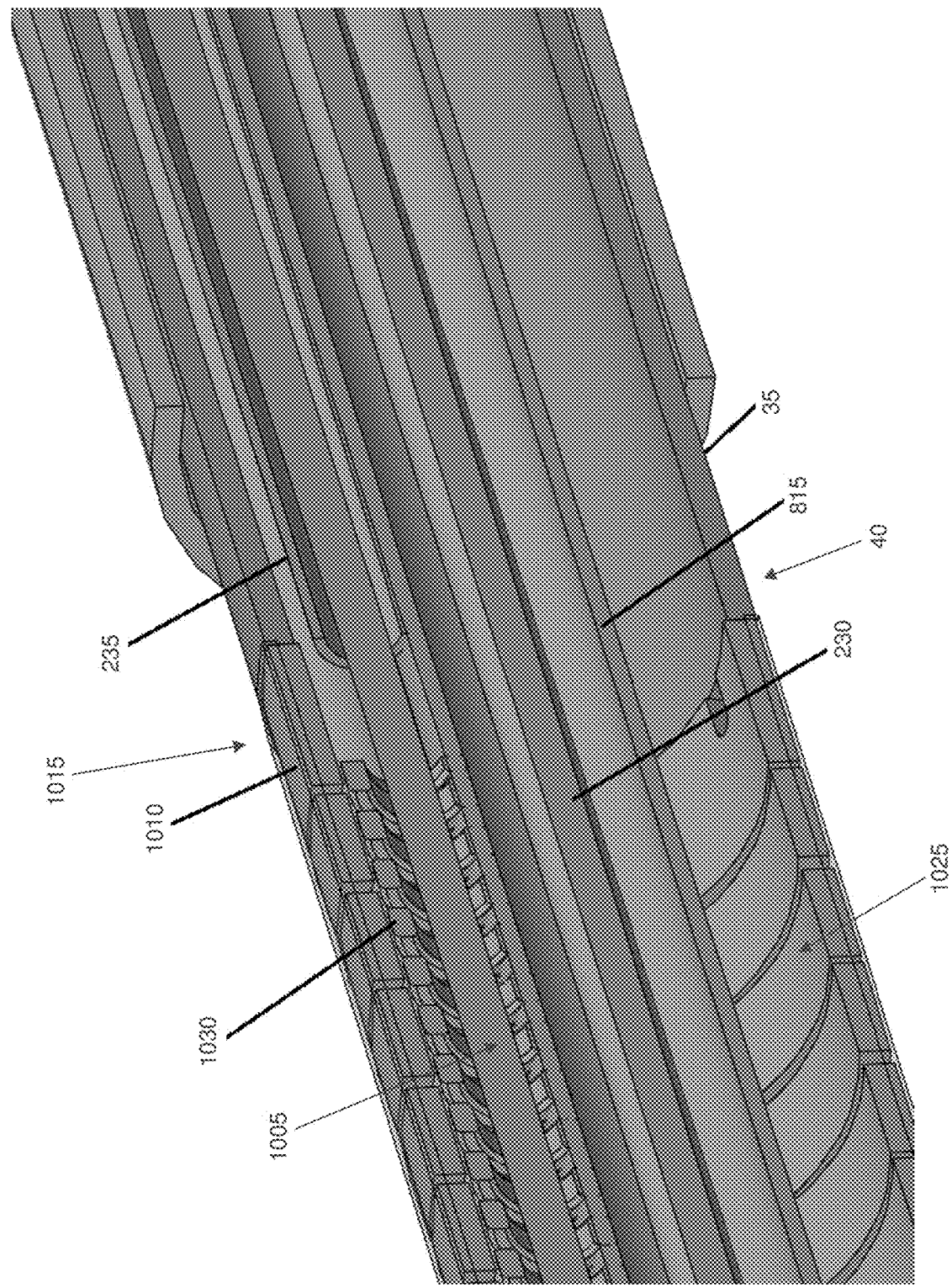
Figure 105:
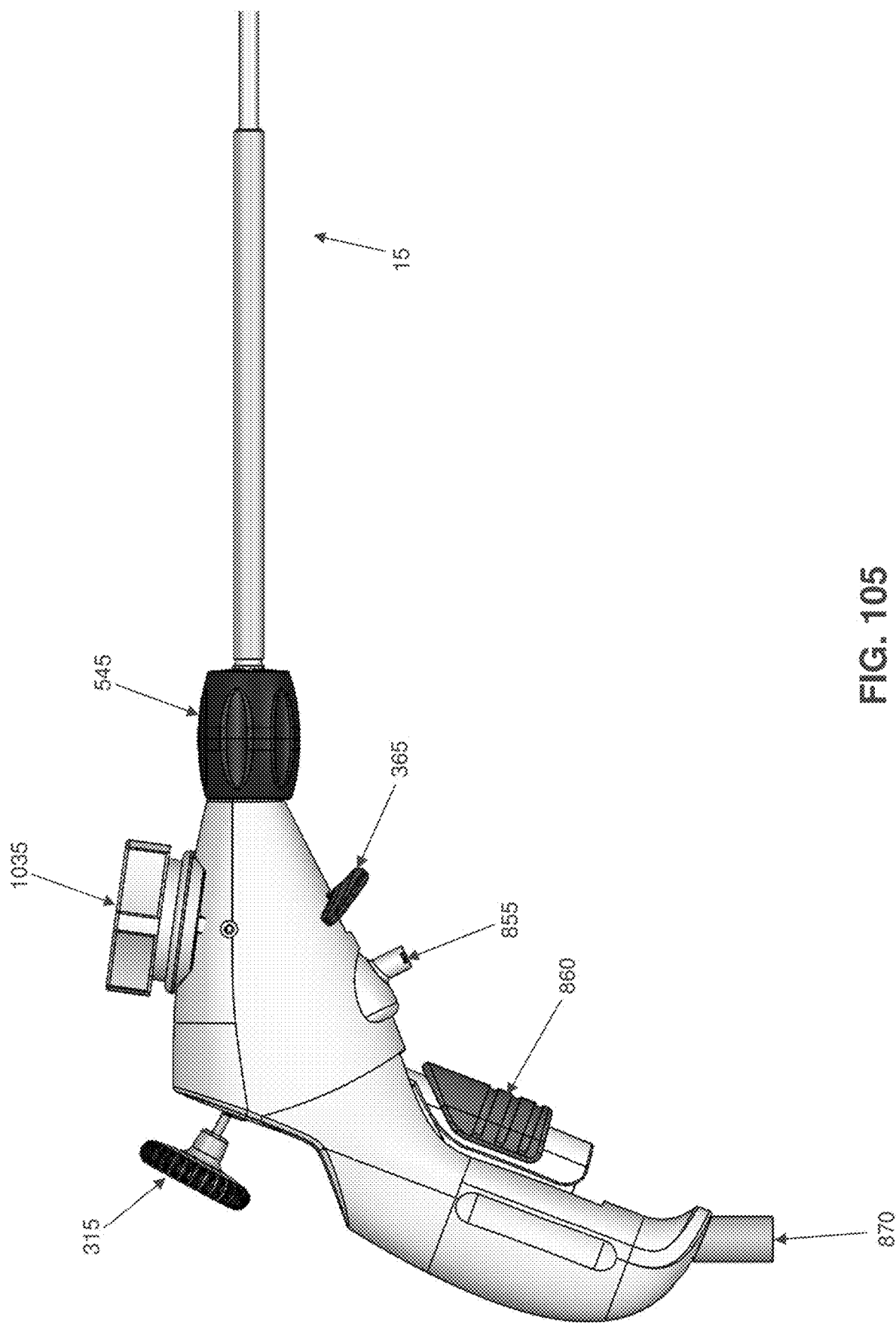
Figure 106:
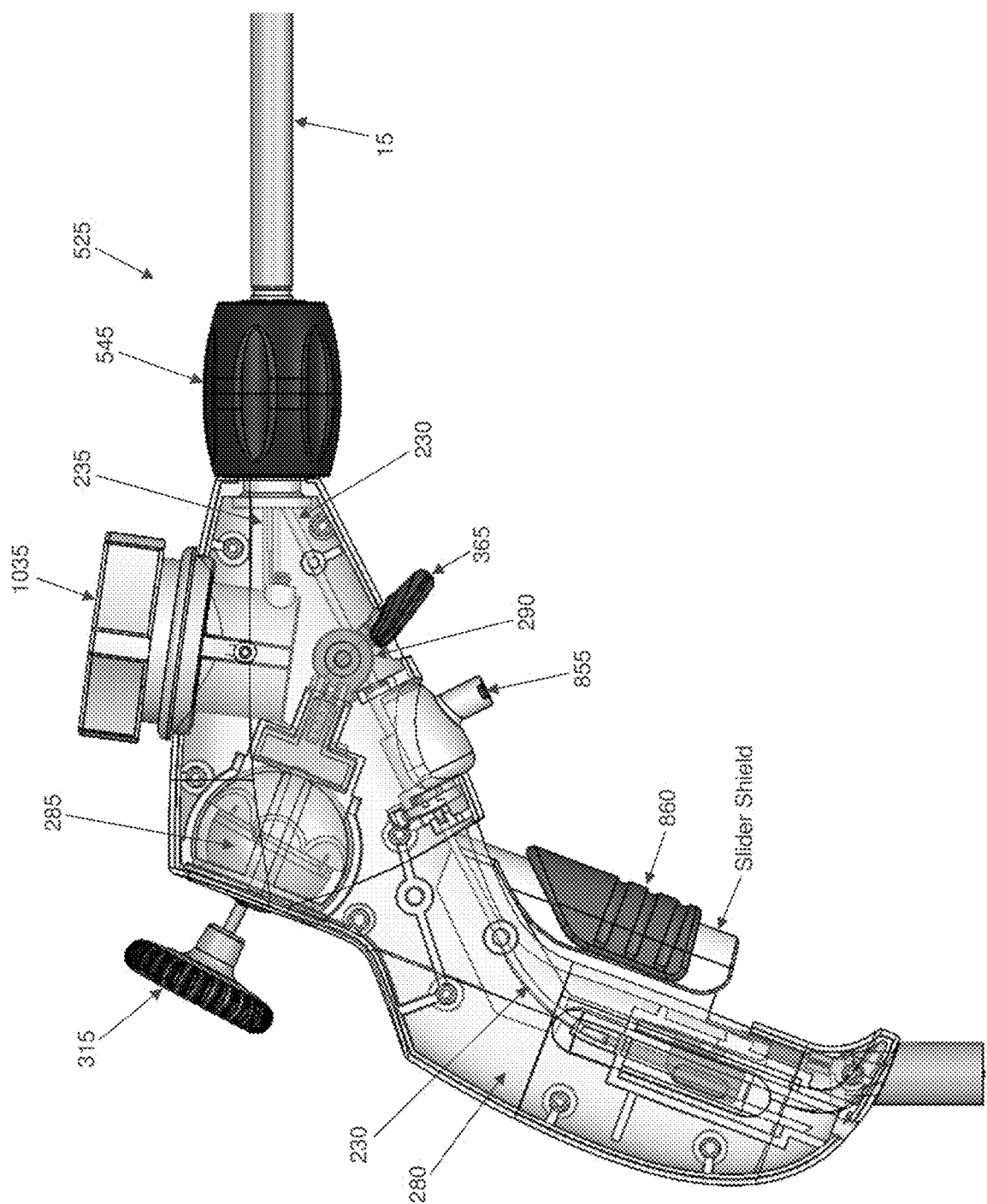

More particularly, and looking next at FIGS. 102-104, in this form of the invention, novel medical instrument 5 comprises (i) four articulation cables 220 for selectively articulating distal articulating portion 25 relative to the distal end of intermediate articulating portion 1000, (ii) a pull wire 230 for selectively moving knife 805 between its extended position and retracted position, and (iii) a gross articulation cable 1005 for selectively articulating intermediate articulating portion 1000 relative to the distal end of flexible proximal portion 20, as will hereinafter be discussed in further detail.

Still looking at FIGS. 102-104, intermediate articulating portion 1000 generally comprises a flex spine 1010 (e.g., a laser-cut hypotube) having a proximal end 1015, a distal end 1020, and a central cavity 1025 disposed therebetween. Proximal end 1015 of intermediate articulating portion 1000 is mounted (e.g., welded, crimping, etc.) to distal end 40 of flexible outer coil 35, and distal end 1020 of intermediate articulating portion 1000 is mounted (e.g., welded, crimping, etc.) to proximal articulation link assembly 75.

Gross articulation cable 1005 runs from distal end 1020 of flex spine 1010 to handle 10. The distal end of gross articulation cable 1005 comprises a crimp (not shown), which is welded to the distal end of gross articulation cable 1005, which is, in turn, mounted to (e.g. welded to) the inside surface of flex spine 1010 proximate distal end 1020 of flex spine 810. The proximal end of gross articulation cable 1005 is attached to a control assembly within handle 10, as will be discussed in further detail below.

The portion of gross articulation cable 1005 which extends between distal end 1020 of flex spine 1010 and proximal end 1015 of flex spine 1010 is slidably disposed within a gross articulation cable conduit 1030 which is disposed within cavity 1025 of flex spine 1010. The portion of gross articulation cable 1005 which extends from distal end 40 of flexible outer coil 35, through flexible proximal portion 20 and through shaft 15 to handle 10 is slidably disposed within an articulation cable housing 235. Gross articulation cable conduit 1030 is welded to proximal end 1015 of flex spine 1010, and articulation cable housing 235 is welded to flexible outer coil 35 of shaft 15, but gross articulation cable conduit 1030 is not connected to articulation cable housing 235.

Gross articulation cable conduit 1030 and articulation cable housing 235 separate gross articulation cable 1005 from articulation cables 220/articulation cable housings 235, whereby to ensure smooth sliding movement of gross articulation cable 1005 within intermediate articulating portion 1000, flexible proximal portion 20 and shaft 15 (i.e., over the distance between distal end 1020 of flex spine 1010 and handle 10, which may be substantial in length (e.g., 95 cm-140 cm) and which often follows a tortuous path when medical instrument 5 is disposed in a patient).

Gross articulation cable conduit 1030 is constructed so as to be more compressible than articulation cable housing 235 so as to ensure that flex spine 1010 can deflect to a desired angle. In one preferred form of the invention, gross articulation cable conduit 1030 comprises a coiled spring such that proximal movement of gross articulation cable 1005 causes flex spine 1010 to articulate relative to distal end 40 of flexible outer coil 35 while allowing gross articulation cable conduit 1030 to compress along its longitudinal dimension.

As a result of this construction, by selectively moving gross articulation cable 1005 proximally, flex spine 1010 of intermediate articulating portion 1000 can be selectively articulated laterally relative to distal end 40 of flexible outer coil 35, whereby to selectively articulate intermediate articulating portion 1000 of shaft 15.

Significantly, inasmuch as only a single gross articulation cable 1005 is provided, intermediate articulating portion 1000 can only be articulated in a single plane. However, if desired, additional gross articulation cables 1005 may be provided if articulation in additional planes is desired, as will be apparent to one skilled in the art in view of the present disclosure.

Looking next at FIGS. 100, 101 and 105-108, a preferred mechanism for selectively moving gross articulation cable 1005 is shown.

More particularly, as discussed above, handle 10 generally comprises an internal cavity 280, an articulation control assembly 285 for selectively moving articulation cables 220 (and hence selectively articulating distal articulating portion 25 of shaft 15), a push rod lock assembly 290 for selectively locking articulation control assembly 285 in a desired position (and hence locking distal articulating portion 25 of shaft 15 in a selected position), a slider 860 for selectively actuating pull wire 230 (and hence selectively moving knife 805 distally and proximally relative to knife housing 820), and a rotatable shaft adapter mechanism 525 for selectively rotating shaft 15 (i.e., flexible proximal portion 20, intermediate articulating portion 1000 and distal articulating portion 25) relative to handle 10.

In this form of the present invention, handle 10 is also provided with a gross articulation control assembly 1035 for selectively moving gross articulation cable 1005 proximally or distally (and hence selectively articulating flex spine 1010 of intermediate articulating portion 1000 of shaft 15 relative to flexible proximal portion 20 of shaft 15).

Gross articulation control assembly 1035 generally comprises a spindle housing 1040 fixedly mounted within internal cavity 280 of handle 10, a spindle 1045 configured to be selectively rotated within spindle housing 1040, and a knob 1050 configured to be engaged by a user.

The proximal end of gross articulation cable 1005 exits the proximal end of shaft 15, passes through a portion of internal cavity 280 of handle 10, and is mounted to spindle 1045 (e.g., via a crimp welded to gross articulation cable 1005 and to spindle 1045, via welding gross articulation cable 1005 directly to spindle 1045, etc.). Cable housing 235 for gross articulation cable 805 preferably terminates at the proximal end of shaft 15, however, if desired, cable housing 235 for gross articulation cable 1005 may extend into internal cavity 280 of handle 10 and terminate at the outer wall of spindle housing 1040.

As a result of this construction, when knob 1050 is rotated in a first direction, the proximal end of gross articulation cable 1005 is pulled proximally, whereby to selectively articulate flex spine 1010 of intermediate articulating portion 1000 of shaft 15 from a straight configuration to an articulated configuration (relative to flexible proximal portion 20 of shaft 15), and when knob 1050 is rotated in a second, opposite direction, the tension on the proximal end of gross articulation cable 1005 is relaxed and allowed to move distally, whereby to enable flex spine 1010 of intermediate articulating portion 1000 of shaft 15 to return to its straight, non-articulated configuration.

It should also be appreciated that, if desired, flex spine 1010 of intermediate articulating portion 1000 can be configured to automatically return to its straight (i.e., non-articulated) configuration when knob 1050 is released by a user. By way of example but not limitation, flex spine 1010 may be formed out of a resilient flexible material that is biased towards assuming a straight configuration. As a result of this construction, releasing knob 1050 of gross articulation control assembly 1035 permits gross articulation cable 1005 to move distally (i.e., under the power of the biasing force provided by the resilient nature of flex spine 1010), whereby to permit flex spine 1010 to return to its straight (i.e., non-articulated) configuration. Alternatively and/or additionally, if desired, an additional gross articulation cable 1005A (not shown) may be provided, wherein the distal end of the additional gross articulation cable 1005A is mounted (e.g., diametrically opposed to gross articulation cable 1005) to the inner surface of flex spine 1010 proximate distal end 1020 of flex spine 1010, whereby to help facilitate returning flex spine 1010 (and hence intermediate articulating portion 1000) to its straight (i.e., non-articulated) configuration and/or articulating flex spine 1010 in a second, opposite direction.

It is important to note that rotating knob 1050 of gross articulation control assembly 1035 so as to articulate flex spine 1010 of intermediate articulating portion 1000 typically requires the use of two hands (i.e., one hand to grip handle 10, and the other hand to rotate knob 1050). However, it should be appreciated that, if desired, knob 1050 could be replaced with a lever (not shown) or other actuation means, so as to facilitate one-handed articulation of flex spine 1010 of intermediate articulating portion 1000.

In an exemplary use of this form of novel medical instrument 5 in a minimally-invasive procedure, knife 805 is retracted; shaft 15 is straightened; handle 10 is longitudinally advanced so as to longitudinally advance knife 805 through a portal and into the body (e.g., along a tortuous path); handle 10 is longitudinally advanced and/or rotated, and/or distal articulating portion 25 of shaft 15 is articulated, and/or intermediate articulating portion 1000 is articulated so that knife 805 is adjacent to the target tissue inside the body; knife 805 is extended; monoelectric power is delivered to knife 805; knife 805 is used to perform the desired procedure (e.g., mark tissue, cut tissue, etc.); knife 805 is retracted; and medical instrument 5 is withdrawn from the body, e.g., handle 10 is longitudinally withdrawn through the portal (during which the handle may also be rotated, and/or distal articulating portion 25 of shaft 15 is straightened (i.e., moved so as to assume its non-articulated configuration), and/or flex spine 1010 of intermediate articulating portion 1000 is straightened (i.e., moved so as to assume its non-articulated configuration).

If desired, a syringe (or another suitable pressurized liquid source) filled with sterile water (or another fluid) may be used to inject fluid into fluid inlet port 855 to flush water out of the distal end of knife housing 820 to clean knife 805 (or the surrounding tissue) while knife 805 is being used to perform the desired procedure.

It will be appreciated by those skilled in the art that, if desired, the medical instrument may be modified so as to provide less (or more) than the aforementioned motions, e.g., the roticulation function may be added, an additional rotational function such as selective rotation of shaft 15 may be added, etc.

Modifications of the Preferred Embodiments

It should be understood that many additional changes in the details, materials, steps and arrangements of parts, which have been herein described and illustrated in order to explain the nature of the present invention, may be made by those skilled in the art while still remaining within the principles and scope of the invention.

What is claimed is:

1. Apparatus for performing a minimally-invasive procedure, the apparatus comprising:
   a shaft having a distal end and a proximal end;
   a monopolar knife assembly attached to the distal end of the shaft, the monopolar knife assembly comprising a knife;
   a handle attached to the proximal end of the shaft;
   wherein the shaft comprises a flexible portion and a first articulating portion, wherein the flexible portion extends distally from the handle and the first articulating portion extends distally from the flexible portion;
   wherein the shaft comprises a second articulating portion, wherein the second articulating portion is disposed between the flexible portion and the first articulating portion;
   wherein at least one first articulation cable extends from the handle to the first articulating portion, such that when tension is applied to the at least one first articulation cable, the first articulating portion deflects;
   wherein at least one second articulation cable extends from the handle to the second articulating portion, such that when tension is applied to the at least one second articulation cable, the second articulating portion deflects;
   wherein an actuation element extends through the shaft from the handle to the knife, such that when the actuation element is moved, the knife is moved; and
   wherein the actuation element transmits electrical power from the handle to the knife.

2. Apparatus according to claim 1 wherein the knife comprises a distal end and a proximal end, and further wherein the distal end of knife comprises a rounded front portion and a flattened back portion.

3. Apparatus according to claim 1 wherein the knife comprises a distal end and a proximal end, and further wherein the proximal end of the knife comprises a mount.

4. Apparatus according to claim 3 wherein the mount comprises a distal end, a proximal end and a cylindrical wall extending between the distal end and the proximal end, and further wherein the cylindrical wall is recessed to provide a plurality of concave portions and a plurality of convex portions.

5. Apparatus according to claim 1 wherein the knife is received in a knife housing, and further wherein the actuation element extends and retracts the knife relative to the knife housing.

6. Apparatus according to claim 5 wherein the knife housing comprises a stepped bore having a first portion and a second portion, wherein the first portion is distal to the second portion, and further wherein the first portion has a smaller diameter than the second portion.

7. Apparatus according to claim 6 wherein the second portion limits extension of the knife relative to the knife housing.

8. Apparatus according to claim 1 further comprising a tube extending from the handle to the distal end of the shaft.

9. Apparatus according to claim 8 wherein the actuation element extends through the tube.

10. Apparatus according to claim 8 wherein the tube is configured so that fluid can be passed through the tube from the handle to the distal end of the shaft.

11. Apparatus according to claim 10 wherein the handle comprises a fluid inlet port for receiving fluid.

12. Apparatus according to claim 1 wherein the articulating portion and the second articulating portion articulate independently of one another.

* * * * *